United States Patent
Briles et al.

(12) 
(10) Patent No.: US 6,500,613 B1
(45) Date of Patent: Dec. 31, 2002

(54) PNEUMOCOCCAL SURFACE PROTEINS AND USES THEREOF

(75) Inventors: David E. Briles, Birmingham, AL (US); Larry S. McDaniel, Ridgland, MS (US); Edwin Swiatlo, Birmingham, AL (US); Janet Yother, Birmingham, AL (US); Marilyn J. Crain, Birmingham, AL (US); Susan Hollingshead, Birmingham, AL (US); Rebecca Tart, Benson, NC (US); Alexis Brooks-Walter, Birmingham, AL (US)

(73) Assignee: University of Alabama at Birmingham, Birmingham, AL (US)

( * ) Notice: Subject to any disclaimer, the term of this patent is extended or adjusted under 35 U.S.C. 154(b) by 0 days.

(21) Appl. No.: 08/714,741

(22) Filed: Sep. 16, 1996

Related U.S. Application Data

(63) Continuation-in-part of application No. 08/529,055, filed on Sep. 15, 1995.

(51) Int. Cl.⁷ .......................... C12Q 1/68; A61K 39/00; A61K 39/09; C07H 21/04
(52) U.S. Cl. ...................... 435/6; 424/184.1; 424/244.1; 536/23.7
(58) Field of Search ................... 424/184.1, 244.1; 435/6; 536/23.7

(56) References Cited

PUBLICATIONS

McDaniel et al, "Use of insertional inactivaion to facilitate studies of biological properties of pneumococcal surface protein A (PspA)", Journal of Experimental Medicine, vol. 165, No. 2, pp. 381–394, Feb. 1, 1987.*

* cited by examiner

*Primary Examiner*—James C. Housel
*Assistant Examiner*—Rodney P. Swartz
(74) *Attorney, Agent, or Firm*—Frommer Lawrence & Haug LLP; William S. Frommer; Thomas J. Kowalski

(57) ABSTRACT

The present invention relates to pneumococcal genes, portions thereof, expression products therefrom and uses of such genes, portions and products; especially to genes of *Streptococcus pneumoniae,* e.g., the gene encoding pneumococcal surface protein A (PspA), i.e., the pspA gene, the gene encoding pneumococcal surface protein A-like proteins, such as pspA-like genes, e.g., the gene encoding pneumococcal surface protein C (PspC), i.e., the pspC gene, portions of such genes, expression products therefrom, and the uses of such genes, portions thereof and expression products therefrom.

9 Claims, 69 Drawing Sheets

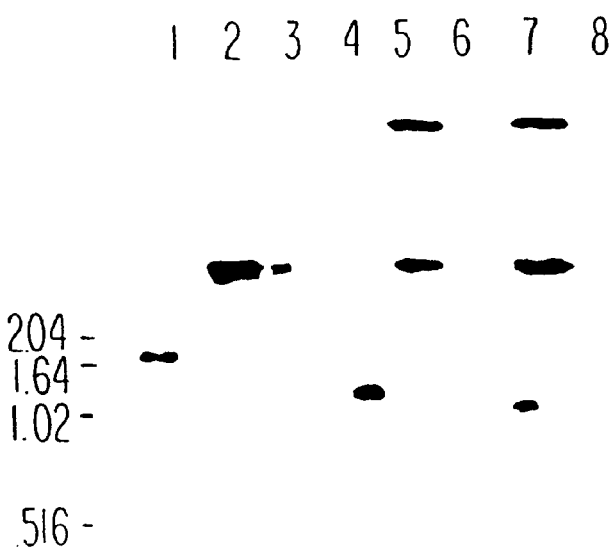
FIG. IA
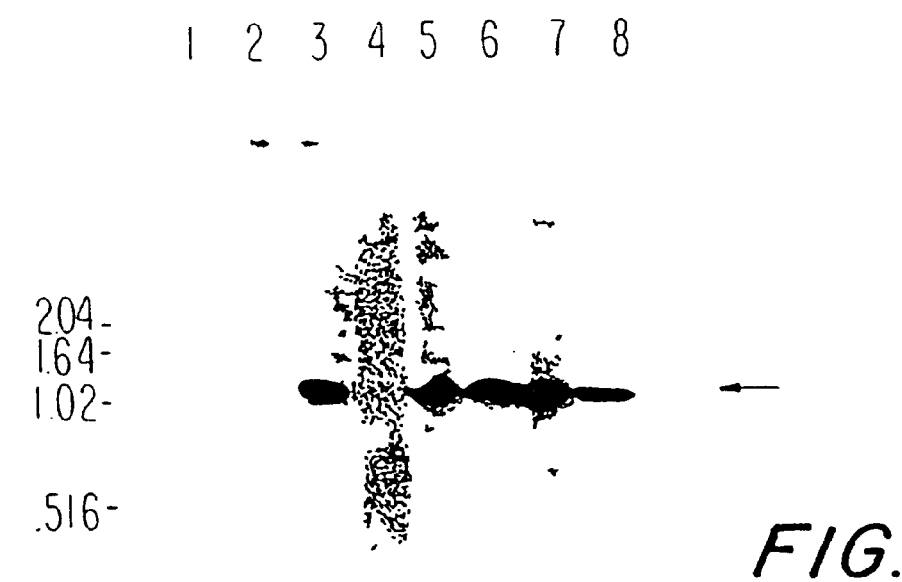
FIG. IB pLSMpspA13/2

FIG. 5A pLSMpspA12/6

FIG. 5B

AMINO ACID SEQUENCES IN THE NH2-TERMINAL END OF DIFFERENT PSPA GENES.
Gap inserted to maximize alignment with related PspA sequences).

```
AtCC6303   MNKKKMILTS LASVAILGTG FVASPPTLVR AEESPQVVEK SSLEKKYEEA
           KAKADTAKKD YETAKK...K AEDAQKKYDE DQKKTEDKAK A.VKKVDEER
           QKAILAVQKA YVEY....RE AKDKASAEKQ IAEAKRKT.. ..........
           .......... .......... .......... .......... :

Ac94...    MNKKKMILTS LASVAILGAG LVTAQPTLVR AEEAP.VASQ SKAEKDYDTA
           KRDAENAKKA LEEAKR.... ..AQKKYED DQKKTEEKAK E.EKQASEAE
           QKANLQYQLK LREYIQ..KT GDRSKIQTEM EEAEKKHKTA KAEFDKVRGT
           VIPSAARV.. .......... .......... .......... :

Bg11703pro MNKKKMILTS LASVAILGAG LVTSQPTLVR AEEAP.VASQ SKAEKDYDAA
           VKKSEAAKKA YEEAKK...K AEDAQKKYDE DQKKTEEKA. ENEKKAAADL
           TEATEVHQKA YVRYSGSNEQ KIKNFKILAI .......... ..........
           .......... .......... .......... .......... :

Bg7322pro  MXKKKMILTS LASVAILGAG XVASQPTXVR AEDAP.VANQ SQAEKDYXAA
           XXXKSEAAKKX YXXAKKVLAE AEAAQKXXED XQKKPEEKA. EKAKAASEEI
           VKATEEVQXA A......... .......... .......... ..........
           .......... .......... .......... .......... :
```

*FIG. 13A*

```
Bg7561pro  MNKKKMILTS LASVAILGAG LVTSQPTLVR AEEAP.GASQ SKAEKDYXAA
           XKKSEAAKKA YEEAAKK...K AEDAQKKYDE GQKKTEEKA. RKAEEASKEL
           AKATSEVQNA YVKYQGVQRN SRLNEKERKK QLAEIDEEIN KAKQIWNEKN
           EDFKKVREEV IPEPTELAKD QRKAEEEAKAE EKVAKRKYDY ATLKVALAKS
           YVEAEEAXL. .........  .........  .........  .........

Bg8090pro  MNKKKMILTS LASVAILGAG LVTSQPTFVR AEEAP.VASQ PKAEKDYDPA
           GKKSEAATKA YEDAKP...T AEDAQKKYDE AQKKPDAER. .........

Bg8743pro  MNKKKMILTS LASVAILGAG LVASQPTVVR AEEAP.VAKQ SQAERDYDAA
           MKKSEAAKKE YEEAAKKDLEE AKAAQKKYGG DPKKTGEETK LVPK.ADGER
           PKANVAVPKA YLKLREAQEQ LNQSPNNKKN SAQQKLKDAL AHIDEVTLNQ
           KEAEA..... .........  .........  .........  .........

Bg8838pro  MNKKKMILTS LASVAILGAG LVTSQPTVVR AEESP.VASQ SKAEKDYDAA
           VKNATAAKKA AEDAHRALDE AKAAQKNYDE DQKKPEEKAK EVPKAPAEE.
```

FIG. 13B

```
Bg9163pro    MNKKKMILTS LASVAILGAG LVASQPTLVR AEDAP.VANQ SQAEKDYDAA
             MKKSEAAKKE YEDAKKVLAE AEAAQKKYED DQKKTEEKA. ENANAASEEI
             AKATEEVH.. .......... .......... .......... ..........

Bg9739pro    .....MNKKK MILTS LASVAILGAG LVASSPTVVR AEEAP.VASQ SKAEKDYDTA
             KRDAENAKKA LEEEAKR.... ..AQEKYAD YQRRIEEKAA K.ETQASLEQ
             QEANKDYQLK LKKYLDGRNL SNSSVLKKEM EEAEKKDKEN QAEFNKIRRE
             IVVPNPQELE MARRKSEVVK ATESGLVTRV EEAEKNVTDA RQKLVLKCNE
             VVLQAXXAEL ESGGHKLEPK .......... .......... ..........

Db11pro      MNKKKMILTS LASXAILGAG LVASQPTVVR AEEAP.VASQ SKAEKDYDAA
             KRDAENAKKA LEEEAKR.... ..AQKXXED DQKKTEEKAK X.DXQASEAE
             QKANLXYQLL LQKYVSESDG KKKKEXEXXA DAAKKEIELK XADLXKIXQE Db15pro      MNKKKMILTS LASVAILGAG LVASQPTVVR AEEAP.VASQ SKAEKDYDAA
             VEKSKAAEED LE.....E AEAAQRKYDE DQKKSEENEK E.TEEASERQ
             QAATLKYHLE SXEFLNYFQD NHR....... .......... ..........

Db16aapro    MNKKKMILTS LASVAILGAG LVASPPTVVR AEEAP.VASQ SKAEKDYDTA
             KRDAENAKKA LEEEAKR.... ..AQEKYAD YQRRIEEKAA K.ETHASLEQ
             QEANKDYQLK LKKYLDGRNL SNSSVLKKEM EEAEKKDKEK PAEFNKIRRE
             IVVPNPQELE MARRKSEVAK TKESGLVKRV EEAEKKVTEA RPKLDAERAK
             EVVLQAQIA. .......... .......... .......... ..........
```

FIG. 13C

```
Db16apro    MNKKKMILTS LASVAILGAG LVASPPTVVR AEEAP.VASQ SKAEKDYDTA
            KRDAENAKKA LEEAKR.... ..AQEKYAD YQRRIEEKAA K.ETHASLEQ
            QEANKDYQLK LKKYLDGRNL SNSSVLKKEM EEAEKKDKEK QAGL......
            .......... .......... .......... .......... ..........

Ef10197pro  MNKKKMILTS LASVAILGAG LVTSQPTLVR AEESP.VASQ SKAEKDYDAA
            KRDAENAKKA LEEAKR.... ..AQEKYAD YQRRIEEKAA K.EQQASLEQ
            QEANKDYQLK LKKYLDGRNL SNSSVLKKEM EEAEKKDKEK QAEFNKIRRE
            IVVPNPQELE MARRKSEVVK AKESGLVKRV EEAEKKVTEA RQKLDAERAK
            EVVLQPTR*V ENEVHKLXQK Ef3296pro   MNKKKMILTS LASVAILGAG LVTSQPTFVR AEESPQVVEK SSLEKKYEEA
            KAKADTAKKD YETAKK...K AEDAQKKYED DQKRTEEKAR K.EAEASQKL
            IDVALVVQNA YKEY....RE VQNQRSKYKS DADYQKKLTE VDSKIEKARK
            EQQDLQNNFN EVRAVVAPDP TCVGXDXR..

Ef6796pro   MNKKKMILTS LASVAILGAG XVTSQPTXVR AEEAPQVVEK SSLEKKYEEA
            KAKYDAAKKD YDEAKK...K AAEAQKKYEE DQKKTEEKAE K.AKAASEEI
            AKATEEVQKA VLDYITAIRN HNDSGKTSAE EAENKAKERD YCCAGKKFDP
            IQTPFVASLT QMIL......

L81905pro   MNKKKMILTS LASVAILGAG LVASSPTVVR AEEAP.VASQ SKAEKDYDTA
            KRDAENAKKA LEEAKR.... ..AQEKYAD YQRRIEEKAA K.ETQASLEQ
            QEANKDYQLK LKKYLDGRNL SNSSVLKKEM EEAEKKDKEN QAEFNKIRRE
            IVVPNPQELE MA........
```

*FIG. 13D*

```
Rx1pro    MNKKKMILTS LASVAILGAG FVASQPTVVR AEESP.VASQ SKAEKDYDAA
          KKDAKNAKKA VEDAQKALDD AKAAQKKYDE DQKKTEEKA. ALEKAASEEM
          DKAVAAVQQA YLAYQQATDK AAKDAADKMI DEAKKREEEA KTKFNTVRAM
          VVPEPEQLAE TKKKSEEAKQ KAPELTKKLE EAKAKLEEAE KKATEAKQKV
          DA........ .......... .......... .......... ..........

Wu2pro    MNKKKMILTS LASVAILGAG LVASQPTLVR AEESP.VASQ SKAEKDYDAA
          VKKSEAAKKA YEEAKKALEE AKVAQKKYED DQKKTEEKA. ELEKEASEAI
          AKATEEVQQA YLAYQRASNK A..EAAKMIE EAQRRENEAR AKFTTIRTTM
          VVPEPEQLAE TKKKAEEAKA KEPKLAKKAA EAKAKLEEAE KKATEANPQV
          DA........ .......... .......... .......... ..........

Ef5668pro MNKKKMILTS LASVAILGAG FVASSPTFVR AEEAP.VANQ SKAEKDYDAA
          VKKSEAAKKD YETAKK...K AEDAQKKYDE DQKKTEAKAE K.ERKASEKI
          AEATKEVQQA YLAYLQASNE SQRKEADKKI KEATHAKMRR TCNLTIEFEQ
          QLYFLNQVSY LRLRKKQKRQ QKKQKYLRKN LKRQLKRYKY RKIKYLNKML
          KTKRKL.... .......... .......... .......... ..........

Bg6692pro MNKKKLIVTS LASVAILGAD SVTSPPALVR ADEASLIASQ SKAEKDYDAA
          KKDAKNAKKA VEDAQKALDD AKAAQKKYDE DQKKTEKKAA AV.KKIDEEH
          QAANLKSQQA LVEFLAAQRE GNPKKKKAAQ ATLEEAENAE KETK......
```

*FIG. 13E*

```
Ac122pro     MNKKKMIKTS LASAAIFGAX SETSQPTRVR PVEAPE.ARH PKVDKYYDAE
             ADEY...... .......... .......... .......... ..........
             .......... .......... .......... .......... ..........
             .......... .......... .......... .......... ..........
             .......... ..........
A66pro       MNKKKMILTS LASVAILGAG FGCVSAYSCK SRRISRS*SA *SSQRL....
             .......... .......... .......... .......... ..........
             .......... .......... .......... .......... ..........
             .......... .......... .......... .......... ..........
             .......... ..........
L82013pro    MNKKKMILKS LASAAISGAX LVXPQPTLVR AEESP.AASQ SHPEQDYDXX
             XXLCXXLXHQ PSXGRTLLXX XXSXPXSPTP XXXXXXPXSX LTXLXPLXXX
             LKPFPLPXSX PXPPXPPXSP PSPPPRPXLY XXPPXPXPXL SLXLIPFLLL
             XLPPPXXXLP HLXSPPXPXL PPSPTPX... .......... ..........
             .......... ..........
```

*FIG. 13F*

SEQUENCES IN THE CENTRAL REGION - (Includes Carboxy-terminus of alpha-helix region and some of the proline-rich region. Gaps are inserted to maximize alignment related PspA sequences.)

```
30 336
0922134c
             ..........  ..........  ..........  ..........  ..........
             ........L   KEIDESDSED  YLKEGLRAPL  QSKLDTKKAK  LSKLEELSDK
             IDELDAEIAK  LEVQLKDAEG  NNNVE.....  A.YFKEGLEK  TTAEKKAELE
             KAEADLKKAV  DEPETPAPA.  ......PQPA  PAPEKPAE..  .........K
             PAPAPAP...  EKPAPAPE..  ...K.PAEK   PAEKPAEEPA  EKPAPAPEK.
             ..........  ...PAPTPE   .KPAPTPETP  KTGWKQENGM  ..........

Atcc6303c
             ..........  ..........  ..........  .........V  LDXTIAEGKA  GIAAXPPNID
             KT....PKDL  EDSGLGLEKV  LATLDPGGET  PDGLDKEASE  DSNIGALPNQ
             VSDLENQVSE  LDREVTRLPS  DLKDTEGNNV  GDYVKGGLEK  ALTDEKVGLN
             NTPKALDTAP  KALDTALNEL  G.PDGDEEET  PAPAPKPE..  .....QPA
             EQP....K..  ..........  ...PAPAPK   PEKTDDQQAE  EDYARRSEEE
             YNRLPQQQPP  KAEK..PAPA  PKPEQPVPAP  ..........  ..........

Ac122c
             ..........  ..........  ..........  ....GGW     SWR*ILLARP
             DRLAARQAEL  AQKQTELGKL  LDSLDPEGKT  QDELDKEAGE  ...AELDKK
             ADGLPNKVSD  LEKEISNLEI  LLGGADSEDD  T...AALPN   KLATKKAELE
             KTQKELDAAL  NELG......  ...PDGDEEET  PAPAPQPE..  .........Q
             PAPAPKPEQ.  ..........  ...PTPAPK   PEQPTPAPKP  EQ..PAP...
             .......AP   KPEQ..PAPA  PKPEQPAPAP  KP.EQPTPGP  KIE.......
```

*FIG. 13G*

```
A66c    ..........  ..........  ..........  ..........  ..........  ..........  ..........
        ..........  KAGADLKEAV  NEPGESAGEP  SQPEEPAEEA  PAPEQPTEPT  ..........  ..........
        ..........  ...QPEEP    AGETPAPKPE  K..PAGQPK   AEKTDDQQAE  EDYARRSEEE  E.........
        ..........  ..........  ..........  ..........  ..........  ..........  LLLLEKAGLG
        YNRLTQQQPP  KAEKPAPA..  PQPEQPAPAP  K.........  ..........

Ac94c   ..........  ..........  ..........  ..........  ..........  ..........  ..........
        ........L   KEIDESDSED  YVKEGLRVPL  QSELDVKQAK  LLKLEELSDK
        IDELDAEIAK  NLKKDVEDFQ  NSGGGYS...  .ALYLEAAEK  DLVAKKAELE
        KTEADLKKAV  NEPEKPAEE.  ..........  .PENPAP...  ..........  .APK
        PAPAPQP...  .EKPA.....  ..PAPAPK    PEKSADQQAE  EDYARRSEEE
        YNRLTQQQPP  KAEKPAPAPV  PKPEQPAPAP  KSR.......  ..........

Bg8090c ..........  ..........  ..........  ..........  ..........  ..........  ..........
        VXLDRGPAEA  AVKEQVDSPP  QQLAD*VKEI  STRGKFLGGA  ATEDETSALP
        NKITAKQAEL  AKKQTELEKL  LDNLDPEGKT  QDELDKEAAE  ..AELDKK
        ADELPNKVAD  LEKEISNLEI  LLGGADPEDD  T...AALPN   KLATKKAEFE
        KTPKELDAAL  NELG......  .PDGDEEET   PA........  ..........
        PAPAPKPEQ.  ..........  .PAPA.....  PAPKP       EQPAPAP...
        ..........  AP  KPEQPAPAPA  PKPEQPTPAP  K.........
```

FIG. 13H

```
Bg8743c  ..........  ..........  .L KEIDESDSED  YIKEGLRAPL  .QSKLDAKKAK  .LSKLDELSDK
         IDELDAEIAK  LEKDVGDFPN  SDGEQ.....  AGQYLVAAEK  DLDAKEAELG
         NTGADLKKAV  DEPETPAPA.  ......PAPK  PAPAPAPT..  .........P
         EAPAPA....  PKPAPAPK..  .PAPAPK...  PAPAPKPAPA  PKPAPAPK..
         ..........  ..PAPAPKPE  RT........  ..........  ..........

Bg9163c  ..........  ..........  GVQRTRKRAP  KRIMSLSQKV  XLKXVCRAPL  .QSKLDAQKAE  ......END
         IEELDAEIAE  LEVQLKDAEG  NNNVE.....  A.YFKEGLEK  TTAEKKAELE  LLKLEELSGK
         XAXADLKKAV  DEPETPAPA.  ......PAPA  PAP.......  .........A
         PAPAPA....  PAPAPAPK..  .PAPAPK...  PAPAPAPAPA  PKPAPAPK..
         ..........  ..PAPAPAPA  PKPEKPAEKP  APAPKPETXX  TYG.......

Bg9739c  ..........  ..........  .L KEIDESDSED  YVREGFRAPL  .QSELDAKQAK  .LSKLEELSDK
         IDELDAEIAK  LEKDVEDFQN  SDGEQ.....  AGQYLAAAGE  DLIAKKAELE
         KAEADLKKAV  DEPETPAPA.  ......PAPK  PAPAPAPT..  .........P
         EAPAPAPA..  PKPAPAPK..  .PAPAPK...  PAPAPKPAPA  PKPAPAPK..
         ..........  ..PAPAPAPA  PKPEKPAEKP  APAPKPE...  ..........
```

FIG. 13I

```
Ef1019c    .......    .......    .......    .......    .......    .......
           .......L   KEIDESDSED YVKEGFRAPL .......    QSELDAKQAK .LSKLEELSDK
           IDELDAEIAK LEDQLKAAEE NNNVE...... .......    .DYFKEGLEK TIAAKKAELE
           KTEADLKKAV NEPEKPAEEP SQPEKPAEEA  PAPEQPTEPT QPEKPAEQPQ
           PAPAPQPEKP AEETPAPKPE K...PAEQPK  .......    .......
           YNRLTQQQPP KAEKPAPA.. PKTK......  .......    .......

Ef3296c    .......GGS ALDQEAAAPP HQVADLEKQI  TGPEIFLGGA DPEADIAARP
           NELAAKQAEL AQKPTGLEKL LDSLDPGGKT  QDELDKEAGE ...AELDKK
           ADELPNKVAD LEKEISNLEI LLGGADSEDD  T...AALPN  KLAXKXAELE
           KTQKELDAAP NELG...... PDGDEEET    PAPAPQPE.. .......Q
           PAPAPKPEQ. .......    ..PAPAPK    PEQPAPAPKP EQ..PAP...
           ...AP      KPEQ..PAPA PKPEQPAKPE  KPAEEPTQPE KPATPKT...

Ef6796xc   .......    .......    .......    .......    .......R
           VRAL..KVAE FGVQLRDAGG SNNVG......A.YFKEGLEE  TTAEXEAGLG
           KAEADLKKAV DEPET..... .......     PAP....... A.........
           PAPAPA...  PAPAPAPK.. ..PAPAPK    PAPAPAPAPA PKPAPAPK..
           .......    ..PAPAPAPA PKPEKPAEKP  APAPKPETPK T.........
```

FIG. 13J

```
Db15c    ......L  KDIDESDSED  YAKEGLRAPL  QSELDTKKAK  LLKLEELSGK
         IEELDAEIXE  LEVQLKDAEG  NNNVE.....  A.YFKEGLEK  TTAEKKAELE
         KAEADLKKAV  DEPETPAPA.  ....PAPA    PAPAPTPE..  .......A
         PAPAPA....  PKPAPAPK..  .PAPAPK     PAPAPKPAPA  PKPAPAPKPA
         PAPAPAPAPK  PAPAPAPAPA  PKPEKPAEKP  APAPKPETPK  TGWKQENGM.

L81905c  ......L  KEIDESDSED  YVKEGFRAPL  QSELDAKQAK  LSKLEEXSDK
         XDELDAEIAK  LEKDVEDFKN  SDGEQ.....  AGQYLAAAEE  DLIAKKAXLE
         KAEADLKKAV  DEPETPAPA.  ....PA....  .PAPAPAPT.  .........P
         EAPAPA....  .PAPAPK...  .PAPAPK     PAPAPKPAPA  PKPAPAPK..
         .........   .PAPAPAPA  PKPEKPAA..  ........    ..........

Rct115c  SKKAEATRLE  LKEIDESDVE  VKKAELELVK  EEAKEPRNEE  KVKQAKAEVE
         ..PAPKPEN.  KIKTDRKKAE  EAKRKAAEED  KVKEK.....  ..........
         YXRLTQQQPP  KTEKPAQPST  PKT.......  ..PAEQPK   AEKPADQQAE  EDYARRSEEE
```

*FIG. 13K*

```
Rct121c   ..........  ..........  ..........  ..........  ..........
          SKKXEATRLE  KIKTDRKKAE  EAXRKAAEED  ..........  .K GEARESRXEE
          PAPAPKPEN.  ..........  ...PAEQPK   KVKEKPAEQP  QPAPAPQPEK
          YNRLTQQQPP  KTEKPAQPST  AEKPADQQAE  EDYARRSEEE  KVNQPKXEVE
          ..........  XK........  ..........  ..........  ..........

Rct123c   ..........  .........I  KEXDESXSED  YLKEGLRAPL  QSKLDTKKAK  LSKLEELSDK
          IDELDAEIAK  LEVQLKDAEG  NNNVE.....  A.YFKEGLEK  TTAEKKAELE
          KAEADLKKAV  DEPETPAPA.  ......PQPA  PAPEKPAE..  .........K
          PAPAPAP...  ......PAPTPE  .KPAPTPETP  KTGWKQENGM  WYFYNTDGSM
          .ATGWLQNNGS  WYYLNSNGAM  ATGWHQNNGS  WYYLNS....  ..........
          .EKPAPAPEK.

Rct129c   ..........  .........L  KEIDESDSED  YLKEGLRAPL  QSKLDTKKAK  LSKLEELSDK
          IDELDAEIAK  LEVQLKDAEG  NNNVE.....  A.YFKEGLEK  TTAEKKAELE
          KAEADLKKAV  DEPDTPAPA.  ......PQPA  PAPEKPAE..  .........K
          PAPAPAP...  EKPAPAPE..  .K.PAPA     PEKPAP..AP  EKPAPAPEK.
          ..........  ..PAPAPE    .KPAPAPEKP  APAPKPETPE  TRLETRKRY.
```

FIG. 13L

```
Rct135c   ........L  .KEIDESDSED  YLKEGLRAPL  .QSKLDTKKAK  .LSKLEELSDK
          IDELDAEIAK  LEVQLKDAEG  NNNVE.....  A.YFKEGLEK   TTAEKKAELE
          KAEADLKKAV  DEPETPAPA.  ...PQPA     PAPEKPAE..  .......K
          ..PAPAP...  EKPAPAPE..  ..K.PAPA    P.........  EKPAPAPEK.
          ..........  ......PAPAPE  .KPAPTPETP  KTGWKQENGM  ..........

RX1c      ........L  .KEIDESESED  YAKEGFRAPL  .QSKLDAKKAK  .LSKLEELSDK
          IDELDAEIAK  LEDQLKAAEE  NNNVE.....  .DYFKEGLEK   TIAAKKAELE
          KTEADLKKAV  NEPEKPA...  ...PAPET    PAPEAPAE..  .......QPK
          PAPAPQP...  ..APAPKPE   K..PAEQPK   PEKTDDQQAE  EDYARRSEEE
          YNRLTQQQPP  KAEKPAPA..  PKTGWKQENG  MWYFYNTDGS  M.........

Bg6692c   ........KTEADLKKAV  NEPEK..PA  ...GEQA...  .GQYRAAAEG  DLAAKQAELE
          PAPAPQP...  ..APAPKPE   K..PAEQPK   PAPEAPAE..  .......QPK
          YNRLTQQQPP  KAEKPAPA..  PKPEQPAPA.  AEKTDDQQAE  EDYARRSEEE
          ..........  ..........  PKPEQPAPA.  ..........  ..........
```

FIG. 13M

```
Bg8838c   ........ ........   ........PK .NSKGEQA..  .EQYRSAAGG DLAAKQVELE
          KTEADLKKAV NEPEK..PA.  ....PAPET  PAPEAPAE..  ........QPK
          PAPAPQP...  .APAPKPE    K..PAEQPK  AEKPADQQAE EDYDRRSEEE
          YNRLTQQQPP KAEKPAPA..   PQPEQPAPAP KS........

Db16ac    ........L  KEIDESDSED YVKEGFRAPL QSELDAKQAK LSKLEELSDK
          IDELDAEIAK .LEKDVEDFK XSDGEQA... .GQYLAAAEE DLIAKKAELE
          QTEADLKKAV NEPGKPAPA.  ....PAPET  PAPEAPAE..  ........QPK
          PAPET.P... .APAPKPE    K..PAEQPK  PEKPADQQAE EDYARRSEEE
          YNRLTQQQPA PAQKPEQP..  AKPEKPAEEP TQPEK.....

Db11c     ...DAEIAK  .LEKNVEYFK KTDAEQT...  .EQYLAAAEK DLADKKAELE
          KTEADLKKAV NEPEKPAEE.  ....TPAPA  PKPEQPAE..  ........QPK
          PAPAPQP... .APAPKP...  ....        EKTDDDQQAE EDYARRSEEE
          YNRLPQQQPP KAEKPAPA..  PKPEQPVP..
```

FIG. 13N

```
L820131c   .........  .........  .........  .........  .........  ...
           .........  .........  .........  .........  ....A      ....
           PAXAPQPLKP EEPAEQPKPE .........  .........  .EXPENPAP  .APK
           YNRFPQQQPP KAEKPAPA.. KPEEPAGQPE PEKPDDQQAG EDYARRSGGE
           .........  PKPEQPVPAP KT.......

Bg11703c   .........  .........  .........  .........  .LLKKA     KLAGAKSKAA
           TKKAELEPEL EKAEAELENL LSTLDPEGKT QDELDKEAAE ...AELNKK
           VEALPNQVSE LEEELSKLED NLKDAETNNV EDYIKEGLEE AIATKQAELE
           KT....P    KELDAALNEL G.PDGDEEET PPPEAPAE   ....QPK
           PEK.PAEET. .........  .PAPAPK    PEKSADQQAE EDYARRSEEE
           YNRLTQQQPP KAEKPAPAPA PKPEQPAPAP KSR......

Bg7817c    .........  .........  .........  .........  .GLATKKKL  NLAEARIELL
           LKKLGLEPGL EKAGAGLGNL LEEELSKLED QDELDKEAAE ...AELNKK
           VEALPNQVAE LEEELSKLED NLKDAETNHV EDYIKEGLEE AIATKQAELE
           KT....P    KELDAALNEL G.PDGDEEET PAPEAPAE   ....QPK
           PEK.PAEET. .........  .PAPAPK    PEKSADQQAE EDYARRSEEE
           YNRLTQQQPP KAEKPAPAPA PKPEQPAPAP K........
```

FIG. 130

```
Bg7561c  ............  ............  .KKQKVNLENL  LSTLDPGGKT  QDELDKGAAE  ..AELNKK
         VEALPNPVXE    LEEELSPPED    NLKDAETNHV   EDYIKEGLEE   AIATKQAELE
         ET.......P    QEVDAALNDL    V.PDGGEEET   PAPAPQPD..   .EPA
         PAPAPNAEQ.    ..........    ..PAPAPK     PEKSADQQAE   EDYARRSEGE
         YNRLTQQQPP    KAEKPAPAPA    PKPEQPAPAP   N........    ....

Ef5668c  ............  ....KEIAR     LQSDLKDAEE   NNVEDYIKEG   LEQAITNKKA  ELATTQQNID
         KT....QKDL    EDAELELEKV    LATLDPEGKT   QDELDKEAAE   ..AELNEK
         VEALQNQVAE    LEEELSKLED    NLKDAETNNV   EDYIKEGLEE   AIATKKAELE
         KT......Q     KELDAALNEL    G.PDGDEEET   PAPAPQPE..   ...KPA
         EEP....EN     ..........    ..PAPAPK     PEKSADQQAE   EDYARRSEEE
         YNRLTQQQPP    KAEK..PAPA    PQPEQPAPAP   KIE......    ....

Wu2c     ............  .L KEIDESESED  YAKEGFRAPL   HSKLDAKKAK   LSKLEELSDK
         IDELDAEIAK    LEDQLKAVEE    NNNVE.....   .DYSTEGLEK   TIAAKTELE
         KTEADLKKAV    NEPEKSAEEP    SQPEKPAEEA   PAPEQPTEPT   .
         ..QPEKP       AEETPAPKPE    K..PAEQPN    AEKTDDQQAE   EDYARRSEEE
         YNRLTQQQPP    KAEKPAPA..    PQPEQTSSLH   ........    ....
```

```
Complete sequence for EF5668 pspA
Sequence Range: 1 to 1453
            10          20          30          40          50          60          70
             *           *           *           *           *           *           *
TTGACAAATA TTTACGGAGG AGGCTTATGC TTAATATAAG TATAGGCTAA AAATGATTAT CAGAAAAGAG
            80          90         100         110         120         130
             *           *           *           *           *           *
GTAAATTTAG ATG AAT AAG AAA ATG ATT TTA ACA AGC CTA GCC AGC GTC GCT ATC TTA GGG
           M   N   K   K   M   I   L   T   S   L   A   S   V   A   I   L   G>
          140         150         160         170         180         190
           *           *           *           *           *           *
GCT GGT TTT GTT GCG TCT TCG CCT ACT TTT GTA AGA GCA GAA GAA GCT CCT GTA GCT AAC
 A   G   F   V   A   S   S   P   T   F   V   R   A   E   E   A   P   V   A   N>
200         210         220         230         240         250
 *           *           *           *           *           *
CAG TCT AAA GCT GAG ACG GCT AAA GAC TAT GAT GCA GAA GAC AAA AAG AAA TCT GAA GCT AAG AAA
 Q   S   K   A   E   T   A   K   D   Y   D   A   E   D   K   K   K   S   E   A   K   K>
260         270         280         290         300         310
 *           *           *           *           *           *
GAT TAC GAA AAA GCT AAA GCA GAA AAG GCG GAA AAA GAA AGA AAG GCT CAG AAG AAA TAT GAT GAG GAT CAG
 D   Y   E   K   A   K   A   E   K   A   E   K   E   R   K   A   Q   K   K   Y   D   E   D   Q>
320         330         340         350         360         370
 *           *           *           *           *           *
AAG AAA ACT GAG GCA AAA GCG GAA AAA GAA AGA AAG GCT AAA AAA GCT TCT GAA AAG ATA GCT GAG GCA
 K   K   T   E   A   K   A   E   K   E   R   K   A   K   K   A   S   E   K   I   A   E   A>
380         390         400         410         420         430
 *           *           *           *           *           *
```

```
ACA AAA GAA GTT CAA CAA TAC CTA GCT TAT CTA CAA GCT AGC AAC GAA AGT CAG AGA
 T   K   E   V   Q   Q   Y   L   A   Y   L   Q   A   S   N   E   S   Q   R>
         440         450         460         470         480         490
          *           *           *           *           *           *

AAA GAG GCA GAT AAG AAG ATA AAA AAG ATA ACG GAA GCT ACG CAC GAA AGG ACG TGC AAT
 K   E   A   D   K   K   I   K   K   I   T   E   A   T   H   E   R   T   C   N>
         500         510         520         530         540         550
          *           *           *           *           *           *

TTG ACT ATC GAA TTC GAA CAA CAA TTG TAC TTC CTG AAC CAA GTG AGT TAC CTG AGA CTA
 L   T   I   E   F   E   Q   Q   L   Y   F   L   N   Q   V   S   Y   L   R   L>
         560         570         580         590         600         610
          *           *           *           *           *           *

AGA AAG CAG AAG AGG CAA AAG AAG AAG CAG AAG GTG AGA AAA ATG CTG AAG AGG
 R   K   Q   K   R   Q   K   K   K   Q   K   V   R   K   M   L   K   R>
         620         630         640         650         660         670
          *           *           *           *           *           *

CAG CTA AAG AGG TAT AAG CAG TAT AGA AAC ACA AAG TCG CTG ATT TAC TTG AAC ATG CTC TCC ATC
 Q   L   K   R   Y   K   Q   Y   R   N   T   K   S   L   I   Y   L   N   M   L   S   I>
         680         690         700         710         720         730
          *           *           *           *           *           *

AGA AAA TTG ACG TAC TTC AAA ACA AAG TCG CTG ATT TAT AAA AAG GAA TTG CTC TCC ATC
 R   K   L   T   Y   F   K   T   K   S   L   I   Y   K   K   E   L   L   S   I>
         740         750         760         770         780         790
          *           *           *           *           *           *

AAA ACA GTC GCT GAA TTA AAT AAA GAA ATT GCT AGA CTT CAA AGC GAT TTA AAA GAT GCT
 K   T   V   A   E   L   N   K   E   I   A   R   L   Q   S   D   L   K   D   A>
         800         810         820         830         840         850
          *           *           *           *           *           *
```

FIG. 13R

```
GAA GAA AAT GTA GAA GAC TAC ATT AAA GAA GGT TTA GAG CAA GCT ATC ACT AAT AAA
 E   E   N   V   E   D   Y   I   K   E   G   L   E   Q   A   I   T   N   K>
    860         870         880         890         900         910
     *           *           *           *           *           *

AAA GCT GAA TTA GCT ACA ACT CAA CAA AAC ATA GAT AAA ACT CAA AAA GAT TTA GAG GAT
 K   A   E   L   A   T   T   Q   Q   N   I   D   K   T   Q   K   D   L   E   D>
    920         930         940         950         960         970
     *           *           *           *           *           *

GCT GAA TTA GAT AAA CTT GAA GAA GTA TTA GCT ACA TTA GAC CCT GAA AAA GGT GAA ACT CAA GAT
 A   E   L   D   K   L   E   E   V   L   A   T   L   D   P   E   K   G   E   T   Q   D>
    980         990         1000        1010        1020        1030
     *           *           *           *           *           *

GAA TTA GAT AAA GAA GCT GCT GAA TTA TCA AAA CTT GAG TTG AAT GAA AAA GTT GAA GCT CTT CAA AAC
 E   L   D   K   E   A   A   E   L   S   K   L   E   L   N   E   K   V   E   A   L   Q   N>
    1040        1050        1060        1070        1080        1090
     *           *           *           *           *           *

CAA GTT GCT GAA TTA GAA GAA GAA CTT TCA AAA CTT AAA GAT AAT CTT AAA GAT GCT GAA
 Q   V   A   E   L   E   E   E   L   S   K   L   K   D   N   L   K   D   A   E>
    1100        1110        1120        1130        1140        1150
     *           *           *           *           *           *
```

FIG. 13S

```
ACA AAC GTT GAA GAC TAC ATT AAA GAA GGT TTA GAA GAA GCT ATC GCG ACT AAA AAA
 T   N   V   E   D   Y   I   K   E   G   L   E   E   A   I   A   T   K   K>
             1160        1170        1180        1190        1200        1210
               *           *           *           *           *           *
GCT GAA TTG GAA AAA ACT CAA AAA GAA TTA GAT GCA GCT CTT AAT GAG TTA GGC CCT GAT
 A   E   L   E   K   T   Q   K   E   L   D   A   A   L   N   E   L   G   P   D>
         1220        1230        1240        1250        1260        1270
           *           *           *           *           *           *
GGA GAT GAA GAA GAG ACT CCA GCG CCG GCT CAA CCA GAA AAA CCA GCT GAA GAG CCT
 G   D   E   E   E   T   P   A   P   A   Q   P   E   K   P   A   E   E   P>
         1280        1290        1300        1310        1320        1330
           *           *           *           *           *           *
GAG AAT CCA GCT CGA GCA CGA ACT GAG AAG TCA GCA GAT CAA CAA GCT GAA GAA GAC
 E   N   P   A   R   A   R   T   E   K   S   A   D   Q   Q   A   E   E   D>
         1340        1350        1360        1370        1380        1390
           *           *           *           *           *           *
TAT GCT CGT AGA GAA GAA TAT AAT CGC TTG ACC CAA CAG CAA CCA CCA AAA GCA
 Y   A   R   R   S   E   E   E   Y   N   R   L   T   Q   Q   Q   P   P   K   A>
         1400        1410        1420        1430        1440        1450
           *           *           *           *           *           *
GAA AAA CCA GCT CCT GCA CCA CCA CAA CCA GAG CAA CCA GCT CCT GCA CCA ATA GAG GC
 E   K   P   A   P   A   P   P   Q   P   E   Q   P   A   P   A   P   I   E   A>
```

*FIG. 13T*

LSMpspA13/2

RXI   MC26   MC28
  MC25   MC27

LSMpspA12/6

RXI   MC26   MC28
  MC25   MC27

```
Primer LSM13:      gcaagcttatgatatagaaatttgtaac
Primer LSM2:  gcgcgtcgacggcttaaccattcaccattgg Probe LSMpspAl3/2 (from RX1 sequence):
aagcttatga tatagaaatt tgtaacaaaa atgtaatata aaacacttga
caaatattta cggaggaggc ttatacttaa tataagtata gtctgaaaat
gactatcaga aaagaggtaa atttagatga ataagaaaaa aatgatttta
acaagtctag ccagcgtcgc tatcttaggg gctggttttg ttgcgtctca
gcctactgtt gtaagagcag aagaatctcc cgtagccagt cagtctaaag
ctgagaaaga ctatgatgca gcgaagaaag atgctaagaa tgcgaaaaaa
gcagtagaag atgctcaaaa ggctttagat gatgcaaaag ctgctcagaa
aaaatatgac gaggatcaga agaaaactga ggagaaaagc gcgctagaaa
aagcagcgtc tgaagagatg gataaggcag tggcagcagt tcaacaagcg
tatctagcct atcaacaagc tacagacaaa gccgcaaaag acgcagcaga
taagatgata gatgaagcta agaaacgcga agaagaggca aaaactaaat
ttaatactgt tcgagcaatg gtagttcctg agccagagca gttggctgag
actaagaaaa aatcagaaga agctaaacaa aaagcaccag aacttactaa
aaaactagaa gaagctaaag caaaattaga agaggctgag aaaaagcta
ctgaagccaa acaaaaagtg gatgctgaag aagtcgctcc tcaagctaaa
atcgctgaat tggaaaatca agttcataga agttcataga ctaaacaag agctcaaaga
gattgatgag tctgaatcag aagattatgc taagagaggt ttccgtgctc
ctcttcaatc taaattggat gccaaaaaag ctaaactatc aaaacttgaa
```

FIG. 15C

```
gagttaagtg ataagattga tgagttagac gctgaaattg caaaacttga
agatcaactt aaagctgctg aagaaaacaa taatgtagaa gactacttta
aagaaggttt agagaaaact attgctgcta aaaaagctga attagaaaaa
actgaagctg accttaagaa agcagttaat gagccagaaa aaccagctcc
agctccagaa actccagccc cagaagcacc agctgaacaa ccaaaaccag
cgccggctcc tcaaccagct cccgcaccaa aaccagagaa gccagctgaa
caaccaaaac cagaaaaaac agatgatcaa caagctgaag aagactatgc
tcgtagatca gaagaagaat ataatcgctt gactcaacag caaccgccaa
aagctgaaaa accagctcct gcaccaaaaa caggctggaa acaagaaaac
ggtatgtggt acttctacaa tactgatggt tcaatggcga caggatggct
ccaaaacaac ggttcatggt actacctcaa cagcaatggt gctatggcta
caggttggct ccaatacaat ggttcatggt attacctcaa cgctaacggc
gctatggcaa caggttgggc taaagtcaac ggttcatggt actacctcaa
cgctaacggc gctatggcta caggttggca ccaatacaac ggttcatggt
attacctcaa cgctaacggc gctatggcta caggttgggc taaagtcaac
ggttcatggt actacctcaa cagcaatggt gctatggcta caggttggct
ccaatacaac ggttcatggt actacctcaa cgctaacggc gctatggcta
caggttggct ccaatacaac ggttcatggt actacctgga gatacctgga actatcttga
agcatcaggt gctatgaaag caagccaatg gttcaaagta tcagataaat
ggtactatgt caatggttta ggtgcccttg cagtcaacac aactgtagat
ggctataaag tcaatgccaa tcaatgccaa tggtgaatgg gttaagccg
```

FIG. 15D

Primer LSM12:  ccggatccagcgtcgctatcttaggggctggtt
Primer LSM6:   ctgagtcgactggagtttctggagctggagc Probe LSMpspA12/6 (from RX1 sequence):

ccagcgtcgc tatcttaggg gctggttttg ttgcgtctca gcctactgtt
gtaagagcag aagaatctcc cgtagccagt cagtctaaag ctgagaaaga
ctatgatgca gcgaagaaag atgctaagaa tgcgaaaaaa gcagtagaag
atgctcaaaa ggctttagat gatgcaaaag ctgctcagaa aaaatatgac
gaggatcaga agaaaactga ggagaaagcc gcgctagaaa aagcagcgtc
tgaagagatg gataaggcag tggcagcagt tcaacaagcg tatctagcct
atcaacaagc tacagacaaa gccgcaaaag acgcagcaga taagatgata
gatgaagcta agaaacgcga agaagaggca aaaactaaat ttaatactgt
tcgagcaatg gtagttcctg agccagagca gttggctgag actaagaaaa
aatcagaaga agctaaacaa aaagcaccag aacttactaa aaaactagaa
gaagctaaag caaaattaga agaggctgag aaaaaagcta ctgaagccaa
acaaaaagtg gatgctgaag aagtcgctcc tcaagctaaa atcgctgaat
tggaaaatca agttcataga ctagaacaag agctcaaaga gattgatgag
tctgaatcag aagattatgc taaagaaggt ttccgtgctc ctcttcaatc
taaattggat gccaaaaaag ctaaactatc aaaacttgaa gagttaagtg
ataagattga tgagttagac gctgaaattg caaaacttga agatcaactt
aaagctgctg aagaaaacaa taatgtagaa gactacttta aagaaggttt
agagaaaact attgctgcta aaaaagctga attagaaaaa actgaagctg
aacttaagaa agccagaaaa gagccagaaa aaccagctcc agctccagaa
actccag

FIG. 15E

SKH2    5' CAT ACC gTT TTC TTg TTT CCA gCC -3'

LSM13   5' gCA AgC TTA TgA TAT AgA AAT TTg TAA C -3'

N192    5' ggA AggCCATATgCTCAAAgAgATTgATgAgTCT -3'

C588    5' CCAAggATCCTTAAACCCATTCACCATTggC -3'

FIG. 19

```
AAGCTTATGC TTGTCAATAA TCACAAATAT GTAGATCATA TCTTGTTTAG GACAGTAAAA CATCCTAATT ACTTTTTAAA         80

TATTTACCT GAGTTGATTG GCTTGACCTT GTTGAGTCAT GCCTATATGA CTTTTGTTTT AGTTTTTCCA GTTTATGCAG         160

TTATTTTGTA TCGACGAATA GCTGAAGAGG AAAAGTTATT ACATGAAGTT ATAATCCCAA ATGGAAGCAT AAAGAGATAA         240

ATACAAAATT CGATTATATAT ACAGTTCATA TTGAAGTGAT ATAGTAAGGT TAAAGAAAAA ATATagaagg aAATAAACAT         320
                                                                                    Met>       -37

GTTGCATCA AAAAGCGAAA GAAAAGTACA TTATTCAATT CGTAAATTTA GTATTGGAGT AGCTAGTGTA GCTGTTGCCA          400
PheAlaSer LysSerGlu ArgLysValHis TyrSerIle ArgLysPhe SerIleGlyVal AlaSerVal AlaValAla>          -11

GCTTGTTCTT AGGAGGAGTA GTCCATGCAG AAGTGGGAAT AACCTCACGG TTACATCTAG TGGGCAAGAT                    480
SerLeuPheLeu GlyGlyVal ValHisAla GluValGly AsnLeuThr ValThrSerSer GlyGlnAsp>                    17

ATATCGAAGA AGTATGCTGA TGAAGTCGAG TCGCATCTAG AAAGTATATT GAAGGATGTC AAAAAAAATT TGAAAAAAGT          560
IleSerLys LysTyrAlaAsp GluValGlu SerHisLeu GluSerIleLeu LysAspVal LysLysAsn LeuLysLysVal>       44

TCAACATACC CAAAATGTCG GCTTAATTAC AAAGTTGAGC GAAATTAAAA AGAAGTATTT GTATGACTTA AAAGTTAATG         640
GluHisThr GlnAsnVal GlyLeuIleThr LysLeuSer GluIleLys LysLysTyrLeu TyrAspLeu LysValAsn>         70

TTTTATCGGA AGTGAGTTG ACGTCAAAAA CAAAAGAAAC AAAAGAAAAG TTAACCGCAA CTTTTGAGCA GTTAAAAAAA         720
ValLeuSerGlu AlaGluLeu ThrSerLys ThrLysGluThr LysGluLys LeuThrAla ThrPheGluGln PheLysLys>      97

GATACATTAC CAACAGAACC AGAAAAAAAG GTAGCAGAAG CTCAGAAGAA GGTTGAAGAA GCTAAGAAAA AAGCCGAGGA         800
AspThrLeu ProThrGluPro GluLysLys ValAlaGlu AlaGlnLysLys ValGluGlu AlaLysLys LysAlaGluAsp>      124
```

FIG. 21A

```
TCAAAAGAA AAAGATCGCC GTAACTACCC AACCATTACT TACAAAAGC TTGAACTTGA AATTGCTGAG TCCGATGTGG    880
GlnLysGlu LysAspArg ArgAsnTyrPro ThrIleThr TyrLysThr LeuGluLeuGlu IleAlaGlu SerAspVal>   150

AAGTTAAAAA AGCGGAGCTT GAACTAGTAA AAGTGAAAGC TAAGGAATCT CAAGACGAGG AAAAAATTAA GCAAGCAGAA    960
GluValLysLys AlaGluLeu GluLeuVal LysValLysAla LysGluSer GlnAspGlu GluLysIleLys GlnAlaGlu>  177

GCGGAAGTTG AGAGTAAACA AGCTGAGGCT ACAAGGTTAA AAAAAATCAA GACAGATCGT GAAGAAGCTA AACGAAAAGC   1040
AlaGluVal GluSerLysGln AlaGluAla ThrArgLeu LysLysIleLys ThrAspArg GluGluAla LysArgLysAla>  204

AGATGCTAAG TTGAAGGAAG CTGTTGAAAA GAATGTAGCG ACTTCAGAGC AAGATAAACC AAAGAGGGCG GCAAAACGAG   1120
AspAlaLys LeuLysGlu AlaValGluLys AsnValAla ThrSerGlu GlnAspLysPro LysArgArg AlaLysArg>    230

GAGTTTCTGG AGAGCTAGCA ACACCTGATA AAAAAGAAAA TGATGCGAAG TCTTCAGATT CTAGCGTAGG TGAAGAAACT   1200
GlyValSerGly GluLeuAla ThrProAsp LysLysGluAsn AspAlaLys SerSerAsp SerSerValGly GluGluThr> 257

CTTCCAAGCC CATCCCTTAA TATGGCAAAT CAGAACATAG GAAAGTCAGA GAAAGATGTC GATGAATATA TAAAAAAAAT   1280
LeuProSer ProSerLeuAsn MetAlaAsn GlnAsnIleGly ThrGluHisArg LysAspVal AspGluTyr IleLysLysMet> 284

GTTGAGTGAG ATCCAATTAG ATAGAAGAAA AATGTCAACT TAAACATAAA GTTGAGCGCA ATTAAAACGA              1360
LeuSerGlu IleGlnLeu AspArgArgLys HisThrGln AsnValAsn LeuAsnIleLys LeuSerAla IleLysThr>    310

AGTATTTGTA TGAATTAAGT GTTTTAAAAG AGAACTCGAA AAAAGAAGAG TTGACGTCAA AAACCAAAGC AGAGTTAACC   1440
LysTyrLeuTyr GluLeuSer ValLeuLys GluAsnSerLys LysGluGlu LeuThrSer LysThrLysAla GluLeuThr> 337

GCAGCTTTTG AGCAGTTTAA AAAAGATACA TTGAAACCAG AAAAAAAGGT AGCAGAAGCT GAGAAGAAGG TTGAAGAAGC   1520
AlaAlaPhe GluGlnPheLys LysAspThr LeuLysPro GluLysLysVal AlaGluAla GluLysLys ValGluGluAla> 364
```

*FIG. 21B*

```
TAAGAAAAAA GCCAAGGATC AAAAAGAAGA AGATGCGCCGT AACTACCCAA CCAATACTTA CAAAACGCTT GAACTTGAAA      1600
LysLysLys AlaLysAsp GlnLysGluGlu AspArgArg AsnTyrPro ThrAsnThrTyr LysThrLeu GluLeuGlu>       390

TTGCTGAGTC CGATGTGAAA GTTAAAGAAG CGGAGCTTGA ACTAGTAAAA GAGGAAGCTA ACGAATCTGA AAACGAGGAA      1680
IleAlaGluSer AspValLys ValLysGlu LeuValLys AlaGluLeuGlu GluGluAla AsnGluSerArg AsnGluGlu>   417

AAAATTAAGC AAGCAAAAGA GAAAGTTGAG AGTAAAAAAG CTGAGGCTAC AAGGTTAGAA AAAATCAAGA CAGATCGTAA      1760
LysIleLys GlnAlaLysGlu LysValGlu SerLysLys AlaGluAlaThr ArgLeuGlu LysIleLys ThrAspArgLys>   444

AAAAGCAGAA GAAGAAGCTA AACGAAAAGC AGAAGAATCT GAGAAAAAAG CTGCTGAAGC CAAACAAAAA GTGGATGCTG      1840
LysAlaGlu GluGluAla LysArgLysAla GluGluSer GluLysLys AlaAlaGluAla LysGlnLys ValAspAla>      470

AAGAATATGC TCTTGAAGCT AAAATCGCTG AGTTGGAATA TGAAGTTCAG AGACTAGAAA AAGAGCTCAA AGAGATTGAT      1920
GluGluTyrAla LeuGluAla LysIleAla GluLeuGluTyr GluValGln ArgLeuGlu LysGluLeuLys GluIleAsp>   497

GAGTCTGACT CAGAAGATTA TCTTAAAGAA GGCCTCCGTG CTCCTCTTCA ATCTAAATTG GATACCAAAA AAGCTAAACT      2000
GluSerAsp SerGluAspTyr LeuLysGlu GlyLeuArg AlaProLeuGln SerLysLeu AspThrLys LysAlaLysLeu>  524

ATCAAAACTT GAAGAGTTGA GTGATAAGAT TGATGAGTTA GACGCTGAAA TTGCAAAACT TGAAGTTCAA CTTAAAGATG      2080
SerLysLeu GluGluLeu SerAspLysIle AspGluLeu AspAlaGlu IleAlaLysLeu GluValGln LeuLysAsp>     550

CTGAAGGAAA CAATAATGTA GAAGCCTACT TTAAAGAAGG TTTAGAGAAA ACTACTGCTG AGAAAAAAGC TGAATTAGAA      2160
AlaGluGlyAsn AsnAsnVal GluAlaTyr PheLysGluGly LeuGluLys ThrThrAla GluLysLysAla GluLeuGlu>   577

AAAGCTGAAG CTGACCTTAA GAAAGCAGTT GATGAGCCAG AAACTCCAGC TCCGGCTCCT CAACCAGCTC CAGCTCCAGA      2240
LysAlaGlu AlaAspLeuLys LysAlaVal AspGluPro GluThrProAla ProAlaPro GlnProAla ProAlaProGlu>  604
```

*FIG. 21C*

```
AAACCAGCT GAAAAACCAG CTCCAGCTCC AGAAAAACCA GCTCCAGCTC CAGAAAAACC AGCTCCAGCT CCAGAAAAAC    2320
LysProAla GluLysPro AlaProAla ProGluLysPro AlaProAla ProGluLysPro AlaProAla ProGluLys>    630

CAGCTCCAGC TCCAGAAAAA CCAGCTCCAG CTCCAGAAAA ACCAGCTCCA ACTCCAGAAA CTCCAAAAAC AGGCTGGAAA    2400
ProAlaProAla ProGluLys ProAlaPro AlaProGluLys ProAlaPro ThrProGlu ThrProLysThr GlyTrpLys>  657
CAAGAAAACG GTATGTGGTA CTTCTACAAT ACTGATGGTT CAATGGCAAC AGGCTGGCTC CAAAACAATG GCTCATGGTA    2480
GlnGluAsn GlyMetTrpTyr PheTyrAsn ThrAspGly SerMetAlaThr GlyTrpLeu GlnAsnAsn GlySerTrpTyr>  684

CTACCTCAAC AGCAATGGCG CTATGGCGAC AGGATGGCTC CAAAACAATG GCTCATGGTA CTACCTCAAC AGCAATGGCG    2560
TyrLeuAsn SerAsnGly AlaMetAlaThr GlyTrpLeu GlnAsnAsn GlySerTrpTyr TyrLeuAsn SerAsnGly>     710

CTATGGCGAC AGGATGGCTC CAATACAATG GTTCATGGTA CTACCTCAAC GCTAATGGTG ATATGGCGAC AGGATGGCTC    2640
AlaMetAlaThr GlyTrpLeu GlnTyrAsn GlySerTrpTyr TyrLeuAsn AlaAsnGly AspMetAlaThr GlyTrpLeu>  737

CAATACAATG GTTCATGGTA CTACCTCAAC GCTAATGGTG ATATGGCGAC AGGATGGTTC CAATACAATG GTTCATGGTA    2720
GlnTyrAsn GlySerTrpTyr TyrLeuAsn AlaAsnGly AspMetAlaThr GlyTrpPhe GlnTyrAsn GlySerTrpTyr>  764

CTACCTCAAC GCTAATGGTG ATATGGCGAC AGGATGGTTC CAATACAATG GTTCATGGTA CTACCTCAAC GCTAATGGTG    2800
TyrLeuAsn AlaAsnGly AspMetAlaThr GlyTrpPhe GlnTyrAsn GlySerTrpTyr TyrLeuAsn AlaAsnGly>     790

ATATGGCGAC AGGATGGCTC CAATACAATG GTTCATGGTA CTACCTAAAC AGCAATGGTG CTATGGTAAC AGGATGGCTC    2880
AspMetAlaThr GlyTrpLeu GlnTyrAsn GlySerTrpTyr TyrLeuAsn SerAsnGly AlaMetValThr GlyTrpLeu>  817

CAAAACAATG GCTCATGGTA CTACCTAAAC GCTAACGGTT CAATGGCAAC AGATTGGGTG AAAGATGGAG ATACCTGGTA    2960
GlnAsnAsn GlySerTrpTyr TyrLeuAsn AlaAsnGly SerMetAlaThr AspTrpVal LysAspGly AspThrTrpTyr>  844
```

*FIG. 21D*

```
CTATCTTGAA GCATCAGGTG CTATGAAAGC AAGCCAATGG TTCAAAGTAT CAGATAAATG GTACTATGTC AATGGCTCAG    3040
 TyrLeuGlu AlaSerGly AlaMetLysAla SerGlnTrp PheLysVal SerAspLysTrp TyrTyrVal AsnGlySer>     870

GTGCCCTTGC AGTCAACACA ACTGTAGATA GCTATAGAGT CAATGCCAAT GGTGAATGGG TAAACTAAAC TTAATATAAC    3200
 GlyAlaLeuAla ValAsnThr ThrValAsp SerTyrArgVal AsnAlaAsn GlyGluTrp ValAsn>                   892

TAGTTAATAC TGACTTCCTG TAAGAACTCT TTAAAGTATT CCCTACAAAT ACCATATCCT TTCAGTAGAT AATATACCCT    3200

TGTAGGAAGT TTAGATTAAA AAATAACTCT GTAATCTCTA GCCGGATTTA TAGCGCTAGA GACTACGGAG TTTTTTTGAT    3280

GAGGAAAGAA TGGCGGCATT CAAGAGACTC TTTAAGAGAG TTACGGGTTT TAAACTATTA AGCTTTCTCC AATTGCAAGA    3360

GGGCTTCAAT CTCTGCTAGG TGCTAGCTTG CGAAATGGCT CCCACGGAGT TGGCRGCGC CAGATGTTCC ACGGAGGTAG    3440

TGAGGAGCGA GGCCGCGGAA TTC
```

*FIG. 21E*

```
249 SDSSVGEETLPSPSPSLNMANESQTEHRKDVDEYIKKMLSEIQLDRRKHTQN 298
      :·|··  ··:·||·   ·   ·:| ·:  ·|· :|·  ··  :: ··
  1 EESPVASQSKAEKDYDAAKKDAKNAKKAVED.AQKALDDAKAAQKKYDED    49

299 VNLNIKLSAIKTKYLYELSVLKENSKKEELTSKTKAELTAAFEQFKKDTL  348
                      ··  :·| :|·  ·|| ·  ·:·| ··  ·|
 50 QKKTEEKAAL..........EKAASEEM.DKAVAAVQQAYLAYQQATD    86

349 KPEKKVAEAEKKVEEAAKKKAKDQKEEDRRNYPTNTYKTLELEIAESDVKV 398
    |·: · ·  ·|·|· :|||·   ·· ·  ·            ·· ·
 87 KAAK..DAADKMIDEAKKREEEAKTK.......FNTVRAMVV.........  119

399 KEAELELVKEEANESRNEEKIKQAKEKVESKKAEATRLEKIKTDRKKAEE  448
                                    ·             |
120 .........................PEPEQLAETKKKSEEAKQKAPEL.......TKKLE  147

449 EAKRKAEESEKKAAEAKQKVDAEEYALEAKIAELEYEVQRLEKELKEIDE  498
    |·|· · ·|·|·||  ·||||| ·  :  ·   :  ·: ··|··|||||
148 EAKAKLEEAEKKATEAKQKVDAEEVAPQAKIAELENQVHRLEQELKEIDE  197
```

FIG. 22A

```
499 SDSEDYLKEGLRAPLQSKLDTKKAKLSKLEELSDKIDELDAEIAKLEVQL 548
    :|::||||||:|||||||||||||||||||||||||||||||||:|:||
198 SESEDYAKEGFRAPLQSKLDAKKAKLSKLEELSDKIDELDAEIAKLEDQL 247

549 KDAEGNNNVEAYFKEGLEKTTAEKKAELEKAEADLKKAVDEPETPAPAPQ 598
    |:||:|||||:|||||||||:|:|||||:|||||||||:||||:|||||
248 KAAEENNNVEDYFKEGLEKTIAAKKAELEKTEADLKKAVNEPEKPAPAPE 297

599 PAPAPEKPAE..KPAPAPEK.PAPAPEKPA..PAPEKPAPA......... 634
    ||||||||:|  ||||||| ||||||||   |||||||||
298 .TPAPEAPAEQPKPAPAPQPAPAPKPEKPAEQPKPEKTDDQQAEEDYARR 346

635 .........PEKPAPAPEKPAPTPETPKTGWKQENGMWYFYNTDGSMATGW 676
             |||||||:||:    ||||||||||||||||||||||
347 SEEEYNRLTQQQPPKAEKPAP...APKTGWKQENGMWYFYNTDGS..... 388

677 LQNNGSWYYLNSNGAMATGWLQYNGSWYYL 726
    ||||||||||||||||||||||||||||||
389 ..........MATGWLQNNGSWYYLNSNGAMATGWLQYNGSWYYL 423
```

FIG. 22B

```
727 NANGDMATGWLQYNGSWYYLNANGDMATGWFQYNGSWYYLNANGDMATGW 776
    |||.|||.||||||||||||||||||.|||:|||||||||||||||.|||
424 NANGAMATGWAKVNGSWYYLNANGAMATGWLQYNGSWYYLNANGAMATGW 473

777 FQYNGSWYYLNANGDMATGWLQYNGSWYYLNSNGAMVTGWLQNNGSWYYL 826
    |||||||||||||.|||||||||||||||||:|||||.||||.||||||
474 AKVNGSWYYLNANGAMATGWLQYNGSWYYLNANGAMATGWAKVNGSWYYL 523

827 NANGSMATDWVKDGDTWYYLEASGAMKASQWFKVSDKWYYVNGSGALAVN 876
    |||.|||||||||||||||||||||||||||||||||||||:|||||||
524 NANGAMATGWVKDGDTWYYLEASGAMKASQWFKVSDKWYYVNGLGALAVN 573

877 TTVDSYRVNANGEWV 891
    ||||..|:|||||||
574 TTVDGYKVNANGEWV 588
```

```
        a   b   c   d   e   f   g
  1                                     Glu Gly Val Arg Ser Gly Asn Asn Leu Thr
 11                                     Val Thr Ser Ser Gly
 16                 Gln Asp Ile Ser Lys Lys
 22     Tyr Ala Asp Glu Val Glu Ser
 29                 His Leu Glu Ser Ile
 34     Leu Lys Asp Val Lys Lys Asn
 41     Leu Lys Lys
 44     Val Gln His Thr Gln Asn Val
 51                 Gly Leu Thr Lys
 56     Leu Ser Glu Ile Lys Lys Tyr
 63
 64     Leu Tyr Asp Leu Lys
 69     Val Asn Val Leu Ser Glu Ala
 76                 Glu Leu Thr Ser Lys
 81                         Thr Lys Glu Thr
 85     Lys Glu Lys Leu Thr Ala Thr
 92     Phe Glu Gln Phe Lys Asp
 99                                     Thr Leu Pro Thr Glu Pro
105                 Glu Lys Lys
108     Val Ala Glu Ala Gln Lys
115     Val Glu Glu Ala Lys Lys Lys
```

FIG. 23B

```
122                     Ala Glu Asp Gln
126 Lys Glu Lys Asp Arg Arg Asn
133 Tyr Pro Thr Ile Thr
138 Tyr Lys Thr Leu Glu Leu Glu
145 Ile Ala Glu Ser Asp Val Glu
152 Val Lys Lys Ala Glu Leu Glu
159 Leu Val Lys Val Lys Ala Lys
166 Glu Ser Gln Asp Glu Glu Lys
173 Ile Lys Gln Ala Glu Ala Glu
180 Val Glu Ser Lys Gln Ala Glu
187             Ala Thr Arg
190 Leu Lys Lys Ile Lys Thr Asp
197 Arg Glu Gln Ala Lys Arg Lys
204     Ala Asp Ala Lys Leu Lys
210     Glu Ala Val Glu Lys Asn
216 Val Ala Thr Ser Gln Gln Asp
223 Lys
224         Pro Lys Arg Arg Arg Ala Lys Arg Gly Val Ser
234         Gly Glu Leu Ala Thr Pro Asp Lys Lys Glu
244         Asn Asp Ala Lys Ser Ser Asp Ser Ser Val
254
```

FIG. 23C

```
                                              Gly Glu Glu Thr Leu Pro Ser Pro Ser Leu
                                              Asn Met Ala Asn
264                         Glu Ser Gln
268  Thr Glu His            Arg Lys Asp
271  Val Asp Glu Tyr
277  Ile Lys Lys Met        Leu Ser Glu
281  Ile Gln Leu Asp        Arg Arg Lys
288          His Thr        Gln Asn Val
295              Asn        Leu Asn Ile Lys
300  Leu Ser Ala Ile        Lys Thr Lys
305              Tyr        Leu Tyr Glu
312  Leu Ser Val Leu        Lys Glu Asn
316                             Ser Lys
323  Lys Glu Glu Leu        Thr Ser Lys
325              Thr        Lys Ala Glu
332  Leu Thr Ala Ala        Phe Glu Gln
336  Phe Lys Lys
343                         Glu Lys Lys      Asp Thr Leu Lys Pro
346  Val Ala Glu Ala        Glu Lys Lys
351  Val Glu Glu Ala        Lys Lys Lys
354              Ala        Lys Asp Gln
361  Lys Glu Glu Asp        Arg Arg Asn
368
372
```

```
379                            Tyr
380                        Pro Thr Asn Thr
384 Tyr Lys Thr Leu Glu Leu Glu
391 Ile Ala Glu Ser Asp Val Lys
398 Val Lys Glu Ala Glu
403 Leu Glu Leu Val Lys Glu Glu
410 Ala Asn Glu Ser Arg Asn Glu
417     Glu Lys Ile Lys Gln Ala
423 Lys Glu Lys Val Glu Ser Lys
430 Lys Ala Glu Ala Thr Arg
436 Leu Glu Lys Ile Lys Thr Asp
443 Arg Lys Lys Ala Glu Glu Glu
450         Ala Lys Glu Arg Lys
454 Ala Glu Glu Ser Glu Lys Lys
461 Ala Ala Glu Ala Lys Gln Lys
468 Val Asp Ala Glu Glu Tyr Ala
475         Leu Glu Ala Lys
479 Ile Ala Glu Leu Glu Tyr Glu
486 Val Gln Arg Leu Glu Lys Glu
```

*FIG. 23D*

```
493 Leu Lys Glu
496 Ile Asp Glu Ser Asp Ser Glu
503         Asp Tyr Leu Lys Glu Gly
509 Leu Arg Ala
512         Pro Leu Gln Ser Lys
517 Leu Asp Thr Lys Lys Ala Lys
524 Leu Ser Lys
527 Leu Glu Glu Leu Ser Asp Lys
534 Ile Asp Glu Leu Asp Ala Glu
541 Ile Ala Lys Leu Glu Val Gln
548 Leu Lys Asp Ala Gly Gly Asn
555                     Asn Asn
557 Val Glu Ala Tyr Phe Lys Glu
564         Gly Leu Glu Lys Thr
569         Thr Ala Glu Lys Lys
574     Ala Glu Leu Glu Lys Ala
580 Glu Ala Asp Leu Lys Lys Ala
587 Val Asp Glu
```

FIG. 23E

```
  1  CCAAGCTATT AGGTGACACT ATAGAATACT CAAGCTATGC ATCAAGCTTA
 51  TGCTTGTCAA TAATCACAAA TATGTAGATC ATATCTTGTT TAGGACAGTA
101  AAACATCCTA ATTACTTTTT AAATATTCTT CCTGAGTTGA TTGGCTTGAC
151  CTTGTTGAGT CATGCTTATG TGACTTTTGT TTTAGTTTTT CCAGTTTATG
201  CAGTTATTTT GTATCGACGA ATAGCTGAAG AGGAAAAGCT ATTACATGAA
251  GTTATAATCC CAAATGGAAG CATAAAGAGA TAAATACAAA ATTCGATTTA
301  TATACAGTTC ATATTGAAGT AATATAGTAA GGTTAAAGAA AAAATATAGA
351  AGGAAATAAA CATGTTTGCA TCAAAAAGCG AAAGAAAAGT ACATTATTCA
401  ATTCGTAAAT TTAGTATTGG AGTANCTAGT GTAGCTGTTG CCAGTCTTGT
451  TATGGGAAGT GTGGTTCATG CSACCAGARA AACGARGGAA GTACCCAAGC
```

FIG. 25A

```
501  AGCCMCTTCT TCTAATATGG CAAAGACAGA ACATAGGAAA GCYGCTAAAC
551  MAGTCGTCGA TGAATATATA GAAAAAATGT TGAGGGAGAT TCAACTAGAT
601  AGAAGAAAAC ATACCCAAAA TGTCGCCTTA AACATAAAGT TGAGCGCAAT
651  TANAACGAAG TATTTGCGTG AATTAANTGT TNTAGAAGAG AAGTCGAANN
701  ATGAGTTGCC GTCAGAAAATA AAAGCGAAGT TAGACGCCGC TTTTGANAAG
751  TTTAAAAAAG ATACATTGAA ACCAGGAGAA AAGGTAGCNG AAGCTAAGAA
801  GAANGTTGAA GAAGCTAAGA AWAAAGCCRA GGATCAAAAA GAAGAAGATC
851  GYCGTAACTA CCCAACCAAT ACTTRCAAAA CGCTTGACCT TGAAATTGCT
901  GAGTYCGATG TGAAAGTTAA AGAAGCGGAG CTTGAACTAG TAAARGAGGA
```

FIG. 25B

```
 951  AGCTMMRGAA YCTCGAGACG AGGAAAAAAT TAAGCAAGCA AAAGCGAAAG
1001  TTGAGAGTAA AAAAGCTGAG GCTACAAGGT TAGAAAACAT CAAGACAGAT
1051  NGTAAAAAAG CAGAAGAAGA AGNTAAACGA AAAGCAGCAG AAGAAGATAA
1101  AGTTAAAGAA AAACCAGCTG AACAACCACA ACCAGGCCCG GNTACTCAAC
1151  CAGAAAAACC AGCTCCAAAA CCAGAGAAGC CAGCTGAACA ACCAAAAGCA
1201  GAAAAAAACAG ATGATCAACA AGCTGAAGAA GACTATGCTC GTAGATCAGA
1251  AGAAGAATAT AATCGCTTGA NTCAACAGCA ACCGCCAAAA ACTGAAAAAC
1301  CAGCACAACC ATNTACTCCA AAAACA
```

FIG. 25C

```
875  AAAAAGCTAAACTATCAAAACTTGAAGAGTTAAGTGATAAGATTGATGAG  924
        ||||  ||  |||  |||    ||||  ||   ||||    ||  ||
877  AAAACGCTTGACCTTGAAA..TTGCTGAGTYCGATGTGAAAGTTAAAGAA  924

925  TTAGACGCTGAAATTGCAAAACTTGAAGATCAACTTAAAGCTGCTGAAGA  974
        ||| ||||||  ||| |||   |||  ||| |:::  |||||| ||
925  GCGGAGCTTGAACTAGTAAAARGAGGAAGCTMMRGAAYCTCGAGACGAGGA  974

975  AAACAATAATGTAGAAGAGACTACTTTAAAGAAGGTTTAGAGAAAACTATTG  1024
        |   |   ||| || |||      ||||  ||||  |||||
975  AAAATTAAGCAAA.........AGCGAAAGTTGAGAG.............  1007

1025 CTGCTAAAAAGCTGA.............ATTAGAAAAACTGAAGCTGACCTT  1065
        ||||||||||||||              |||||||||||||||||||||
1008 ....TAAAAAGCTGAGGCTACAAGGTTAGAAAACATCAAGACAGATNGT   1053
```

FIG. 26A

```
1066  AAGAAAGCAGTTAATGAGCCAGAAAAACCAGCTCCAGAAACTCC  1115
      ||| || ||||||    ||  |: ||   ||||||  |||||||
1054  AAAAAAGCAG...AAGAAGAAGNTAAACGCAGAAGCAGAAGATAA  1100

1116  AGCCCCAGAAGCACCAGCAAAAACCAAACCAGCGCCCGGCTCCTCAAC  1165
      ||  || ||| || |  ||||| |||| |||||||||||| | ||||:
1101  AGTTAAAGAAGAAAAACCAGCTCCAAAAACCAGCGCCCGGNTACTCAAC  1150

1166  CAG....CTCCCGCACCAAAACCAGAGAAGCCAGCTGAACAACCAAAACCA  1212
      |||    ||  |  |||||||||||||||||||||||||||||||| |||
1151  CAGAAAAACCAGCTCCAAAAACCAGAGAAGCCAGCTGAACAACCAAAAGCA  1200

1213  GAAAAAACAGATGATCAACAAGCTGACTCAACAGCTCGTAGATCAGA  1262
      ||||||||||||||||||||||||| ||| |||||||||||||||||
1201  GAAAAAACAGATGATCAACAAGCTGAACAAGCTCGTAGATCAGA  1250

1263  AGAAGAATATAATCGCTTGACTCAACAACCGCCAACCGCTGAAAAAC  1312
      |||||||||||||||||||| |||| ||||||||||||||||||||
1251  AGAAGAATATAATCGCTTGANTCAACAGCAACCGCCAAAAACTGAAAAAC  1300

1313  CAGCTC......CTGCACCAAAAACA  1332
      ||||||      :|  ||||||| ||
1301  CAGCACAACCATNTACTCCAAAACA  1326
```

FIG. 26B

```
  1 AAGCTTATGCTTGTCAATAATCACAAATATGTAGATCATATCTTGTTTAG   50
    ||||||||||||||||||||||||||||||||||||||||||||||||||
 44 AAGCTTATGCTTGTCAATAATCACAAATATGTAGATCATATCTTGTTTAG   93

51 GACAGTAAAACATCCCTAATTACTTTTTAAATATTTTACCTGAGTTGATTG  100
    ||||||||||||||||||||||||||||||||||||||||||||||||||
 94 GACAGTAAAACATCCCTAATTACTTTTTAAATATTCTTCCTGAGTTGATTG  143

101 GCTTGACCTTGTTGAGTCATGCCTATATGACTTTTGTTTTAGTTTTTTCCA  150
    ||||||||||||||||||||||||||||||||||||| |||||||| |||
144 GCTTGACCTTGTTGAGTCATGCCTATATGTGACTTTTGTTTTTAGTTTTCCA  193

151 GTTTATGCAGTTATTTTGTATCGACGAATAGCTGAAGAGGAAAAGTTATT  200
    ||||||||||||||||||||||||||||||||||||||||||||| ||||
194 GTTTATGCAGTTATTTTGTATCGACGAATAGCTGAAGAGGAAAAGCTATT  243
```

FIG. 27A

```
201  ACATGAAGTTATATAATCCCAAATGGAAGCATAAAGAGATAAATACAAAATT  250
     |||||||||||||||||||||||||||||||||||||||||||||||||||
244  ACATGAAGTTATATAATCCCAAATGGAAGCATAAAGAGATAAATACAAAATT  293

251  CGATTTATATACAGTTCATATTGAAGTGATATAGTAAGGTTAAAGAAAAA   300
     |||||||||||||||||||||||||||||||||||||||||||||||||
294  CGATTTATATACAGTTCATATTGAAGTAATATAGTAAGGTTAAAGAAAAA   343

301  ATATAGAAGGAAATAAACATGTTTGCATCAAAAAGCGAAAGAAAAGTACA   350
     |||||||||||||||||||||||||||||||||||||||||||||||||
344  ATATAGAAGGAAATAAACATGTTTGCATCAAAAAGCGAAAGAAAAGTACA   393

351  TTATTCAATTCGTAAATTTAGTATTGGAGTAGCTGTAGCTGTGTTGCCA   400
     ||||||||||||||||||||||||||||||||| |||||||||||||
394  TTATTCAATTCGTAAATTTAGTATTGGAGTAGTANCTAGTGTTGCCA    443

401  GCTTGTGTCTTAGGAGGAGTAGTCCATGCAGAAGGGGTTAGAAGTGGAAT   450
                                                     :||
444  GTCTTGTTATGGGAAGTGTGGTTCATGC..SACCAGARAAACGARGGAAG  491

451  AACCTCA.....CGGTTACATCTAGTGGGCAAGATATATCGAAGAAGTATG  496
                |    |  ||                  |
492  TACCCAAGCAGCAGCCMCTTCTTCTAATATGGCAAAGACAGAACATAGGAAAG  541
```

FIG. 27B

```
497  CTGATGAA......GTCGAGTCGCATCTAGAAAGTATATTGAAGGATGTC  540
      |:| ||      |||||||| |||||||||||||| |||||||| |||
542  CYGCTAAACMAGTCGTCGATGAATATAGAAAAAATGTTGAGGGAGATT  591

541  AAAAAAATTTGAAAAAAGTTCAACATACCCAAAATGTCGGCTTAATTAC  590
      |||||||          ||  |||||||||||||||||| ||||| ||
592  CAACTAGATAGAAGAA......AACATACCCAAAATGTCGCCTTAAACAT  635

591  AAAGTTGAGCGAAATTAAAAAGAAGTATTTGTATGACTTAAAAGTTA...  637
     |||||||||||  |||||| ||  ||:  ||| |: ||||
636  AAAGTTGAGCGCAATTANAACGAAGTATTGCGTGAATTAANTGTTNTAG  685

638  ATGTTTTATCGGAAGCTGAGTTGACGTCAAAAAACAAAAGAAACAAAAGAA  687
         ||:  ||||||  ||||  ||||                 |||| ||
686  AAGAGAAGTCGAANNATGAGTTGCCGTC..........AGAAATAAAGCG  726

688  AAGTTAACCGCAACTTTTGAGCAGTTTAAAAAAGATACATTACCAACAGA  737
     |||||   ||  ||  |||| |:  |||||||||||||||||||||
727  AAGTTAGACGCCGCTTTTGANAAGTTTAAAAAAAGATACATT.......GAA  770

738  ACCAGAAAAAAGGTAGCAGAAGCTCAGAGAAGAAGGTTGAAGAAGCTAAGA  787
     ||||||||| ||||||||| ||||||||||||||||||||:|||||||||
771  ACCAGGAGAAAAGGTAGCNGAAGCTAAGAAGAANGTTGAAGAAGCTAAGA  820
```

FIG. 27C

```
 788  AAAAGCCGAGGATCAAAAGAAAAAGATCGCCGTAACTACCCAACCATT  837
      |:||||||:||||||| ||||||||| ||||:|| ||||||||||||:
 821  AWAAAGCCRAGGATCAAAAGAAGAAGATCGYCGTAACTACCCAACCAAT 870

838  ACTTACAAAACGCTTGAACTTGAAATTGCTGAGTCCGATGTGGAAGTTAA 887
      ||||:||||||||||||||||||||||||||||||| ||:||||||||||
 871  ACTTRCAAAACGCTTGACCTTGAAATTGCTGAGTYCGATGTGAAAGTTAA 920

888  AAAAGCGGAGCTTGAACTAGTAAAAGTGAAAGCTAAGGAATCTCAAGACG 937
      ||:||||||||||||||||| |||||||||:||:|||||||:|||||||
 921  AGAAGCGGAGCTTGAACTAGTAAAARGAGGAAGCTMMRGAAYCTCGAGACG 970

938  AGGAAAAATTAAGCAAGCAGAAGTTGAGAGTAAACAAGCTGAG 987
      |||||||| |||||||||||||||||||||||||||||||||||
 971  AGGAAAAATTAAGCAAGCAGAAGTTGAGAGTAAAAAAGCTGAG 1020

988  GCTACAAGGTTAAAAAAATCAAGACAGATCGT.........GAAGA 1025
      |||||||||||| ||:||||||||||||||:||        |||||
 1021 GCTACAAGGTTAGAAACATCAAGACAGATNGTAAAAAAGCAGAAGAAGA 1070

1026 AGCTAAAAGCGAAAAGCAG 1042
      ||:||||||||||||||||
 1071 AGNTAAAAGCGAAAAGCAG 1087
```

FIG. 27D

```
306 SQTEHRKD.....VDEYIKKMLSEIQLDRRKHTQNVNLNIKLSAIKTKYLY 351
        ..|||.     |||||||||||.||.|||||.||||||||.|||||||
  2 AKTEHRKAAKXVVDEYIEKMLREIQLDRRKHTQNVALNIKLSAIXTKYLR  51

352 ELSVLKENSKKEELTSKTKAELTAAFEQFKKDTLKPEKKVAEAEKKVEEA 401
    ||.|.|.||..|| |.||.|||||||.||||||||||.||||.||||||
 52 ELXVXEEKS.XXELPSEIKAKLDAAFXKFKKDTLKPGEKVAEAKKXVEEA 100

402 KKKAKDQKEEDRRNYPTNTYKTLELEIAESDVKVKEAELELVKEEANESR 451
    ||.|.|||||||||||||.|.|||||||.|||||||||||||||.|..|
101 KXKAXDQKEEDRRNYPTNTXKTLDLEIAEXDVKVKEAELELVKEEAXEXR 150
```

*FIG. 28A*

```
452 NEEKIKQAKEKVESKKAEATRLEKIKTDRKKAEEEAKRKAEESEKKAAEA 501
    :  ||||| . |||| ||||||||||||| |||  . | . :
151 DEEKIKQAKAKVESKKAEATRLENIKTDXKKAEEEXKRKAAEEDK...... 195

552 SKLDTKKAKLSKLEELSDKIDELDAEIAKLEVQLKDAEGNNNVEAYFKEG 601
                               | . ||.
196 ............................VKEKPAEQ.............. 203

602 LEKTTAEKKAELEKAEADLKKAVDEPETPAPAPQPAPAPEKPAEKPAPAP 651
     : . :: .  ||  ||||    .: ||||||||| . ||||
204 ..........................PQPAPXTQPEKPAPKPEKPAEQPKAEK 230

652 EKPAPAPEKPAPAPEKP.APAPEKPAPAPEKPAPTPETPKT 691
     ||||. | . . :|  :| ||||| . |||| ||||
231 TDDQQAEEDYARRSEEEYNRLXQQQPPKTEKPAQ.PXTPKT 270
```

FIG. 28B

```
 91 AKKDAKNAKKAVEDAQKALDDAKAAQKKYDEDQKKTEEKAALEKAASEEM 140
    ||| :: :| ||| |        :    |:|  ::::  |:  |: |: :
  2 AKTEHRKAAKXVVD.......EYIEKMLREIQLDRRKHTQNVALNIKLSAIX 46

141 DKAVAVQQAYLAYQQATDKAAKDAADKMIDEAKKREEEAKTKFNTVRAM 190
           :   :             | :|   |  :| | ||
 47 TK............YLRELXVEEKSXXELPSEIKAKLDAAFXKF...KKD 82

191 VVPEPEQLAETKKKSEEAKQKAPELTKKLEEAKAKLEEAEKKATEAKQKV 240
    ::|:: |:|| ||| ||||||                |:  |:  |  :
 83 TLKPGEKVAEAKKXVEEAKKXKAXD............QKEEDRRNYPTNTXKTL 123
```

FIG. 29A

```
241 DAEEVAPQAKIAELENQVHRLEQELKEIDESESEDYAKEGFRAPLQSKLD 290
     |  ..:|  :|  —  | : ..:  ..|.|.
124 DLEIAEXDVKVKEAELEL..VKEEAXEXRDEEKIKQAK........AKVE 163

291 AKKAKLSKLEELSDKIDELDAEIAKLEDQLKAAEENNNVEDYFKEGLEKT 340
     |||. .:||  .:||  ::
164 SKKAEATRLENI...................................  175

341 IAAKKAELEKTEADLKKAVNEPEKPAPAPAPETPAPEAPAEQPKPAPAPQPA 390
     |:..| ::|  |.|:  |—  .|—.||.
176 .....KTDXKKAEEEXKRKAAEEDK............VKEKPAEQPQPAPXTQPE 213

391 .PAPKPEKPAEQPKPEKTDDQQAEEDYARRSEEEYNRLTQQQPPKAEKPA 439
    ||||||||||||||||||||||||||||||||||||||||.|||||
214 KPAPKPEKPAEQPKAEKTDDQQAEEDYARRSEEEYNRLXQQQPPKTEKPA 263

440 PA...PKT 444
    ||   :|
264 QPXTPKT  270
```

FIG. 29B

```
                          SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

CCGGATCCAG CTCCTGCACC AAAAAC                                            26

(2) INFORMATION FOR SEQ ID NO:2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GCGCGTCGAC GGCTTAAACC CATTCACCAT TGG                                    33

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCGGATCCTG AGCCAGAGCA GTTGGCTG                                          28

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CCGGATCCGC TCAAAGAGAT TGATGAGTCT G                                      31

(2) INFORMATION FOR SEQ ID NO:5:
```

```
    (i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCGGATCCCG TAGCCAGTCA GTCTAAAGCT G                                31

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CTGAGTCGAC TGGAGTTTCT GGAGCTGGAG C                                31

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CCGGATCCAG CTCCAGCTCC AGAAACTCCA G                                31

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GCGGATCCTT GACCAATATT TACGGAGGAG GC                               32

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GTTTTTGGTG CAGGAGCTGG                                             20

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:10:

GCTATGGGCT ACAGGTTG                                                        18

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CCACCTGTAG CCATAGC                                                         17

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CCGCATCCAG CGTGCCTATC TTAGGGGCTG GTT                                       33

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCAAGCTTAT GATATAGAAA TTTGTAAC                                             28

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGAAGGCCAT ATGCTCAAAG AGATTGATGA GTCT                                      34

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CCAAGGATCC TTAAACCCAT TCACCATTGG C                                31

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CCGGATCCGC TCAAAGAGAT TGATGAGTCT G                                31

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CTGAGTCGAC TGAGTTTCTG GAGCTGGAGC                                  30

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GCGCGTCGAC GGCTTAAACC CATTCACCAT TGG                              33

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CCGGATCCAG CTCCTGCACC AAAAAC                                      26

(2) INFORMATION FOR SEQ ID NO:20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GCAAGCTTAT GATATAGAAA TTTGTAAC                                    28

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
CCACATACCG TTTTCTTGTT TCCAGCC                                 27
```

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
CCGGATCCAG CTCCTGCACC AAAAC                                  25
```

(2) INFORMATION FOR SEQ ID NO:23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
CCGGATCCTG AGCCAGAGCA GTTGGCTG                               28
```

(2) INFORMATION FOR SEQ ID NO:24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
CCGGATCCGC TCAAAGAGAT TGATGAGTCT G                           31
```

(2) INFORMATION FOR SEQ ID NO:25:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
GCGGATCCCG TAGCCAGTCA GTCTAAAGCT G                           31
```

(2) INFORMATION FOR SEQ ID NO:26:

(i) SEQUENCE CHARACTERISTICS:

```
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CTGAGTCGAC TGGAGTTTCT GGAGCTGGAG C                               31

(2) INFORMATION FOR SEQ ID NO:27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CCGGATCCAG CTCCAGCTCC AGAAACTCCA G                               31

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GTTTTTGGTG CAGGAGCTGG                                            20

(2) INFORMATION FOR SEQ ID NO:29:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GCTATGGCTA CAGGTTG                                               17

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CCGGATCCAG CGTGCCTATC TTAGGGGCTG GT                              32

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:31:

GCGGATCCTT GACCAATAAC GGAGGAGGC                                                        29

(2) INFORMATION FOR SEQ ID NO:32:

(i) SEQUENCE CHARACTERISTICS:
                (A) LENGTH: 8991 amino acids
                (B) TYPE: amino acid
                (C) STRANDEDNESS: single
                (D) TOPOLOGY: linear (ii) MOLECULE TYPE: amino acid (xi) SEQUENCE DESCRIPTION: SEQ ID NO:32:

Met Asn Lys Lys Met Ile Leu Thr Ser Leu Ala Ser Val Ala Ile
1               5                   10                  15

Leu Gly Thr Gly Phe Val Ala Ser Pro Thr Leu Val Arg Ala Glu
            20                  25                  30

Glu Ser Pro Gln Val Val Glu Lys Ser Leu Glu Lys Lys Tyr Glu
        35                  40                  45

Glu Ala Lys Ala Lys Ala Asp Thr Ala Lys Lys Asp Tyr Glu Thr Ala
    50                  55                  60

Lys Lys Ala Glu Asp Ala Gln Lys Lys Tyr Asp Glu Asp Gln Lys
65                  70                  75                  80

Lys Thr Glu Asp Lys Ala Lys Ala Val Lys Val Asp Glu Glu Arg
                85                  90                  95

Gln Lys Ala Ile Leu Ala Val Gln Lys Ala Tyr Val Glu Tyr Arg Glu
                100                 105                 110

Ala Lys Asp Lys Ala Ser Ala Glu Lys Gln Ile Ala Glu Ala Lys Arg
            115                 120                 125

Lys Thr Met Asn Lys Lys Met Ile Leu Thr Ser Leu Ala Ser Val
130                 135                 140

Ala Ile Leu Gly Ala Gly Leu Val Thr Ala Gln Pro Thr Leu Val Arg
145                 150                 155                 160

Ala Glu Glu Ala Pro Val Ala Ser Gln Ser Lys Ala Glu Lys Asp Tyr
                165                 170                 175

Asp Thr Ala Lys Arg Asp Ala Glu Asn Ala Lys Lys Ala Leu Glu Glu
            180                 185                 190

Ala Lys Arg Ala Gln Lys Lys Tyr Glu Asp Gln Lys Lys Thr Glu
            195                 200                 205

Glu Lys Ala Lys Glu Glu Lys Gln Ala Ser Glu Ala Glu Gln Lys Ala
    210                 215                 220

Asn Leu Gln Tyr Gln Leu Lys Leu Arg Glu Tyr Ile Gln Lys Thr Gly
225                 230                 235                 240

Asp Arg Ser Lys Ile Gln Thr Glu Met Glu Glu Ala Glu Lys Lys His
                245                 250                 255

Lys Thr Ala Lys Ala Glu Phe Asp Lys Val Arg Gly Thr Val Ile Pro
                260                 265                 270

Ser Ala Ala Arg Val Met Asn Lys Lys Met Ile Leu Thr Ser Leu
                275                 280                 285

Ala Ser Val Ala Ile Leu Gly Ala Gly Leu Val Thr Ser Gln Pro Thr
            290                 295                 300

Leu Val Arg Ala Glu Glu Ala Pro Val Ala Ser Gln Ser Lys Ala Glu
305                 310                 315                 320

```
Lys Asp Tyr Asp Ala Ala Val Lys Lys Ser Glu Ala Ala Lys Lys Ala
                325                 330                 335

Tyr Glu Glu Ala Lys Lys Lys Ala Glu Asp Ala Gln Lys Lys Tyr Asp
            340                 345                 350

Glu Asp Gln Lys Lys Thr Glu Glu Lys Ala Glu Asn Glu Lys Lys Ala
            355                 360                 365

Ala Ala Asp Leu Thr Glu Ala Thr Glu Val His Gln Lys Ala Tyr Val
        370                 375                 380

Arg Tyr Ser Gly Ser Asn Glu Gln Lys Ile Lys Asn Phe Lys Ile Leu
385                 390                 395                 400

Ala Ile Met Xaa Lys Lys Met Ile Leu Thr Ser Leu Ala Ser Val
                405                 410                 415

Ala Ile Leu Gly Ala Gly Xaa Val Ala Ser Gln Pro Thr Xaa Val Arg
            420                 425                 430

Ala Glu Asp Ala Pro Val Ala Asn Gln Ser Gln Ala Glu Lys Asp Tyr
            435                 440                 445

Xaa Ala Ala Xaa Xaa Lys Ser Glu Ala Ala Lys Lys Xaa Tyr Xaa Xaa
        450                 455                 460

Ala Lys Lys Val Leu Ala Glu Ala Glu Ala Ala Gln Lys Xaa Xaa Glu
465                 470                 475                 480

Asp Xaa Gln Lys Lys Pro Glu Glu Lys Ala Glu Lys Ala Lys Ala Ala
            485                 490                 495

Ser Glu Glu Ile Val Lys Ala Thr Glu Glu Val Gln Xaa Ala Ala Met
            500                 505                 510

Asn Lys Lys Lys Met Ile Leu Thr Ser Leu Ala Ser Val Ala Ile Leu
            515                 520                 525

Gly Ala Gly Leu Val Thr Ser Gln Pro Thr Leu Val Arg Ala Glu Glu
            530                 535                 540

Ala Pro Gly Ala Ser Gln Ser Lys Ala Glu Lys Asp Tyr Xaa Ala Ala
545                 550                 555                 560

Xaa Lys Lys Ser Glu Ala Ala Lys Lys Ala Tyr Glu Glu Ala Lys Lys
            565                 570                 575

Lys Ala Glu Asp Ala Gln Lys Lys Tyr Asp Glu Gly Gln Lys Lys Thr
            580                 585                 590

Glu Glu Lys Ala Arg Lys Ala Glu Glu Ala Ser Lys Glu Leu Ala Lys
            595                 600                 605

Ala Thr Ser Glu Val Gln Asn Ala Tyr Val Lys Tyr Gln Gly Val Gln
            610                 615                 620

Arg Asn Ser Arg Leu Asn Glu Lys Glu Arg Lys Lys Gln Leu Ala Glu
625                 630                 635                 640

Ile Asp Glu Glu Ile Asn Lys Ala Lys Gln Ile Trp Asn Glu Lys Asn
                645                 650                 655

Glu Asp Phe Lys Lys Val Arg Glu Glu Val Ile Pro Glu Pro Thr Glu
            660                 665                 670

Leu Ala Lys Asp Gln Arg Lys Ala Glu Glu Ala Lys Ala Glu Glu Lys
            675                 680                 685

Val Ala Lys Arg Lys Tyr Asp Tyr Ala Thr Leu Lys Val Ala Leu Ala
        690                 695                 700

Lys Ser Tyr Val Glu Ala Glu Ala Xaa Leu Met Asn Lys Lys Lys
705                 710                 715                 720

Met Ile Leu Thr Ser Leu Ala Ser Val Ala Ile Leu Gly Ala Gly Leu
                725                 730                 735
```

-continued

```
Val Thr Ser Gln Pro Thr Phe Val Arg Ala Glu Glu Ala Pro Val Ala
            740                 745                 750

Ser Gln Pro Lys Ala Glu Lys Asp Tyr Asp Pro Ala Gly Lys Lys Ser
            755                 760                 765

Glu Ala Ala Thr Lys Ala Tyr Glu Asp Ala Lys Pro Thr Ala Glu Asp
            770                 775                 780

Ala Gln Lys Lys Tyr Asp Glu Ala Gln Lys Lys Pro Asp Ala Glu Arg
785                 790                 795                 800

Met Asn Lys Lys Met Ile Leu Thr Ser Leu Ala Ser Val Ala Ile
                    805                 810                 815

Leu Gly Ala Gly Leu Val Ala Ser Gln Pro Thr Val Val Arg Ala Glu
            820                 825                 830

Glu Ala Pro Val Ala Lys Gln Ser Gln Ala Glu Arg Asp Tyr Asp Ala
            835                 840                 845

Ala Met Lys Lys Ser Glu Ala Ala Lys Lys Glu Tyr Glu Glu Ala Lys
            850                 855                 860

Lys Asp Leu Glu Glu Ala Lys Ala Ala Gln Lys Lys Tyr Gly Gly Asp
865                 870                 875                 880

Pro Lys Lys Thr Gly Glu Glu Thr Lys Leu Val Pro Lys Ala Asp Gly
                    885                 890                 895

Glu Arg Pro Lys Ala Asn Val Ala Val Pro Lys Ala Tyr Leu Lys Leu
            900                 905                 910

Arg Glu Ala Gln Glu Gln Leu Asn Gln Ser Pro Asn Asn Lys Lys Asn
            915                 920                 925

Ser Ala Gln Gln Lys Leu Lys Asp Ala Leu Ala His Ile Asp Glu Val
            930                 935                 940

Thr Leu Asn Gln Lys Glu Ala Glu Ala Met Asn Lys Lys Lys Met Ile
945                 950                 955                 960

Leu Thr Ser Leu Ala Ser Val Ala Ile Leu Gly Ala Gly Leu Val Thr
                    965                 970                 975

Ser Gln Pro Thr Val Val Arg Ala Glu Glu Ser Pro Val Ala Ser Gln
            980                 985                 990

Ser Lys Ala Glu Lys Asp Tyr Asp Ala Ala Val Lys Asn Ala Thr Ala
            995                 1000                1005

Ala Lys Lys Ala Ala Glu Asp Ala His Arg Ala Leu Asp Glu Ala Lys
            1010                1015                1020

Ala Ala Gln Lys Asn Tyr Asp Glu Asp Gln Lys Lys Pro Glu Glu Lys
1025                1030                1035                1040

Ala Lys Glu Val Pro Lys Ala Pro Ala Glu Glu Met Asn Lys Lys Lys
                    1045                1050                1055

Met Ile Leu Thr Ser Leu Ala Ser Val Ala Ile Leu Gly Ala Gly Leu
            1060                1065                1070

Val Ala Ser Gln Pro Thr Leu Val Arg Ala Glu Asp Ala Pro Val Ala
            1075                1080                1085

Asn Gln Ser Gln Ala Glu Lys Asp Tyr Asp Ala Ala Met Lys Lys Ser
            1090                1095                1100

Glu Ala Ala Lys Lys Glu Tyr Glu Asp Ala Lys Lys Val Leu Ala Glu
1105                1110                1115                1120

Ala Glu Ala Ala Gln Lys Lys Tyr Glu Asp Asp Gln Lys Lys Thr Glu
                    1125                1130                1135

Glu Lys Ala Glu Asn Ala Asn Ala Ala Ser Glu Glu Ile Ala Lys Ala
            1140                1145                1150

Thr Glu Glu Val His Met Asn Lys Lys Lys Met Ile Leu Thr Ser Leu
```

-continued

```
                    1155                1160                1165

Ala Ser Val Ala Ile Leu Gly Ala Gly Leu Val Ala Ser Ser Pro Thr
           1170                1175                1180

Val Val Arg Ala Glu Glu Ala Pro Val Ala Ser Gln Ser Lys Ala Glu
1185                1190                1195                1200

Lys Asp Tyr Asp Thr Ala Lys Arg Asp Ala Glu Asn Ala Lys Lys Ala
                1205                1210                1215

Leu Glu Glu Ala Lys Arg Ala Gln Glu Lys Tyr Ala Asp Tyr Gln Arg
           1220                1225                1230

Arg Ile Glu Glu Lys Ala Ala Lys Glu Thr Gln Ala Ser Leu Glu Gln
           1235                1240                1245

Gln Glu Ala Asn Lys Asp Tyr Gln Leu Lys Leu Lys Lys Tyr Leu Asp
           1250                1255                1260

Gly Arg Asn Leu Ser Asn Ser Ser Val Leu Lys Lys Glu Met Glu Glu
1265                1270                1275                1280

Ala Glu Lys Lys Asp Lys Glu Asn Gln Ala Glu Phe Asn Lys Ile Arg
                1285                1290                1295

Arg Glu Ile Val Val Pro Asn Pro Gln Glu Leu Glu Met Ala Arg Arg
           1300                1305                1310

Lys Ser Glu Val Val Lys Ala Thr Glu Ser Gly Leu Val Thr Arg Val
           1315                1320                1325

Glu Glu Ala Glu Lys Asn Val Thr Asp Ala Arg Gln Lys Leu Val Leu
           1330                1335                1340

Lys Cys Asn Glu Val Val Leu Gln Ala Xaa Xaa Ala Glu Leu Glu Ser
1345                1350                1355                1360

Gly Gly His Lys Leu Glu Pro Lys Met Asn Lys Lys Met Ile Leu
                1365                1370                1375

Thr Ser Leu Ala Ser Xaa Ala Ile Leu Gly Ala Gly Leu Val Ala Ser
           1380                1385                1390

Gln Pro Thr Val Val Arg Ala Glu Glu Ala Pro Val Ala Ser Gln Ser
           1395                1400                1405

Lys Ala Glu Lys Asp Tyr Asp Ala Ala Lys Arg Asp Ala Glu Asn Ala
           1410                1415                1420

Lys Lys Ala Leu Glu Glu Ala Lys Arg Ala Gln Lys Xaa Xaa Glu Asp
1425                1430                1435                1440

Asp Gln Lys Lys Thr Glu Glu Lys Ala Lys Xaa Asp Xaa Gln Ala Ser
                1445                1450                1455

Glu Ala Glu Gln Lys Ala Asn Leu Xaa Tyr Gln Leu Leu Gln Lys
           1460                1465                1470

Tyr Val Ser Glu Ser Asp Gly Lys Lys Lys Glu Xaa Glu Xaa Xaa
           1475                1480                1485

Ala Asp Ala Ala Lys Lys Glu Ile Glu Leu Lys Xaa Ala Asp Leu Xaa
           1490                1495                1500

Lys Ile Xaa Gln Glu Met Asn Lys Lys Met Ile Leu Thr Ser Leu
1505                1510                1515                1520

Ala Ser Val Ala Ile Leu Gly Ala Gly Leu Val Ala Ser Gln Pro Thr
                1525                1530                1535

Val Val Arg Ala Glu Glu Ala Pro Val Ala Ser Gln Ser Lys Ala Glu
           1540                1545                1550

Lys Asp Tyr Asp Ala Ala Val Glu Lys Ser Lys Ala Ala Glu Glu Asp
           1555                1560                1565

Leu Glu Glu Ala Glu Ala Ala Gln Arg Lys Tyr Asp Glu Asp Gln Lys
           1570                1575                1580
```

-continued

```
Lys Ser Glu Glu Asn Glu Lys Glu Thr Glu Ala Ser Glu Arg Gln
1585                1590                1595                1600

Gln Ala Ala Thr Leu Lys Tyr His Leu Glu Ser Xaa Glu Phe Leu Asn
            1605                1610                1615

Tyr Phe Gln Asp Asn His Arg Met Asn Lys Lys Met Ile Leu Thr
        1620                1625                1630

Ser Leu Ala Ser Val Ala Ile Leu Gly Ala Gly Leu Val Ala Ser Pro
        1635                1640                1645

Pro Thr Val Val Arg Ala Glu Glu Ala Pro Val Ala Ser Gln Ser Lys
        1650                1655                1660

Ala Glu Lys Asp Tyr Asp Thr Ala Lys Arg Asp Ala Glu Asn Ala Lys
1665                1670                1675                1680

Lys Ala Leu Glu Glu Ala Lys Arg Ala Gln Glu Lys Tyr Ala Asp Tyr
            1685                1690                1695

Gln Arg Arg Ile Glu Glu Lys Ala Ala Lys Glu Thr His Ala Ser Leu
        1700                1705                1710

Glu Gln Gln Glu Ala Asn Lys Asp Tyr Gln Leu Lys Leu Lys Lys Tyr
        1715                1720                1725

Leu Asp Gly Arg Asn Leu Ser Asn Ser Ser Val Leu Lys Lys Glu Met
    1730                1735                1740

Glu Glu Ala Glu Lys Lys Asp Lys Glu Lys Pro Ala Glu Phe Asn Lys
1745                1750                1755                1760

Ile Arg Arg Glu Ile Val Val Pro Asn Pro Gln Glu Leu Glu Met Ala
            1765                1770                1775

Arg Arg Lys Ser Glu Val Ala Lys Thr Lys Glu Ser Gly Leu Val Lys
            1780                1785                1790

Arg Val Glu Glu Ala Glu Lys Lys Val Thr Glu Ala Arg Pro Lys Leu
        1795                1800                1805

Asp Ala Glu Arg Ala Lys Glu Val Val Leu Gln Ala Gln Ile Ala Met
        1810                1815                1820

Asn Lys Lys Lys Met Ile Leu Thr Ser Leu Ala Ser Val Ala Ile Leu
1825                1830                1835                1840

Gly Ala Gly Leu Val Ala Ser Pro Pro Thr Val Val Arg Ala Glu Glu
            1845                1850                1855

Ala Pro Val Ala Ser Gln Ser Lys Ala Glu Lys Asp Tyr Asp Thr Ala
            1860                1865                1870

Lys Arg Asp Ala Glu Asn Ala Lys Lys Ala Leu Glu Glu Ala Lys Arg
        1875                1880                1885

Ala Gln Glu Lys Tyr Ala Asp Tyr Gln Arg Arg Ile Glu Glu Lys Ala
        1890                1895                1900

Ala Lys Glu Thr His Ala Ser Leu Glu Gln Gln Glu Ala Asn Lys Asp
1905                1910                1915                1920

Tyr Gln Leu Lys Leu Lys Lys Tyr Leu Asp Gly Arg Asn Leu Ser Asn
            1925                1930                1935

Ser Ser Val Leu Lys Lys Glu Met Glu Glu Ala Glu Lys Lys Asp Lys
        1940                1945                1950

Glu Lys Gln Ala Gly Leu Met Asn Lys Lys Met Ile Leu Thr Ser
        1955                1960                1965

Leu Ala Ser Val Ala Ile Leu Gly Ala Gly Leu Val Thr Ser Gln Pro
    1970                1975                1980

Thr Leu Val Arg Ala Glu Glu Ser Pro Val Ala Ser Gln Ser Lys Ala
1985                1990                1995                2000
```

```
Glu Lys Asp Tyr Asp Ala Ala Lys Arg Asp Ala Glu Asn Ala Lys Lys
            2005                2010                2015

Ala Leu Glu Glu Ala Lys Arg Ala Gln Glu Lys Tyr Ala Asp Tyr Gln
            2020                2025                2030

Arg Arg Ile Glu Glu Lys Ala Lys Glu Gln Gln Ala Ser Leu Glu
            2035                2040                2045

Gln Gln Glu Ala Asn Lys Asp Tyr Gln Leu Lys Leu Lys Lys Tyr Leu
            2050                2055                2060

Asp Gly Arg Asn Leu Ser Asn Ser Ser Val Leu Lys Lys Glu Met Glu
2065                2070                2075                2080

Glu Ala Glu Lys Lys Asp Lys Glu Lys Gln Ala Glu Phe Asn Lys Ile
            2085                2090                2095

Arg Arg Glu Ile Val Val Pro Asn Pro Gln Leu Glu Met Ala Arg
            2100                2105                2110

Arg Lys Ser Glu Val Val Lys Ala Lys Glu Ser Gly Leu Val Lys Arg
            2115                2120                2125

Val Glu Glu Ala Glu Lys Lys Val Thr Glu Ala Arg Gln Lys Leu Asp
            2130                2135                2140

Ala Glu Arg Ala Lys Glu Val Val Leu Gln Pro Thr Arg Val Glu Asn
2145                2150                2155                2160

Glu Val His Lys Leu Xaa Gln Lys Met Asn Lys Lys Met Ile Leu
            2165                2170                2175

Thr Ser Leu Ala Ser Val Ala Ile Leu Gly Ala Gly Leu Val Thr Ser
            2180                2185                2190

Gln Pro Thr Phe Val Arg Ala Glu Glu Ser Pro Gln Val Val Glu Lys
            2195                2200                2205

Ser Ser Leu Glu Lys Lys Tyr Glu Glu Ala Lys Ala Lys Ala Asp Thr
            2210                2215                2220

Ala Lys Lys Asp Tyr Glu Thr Ala Lys Lys Ala Glu Asp Ala Gln
2225                2230                2235                2240

Lys Lys Tyr Glu Asp Asp Gln Lys Arg Thr Glu Lys Ala Arg Lys
            2245                2250                2255

Glu Ala Glu Ala Ser Gln Lys Leu Ile Asp Val Ala Leu Val Val Gln
            2260                2265                2270

Asn Ala Tyr Lys Glu Tyr Arg Gly Val Gln Asn Gln Arg Ser Lys Tyr
            2275                2280                2285

Lys Ser Asp Ala Asp Tyr Gln Lys Lys Leu Thr Glu Val Asp Ser Lys
            2290                2295                2300

Ile Glu Lys Ala Arg Lys Glu Gln Gln Asp Leu Gln Asn Asn Phe Asn
2305                2310                2315                2320

Glu Val Arg Ala Val Val Ala Pro Asp Pro Thr Cys Val Gly Xaa Asp
            2325                2330                2335

Xaa Arg Met Asn Lys Lys Met Ile Leu Thr Ser Leu Ala Ser Val
            2340                2345                2350

Ala Ile Leu Gly Ala Gly Xaa Val Thr Ser Gln Pro Thr Xaa Val Arg
            2355                2360                2365

Ala Glu Glu Ala Pro Gln Val Val Glu Lys Ser Ser Leu Glu Lys Lys
            2370                2375                2380

Tyr Glu Glu Ala Lys Ala Lys Tyr Asp Ala Ala Lys Lys Asp Tyr Asp
2385                2390                2395                2400

Glu Ala Lys Lys Lys Ala Ala Glu Ala Gln Lys Lys Tyr Glu Glu Asp
            2405                2410                2415

Gln Lys Lys Thr Glu Glu Lys Ala Glu Lys Ala Lys Ala Ala Ser Glu
```

```
                  2420               2425                2430
Glu Ile Ala Lys Ala Thr Glu Glu Val Gln Lys Ala Val Leu Asp Tyr
            2435                2440                2445
Ile Thr Ala Ile Arg Asn His Asn Asp Ser Gly Lys Thr Ser Ala Glu
        2450                2455                2460
Glu Ala Glu Asn Lys Ala Lys Glu Arg Asp Tyr Cys Cys Ala Gly Lys
2465                2470                2475                2480
Lys Phe Asp Pro Ile Gln Thr Pro Phe Val Ala Ser Leu Thr Gln Met
            2485                2490                2495
Ile Leu Met Asn Lys Lys Met Ile Leu Thr Ser Leu Ala Ser Val
        2500                2505                2510
Ala Ile Leu Gly Ala Gly Leu Val Ala Ser Ser Pro Thr Val Val Arg
        2515                2520                2525
Ala Glu Glu Ala Pro Val Ala Ser Gln Ser Lys Ala Glu Lys Asp Tyr
        2530                2535                2540
Asp Thr Ala Lys Arg Asp Ala Glu Asn Ala Lys Lys Ala Leu Glu Glu
2545                2550                2555                2560
Ala Lys Arg Ala Gln Glu Lys Tyr Ala Asp Tyr Gln Arg Arg Ile Glu
            2565                2570                2575
Glu Lys Ala Ala Lys Glu Thr Gln Ala Ser Leu Glu Gln Gln Glu Ala
            2580                2585                2590
Asn Lys Asp Tyr Gln Leu Lys Leu Lys Lys Tyr Leu Asp Gly Arg Asn
            2595                2600                2605
Leu Ser Asn Ser Ser Val Leu Lys Lys Glu Met Glu Glu Ala Glu Lys
        2610                2615                2620
Lys Asp Lys Glu Asn Gln Ala Glu Phe Asn Lys Ile Arg Arg Glu Ile
2625                2630                2635                2640
Val Val Pro Asn Pro Gln Glu Leu Glu Met Ala Met Asn Lys Lys Lys
            2645                2650                2655
Met Ile Leu Thr Ser Leu Ala Ser Val Ala Ile Leu Gly Ala Gly Phe
            2660                2665                2670
Val Ala Ser Gln Pro Thr Val Val Arg Ala Glu Glu Ser Pro Val Ala
        2675                2680                2685
Ser Gln Ser Lys Ala Glu Lys Asp Tyr Asp Ala Ala Lys Lys Asp Ala
        2690                2695                2700
Lys Asn Ala Lys Lys Ala Val Glu Asp Ala Gln Lys Ala Leu Asp Asp
2705                2710                2715                2720
Ala Lys Ala Ala Gln Lys Lys Tyr Asp Glu Asp Gln Lys Lys Thr Glu
            2725                2730                2735
Glu Lys Ala Ala Leu Glu Lys Ala Ala Ser Glu Glu Met Asp Lys Ala
            2740                2745                2750
Val Ala Ala Val Gln Gln Ala Tyr Leu Ala Tyr Gln Gln Ala Thr Asp
        2755                2760                2765
Lys Ala Ala Lys Asp Ala Ala Asp Lys Met Ile Asp Glu Ala Lys Lys
        2770                2775                2780
Arg Glu Glu Glu Ala Lys Thr Lys Phe Asn Thr Val Arg Ala Met Val
2785                2790                2795                2800
Val Pro Glu Pro Glu Gln Leu Ala Glu Thr Lys Lys Lys Ser Glu Glu
            2805                2810                2815
Ala Lys Gln Lys Ala Pro Glu Leu Thr Lys Lys Leu Glu Glu Ala Lys
            2820                2825                2830
Ala Lys Leu Glu Glu Ala Glu Lys Lys Ala Thr Glu Ala Lys Gln Lys
            2835                2840                2845
```

```
Val Asp Ala Met Asn Lys Lys Met Ile Leu Thr Ser Leu Ala Ser
2850                2855                2860

Val Ala Ile Leu Gly Ala Gly Leu Val Ala Ser Gln Pro Thr Leu Val
2865                2870                2875                2880

Arg Ala Glu Glu Ser Pro Val Ala Ser Gln Ser Lys Ala Glu Lys Asp
        2885                2890                2895

Tyr Asp Ala Ala Val Lys Lys Ser Glu Ala Ala Lys Lys Ala Tyr Glu
            2900                2905                2910

Glu Ala Lys Lys Ala Leu Glu Glu Ala Lys Val Ala Gln Lys Lys Tyr
        2915                2920                2925

Glu Asp Asp Gln Lys Lys Thr Glu Glu Lys Ala Glu Leu Glu Lys Glu
        2930                2935                2940

Ala Ser Glu Ala Ile Ala Lys Ala Thr Glu Glu Val Gln Gln Ala Tyr
2945                2950                2955                2960

Leu Ala Tyr Gln Arg Ala Ser Asn Lys Ala Glu Ala Ala Lys Met Ile
            2965                2970                2975

Glu Glu Ala Gln Arg Arg Glu Asn Glu Ala Arg Ala Lys Phe Thr Thr
        2980                2985                2990

Ile Arg Thr Thr Met Val Val Pro Glu Pro Glu Gln Leu Ala Glu Thr
        2995                3000                3005

Lys Lys Lys Ala Glu Glu Ala Lys Ala Lys Glu Pro Lys Leu Ala Lys
        3010                3015                3020

Lys Ala Glu Ala Lys Ala Lys Leu Glu Glu Ala Glu Lys Lys Ala
3025                3030                3035                3040

Thr Glu Ala Asn Pro Gln Val Asp Ala Met Asn Lys Lys Met Ile
            3045                3050                3055

Leu Thr Ser Leu Ala Ser Val Ala Ile Leu Gly Ala Gly Phe Val Ala
        3060                3065                3070

Ser Ser Pro Thr Phe Val Arg Ala Glu Glu Ala Pro Val Ala Asn Gln
        3075                3080                3085

Ser Lys Ala Glu Lys Asp Tyr Asp Ala Ala Val Lys Lys Ser Glu Ala
        3090                3095                3100

Ala Lys Lys Asp Tyr Glu Thr Ala Lys Lys Ala Glu Asp Ala Gln
3105                3110                3115                3120

Lys Lys Tyr Asp Glu Asp Gln Lys Lys Thr Glu Ala Lys Ala Glu Lys
            3125                3130                3135

Glu Arg Lys Ala Ser Glu Lys Ile Ala Glu Ala Thr Lys Glu Val Gln
        3140                3145                3150

Gln Ala Tyr Leu Ala Tyr Leu Gln Ala Ser Asn Glu Ser Gln Arg Lys
        3155                3160                3165

Glu Ala Asp Lys Lys Ile Lys Glu Ala Thr His Ala Lys Met Arg Arg
        3170                3175                3180

Thr Cys Asn Leu Thr Ile Glu Phe Glu Gln Gln Leu Tyr Phe Leu Asn
3185                3190                3195                3200

Gln Val Ser Tyr Leu Arg Leu Arg Lys Lys Gln Lys Arg Gln Gln Lys
            3205                3210                3215

Lys Gln Lys Tyr Leu Arg Lys Asn Leu Lys Arg Gln Leu Lys Arg Tyr
        3220                3225                3230

Lys Tyr Arg Lys Ile Lys Tyr Leu Asn Lys Met Leu Lys Thr Lys Arg
        3235                3240                3245

Lys Leu Met Asn Lys Lys Leu Ile Val Thr Ser Leu Ala Ser Val
3250                3255                3260
```

-continued

```
Ala Ile Leu Gly Ala Asp Ser Val Thr Ser Pro Pro Ala Leu Val Arg
3265                3270                3275                3280

Ala Asp Glu Ala Ser Leu Ile Ala Ser Gln Ser Lys Ala Glu Lys Asp
            3285                3290                3295

Tyr Asp Ala Ala Lys Lys Asp Ala Lys Asn Ala Lys Lys Ala Val Glu
        3300                3305                3310

Asp Ala Gln Lys Ala Leu Asp Asp Ala Lys Ala Ala Gln Lys Lys Tyr
    3315                3320                3325

Asp Glu Asp Gln Lys Lys Thr Glu Lys Lys Ala Ala Val Lys Lys
3330                3335                3340

Ile Asp Glu Glu His Gln Ala Ala Asn Leu Lys Ser Gln Gln Ala Leu
3345                3350                3355                3360

Val Glu Phe Leu Ala Ala Gln Arg Glu Gly Asn Pro Lys Lys Lys
            3365                3370                3375

Ala Ala Gln Ala Thr Leu Glu Glu Ala Glu Asn Ala Glu Lys Glu Thr
        3380                3385                3390

Lys Met Asn Lys Lys Met Ile Lys Thr Ser Leu Ala Ser Ala Ala
    3395                3400                3405

Ile Phe Gly Ala Xaa Ser Glu Thr Ser Gln Pro Thr Arg Val Arg Pro
3410                3415                3420

Val Glu Ala Pro Glu Ala Arg His Pro Lys Val Asp Lys Tyr Tyr Asp
3425                3430                3435                3440

Ala Glu Ala Asp Glu Tyr Met Asn Lys Lys Met Ile Leu Thr Ser
            3445                3450                3455

Leu Ala Ser Val Ala Ile Leu Gly Ala Gly Phe Gly Cys Val Ser Ala
        3460                3465                3470

Tyr Ser Cys Lys Ser Arg Arg Ile Ser Arg Ser Ser Ala Ser Ser Gln
    3475                3480                3485

Arg Leu Met Asn Lys Lys Met Ile Leu Lys Ser Leu Ala Ser Ala
    3490                3495                3500

Ala Ile Ser Gly Ala Xaa Leu Val Xaa Pro Gln Pro Thr Leu Val Arg
3505                3510                3515                3520

Ala Glu Glu Ser Pro Ala Ala Ser Gln Ser His Pro Glu Gln Asp Tyr
            3525                3530                3535

Asp Xaa Xaa Xaa Xaa Leu Cys Xaa Xaa Leu Xaa His Gln Pro Ser Xaa
        3540                3545                3550

Gly Arg Thr Leu Leu Xaa Xaa Xaa Ser Xaa Pro Xaa Ser Pro Thr
    3555                3560                3565

Pro Xaa Xaa Xaa Xaa Xaa Xaa Pro Xaa Ser Xaa Leu Thr Xaa Leu Xaa
    3570                3575                3580

Pro Leu Xaa Xaa Xaa Leu Lys Pro Phe Pro Leu Pro Xaa Ser Xaa Pro
3585                3590                3595                3600

Xaa Pro Pro Xaa Pro Pro Xaa Ser Pro Pro Ser Pro Pro Arg Pro
        3605                3610                3615

Xaa Leu Tyr Xaa Xaa Pro Pro Xaa Pro Xaa Pro Xaa Leu Ser Leu Xaa
        3620                3625                3630

Leu Ile Pro Phe Leu Leu Leu Xaa Leu Pro Pro Pro Xaa Xaa Xaa Leu
        3635                3640                3645

Pro His Leu Xaa Ser Pro Pro Xaa Pro Xaa Leu Pro Pro Ser Pro Thr
    3650                3655                3660

Pro Xaa Leu Lys Glu Ile Asp Glu Ser Asp Ser Glu Asp Tyr Leu Lys
3665                3670                3675                3680

Glu Gly Leu Arg Ala Pro Leu Gln Ser Lys Leu Asp Thr Lys Lys Ala
```

```
                   3685              3690                 3695
Lys Leu Ser Lys Leu Glu Glu Leu Ser Asp Lys Ile Asp Glu Leu Asp
            3700              3705                 3710
Ala Glu Ile Ala Lys Leu Glu Val Gln Leu Lys Asp Ala Glu Gly Asn
            3715              3720                 3725
Asn Asn Val Glu Ala Tyr Phe Lys Gly Leu Glu Lys Thr Thr Ala
            3730              3735                 3740
Glu Lys Lys Ala Glu Leu Glu Lys Ala Glu Ala Asp Leu Lys Lys Ala
3745              3750                 3755                  3760
Val Asp Glu Pro Glu Thr Pro Ala Pro Ala Pro Gln Pro Ala Pro Ala
                3765              3770                  3775
Pro Glu Lys Pro Ala Glu Lys Pro Ala Pro Ala Pro Glu Lys
            3780              3785                 3790
Pro Ala Pro Ala Pro Glu Lys Pro Ala Glu Lys Pro Ala Glu Lys Pro
            3795              3800                 3805
Ala Glu Glu Pro Ala Glu Lys Pro Ala Pro Ala Pro Glu Lys Pro Ala
            3810              3815                 3820
Pro Thr Pro Glu Lys Pro Ala Pro Thr Pro Glu Thr Pro Lys Thr Gly
3825              3830                 3835                  3840
Trp Lys Gln Glu Asn Gly Met Val Leu Asp Xaa Thr Ile Ala Glu Gly
            3845              3850                 3855
Lys Ala Gly Ile Ala Ala Xaa Pro Pro Asn Ile Asp Lys Thr Pro Lys
            3860              3865                 3870
Asp Leu Glu Asp Ser Gly Leu Gly Leu Glu Lys Val Leu Ala Thr Leu
            3875              3880                 3885
Asp Pro Gly Gly Glu Thr Pro Asp Gly Leu Asp Lys Glu Ala Ser Glu
            3890              3895                 3900
Asp Ser Asn Ile Gly Ala Leu Pro Asn Gln Val Ser Asp Leu Glu Asn
3905              3910                 3915                  3920
Gln Val Ser Glu Leu Asp Arg Glu Val Thr Arg Leu Pro Ser Asp Leu
            3925              3930                 3935
Lys Asp Thr Glu Gly Asn Asn Val Gly Asp Tyr Val Lys Gly Gly Leu
            3940              3945                 3950
Glu Lys Ala Leu Thr Asp Glu Lys Val Gly Leu Asn Asn Thr Pro Lys
            3955              3960                 3965
Ala Leu Asp Thr Ala Pro Lys Ala Leu Asp Thr Ala Leu Asn Glu Leu
            3970              3975                 3980
Gly Pro Asp Gly Asp Glu Glu Thr Pro Ala Pro Ala Pro Lys Pro
3985              3990                 3995                  4000
Glu Gln Pro Ala Glu Gln Pro Lys Pro Ala Pro Ala Pro Lys Pro Glu
            4005              4010                 4015
Lys Thr Asp Asp Gln Gln Ala Glu Glu Asp Tyr Ala Arg Arg Ser Glu
            4020              4025                 4030
Glu Glu Tyr Asn Arg Leu Pro Gln Gln Gln Pro Pro Lys Ala Glu Lys
            4035              4040                 4045
Pro Ala Pro Ala Pro Lys Pro Glu Gln Pro Val Pro Ala Pro Gly Gly
            4050              4055                 4060
Trp Ser Trp Arg Ile Leu Leu Ala Arg Pro Asp Arg Leu Ala Ala Arg
4065              4070                 4075                  4080
Gln Ala Glu Leu Ala Gln Lys Gln Thr Glu Leu Gly Lys Leu Leu Asp
            4085              4090                 4095
Ser Leu Asp Pro Glu Gly Lys Thr Gln Asp Glu Leu Asp Lys Glu Ala
            4100              4105                 4110
```

-continued

```
Gly Glu Ala Glu Leu Asp Lys Lys Ala Asp Gly Leu Pro Asn Lys Val
        4115                4120                4125

Ser Asp Leu Glu Lys Glu Ile Ser Asn Leu Glu Ile Leu Leu Gly Gly
        4130                4135                4140

Ala Asp Ser Glu Asp Asp Thr Ala Ala Leu Pro Asn Lys Leu Ala Thr
4145                4150                4155                4160

Lys Lys Ala Glu Leu Glu Lys Thr Gln Lys Glu Leu Asp Ala Ala Leu
                4165                4170                4175

Asn Glu Leu Gly Pro Asp Gly Asp Glu Glu Thr Pro Ala Pro Ala
        4180                4185                4190

Pro Gln Pro Glu Gln Pro Ala Pro Ala Pro Lys Pro Glu Gln Pro Thr
        4195                4200                4205

Pro Ala Pro Lys Pro Glu Gln Pro Thr Pro Ala Pro Lys Pro Glu Gln
        4210                4215                4220

Pro Ala Pro Ala Pro Lys Pro Glu Gln Pro Ala Pro Ala Pro Lys Pro
4225                4230                4235                4240

Glu Gln Pro Ala Pro Ala Pro Lys Pro Glu Gln Pro Thr Pro Gly Pro
                4245                4250                4255

Lys Ile Glu Glu Leu Leu Leu Glu Lys Ala Gly Leu Gly Lys Ala
        4260                4265                4270

Gly Ala Asp Leu Lys Glu Ala Val Asn Glu Pro Gly Glu Ser Ala Gly
        4275                4280                4285

Glu Pro Ser Gln Pro Glu Glu Pro Ala Glu Glu Ala Pro Ala Pro Glu
        4290                4295                4300

Gln Pro Thr Glu Pro Thr Gln Pro Glu Glu Pro Ala Gly Glu Thr Pro
4305                4310                4315                4320

Ala Pro Lys Pro Glu Lys Pro Ala Gly Gln Pro Lys Ala Glu Lys Thr
                4325                4330                4335

Asp Asp Gln Gln Ala Glu Glu Asp Tyr Ala Arg Arg Ser Glu Glu Glu
        4340                4345                4350

Tyr Asn Arg Leu Thr Gln Gln Pro Pro Lys Ala Glu Lys Pro Ala
        4355                4360                4365

Pro Ala Pro Gln Pro Glu Gln Pro Ala Pro Ala Pro Lys Leu Lys Glu
        4370                4375                4380

Ile Asp Glu Ser Asp Ser Glu Asp Tyr Val Lys Glu Gly Leu Arg Val
4385                4390                4395                4400

Pro Leu Gln Ser Glu Leu Asp Val Lys Gln Ala Lys Leu Leu Lys Leu
                4405                4410                4415

Glu Glu Leu Ser Asp Lys Ile Asp Glu Leu Asp Ala Glu Ile Ala Lys
        4420                4425                4430

Asn Leu Lys Lys Asp Val Glu Asp Phe Gln Asn Ser Gly Gly Gly Tyr
        4435                4440                4445

Ser Ala Leu Tyr Leu Glu Ala Ala Glu Lys Asp Leu Val Ala Lys Lys
        4450                4455                4460

Ala Glu Leu Glu Lys Thr Glu Ala Asp Leu Lys Lys Ala Val Asn Glu
4465                4470                4475                4480

Pro Glu Lys Pro Ala Glu Glu Pro Glu Asn Pro Ala Pro Ala Pro Lys
                4485                4490                4495

Pro Ala Pro Ala Pro Gln Pro Glu Lys Pro Ala Pro Ala Pro Ala Pro
        4500                4505                4510

Lys Pro Glu Lys Ser Ala Asp Gln Gln Ala Glu Glu Asp Tyr Ala Arg
        4515                4520                4525
```

-continued

```
Arg Ser Glu Glu Glu Tyr Asn Arg Leu Thr Gln Gln Gln Pro Pro Lys
    4530                4535                4540

Ala Glu Lys Pro Ala Pro Ala Pro Val Pro Lys Pro Glu Gln Pro Ala
4545                4550                4555                4560

Pro Ala Pro Lys Ser Arg Val Xaa Leu Asp Arg Gly Pro Ala Glu Ala
                4565                4570                4575

Ala Val Lys Glu Gln Val Asp Ser Pro Pro Gln Gln Leu Ala Asp Val
            4580                4585                4590

Lys Glu Ile Ser Thr Arg Gly Lys Phe Leu Gly Gly Ala Ala Thr Glu
        4595                4600                4605

Asp Glu Thr Ser Ala Leu Pro Asn Lys Ile Thr Ala Lys Gln Ala Glu
    4610                4615                4620

Leu Ala Lys Lys Gln Thr Glu Leu Glu Lys Leu Leu Asp Asn Leu Asp
4625                4630                4635                4640

Pro Glu Gly Lys Thr Gln Asp Glu Leu Asp Lys Glu Ala Ala Glu Ala
                4645                4650                4655

Glu Leu Asp Lys Lys Ala Asp Glu Leu Pro Asn Lys Val Ala Asp Leu
            4660                4665                4670

Glu Lys Glu Ile Ser Asn Leu Glu Ile Leu Leu Gly Gly Ala Asp Pro
        4675                4680                4685

Glu Asp Asp Thr Ala Ala Leu Pro Asn Lys Leu Ala Thr Lys Lys Ala
    4690                4695                4700

Glu Phe Glu Lys Thr Pro Lys Glu Leu Asp Ala Ala Leu Asn Glu Leu
4705                4710                4715                4720

Gly Pro Asp Gly Asp Glu Glu Thr Pro Ala Pro Ala Pro Ala Pro Ala
                4725                4730                4735

Lys Pro Glu Gln Pro Ala Pro Ala Pro Lys Pro Glu Gln Pro
            4740                4745                4750

Ala Pro Ala Pro Ala Pro Lys Pro Glu Gln Pro Ala Pro Ala Pro Ala
        4755                4760                4765

Pro Lys Pro Glu Gln Pro Thr Pro Ala Pro Lys Leu Lys Glu Ile Asp
    4770                4775                4780

Glu Ser Asp Ser Glu Asp Tyr Ile Lys Glu Gly Leu Arg Ala Pro Leu
4785                4790                4795                4800

Gln Ser Lys Leu Asp Ala Lys Lys Ala Lys Leu Ser Lys Leu Asp Glu
                4805                4810                4815

Leu Ser Asp Lys Ile Asp Glu Leu Asp Ala Glu Ile Ala Lys Leu Glu
            4820                4825                4830

Lys Asp Val Gly Asp Phe Pro Asn Ser Asp Gly Glu Gln Ala Gly Gln
        4835                4840                4845

Tyr Leu Val Ala Ala Glu Lys Asp Leu Asp Ala Lys Glu Ala Glu Leu
    4850                4855                4860

Gly Asn Thr Gly Ala Asp Leu Lys Lys Ala Val Asp Glu Pro Glu Thr
4865                4870                4875                4880

Pro Ala Pro Ala Pro Ala Pro Lys Pro Ala Pro Ala Pro Ala Pro Thr
                4885                4890                4895

Pro Glu Ala Pro Ala Pro Ala Pro Lys Pro Ala Pro Ala Pro Lys Pro
            4900                4905                4910

Ala Pro Ala Pro Lys Pro Ala Pro Ala Pro Lys Pro Ala Pro Ala Pro
        4915                4920                4925

Lys Pro Ala Pro Ala Pro Lys Pro Ala Pro Ala Pro Lys Pro Glu Arg
    4930                4935                4940

Thr Glu Asn Asp Gly Val Gln Arg Thr Arg Lys Arg Ala Pro Lys Arg
```

-continued

```
4945                4950                4955                4960

Ile Met Ser Leu Ser Gln Lys Val Xaa Leu Lys Xaa Val Cys Arg Ala
                4965                4970                4975

Pro Leu Gln Ser Lys Leu Asp Ala Gln Lys Ala Glu Leu Leu Lys Leu
                4980                4985                4990

Glu Glu Leu Ser Gly Lys Ile Glu Glu Leu Asp Ala Glu Ile Ala Glu
            4995                5000                5005

Leu Glu Val Gln Leu Lys Asp Ala Glu Gly Asn Asn Asn Val Glu Ala
        5010                5015                5020

Tyr Phe Lys Glu Gly Leu Glu Lys Thr Thr Ala Glu Lys Lys Ala Glu
5025                5030                5035                5040

Leu Glu Xaa Ala Xaa Ala Asp Leu Lys Lys Ala Val Asp Glu Pro Glu
                5045                5050                5055

Thr Pro Ala Pro Ala Pro Ala Pro Ala Pro Ala Pro Ala Pro Ala Pro
                5060                5065                5070

Ala Pro Ala Pro Ala Pro Ala Pro Ala Pro Lys Pro Ala Pro Ala Pro
                5075                5080                5085

Lys Pro Ala Pro Ala Pro Ala Pro Ala Pro Ala Pro Lys Pro Ala Pro
                5090                5095                5100

Ala Pro Lys Pro Ala Pro Ala Pro Ala Pro Ala Pro Lys Pro Glu Lys
5105                5110                5115                5120

Pro Ala Glu Lys Pro Ala Pro Ala Pro Lys Pro Glu Thr Xaa Lys Thr
                5125                5130                5135

Tyr Gly Leu Lys Glu Ile Asp Glu Ser Asp Ser Glu Asp Tyr Val Arg
                5140                5145                5150

Glu Gly Phe Arg Ala Pro Leu Gln Ser Glu Leu Asp Ala Lys Gln Ala
            5155                5160                5165

Lys Leu Ser Lys Leu Glu Glu Leu Ser Asp Lys Ile Asp Glu Leu Asp
        5170                5175                5180

Ala Glu Ile Ala Lys Leu Glu Lys Asp Val Glu Asp Phe Gln Asn Ser
5185                5190                5195                5200

Asp Gly Glu Gln Ala Gly Gln Tyr Leu Ala Ala Ala Gly Glu Asp Leu
                5205                5210                5215

Ile Ala Lys Lys Ala Glu Leu Glu Lys Ala Glu Ala Asp Leu Lys Lys
            5220                5225                5230

Ala Val Asp Glu Pro Glu Thr Pro Ala Pro Ala Pro Ala Pro Ala Pro
        5235                5240                5245

Ala Pro Ala Pro Thr Pro Glu Ala Pro Ala Pro Ala Pro Ala Pro Ala
5250                5255                5260

Pro Lys Pro Ala Pro Ala Pro Lys Pro Ala Pro Ala Pro Lys Pro Ala
5265                5270                5275                5280

Pro Ala Pro Lys Pro Ala Pro Ala Pro Lys Pro Ala Pro Ala Pro Lys
                5285                5290                5295

Pro Ala Pro Ala Pro Ala Pro Ala Pro Lys Pro Glu Lys Pro Ala Glu
                5300                5305                5310

Lys Pro Ala Pro Ala Pro Lys Pro Glu Leu Lys Glu Ile Asp Glu Ser
            5315                5320                5325

Asp Ser Glu Asp Tyr Val Lys Glu Gly Phe Arg Ala Pro Leu Gln Ser
        5330                5335                5340

Glu Leu Asp Ala Lys Gln Ala Lys Leu Ser Lys Leu Glu Glu Leu Ser
5345                5350                5355                5360

Asp Lys Ile Asp Glu Leu Asp Ala Glu Ile Ala Lys Leu Glu Asp Gln
                5365                5370                5375
```

-continued

Leu Lys Ala Ala Glu Glu Asn Asn Asn Val Glu Asp Tyr Phe Lys Glu
                5380                5385                5390

Gly Leu Glu Lys Thr Ile Ala Ala Lys Lys Ala Glu Leu Glu Lys Thr
            5395                5400                5405

Glu Ala Asp Leu Lys Lys Ala Val Asn Glu Pro Glu Lys Pro Ala Glu
            5410                5415                5420

Glu Pro Ser Gln Pro Glu Lys Pro Ala Glu Ala Pro Ala Pro Glu
5425            5430                5435                5440

Gln Pro Thr Glu Pro Thr Gln Pro Glu Lys Pro Ala Glu Gln Pro Gln
            5445                5450                5455

Pro Ala Pro Ala Pro Gln Pro Glu Lys Pro Ala Glu Glu Thr Pro Ala
            5460                5465                5470

Pro Lys Pro Glu Lys Pro Ala Glu Gln Pro Lys Ala Glu Lys Pro Ala
            5475                5480                5485

Asp Gln Gln Ala Glu Glu Asp Tyr Ala Arg Arg Ser Glu Glu Glu Tyr
            5490                5495                5500

Asn Arg Leu Thr Gln Gln Gln Pro Pro Lys Ala Glu Lys Pro Ala Pro
5505                5510                5515                5520

Ala Pro Lys Thr Lys Gly Gly Ser Ala Leu Asp Gln Glu Ala Ala Ala
            5525                5530                5535

Pro Pro His Gln Val Ala Asp Leu Glu Lys Gln Ile Thr Gly Pro Glu
            5540                5545                5550

Ile Phe Leu Gly Gly Ala Asp Pro Glu Ala Asp Ile Ala Ala Arg Pro
            5555                5560                5565

Asn Glu Leu Ala Ala Lys Gln Ala Glu Leu Ala Gln Lys Pro Thr Gly
            5570                5575                5580

Leu Glu Lys Leu Leu Asp Ser Leu Asp Pro Gly Gly Lys Thr Gln Asp
5585                5590                5595                5600

Glu Leu Asp Lys Glu Ala Gly Glu Ala Glu Leu Asp Lys Lys Ala Asp
            5605                5610                5615

Glu Leu Pro Asn Lys Val Ala Asp Leu Glu Lys Glu Ile Ser Asn Leu
            5620                5625                5630

Glu Ile Leu Leu Gly Gly Ala Asp Ser Glu Asp Asp Thr Ala Ala Leu
            5635                5640                5645

Pro Asn Lys Leu Ala Xaa Lys Xaa Ala Glu Leu Glu Lys Thr Gln Lys
            5650                5655                5660

Glu Leu Asp Ala Ala Pro Asn Glu Leu Gly Pro Asp Gly Asp Glu Glu
5665                5670                5675                5680

Glu Thr Pro Ala Pro Ala Pro Gln Pro Glu Gln Pro Ala Pro Ala Pro
            5685                5690                5695

Lys Pro Glu Gln Pro Ala Pro Ala Pro Lys Pro Glu Gln Pro Ala Pro
            5700                5705                5710

Ala Pro Lys Pro Glu Gln Pro Ala Pro Ala Lys Pro Glu Gln Pro
            5715                5720                5725

Ala Pro Ala Pro Lys Pro Glu Gln Pro Ala Lys Pro Glu Lys Pro Ala
            5730                5735                5740

Glu Glu Pro Thr Gln Pro Glu Lys Pro Ala Thr Pro Lys Thr Arg Val
5745                5750                5755                5760

Arg Ala Leu Lys Val Ala Glu Phe Gly Val Gln Leu Arg Asp Ala Gly
            5765                5770                5775

Gly Ser Asn Asn Val Gly Ala Tyr Phe Lys Glu Gly Leu Glu Glu Thr
            5780                5785                5790

-continued

Thr Ala Glu Xaa Glu Ala Gly Leu Gly Lys Ala Glu Ala Asp Leu Lys
                5795                5800                5805

Lys Ala Val Asp Glu Pro Glu Thr Pro Ala Pro Ala Pro Ala Pro Ala
5810                5815                5820

Pro Ala Pro Ala Pro Ala Pro Ala Pro Lys Pro Ala Pro Ala Pro Lys
5825                5830                5835                5840

Pro Ala Pro Ala Pro Ala Pro Ala Pro Lys Pro Ala Pro Ala
                5845                5850                5855

Pro Lys Pro Ala Pro Ala Pro Ala Pro Lys Pro Glu Lys Pro
                5860                5865                5870

Ala Glu Lys Pro Ala Pro Ala Pro Lys Pro Glu Thr Pro Lys Thr Leu
                5875                5880                5885

Lys Asp Ile Asp Glu Ser Asp Ser Glu Asp Tyr Ala Lys Glu Gly Leu
                5890                5895                5900

Arg Ala Pro Leu Gln Ser Glu Leu Asp Thr Lys Lys Ala Lys Leu Leu
5905                5910                5915                5920

Lys Leu Glu Glu Leu Ser Gly Lys Ile Glu Glu Leu Asp Ala Glu Ile
                5925                5930                5935

Xaa Glu Leu Glu Val Gln Leu Lys Asp Ala Glu Gly Asn Asn Asn Val
                5940                5945                5950

Glu Ala Tyr Phe Lys Gly Leu Glu Lys Thr Thr Ala Glu Lys Lys
                5955                5960                5965

Ala Glu Leu Glu Lys Ala Glu Ala Asp Leu Lys Lys Ala Val Asp Glu
                5970                5975                5980

Pro Glu Thr Pro Ala Pro Ala Pro Ala Pro Ala Pro Ala Pro Ala Pro
5985                5990                5995                6000

Thr Pro Glu Ala Pro Ala Pro Ala Pro Lys Pro Ala Pro Ala
                6005                6010                6015

Pro Lys Pro Ala Pro Ala Pro Lys Pro Ala Pro Ala Pro Lys Pro Ala
                6020                6025                6030

Pro Ala Pro Lys Pro Ala Pro Ala Pro Lys Pro Ala Pro Ala Pro Ala
                6035                6040                6045

Pro Ala Pro Ala Pro Lys Pro Ala Pro Ala Pro Ala Pro Ala
                6050                6055                6060

Pro Lys Pro Glu Lys Pro Ala Glu Lys Pro Ala Pro Ala Pro Lys Pro
6065                6070                6075                6080

Glu Thr Pro Lys Thr Gly Trp Lys Gln Glu Asn Gly Met Leu Lys Glu
                6085                6090                6095

Ile Asp Glu Ser Asp Ser Glu Asp Tyr Val Lys Glu Gly Phe Arg Ala
                6100                6105                6110

Pro Leu Gln Ser Glu Leu Asp Ala Lys Gln Ala Lys Leu Ser Lys Leu
                6115                6120                6125

Glu Glu Xaa Ser Asp Lys Xaa Asp Glu Leu Asp Ala Glu Ile Ala Lys
                6130                6135                6140

Leu Glu Lys Asp Val Glu Asp Phe Lys Asn Ser Asp Gly Glu Gln Ala
6145                6150                6155                6160

Gly Gln Tyr Leu Ala Ala Ala Glu Glu Asp Leu Ile Ala Lys Lys Ala
                6165                6170                6175

Xaa Leu Glu Lys Ala Glu Ala Asp Leu Lys Lys Ala Val Asp Glu Pro
                6180                6185                6190

Glu Thr Pro Ala Pro Ala Pro Ala Pro Ala Pro Ala Pro Ala Pro Thr
                6195                6200                6205

Pro Glu Ala Pro Ala Pro Ala Pro Ala Pro Ala Pro Lys Pro Ala Pro

```
         6210                6215                6220
Ala Pro Lys Pro Ala Pro Ala Pro Lys Pro Ala Pro Ala Pro Lys Pro
6225                6230                6235                6240

Ala Pro Ala Pro Lys Pro Ala Pro Ala Pro Ala Pro Lys Pro
                    6245                6250                6255

Glu Lys Pro Ala Ala Leu Lys Glu Ile Asp Glu Ser Asp Val Glu Val
            6260                6265                6270

Lys Lys Ala Glu Leu Glu Leu Val Lys Glu Glu Ala Lys Glu Pro Arg
        6275                6280                6285

Asn Glu Glu Lys Val Lys Gln Ala Lys Ala Glu Val Glu Ser Lys Lys
    6290                6295                6300

Ala Glu Ala Thr Arg Leu Glu Lys Ile Lys Thr Asp Arg Lys Lys Ala
6305                6310                6315                6320

Glu Glu Ala Lys Arg Lys Ala Ala Glu Glu Asp Lys Val Lys Glu Lys
            6325                6330                6335

Pro Ala Pro Lys Pro Glu Asn Pro Ala Glu Gln Pro Lys Ala Glu Lys
        6340                6345                6350

Pro Ala Asp Gln Gln Ala Glu Glu Asp Tyr Ala Arg Arg Ser Glu Glu
    6355                6360                6365

Glu Tyr Xaa Arg Leu Thr Gln Gln Gln Pro Pro Lys Thr Glu Lys Pro
6370                6375                6380

Ala Gln Pro Ser Thr Pro Lys Thr Lys Gly Glu Ala Arg Glu Ser Arg
6385                6390                6395                6400

Xaa Glu Glu Lys Val Asn Gln Pro Lys Xaa Glu Val Glu Ser Lys Lys
            6405                6410                6415

Xaa Glu Ala Thr Arg Leu Glu Lys Ile Lys Thr Asp Arg Lys Lys Ala
            6420                6425                6430

Glu Glu Ala Xaa Arg Lys Ala Ala Glu Glu Asp Lys Val Lys Glu Lys
            6435                6440                6445

Pro Ala Glu Gln Pro Gln Pro Ala Pro Ala Pro Gln Pro Glu Lys Pro
    6450                6455                6460

Ala Pro Ala Pro Lys Pro Glu Asn Pro Ala Glu Gln Pro Lys Ala Glu
6465                6470                6475                6480

Lys Pro Ala Asp Gln Gln Ala Glu Glu Asp Tyr Ala Arg Arg Ser Glu
            6485                6490                6495

Glu Glu Tyr Asn Arg Leu Thr Gln Gln Gln Pro Pro Lys Thr Glu Lys
        6500                6505                6510

Pro Ala Gln Pro Ser Thr Xaa Lys Ile Lys Glu Xaa Asp Glu Ser Xaa
    6515                6520                6525

Ser Glu Asp Tyr Leu Lys Glu Gly Leu Arg Ala Pro Leu Gln Ser Lys
    6530                6535                6540

Leu Asp Thr Lys Lys Ala Lys Leu Ser Lys Leu Glu Glu Leu Ser Asp
6545                6550                6555                6560

Lys Ile Asp Glu Leu Asp Ala Glu Ile Ala Lys Leu Glu Val Gln Leu
            6565                6570                6575

Lys Asp Ala Glu Gly Asn Asn Asn Val Glu Ala Tyr Phe Lys Glu Gly
        6580                6585                6590

Leu Glu Lys Thr Thr Ala Glu Lys Lys Ala Glu Leu Glu Lys Ala Glu
            6595                6600                6605

Ala Asp Leu Lys Lys Ala Val Asp Glu Pro Glu Thr Pro Ala Pro Ala
    6610                6615                6620

Pro Gln Pro Ala Pro Ala Pro Glu Lys Pro Ala Glu Lys Pro Ala Pro
6625                6630                6635                6640
```

-continued

```
Ala Pro Ala Pro Glu Lys Pro Ala Pro Ala Pro Glu Lys Pro Ala Pro
            6645                6650                6655
Thr Pro Glu Lys Pro Ala Pro Thr Pro Glu Thr Pro Lys Thr Gly Trp
            6660                6665                6670
Lys Gln Glu Asn Gly Met Trp Tyr Phe Tyr Asn Thr Asp Gly Ser Met
            6675                6680                6685
Ala Thr Gly Trp Leu Gln Asn Asn Gly Ser Trp Tyr Tyr Leu Asn Ser
        6690                6695                6700
Asn Gly Ala Met Ala Thr Gly Trp His Gln Asn Asn Gly Ser Trp Tyr
6705                6710                6715                6720
Tyr Leu Asn Ser Leu Lys Glu Ile Asp Glu Ser Asp Ser Glu Asp Tyr
            6725                6730                6735
Leu Lys Glu Gly Leu Arg Ala Pro Leu Gln Ser Lys Leu Asp Thr Lys
            6740                6745                6750
Lys Ala Lys Leu Ser Lys Leu Glu Glu Leu Ser Asp Lys Ile Asp Glu
            6755                6760                6765
Leu Asp Ala Glu Ile Ala Lys Leu Glu Val Gln Leu Lys Asp Ala Glu
            6770                6775                6780
Gly Asn Asn Val Glu Ala Tyr Phe Lys Glu Gly Leu Glu Lys Thr
6785                6790                6795                6800
Thr Ala Glu Lys Lys Ala Glu Leu Glu Lys Ala Glu Ala Asp Leu Lys
            6805                6810                6815
Lys Ala Val Asp Glu Pro Asp Thr Pro Ala Pro Ala Pro Gln Pro Ala
            6820                6825                6830
Pro Ala Pro Glu Lys Pro Ala Glu Lys Pro Ala Pro Ala Pro Ala Pro
            6835                6840                6845
Glu Lys Pro Ala Pro Ala Pro Glu Lys Pro Ala Pro Ala Pro Glu Lys
            6850                6855                6860
Pro Ala Pro Ala Pro Glu Lys Pro Ala Pro Ala Pro Glu Lys Pro Ala
6865                6870                6875                6880
Pro Ala Pro Glu Lys Pro Ala Pro Ala Pro Glu Lys Pro Ala Pro Ala
            6885                6890                6895
Pro Lys Pro Glu Thr Pro Glu Thr Arg Leu Glu Thr Arg Lys Arg Tyr
            6900                6905                6910
Leu Lys Glu Ile Asp Glu Ser Asp Ser Glu Asp Tyr Leu Lys Glu Gly
            6915                6920                6925
Leu Arg Ala Pro Leu Gln Ser Lys Leu Asp Thr Lys Lys Ala Lys Leu
            6930                6935                6940
Ser Lys Leu Glu Glu Leu Ser Asp Lys Ile Asp Glu Leu Asp Ala Glu
6945                6950                6955                6960
Ile Ala Lys Leu Glu Val Gln Leu Lys Asp Ala Glu Gly Asn Asn Asn
            6965                6970                6975
Val Glu Ala Tyr Phe Lys Glu Gly Leu Glu Lys Thr Thr Ala Glu Lys
            6980                6985                6990
Lys Ala Glu Leu Glu Lys Ala Glu Ala Asp Leu Lys Lys Ala Val Asp
            6995                7000                7005
Glu Pro Glu Thr Pro Ala Pro Ala Pro Gln Pro Ala Pro Ala Pro Glu
            7010                7015                7020
Lys Pro Ala Glu Lys Pro Ala Pro Ala Pro Glu Lys Pro Ala Pro Ala
7025                7030                7035                7040
Pro Glu Lys Pro Ala Pro Ala Pro Glu Lys Pro Ala Pro Ala Pro Glu
            7045                7050                7055
```

-continued

```
Lys Pro Ala Pro Ala Pro Glu Lys Pro Ala Pro Thr Pro Glu Thr Pro
            7060                7065                7070

Lys Thr Gly Trp Lys Gln Glu Asn Gly Met Leu Lys Glu Ile Asp Glu
            7075                7080                7085

Ser Glu Ser Glu Asp Tyr Ala Lys Glu Gly Phe Arg Ala Pro Leu Gln
            7090                7095                7100

Ser Lys Leu Asp Ala Lys Lys Ala Lys Leu Ser Lys Leu Glu Glu Leu
7105                7110                7115                7120

Ser Asp Lys Ile Asp Glu Leu Asp Ala Glu Ile Ala Lys Leu Glu Asp
            7125                7130                7135

Gln Leu Lys Ala Ala Glu Glu Asn Asn Asn Val Glu Asp Tyr Phe Lys
            7140                7145                7150

Glu Gly Leu Glu Lys Thr Ile Ala Ala Lys Lys Ala Glu Leu Glu Lys
            7155                7160                7165

Thr Glu Ala Asp Leu Lys Lys Ala Val Asn Glu Pro Glu Lys Pro Ala
            7170                7175                7180

Pro Ala Pro Glu Thr Pro Ala Pro Glu Ala Pro Ala Glu Gln Pro Lys
7185                7190                7195                7200

Pro Ala Pro Ala Pro Gln Pro Ala Pro Ala Pro Lys Pro Glu Lys Pro
            7205                7210                7215

Ala Glu Gln Pro Lys Pro Glu Lys Thr Asp Asp Gln Gln Ala Glu Glu
            7220                7225                7230

Asp Tyr Ala Arg Arg Ser Glu Glu Tyr Asn Arg Leu Thr Gln Gln
            7235                7240                7245

Gln Pro Pro Lys Ala Glu Lys Pro Ala Pro Ala Pro Lys Thr Gly Trp
            7250                7255                7260

Lys Gln Glu Asn Gly Met Trp Tyr Phe Tyr Asn Thr Asp Gly Ser Met
7265                7270                7275                7280

Gly Glu Gln Ala Gly Gln Tyr Arg Ala Ala Ala Glu Gly Asp Leu Ala
            7285                7290                7295

Ala Lys Gln Ala Glu Leu Glu Lys Thr Glu Ala Asp Leu Lys Lys Ala
            7300                7305                7310

Val Asn Glu Pro Glu Lys Pro Ala Pro Ala Pro Glu Thr Pro Ala Pro
            7315                7320                7325

Glu Ala Pro Ala Glu Gln Pro Lys Pro Ala Pro Ala Pro Gln Pro Ala
            7330                7335                7340

Pro Ala Pro Lys Pro Glu Lys Pro Ala Glu Gln Pro Lys Ala Glu Lys
7345                7350                7355                7360

Thr Asp Asp Gln Gln Ala Glu Glu Asp Tyr Ala Arg Arg Ser Glu Glu
            7365                7370                7375

Glu Tyr Asn Arg Leu Thr Gln Gln Pro Pro Lys Ala Glu Lys Pro
            7380                7385                7390

Ala Pro Ala Pro Lys Pro Glu Gln Pro Ala Pro Ala Pro Lys Asn Ser
            7395                7400                7405

Lys Gly Glu Gln Ala Glu Gln Tyr Arg Ser Ala Ala Gly Gly Asp Leu
            7410                7415                7420

Ala Ala Lys Gln Val Glu Leu Glu Lys Thr Glu Ala Asp Leu Lys Lys
7425                7430                7435                7440

Ala Val Asn Glu Pro Glu Lys Pro Ala Pro Ala Pro Glu Thr Pro Ala
            7445                7450                7455

Pro Glu Ala Pro Ala Glu Gln Pro Lys Pro Ala Pro Ala Pro Gln Pro
            7460                7465                7470

Ala Pro Ala Pro Lys Pro Glu Lys Pro Ala Glu Gln Pro Lys Ala Glu
```

-continued

```
            7475                7480                7485

Lys Pro Ala Asp Gln Gln Ala Glu Glu Asp Tyr Asp Arg Arg Ser Glu
            7490                7495                7500

Glu Glu Tyr Asn Arg Leu Thr Gln Gln Pro Pro Lys Ala Glu Lys
7505                7510                7515                7520

Pro Ala Pro Ala Pro Gln Pro Glu Gln Pro Ala Pro Ala Pro Lys Ser
                7525                7530                7535

Leu Lys Glu Ile Asp Glu Ser Asp Ser Glu Asp Tyr Val Lys Glu Gly
            7540                7545                7550

Phe Arg Ala Pro Leu Gln Ser Glu Leu Asp Ala Lys Gln Ala Lys Leu
            7555                7560                7565

Ser Lys Leu Glu Glu Leu Ser Asp Lys Ile Asp Glu Leu Asp Ala Glu
        7570                7575                7580

Ile Ala Lys Leu Glu Lys Asp Val Glu Asp Phe Lys Xaa Ser Asp Gly
7585                7590                7595                7600

Glu Gln Ala Gly Gln Tyr Leu Ala Ala Ala Glu Glu Asp Leu Ile Ala
                7605                7610                7615

Lys Lys Ala Glu Leu Glu Gln Thr Glu Ala Asp Leu Lys Lys Ala Val
            7620                7625                7630

Asn Glu Pro Gly Lys Pro Ala Pro Ala Pro Glu Thr Pro Ala
            7635                7640                7645

Pro Glu Ala Pro Ala Glu Gln Pro Lys Pro Ala Pro Glu Thr Pro Ala
7650                7655                7660

Pro Ala Pro Lys Pro Glu Lys Pro Ala Glu Gln Pro Lys Pro Glu Lys
7665                7670                7675                7680

Pro Ala Asp Gln Gln Ala Glu Glu Asp Tyr Ala Arg Arg Ser Glu Glu
            7685                7690                7695

Glu Tyr Asn Arg Leu Thr Gln Gln Pro Ala Pro Ala Gln Lys Pro
            7700                7705                7710

Glu Gln Pro Ala Lys Pro Glu Lys Pro Ala Glu Glu Pro Thr Gln Pro
        7715                7720                7725

Glu Lys Asp Ala Glu Ile Ala Lys Leu Glu Lys Asn Val Glu Tyr Phe
    7730                7735                7740

Lys Lys Thr Asp Ala Glu Gln Thr Glu Gln Tyr Leu Ala Ala Ala Glu
7745                7750                7755                7760

Lys Asp Leu Ala Asp Lys Lys Ala Glu Leu Glu Lys Thr Glu Ala Asp
                7765                7770                7775

Leu Lys Lys Ala Val Asn Glu Pro Glu Lys Pro Ala Glu Thr Pro
            7780                7785                7790

Ala Pro Ala Pro Lys Pro Glu Gln Pro Ala Glu Gln Pro Lys Pro Ala
            7795                7800                7805

Pro Ala Pro Gln Pro Ala Pro Ala Pro Lys Pro Glu Lys Thr Asp Asp
        7810                7815                7820

Gln Gln Ala Glu Glu Asp Tyr Ala Arg Arg Ser Glu Glu Tyr Asn
7825                7830                7835                7840

Arg Leu Pro Gln Gln Gln Pro Pro Lys Ala Glu Lys Pro Ala Pro Ala
                7845                7850                7855

Pro Lys Pro Glu Gln Pro Val Pro Ala Glu Xaa Pro Glu Asn Pro Ala
            7860                7865                7870

Pro Ala Pro Lys Pro Ala Xaa Ala Pro Gln Pro Leu Lys Pro Glu Glu
            7875                7880                7885

Pro Ala Glu Gln Pro Lys Pro Glu Lys Pro Glu Glu Pro Ala Gly Gln
        7890                7895                7900
```

```
Pro Glu Pro Glu Lys Pro Asp Asp Gln Gln Ala Gly Glu Asp Tyr Ala
7905                7910                7915                7920

Arg Arg Ser Gly Gly Glu Tyr Asn Arg Phe Pro Gln Gln Gln Pro Pro
            7925                7930                7935

Lys Ala Glu Lys Pro Ala Pro Ala Pro Lys Pro Glu Gln Pro Val Pro
        7940                7945                7950

Ala Pro Lys Thr Leu Leu Lys Lys Ala Lys Leu Ala Gly Ala Lys Ser
        7955                7960                7965

Lys Ala Ala Thr Lys Lys Ala Glu Leu Glu Pro Glu Leu Glu Lys Ala
        7970                7975                7980

Glu Ala Glu Leu Glu Asn Leu Leu Ser Thr Leu Asp Pro Glu Gly Lys
7985                7990                7995                8000

Thr Gln Asp Glu Leu Asp Lys Glu Ala Ala Glu Ala Glu Leu Asn Lys
                8005                8010                8015

Lys Val Glu Ala Leu Pro Asn Gln Val Ser Glu Leu Glu Glu Glu Leu
            8020                8025                8030

Ser Lys Leu Glu Asp Asn Leu Lys Asp Ala Glu Thr Asn Asn Val Glu
            8035                8040                8045

Asp Tyr Ile Lys Glu Gly Leu Glu Glu Ala Ile Ala Thr Lys Gln Ala
        8050                8055                8060

Glu Leu Glu Lys Thr Pro Lys Glu Leu Asp Ala Ala Leu Asn Glu Leu
8065                8070                8075                8080

Gly Pro Asp Gly Asp Glu Glu Thr Pro Pro Glu Ala Pro Ala
            8085                8090                8095

Glu Gln Pro Lys Pro Glu Lys Pro Ala Glu Glu Thr Pro Ala Pro Ala
        8100                8105                8110

Pro Lys Pro Glu Lys Ser Ala Asp Gln Gln Ala Glu Glu Asp Tyr Ala
        8115                8120                8125

Arg Arg Ser Glu Glu Glu Tyr Asn Arg Leu Thr Gln Gln Pro Pro
        8130                8135                8140

Lys Ala Glu Lys Pro Ala Pro Ala Pro Ala Pro Lys Pro Glu Gln Pro
8145                8150                8155                8160

Ala Pro Ala Pro Lys Ser Arg Gly Leu Ala Thr Lys Lys Leu Asn
        8165                8170                8175

Leu Ala Glu Ala Arg Ile Glu Leu Leu Leu Lys Lys Leu Gly Leu Glu
        8180                8185                8190

Pro Gly Leu Glu Lys Ala Gly Ala Gly Leu Gly Asn Leu Leu Ser Thr
        8195                8200                8205

Leu Asp Pro Glu Gly Lys Thr Gln Asp Glu Leu Asp Lys Glu Ala Ala
        8210                8215                8220

Glu Ala Glu Leu Asn Lys Lys Val Glu Ala Leu Pro Asn Gln Val Ala
8225                8230                8235                8240

Glu Leu Glu Glu Glu Leu Ser Lys Leu Glu Asp Asn Leu Lys Asp Ala
                8245                8250                8255

Glu Thr Asn His Val Glu Asp Tyr Ile Lys Glu Gly Leu Glu Glu Ala
                8260                8265                8270

Ile Ala Thr Lys Gln Ala Glu Leu Glu Lys Thr Pro Lys Glu Leu Asp
        8275                8280                8285

Ala Ala Leu Asn Glu Leu Gly Pro Asp Gly Asp Glu Glu Thr Pro
        8290                8295                8300

Ala Pro Glu Ala Pro Ala Glu Gln Pro Lys Pro Glu Lys Pro Ala Glu
8305                8310                8315                8320
```

```
Glu Thr Pro Ala Pro Ala Pro Lys Pro Glu Lys Ser Ala Asp Gln Gln
            8325                8330                8335

Ala Glu Glu Asp Tyr Ala Arg Arg Ser Glu Glu Tyr Asn Arg Leu
        8340                8345                8350

Thr Gln Gln Gln Pro Pro Lys Ala Glu Lys Pro Ala Pro Ala Pro Ala
            8355                8360                8365

Pro Lys Pro Glu Gln Pro Ala Pro Lys Lys Gln Lys Val
        8370                8375                8380

Asn Leu Glu Asn Leu Leu Ser Thr Leu Asp Pro Gly Gly Lys Thr Gln
8385                8390                8395                8400

Asp Glu Leu Asp Lys Gly Ala Ala Glu Ala Glu Leu Asn Lys Lys Val
            8405                8410                8415

Glu Ala Leu Pro Asn Pro Val Xaa Glu Leu Glu Glu Glu Leu Ser Pro
            8420                8425                8430

Pro Glu Asp Asn Leu Lys Asp Ala Glu Thr Asn His Val Glu Asp Tyr
            8435                8440                8445

Ile Lys Glu Gly Leu Glu Glu Ala Ile Ala Thr Lys Gln Ala Glu Leu
            8450                8455                8460

Glu Glu Thr Pro Gln Glu Val Asp Ala Ala Leu Asn Asp Leu Val Pro
8465                8470                8475                8480

Asp Gly Gly Glu Glu Thr Pro Ala Pro Ala Pro Gln Pro Asp Glu
            8485                8490                8495

Pro Ala Pro Ala Pro Ala Pro Asn Ala Glu Gln Pro Ala Pro Ala Pro
            8500                8505                8510

Lys Pro Glu Lys Ser Ala Asp Gln Gln Ala Glu Glu Asp Tyr Ala Arg
            8515                8520                8525

Arg Ser Glu Gly Glu Tyr Asn Arg Leu Thr Gln Gln Pro Pro Lys
        8530                8535                8540

Ala Glu Lys Pro Ala Pro Ala Pro Ala Pro Lys Pro Glu Gln Pro Ala
8545                8550                8555                8560

Pro Ala Pro Asn Lys Glu Ile Ala Arg Leu Gln Ser Asp Leu Lys Asp
            8565                8570                8575

Ala Glu Glu Asn Asn Val Glu Asp Tyr Ile Lys Glu Gly Leu Glu Gln
            8580                8585                8590

Ala Ile Thr Asn Lys Lys Ala Glu Leu Ala Thr Thr Gln Gln Asn Ile
            8595                8600                8605

Asp Lys Thr Gln Lys Asp Leu Glu Asp Ala Glu Leu Glu Leu Glu Lys
            8610                8615                8620

Val Leu Ala Thr Leu Asp Pro Glu Gly Lys Thr Gln Asp Glu Leu Asp
8625                8630                8635                8640

Lys Glu Ala Ala Glu Ala Glu Leu Asn Glu Lys Val Glu Ala Leu Gln
            8645                8650                8655

Asn Gln Val Ala Glu Leu Glu Glu Glu Leu Ser Lys Leu Glu Asp Asn
            8660                8665                8670

Leu Lys Asp Ala Glu Thr Asn Asn Val Glu Asp Tyr Ile Lys Glu Gly
            8675                8680                8685

Leu Glu Glu Ala Ile Ala Thr Lys Lys Ala Glu Leu Glu Lys Thr Gln
            8690                8695                8700

Lys Glu Leu Asp Ala Ala Leu Asn Glu Leu Gly Pro Asp Gly Asp Glu
8705                8710                8715                8720

Glu Glu Thr Pro Ala Pro Ala Pro Gln Pro Glu Lys Pro Ala Glu Glu
            8725                8730                8735

Pro Glu Asn Pro Ala Pro Ala Pro Lys Pro Glu Lys Ser Ala Asp Gln
```

Gln Ala Glu Glu Asp Tyr Ala Arg Arg Ser Glu Glu Tyr Asn Arg
        8755                8760                8765
Leu Thr Gln Gln Gln Pro Pro Lys Ala Glu Lys Pro Ala Pro Ala Pro
    8770                8775                8780
Gln Pro Glu Gln Pro Ala Pro Ala Pro Lys Ile Glu Leu Lys Glu Ile
8785                8790                8795                8800
Asp Glu Ser Glu Ser Glu Asp Tyr Ala Lys Glu Gly Phe Arg Ala Pro
                8805                8810                8815
Leu His Ser Lys Leu Asp Ala Lys Lys Ala Lys Leu Ser Lys Leu Glu
            8820                8825                8830
Glu Leu Ser Asp Lys Ile Asp Glu Leu Asp Ala Glu Ile Ala Lys Leu
        8835                8840                8845
Glu Asp Gln Leu Lys Ala Val Glu Glu Asn Asn Asn Val Glu Asp Tyr
    8850                8855                8860
Ser Thr Glu Gly Leu Glu Lys Thr Ile Ala Ala Lys Lys Thr Glu Leu
8865                8870                8875                8880
Glu Lys Thr Glu Ala Asp Leu Lys Lys Ala Val Asn Glu Pro Glu Lys
                8885                8890                8895
Ser Ala Glu Glu Pro Ser Gln Pro Glu Lys Pro Ala Glu Glu Ala Pro
            8900                8905                8910
Ala Pro Glu Gln Pro Thr Glu Pro Thr Gln Pro Glu Lys Pro Ala Glu
        8915                8920                8925
Glu Thr Pro Ala Pro Lys Pro Glu Lys Pro Ala Glu Gln Pro Asn Ala
    8930                8935                8940
Glu Lys Thr Asp Asp Gln Gln Ala Glu Glu Asp Tyr Ala Arg Arg Ser
8945                8950                8955                8960
Glu Glu Glu Tyr Asn Arg Leu Thr Gln Gln Gln Pro Pro Lys Ala Glu
                8965                8970                8975
Lys Pro Ala Pro Ala Pro Gln Pro Glu Gln Thr Ser Ser Leu His
            8980                8985                8990

(2) INFORMATION FOR SEQ ID NO:33:

(i) SEQUENCE CHARACTERISTICS:
        (A) LENGTH: 1453 base pairs
        (B) TYPE: nucleic acid
        (C) STRANDEDNESS: single
        (D) TOPOLOGY: linear (ii) MOLECULE TYPE: amino acid (xi) SEQUENCE DESCRIPTION: SEQ ID NO:33:

```
TTGACAAATA TTTACGGAGG AGGCTTATGC TTAATATAAG TATAGGCTAA AAATGATTAT    60

CAGAAAAGAG GTAAATTTAG ATGAATAAGA AAAAAATGAT TTTAACAAGC CTAGCCAGCG   120

TCGCTATCTT AGGGGCTGGT TTTGTTGCGT CTTCGCCTAC TTTTGTAAGA GCAGAAGAAG   180

CTCCTGTAGC TAACCAGTCT AAAGCTGAGA AGACTATGA TGCAGCAGTG AAAAAATCTG    240

AAGCTGCTAA GAAAGATTAC GAAACGGCTA AAAAGAAAGC AGAAGACGCT CAGAAGAAAT   300

ATGATGAGGA TCAGAAGAAA ACTGAGGCAA AGCGGAAAA AGAAAGAAAA GCTTCTGAAA    360

AGATAGCTGA GGCAACAAAA GAAGTTCAAC AAGCGTACCT AGCTTATCTA CAAGCTAGCA   420

ACGAAAGTCA GAGAAAAGAG GCAGATAAGA AGATAAAAGA AGCTACGCAC GCAAAGATGA   480

GGCGGACGTG CAATTTGACT ATCGAATTCG AACAACAATT GTACTTCCTG AACCAAGTGA   540

GTTACCTGAG ACTAAGAAAA AAGCAGAAGA GGCAACAAAA GAAGCAGAAG TATCTAAGAA   600
```

```
AAAATCTGAA GAGGCAGCTA AAGAGGTATA AGTATAGAAA AATAAAATAC TTGAACAAGA      660

TGCTGAAAAC GAAAAGAAAA TTGACGTACT TCAAAACAAA GTCGCTGATT TATAAAAAGG      720

AATTGCTCTC CATCAAAACA GTCGCTGAAT TAAATAAAGA AATTGCTAGA CTTCAAAGCG      780

ATTTAAAAGA TGCTGAAGAA AATAATGTAG AAGACTACAT TAAAGAAGGT TTAGAGCAAG      840

CTATCACTAA TAAAAAAGCT GAATTAGCTA CAACTCAACA AAACATAGAT AAAACTCAAA      900

AAGATTTAGA GGATGCTGAA TTAGAACTTG AAAAAGTATT AGCTACATTA GACCCTGAAG      960

GTAAAACTCA AGATGAATTA GATAAAGAAG CTGCTGAAGC TGAGTTGAAT GAAAAAGTTG     1020

AAGCTCTTCA AAACCAAGTT GCTGAATTAG AAGAAGAACT TTCAAAACTT GAAGATAATC     1080

TTAAAGATGC TGAAACAAAC AACGTTGAAG ACTACATTAA AGAAGGTTTA GAAGAAGCTA     1140

TCGCGACTAA AAAAGCTGAA TTGGAAAAAA CTCAAAAAGA ATTAGATGCA GCTCTTAATG     1200

AGTTAGGCCC TGATGGAGAT GAAGAAGAGA CTCCAGCGCC GGCTCCTCAA CCAGAAAAAC     1260

CAGCTGAAGA GCCTGAGAAT CCAGCTCCAG CACCAAAACC AGAGAAGTCA GCAGATCAAC     1320

AAGCTGAAGA AGACTATGCT CGTAGATCAG AAGAAGAATA TAATCGCTTG ACCCAACAGC     1380

AACCGCCAAA AGCAGAAAAA CCAGCTCCTG CACCACAACC AGAGCAACCA GCTCCTGCAC     1440

CAAAAATAGA GGC                                                       1453
```

(2) INFORMATION FOR SEQ ID NO:34:

(i) SEQUENCE CHARACTERISTICS:
        (A) LENGTH: 1241 amino acids
        (B) TYPE: amino acid
        (C) STRANDEDNESS: single
        (D) TOPOLOGY: linear (ii) MOLECULE TYPE: amino acid (xi) SEQUENCE DESCRIPTION: SEQ ID NO:34:

```
Met Glu Thr Ala Ser Asn Leu Tyr Ser Leu Tyr Ser Leu Tyr Ser Met
1               5                   10                  15

Glu Thr Ile Leu Glu Leu Glu Thr His Arg Ser Glu Arg Leu Glu Ala
            20                  25                  30

Leu Ala Ser Glu Arg Val Ala Leu Ala Leu Ala Ile Leu Glu Leu Glu
        35                  40                  45

Gly Leu Tyr Ala Leu Ala Gly Leu Tyr Pro His Glu Val Ala Leu Ala
    50                  55                  60

Leu Ala Ser Glu Arg Ser Glu Arg Pro Arg Thr His Arg Pro His Glu
65                  70                  75                  80

Val Ala Leu Ala Arg Gly Ala Leu Ala Gly Leu Gly Leu Ala Leu Ala
                85                  90                  95

Pro Arg Val Ala Leu Ala Leu Ala Ala Ser Asn Gly Leu Asn Ser Glu
            100                 105                 110

Arg Leu Tyr Ser Ala Leu Ala Gly Leu Leu Tyr Ser Ala Ser Pro Thr
        115                 120                 125

Tyr Arg Ala Ser Pro Ala Leu Ala Ala Leu Ala Val Ala Leu Leu Tyr
    130                 135                 140

Ser Leu Tyr Ser Ser Glu Arg Gly Leu Ala Leu Ala Ala Leu Ala Leu
145                 150                 155                 160

Tyr Ser Leu Tyr Ser Ala Ser Pro Thr Tyr Arg Gly Leu Thr His Arg
                165                 170                 175

Ala Leu Ala Leu Tyr Ser Leu Tyr Ser Leu Tyr Ser Ala Leu Ala Gly
            180                 185                 190
```

-continued

```
Leu Ala Ser Pro Ala Leu Ala Gly Leu Asn Leu Tyr Ser Leu Tyr Ser
            195                 200                 205
Thr Tyr Arg Ala Ser Pro Gly Leu Ala Ser Pro Gly Leu Asn Leu Tyr
        210                 215                 220
Ser Leu Tyr Ser Thr His Arg Gly Leu Ala Leu Ala Leu Tyr Ser Ala
225                 230                 235                 240
Leu Ala Gly Leu Leu Tyr Ser Gly Leu Ala Arg Gly Leu Tyr Ser Ala
                245                 250                 255
Leu Ala Ser Glu Arg Gly Leu Leu Tyr Ser Ile Leu Glu Ala Leu Ala
            260                 265                 270
Gly Leu Ala Leu Ala Thr His Arg Leu Tyr Ser Gly Leu Val Ala Leu
        275                 280                 285
Gly Leu Asn Gly Leu Asn Ala Leu Ala Thr Tyr Arg Leu Glu Ala Leu
        290                 295                 300
Ala Thr Tyr Arg Leu Glu Gly Leu Asn Ala Leu Ala Ser Glu Arg Ala
305                 310                 315                 320
Ser Asn Gly Leu Ser Glu Arg Gly Leu Asn Ala Arg Gly Leu Tyr Ser
                325                 330                 335
Gly Leu Ala Leu Ala Ala Ser Pro Leu Tyr Ser Leu Tyr Ser Ile Leu
            340                 345                 350
Glu Leu Tyr Ser Gly Leu Ala Leu Ala Thr His Arg His Ile Ser Ala
            355                 360                 365
Leu Ala Leu Tyr Ser Met Glu Thr Ala Arg Gly Ala Arg Gly Thr His
        370                 375                 380
Arg Cys Tyr Ser Ala Ser Asn Leu Glu Thr His Arg Ile Leu Glu Gly
385                 390                 395                 400
Leu Pro His Glu Gly Leu Gly Leu Asn Gly Leu Asn Leu Glu Thr Tyr
                405                 410                 415
Arg Pro His Glu Leu Glu Ala Ser Asn Gly Leu Asn Val Ala Leu Ser
            420                 425                 430
Glu Arg Thr Tyr Arg Leu Glu Ala Arg Gly Leu Glu Ala Arg Gly Leu
        435                 440                 445
Tyr Ser Leu Tyr Ser Gly Leu Asn Leu Tyr Ser Ala Arg Gly Gly Leu
    450                 455                 460
Asn Gly Leu Asn Leu Tyr Ser Leu Tyr Ser Gly Leu Asn Leu Tyr Ser
465                 470                 475                 480
Thr Tyr Arg Leu Glu Ala Arg Gly Leu Tyr Ser Ala Ser Asn Leu Glu
            485                 490                 495
Leu Tyr Ser Ala Arg Gly Gly Leu Asn Leu Glu Leu Tyr Ser Ala Arg
            500                 505                 510
Gly Thr Tyr Arg Leu Tyr Ser Thr Tyr Arg Ala Arg Gly Leu Tyr Ser
            515                 520                 525
Ile Leu Glu Leu Tyr Ser Thr Tyr Arg Leu Glu Ala Ser Asn Leu Tyr
        530                 535                 540
Ser Met Glu Thr Leu Glu Leu Tyr Ser Thr His Arg Leu Tyr Ser Ala
545                 550                 555                 560
Arg Gly Leu Tyr Ser Leu Glu Thr His Arg Thr Tyr Arg Pro His Glu
                565                 570                 575
Leu Tyr Ser Thr His Arg Leu Tyr Ser Ser Glu Arg Leu Glu Ile Leu
            580                 585                 590
Glu Thr Tyr Arg Leu Tyr Ser Leu Tyr Ser Gly Leu Leu Glu Leu Glu
        595                 600                 605
```

-continued

Ser Glu Arg Ile Leu Glu Leu Tyr Ser Thr His Arg Val Ala Leu Ala
    610                 615                 620

Leu Ala Gly Leu Leu Glu Ala Ser Asn Leu Tyr Ser Gly Leu Ile Leu
625                 630                 635                 640

Glu Ala Leu Ala Ala Arg Gly Leu Glu Gly Leu Asn Ser Glu Arg Ala
                645                 650                 655

Ser Pro Leu Glu Leu Tyr Ser Ala Ser Pro Ala Leu Ala Gly Leu Gly
            660                 665                 670

Leu Ala Ser Asn Ala Ser Asn Val Ala Leu Gly Leu Ala Ser Pro Thr
                675                 680                 685

Tyr Arg Ile Leu Glu Leu Tyr Ser Gly Leu Gly Leu Tyr Leu Glu Gly
            690                 695                 700

Leu Gly Leu Asn Ala Leu Ala Ile Leu Glu Thr His Arg Ala Ser Asn
705                 710                 715                 720

Leu Tyr Ser Leu Tyr Ser Ala Leu Ala Gly Leu Leu Glu Ala Leu Ala
                725                 730                 735

Thr His Arg Thr His Arg Gly Leu Asn Gly Leu Asn Ala Ser Asn Ile
                740                 745                 750

Leu Glu Ala Ser Pro Leu Tyr Ser Thr His Arg Gly Leu Asn Leu Tyr
            755                 760                 765

Ser Ala Ser Pro Leu Gly Leu Ala Ser Pro Ala Leu Ala Gly Leu
770                 775                 780

Leu Glu Gly Leu Leu Glu Gly Leu Leu Tyr Ser Val Ala Leu Leu Glu
785                 790                 795                 800

Ala Leu Ala Thr His Arg Leu Glu Ala Ser Pro Arg Gly Leu Gly
                805                 810                 815

Leu Tyr Leu Tyr Ser Thr His Arg Gly Leu Asn Ala Ser Pro Gly Leu
                820                 825                 830

Leu Glu Ala Ser Pro Leu Tyr Ser Gly Leu Ala Leu Ala Ala Leu Ala
            835                 840                 845

Gly Leu Ala Leu Ala Gly Leu Leu Glu Ala Ser Asn Gly Leu Leu Tyr
850                 855                 860

Ser Val Ala Leu Gly Leu Ala Leu Ala Leu Glu Gly Leu Asn Ala Ser
865                 870                 875                 880

Asn Gly Leu Asn Val Ala Leu Ala Leu Ala Gly Leu Leu Glu Gly Leu
                885                 890                 895

Gly Leu Gly Leu Leu Glu Ser Glu Arg Leu Tyr Ser Leu Glu Gly Leu
            900                 905                 910

Ala Ser Pro Ala Ser Asn Leu Glu Leu Tyr Ser Ala Ser Pro Ala Leu
            915                 920                 925

Ala Gly Leu Thr His Arg Ala Ser Asn Ala Ser Asn Val Ala Leu Gly
            930                 935                 940

Leu Ala Ser Pro Thr Tyr Arg Ile Leu Glu Leu Tyr Ser Gly Leu Gly
945                 950                 955                 960

Leu Tyr Leu Glu Gly Leu Gly Leu Ala Leu Ala Ile Leu Glu Ala Leu
                965                 970                 975

Ala Thr His Arg Leu Tyr Ser Leu Tyr Ser Ala Leu Ala Gly Leu Leu
                980                 985                 990

Glu Gly Leu Leu Tyr Ser Thr His Arg Gly Leu Asn Leu Tyr Ser Gly
            995                 1000                1005

Leu Leu Glu Ala Ser Pro Ala Leu Ala Ala Leu Ala Leu Glu Ala Ser
      1010                1015                1020

Asn Gly Leu Leu Glu Gly Leu Tyr Pro Arg Ala Ser Pro Gly Leu Tyr

```
                1025            1030            1035            1040
Ala Ser Pro Gly Leu Gly Leu Gly Leu Thr His Arg Pro Arg Ala Leu
                    1045            1050            1055
Ala Pro Arg Ala Leu Ala Pro Arg Gly Leu Asn Pro Arg Gly Leu Leu
                1060            1065            1070
Tyr Ser Pro Arg Ala Leu Ala Gly Leu Gly Leu Pro Arg Gly Leu Ala
            1075            1080            1085
Ser Asn Pro Arg Ala Leu Ala Pro Arg Ala Leu Ala Pro Arg Leu Tyr
        1090            1095            1100
Ser Pro Arg Gly Leu Leu Tyr Ser Ser Glu Arg Ala Leu Ala Ala Ser
1105            1110            1115            1120
Pro Gly Leu Asn Gly Leu Asn Ala Leu Ala Gly Leu Gly Leu Ala Ser
                1125            1130            1135
Pro Thr Tyr Arg Ala Leu Ala Ala Arg Gly Ala Arg Gly Ser Glu Arg
                1140            1145            1150
Gly Leu Gly Leu Gly Leu Thr Tyr Arg Ala Ser Asn Ala Arg Gly Leu
            1155            1160            1165
Glu Thr His Arg Gly Leu Asn Gly Leu Asn Gly Leu Asn Pro Arg Pro
        1170            1175            1180
Arg Leu Tyr Ser Ala Leu Ala Gly Leu Leu Tyr Ser Pro Arg Ala Leu
1185            1190            1195            1200
Ala Pro Arg Ala Leu Ala Pro Arg Gly Leu Asn Pro Arg Gly Leu Gly
                1205            1210            1215
Leu Asn Pro Arg Ala Leu Ala Pro Arg Ala Leu Ala Pro Arg Leu Tyr
            1220            1225            1230
Ser Ile Leu Glu Gly Leu Ala Leu Ala
        1235            1240

(2) INFORMATION FOR SEQ ID NO:35:

(i) SEQUENCE CHARACTERISTICS:
        (A) LENGTH: 1990 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

AAGCTTATGA TATAGAAATT TGTAACAAAA ATGTAATATA AAACACTTGA CAAATATTTA      60

CGGAGGAGGC TTATACTTAA TATAAGTATA GTCTGAAAAT GACTATCAGA AAAGAGGTAA     120

ATTTAGATGA ATAAGAAAAA AATGATTTTA ACAAGTCTAG CCAGCGTCGC TATCTTAGGG     180

GCTGGTTTTG TTGCGTCTCA GCCTACTGTT GTAAGAGCAG AAGAATCTCC CGTAGCCAGT     240

CAGTCTAAAG CTGAGAAAGA CTATGATGCA GCGAAGAAAG ATGCTAAGAA TGCGAAAAAA     300

GCAGTAGAAG ATGCTCAAAA GGCTTTAGAT GATGCAAAAG CTGCTCAGAA AAAATATGAC     360

GAGGATCAGA AGAAAACTGA GGAGAAAGCC GCGCTAGAAA AAGCAGCGTC TGAAGAGATG     420

GATAAGGCAG TGGCAGCAGT TCAACAAGCG TATCTAGCCT ATCAACAAGC TACAGACAAA     480

GCCGCAAAAG ACGCAGCAGA TAAGATGATA GATGAAGCTA AGAAACGCGA AGAAGAGGCA     540

AAAACTAAAT TTAATACTGT TCGAGCAATG GTAGTTCCTG AGCCAGAGCA GTTGGCTGAG     600

ACTAAGAAAA AATCAGAAGA AGCTAAACAA AAAGCACCAG AACTTACTAA AAAACTAGAA     660

GAAGCTAAAG CAAAATTAGA AGAGGCTGAG AAAAAAGCTA CTGAAGCCAA ACAAAAAGTG     720

GATGCTGAAG AAGTCGCTCC TCAAGCTAAA ATCGCTGAAT GGAAAATCA AGTTCATAGA     780
```

-continued

```
CTAGAACAAG AGCTCAAAGA GATTGATGAG TCTGAATCAG AAGATTATGC TAAAGAAGGT    840

TTCCGTGCTC CTCTTCAATC TAAATTGGAT GCCAAAAAAG CTAAACTATC AAAACTTGAA    900

GAGTTAAGTG ATAAGATTGA TGAGTTAGAC GCTGAAATTG CAAAACTTGA AGATCAACTT    960

AAAGCTGCTG AAGAAAACAA TAATGTGAAA GACTACTTTA AGAAGGTTT AGAGAAAACT   1020

ATTGCTGCTA AAAAAGCTGA ATTAGAAAAA ACTGAAGCTG ACCTTAAGAA AGCAGTTAAT   1080

GAGCCAGAAA AACCAGCTCC AGCTCCAGAA ACTCCAGCCC CAGAAGCACC AGCTGAACAA   1140

CCAAAACCAG CGCCGGCTCC TCAACCAGCT CCCGCACCAA ACCAGAGAA GCCAGCTGAA   1200

CAACCAAAAC CAGAAAAAAC AGATGATCAA CAAGCTGAAG AAGACTATGC TCGTAGATCA   1260

GAAGAAGAAT ATAATCGCTT GACTCAACAG CAACCGCCAA AAGCTGAAAA ACCAGCTCCT   1320

GCACCAAAAA CAGGCTGGAA ACAAGAAAAC GGTATGTGGT ACTTCTACAA TACTGATGGT   1380

TCAATGGCGA CAGGATGGCT CCAAAACAAC GGTTCATGGT ACTACCTCAA CAGCAATGGT   1440

GCTATGGCTA CAGGTTGGCT CCAATACAAT GGTTCATGGT ATTACCTCAA CGCTAACGGC   1500

GCTATGGCAA CAGGTTGGGC TAAAGTCAAC GGTTCATGGT ACTACCTCAA CGCTAATGGT   1560

GCTATGGCTA CAGGTTGGCT CCAATACAAC GGTTCATGGT ATTACCTCAA CGCTAACGGC   1620

GCTATGGCAA CAGGTTGGGC TAAAGTCAAC GGTTCATGGT ACTACCTCAA CGCTAATGGT   1680

GCTATGGCTA CAGGTTGGCT CCAATACAAC GGTTCATGGT ACTACCTCAA CGCTAACGGT   1740

GCTATGGCTA CAGGTTGGGC TAAAGTCAAC GGTTCATGGT ACTACCTCAA CGCTAATGGT   1800

GCTATGGCAA CAGGTTGGGT GAAAGATGGA GATACCTGGT ACTATCTTGA AGCATCAGGT   1860

GCTATGAAAG CAAGCCAATG GTTCAAAGTA TCAGATAAAT GGTACTATGT CAATGGTTTA   1920

GGTGCCCTTG CAGTCAACAC AACTGTAGAT GGCTATAAAG TCAATGCCAA TGGTGAATGG   1980

GTTTAAGCCG                                                         1990

(2) INFORMATION FOR SEQ ID NO:36:

(i) SEQUENCE CHARACTERISTICS:
        (A) LENGTH: 956 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CCAGCGTCGC TATCTTAGGG GCTGGTTTTG TTGCGTCTCA GCCTACTGTT GTAAGAGCAG     60

AAGAATCTCC CGTAGCCAGT CAGTCTAAAG CTGAGAAAGA CTATGATGCA GCGAAGAAAG    120

ATGCTAAGAA TGCGAAAAAA GCAGTAGAAG ATGCTCAAAA GGCTTTAGAT GATGCAAAAG    180

CTGCTCAGAA AAAATATGAC GAGGATCAGA AGAAAACTGA GGAGAAAGCC GCGCTAGAAA    240

AAGCAGCGTC TGAAGAGATG GATAAGGCAG TGGCAGCAGT TCAACAAGCG TATCTACCCT    300

ATCAACAAGC TACAGACAAA GCCGCAAAAG ACGCAGCAGA TAAGATGATA GATGAAGCTA    360

AGAAACGCGA AGAAGAGGCA AAAACTAAAT TTAATACTGT TCGAGCAATG GTAGTTCCTG    420

AGCCAGAGCA GTTGGCTGAG ACTAAGAAAA AATCAGAAGA AGCTAAACAA AAAGCACCAG    480

AACTTACTAA AAAACTAGAA GAAGCTAAAG CAAAATTAGA AGACGCTGAG AAAAAAGCTA    540

CTGAAGCCAA ACAAAAAGTG GATGCTGAAG AAGTCGCTCC TCAAGCTAAA ATCGCTGAAT    600

TGGAAAATCA AGTTCATAGA CTAGAACAAG ACTCAAAGAG ATTGATGAGT CTGAATCAGA    660

AGATTATGCT AAAGAAGGTT TCCGTGCTCC TCTTCAATCT AAATTGGATG CCAAAAAAGC    720
```

| | | |
|---|---|---|
| TAAACTATCA AAACTTGAAG AGTTAAGTGA TAAGATTGAT GAGTTAGACG CTGAAATTGC | | 780 |
| AAAACTTGAA GATCAACTTA AAGCTGCTGA AGAAAACAAT AATGTAGAAG ACTACTTTAA | | 840 |
| AGAAGGTTTA GAGAAAACTA TTGCTGCTAA AAAAGCTGAA TTAGAAAAAA CTGAAGCTGA | | 900 |
| CCTTAAGAAA GCAGTTAATG AGCCAGAAAA ACCAGCTCCA GCTCCAGAAA CTCCAG | | 956 |

(2) INFORMATION FOR SEQ ID NO:37:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

| | |
|---|---|
| GGAAGGCCAT ATGCTCAAAG AGATTGATGA GTCT | 34 |

(2) INFORMATION FOR SEQ ID NO:38:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

| | |
|---|---|
| CCAAGGATCC TTAAACCCAT TCACCATTGG C | 31 |

(2) INFORMATION FOR SEQ ID NO:39:

(i) SEQUENCE CHARACTERISTICS:
        (A) LENGTH: 3222 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

| | | |
|---|---|---|
| AAGCTTATGC TTGTCAATAA TCACAAATAT GTAGATCATA TCTTGTTTAG GACAGTAAAA | | 60 |
| CATCCTAATT ACTTTTTAAA TATTTTACCT GAGTTGATTG GCTTGACCTT GTTGAGTCAT | | 120 |
| GCCTATATGA CTTTTGTTTT AGTTTTTCCA GTTTATGCAG TTATTTTGTA TCGACGAATA | | 180 |
| GCTGAAGAGG AAAAGTTATT ACATGAAGTT ATAATCCCAA ATGGAAGCAT AAAGAGATAA | | 240 |
| ATACAAAATT CGATTTATAT ACAGTTCATA TTGAAGTGAT ATAGTAAGGT TAAAGAAAAA | | 300 |
| ATATAGAAGG AAATAAACAT GTTTGCATCA AAAAGCGAAA GAAAAGTACA TTATTCAATT | | 360 |
| CGTAAATTTA GTATTGGAGT AGCTAGTGTA GCTGTTGCCA GCTTGTTCTT AGGAGGAGTA | | 420 |
| GTCCATGCAG AAGGGGTTAG AAGTGGGAAT AACCTCACGG TTACATCTAG TGGGCAAGAT | | 480 |
| ATATCGAAGA AGTATGCTGA TGAAGTCGAG TCGCATCTAG AAAGTATATT GAAGGATGTC | | 540 |
| AAAAAAAATT TGAAAAAAGT TCAAAAAGAA AAAGATCGCC GTAACTACCC AACCATTACT | | 600 |
| TACAAAACGC TTGAACTTGA AATTGCTGAG TCCGATGTGG AAGTTAAAAA AGCGGAGCTT | | 660 |
| GAACTAGTAA AAGTGAAAGC TAAGGAATCT CAAGACGAGG AAAAAATTAA GCAAGCAGAA | | 720 |
| GCGGAAGTTG AGAGTAAACA AGCTGAGGCT ACAAGGTTAA AAAAAATCAA GACAGATCGT | | 780 |
| GAAGAAGCTA AACGAAAAGC AGATGCTAAG TTGAAGGAAG CTGTTGAAAA GAATGTAGCG | | 840 |

```
ACTTCAGAGC AAGATAAACC AAAGAGGCGG GCAAAACGAG GAGTTTCTGG AGAGCTAGCA    900
ACACCTGATA AAAAAGAAAA TGATGCGAAG TCTTCAGATT CTAGCGTAGG TGAAGAAACT    960
CTTCCAAGCC CATCCCTTAA TATGGCAAAT GAAAGTCAGA CAGAACATAG GAAAGATGTC   1020
GATGAATATA TAAAAAAAAT GTTGAGTGAG ATCCAATTAG ATAGAAGAAA ACATACCCAA   1080
AATGTCAACT TAAACATAAA GTTGAGCGCA ATTAAAACGA AGTATTTGTA TGAATTAAGT   1140
GTTTTAAAAG AGAACTCGAA AAAGAAGAG TTGACGTCAA AAACCAAAGC AGAGTTAACC   1200
GCAGCTTTTG AGCAGTTTAA AAAAGATACA TTGAAACCAA AAAAAAGGT AGCAGAAGCT   1260
GAGAAGAAGG TTGAAGAAGC TAAGAAAAAA GCCAAGGATC AAAAAGAAGA AGATCGCCGT   1320
AACTACCCAA CCAATACTTA CAAAACGCTT GAACTTGAAA TTGCTGAGTC CGATGTGAAA   1380
GTTAAAGAAG CGGAGCTTGA ACTAGTAAAA GAGGAAGCTA ACGAATCTCG AAACGAGGAA   1440
AAAATTAAGC AAGCAAAAGA GAAAGTTGAG AGTAAAAAAG CTGAGGCTAC AAGGTTAGAA   1500
AAAATCAAGA CAGATCGTAA AAAAGCAGAA GAAGAAGCTA AACGAAAAGC AGAAGAATCT   1560
GAGAAAAAAG CTGCTGAAGC CAAACAAAAA GTGGATGCTG AAGAATATGC TCTTGAAGCT   1620
AAAATCGCTG AGTTGGAATA TGAAGTTCAG AGACTAGAAA AAGAGCTCAA AGAGATTGAT   1680
GAGTCTGACT CAGAAGATTA TCTTAAAGAA GGCCTCCGTG CTCCTCTTCA ATCTAAATTG   1740
GATACCAAAA AAGCTAAACT ATCAAAACTT GAAGAGTTGA GTGATAAGAT TGATGAGTTA   1800
GACGCTGAAA TTGCAAAACT TGAAGTTCAA CTTAAAGATG CTGAAGGAAA CAATAATGTA   1860
GAAGCCTACT TTAAAGAAGG TTTAGAGAAA ACTACTGCTG AGAAAAAGC TGAATTAGAA   1920
AAAGCTGAAG CTGACCTTAA GAAAGCAGTT GATGAGCCAG AAACTCCAGC TCCGGCTCCT   1980
CAACCAGCTC CAGCTCCAGA AAAACCAGCT GAAAAACCAG CTCCAGCTCC AGAAAAACCA   2040
GCTCCAGCTC CAGAAAAACC AGCTCCAGCT CCAGAAAAAC CAGCTCCAGC TCCAGAAAAA   2100
CCAGCTCCAG CTCCAGAAAA ACCAGCTCCA ACTCCAGAAA CTCCAAAAAC AGGCTGGAAA   2160
CAAGAAAACG GTATGTGGTA CTTCTACAAT ACTGATGGTT CAATGGCAAC AGGCTGGCTC   2220
CAAAACAATG GCTCATGGTA CTACCTCAAC AGCAATGGCG CTATGGCGAC AGGATGGCTC   2280
CAAAACAATG GCTCATGGTA CTACCTCAAC AGCAATGGCG CTATGGCGAC AGGATGGCTC   2340
CAATACAATG GTTCATGGTA CTACCTCAAC GCTAATGGTG ATATGGCGAC AGGATGGCTC   2400
CAATACAATG GTTCATGGTA CTACCTCAAC GCTAATGGTG ATATGGCGAC AGGATGGTTC   2460
CAATACAATG GTTCATGGTA CTACCTCAAC GCTAATGGTG ATATGGCGAC AGGATGGTTC   2520
CAATACAATG GTTCATGGTA CTACCTCAAC GCTAATGGTG ATATGGCGAC AGGATGGCTC   2580
CAATACAATG GTTCATGGTA CTACCTAAAC AGCAATGGTG CTATGGTAAC AGGATGGCTC   2640
CAAAACAATG GCTCATGGTA CTACCTAAAC GCTAACGGTT CAATGGCAAC AGATTGGGTG   2700
AAAGATGGAG ATACCTGGTA CTATCTTGAA GCATCAGGTG CTATGAAAGC AAGCCAATGG   2760
TTCAAAGTAT CAGATAAATG GTACTATGTC AATGGCTCAG GTGCCCTTGC AGTCAACACA   2820
ACTGTAGATA GCTATAGAGT CAATGCCAAT GGTGAATGGG TAAACTAAAC TTAATATAAC   2880
TAGTTAATAC TGACTTCCTG TAAGAACTCT TTAAAGTATT CCCTACAAAT ACCATATCCT   2940
TTCAGTAGAT AATATACCCT TGTAGGAAGT TTAGATTAAA AAATAACTCT GTAATCTCTA   3000
GCCGGATTTA TAGCGCTAGA GACTACGGAG TTTTTTTGAT GAGGAAAGAA TGGCGGCATT   3060
CAAGAGACTC TTTAAGAGAG TTACGGGTTT TAAACTATTA AGCTTTCTCC AATTGCAAGA   3120
GGGCTTCAAT CTCTGCTAGG TGCTAGCTTG CGAAATGGCT CCCACGGAGT TTGGCGCGCC   3180
```

-continued

```
AGATGTTCCA CGGAGGTAGT GAGGAGCGAG GCCGCGGAAT TC                    3222
```

(2) INFORMATION FOR SEQ ID NO:40:

(i) SEQUENCE CHARACTERISTICS:
  (A) LENGTH: 864 amino acids
  (B) TYPE: amino acid
  (C) STRANDEDNESS: single
  (D) TOPOLOGY: linear (ii) MOLECULE TYPE: amino acid (xi) SEQUENCE DESCRIPTION: SEQ ID NO:40:

```
Phe Ala Ser Lys Ser Glu Arg Lys Val His Tyr Ser Ile Arg Lys Phe
1               5                   10                  15

Ser Ile Gly Val Ala Ser Val Ala Val Ala Ser Leu Phe Leu Gly Gly
            20                  25                  30

Val Val His Ala Glu Gly Val Arg Ser Gly Asn Asn Leu Thr Val Thr
        35                  40                  45

Ser Ser Gly Gln Asp Ile Ser Lys Lys Tyr Ala Asp Glu Val Glu Ser
    50                  55                  60

His Leu Glu Ser Ile Leu Lys Asp Val Lys Lys Asn Glu Lys Lys Val
65                  70                  75                  80

Ala Glu Ala Gln Lys Lys Val Glu Glu Ala Lys Lys Ala Glu Asp
                85                  90                  95

Gln Lys Glu Lys Asp Arg Arg Asn Tyr Pro Thr Ile Thr Tyr Lys Thr
            100                 105                 110

Leu Glu Leu Glu Ile Ala Glu Ser Asp Val Glu Val Lys Lys Ala Glu
            115                 120                 125

Leu Glu Leu Val Lys Val Lys Ala Lys Glu Ser Gln Asp Glu Glu Lys
        130                 135                 140

Ile Lys Gln Ala Glu Ala Glu Val Glu Ser Lys Gln Ala Glu Ala Thr
145                 150                 155                 160

Arg Leu Lys Lys Ile Lys Thr Asp Arg Glu Glu Ala Lys Arg Lys Ala
                165                 170                 175

Asp Ala Lys Leu Lys Glu Ala Val Glu Lys Asn Val Ala Thr Ser Glu
            180                 185                 190

Gln Asp Lys Pro Lys Arg Arg Ala Lys Arg Gly Val Ser Gly Glu Leu
        195                 200                 205

Ala Thr Pro Asp Lys Lys Glu Asn Asp Ala Lys Ser Ser Asp Ser Ser
    210                 215                 220

Val Gly Glu Glu Thr Leu Pro Ser Pro Ser Leu Asn Met Ala Asn Glu
225                 230                 235                 240

Ser Gln Thr Glu His Arg Lys Asp Val Asp Glu Tyr Ile Lys Lys Met
                245                 250                 255

Leu Ser Glu Ile Gln Leu Asp Arg Arg Lys His Thr Gln Asn Val Asn
            260                 265                 270

Leu Asn Ile Lys Leu Ser Ala Ile Lys Thr Lys Tyr Leu Tyr Glu Leu
        275                 280                 285

Ser Val Leu Lys Glu Asn Ser Lys Glu Glu Leu Thr Ser Lys Thr
    290                 295                 300

Lys Ala Glu Leu Thr Ala Ala Phe Glu Gln Phe Lys Lys Asp Thr Leu
305                 310                 315                 320

Lys Pro Glu Lys Lys Val Ala Glu Ala Glu Lys Val Glu Glu Ala
                325                 330                 335

Lys Lys Lys Ala Lys Asp Gln Lys Glu Glu Asp Arg Arg Asn Tyr Pro
```

-continued

```
                340                 345                 350
Thr Asn Thr Tyr Lys Thr Leu Glu Leu Glu Ile Ala Glu Ser Asp Val
            355                 360                 365
Lys Val Lys Glu Ala Glu Leu Glu Leu Val Lys Glu Glu Ala Asn Glu
        370                 375                 380
Ser Arg Asn Glu Glu Lys Ile Lys Gln Ala Lys Glu Lys Val Glu Ser
385                 390                 395                 400
Lys Lys Ala Glu Ala Thr Arg Leu Glu Lys Ile Lys Thr Asp Arg Lys
                405                 410                 415
Lys Ala Glu Glu Glu Ala Lys Arg Lys Ala Glu Glu Ser Glu Lys Lys
            420                 425                 430
Ala Ala Glu Ala Lys Gln Lys Val Asp Ala Glu Tyr Ala Leu Glu
        435                 440                 445
Ala Lys Ile Ala Glu Leu Glu Tyr Glu Val Gln Arg Leu Glu Lys Glu
    450                 455                 460
Leu Lys Glu Ile Asp Glu Ser Asp Ser Glu Asp Tyr Leu Lys Glu Gly
465                 470                 475                 480
Leu Arg Ala Pro Leu Gln Ser Lys Leu Asp Thr Lys Lys Ala Lys Leu
                485                 490                 495
Ser Lys Leu Glu Glu Leu Ser Asp Lys Ile Asp Glu Leu Asp Ala Glu
            500                 505                 510
Ile Ala Lys Leu Glu Val Gln Leu Lys Asp Ala Glu Gly Asn Asn Asn
        515                 520                 525
Val Glu Ala Tyr Phe Lys Glu Gly Leu Glu Lys Thr Thr Ala Glu Lys
    530                 535                 540
Lys Ala Glu Leu Glu Lys Ala Glu Ala Asp Leu Lys Lys Ala Val Asp
545                 550                 555                 560
Glu Pro Glu Thr Pro Ala Pro Ala Pro Gln Pro Ala Pro Ala Pro Glu
                565                 570                 575
Lys Pro Ala Glu Lys Pro Ala Pro Ala Pro Glu Lys Pro Ala Pro Ala
            580                 585                 590
Pro Glu Lys Pro Ala Pro Ala Pro Glu Lys Pro Ala Pro Ala Pro Glu
        595                 600                 605
Lys Pro Ala Pro Ala Pro Glu Lys Pro Ala Pro Thr Pro Glu Thr Pro
    610                 615                 620
Lys Thr Gly Trp Lys Gln Glu Asn Gly Met Trp Tyr Phe Tyr Asn Thr
625                 630                 635                 640
Asp Gly Ser Met Ala Thr Gly Trp Leu Gln Asn Asn Gly Ser Trp Tyr
                645                 650                 655
Tyr Leu Asn Ser Asn Gly Ala Met Ala Thr Gly Trp Leu Gln Asn Asn
            660                 665                 670
Gly Ser Trp Tyr Tyr Leu Asn Ser Asn Gly Ala Met Ala Thr Gly Trp
        675                 680                 685
Leu Gln Tyr Asn Gly Ser Trp Tyr Tyr Leu Asn Ala Asn Gly Asp Met
    690                 695                 700
Ala Thr Gly Trp Leu Gln Tyr Asn Gly Ser Trp Tyr Tyr Leu Asn Ala
705                 710                 715                 720
Asn Gly Asp Met Ala Thr Gly Trp Phe Gln Tyr Asn Gly Ser Trp Tyr
                725                 730                 735
Tyr Leu Asn Ala Asn Gly Asp Met Ala Thr Gly Trp Phe Gln Tyr Asn
            740                 745                 750
Gly Ser Trp Tyr Tyr Leu Asn Ala Asn Gly Asp Met Ala Thr Gly Trp
        755                 760                 765
```

```
Leu Gln Tyr Asn Gly Ser Trp Tyr Tyr Leu Asn Ser Asn Gly Ala Met
    770             775                 780
Val Thr Gly Trp Leu Gln Asn Asn Gly Ser Trp Tyr Tyr Leu Asn Ala
785             790                 795                     800
Asn Gly Ser Met Ala Thr Asp Trp Val Lys Asp Gly Asp Thr Trp Tyr
            805                 810                 815
Tyr Leu Glu Ala Ser Gly Ala Met Lys Ala Ser Gln Trp Phe Lys Val
            820                 825                 830
Ser Asp Lys Trp Tyr Tyr Val Asn Gly Ser Gly Ala Leu Ala Val Asn
        835                 840                 845
Thr Thr Val Asp Ser Tyr Arg Val Asn Ala Asn Gly Glu Trp Val Asn
    850                 855                 860

(2) INFORMATION FOR SEQ ID NO:41:

(i) SEQUENCE CHARACTERISTICS:
        (A) LENGTH: 1231 amino acids
        (B) TYPE: amino acid
        (C) STRANDEDNESS: single
        (D) TOPOLOGY: linear (ii) MOLECULE TYPE: amino acid (xi) SEQUENCE DESCRIPTION: SEQ ID NO:41:

Ser Asp Ser Ser Val Gly Glu Glu Thr Leu Pro Ser Pro Ser Leu Asn
1               5                   10                  15
Met Ala Asn Glu Ser Gln Thr Glu His Arg Lys Asp Val Asp Glu Tyr
            20                  25                  30
Ile Lys Lys Met Leu Ser Glu Ile Gln Leu Asp Arg Arg Lys His Thr
        35                  40                  45
Gln Asn Glu Glu Ser Pro Val Ala Ser Gln Ser Lys Ala Glu Lys Asp
    50                  55                  60
Tyr Asp Ala Ala Lys Lys Asp Ala Lys Asn Ala Lys Lys Ala Val Glu
65                  70                  75                  80
Asp Ala Gln Lys Ala Leu Asp Asp Ala Lys Ala Gln Lys Lys Tyr
                85                  90                  95
Asp Glu Asp Val Asn Leu Asn Ile Lys Leu Ser Ala Ile Lys Thr Lys
            100                 105                 110
Tyr Leu Tyr Glu Leu Ser Val Leu Lys Glu Asn Ser Lys Lys Glu Glu
        115                 120                 125
Leu Thr Ser Lys Thr Lys Ala Glu Leu Thr Ala Ala Phe Glu Gln Phe
    130                 135                 140
Lys Lys Asp Thr Leu Gln Lys Lys Thr Glu Glu Lys Ala Ala Leu Glu
145                 150                 155                 160
Lys Ala Ala Ser Glu Glu Met Asp Lys Ala Val Ala Ala Val Gln Gln
                165                 170                 175
Ala Tyr Leu Ala Tyr Gln Gln Ala Thr Asp Lys Pro Glu Lys Lys Val
            180                 185                 190
Ala Glu Ala Glu Lys Lys Val Glu Glu Ala Lys Lys Ala Lys Lys Asp
        195                 200                 205
Gln Lys Glu Glu Asp Arg Arg Asn Tyr Pro Thr Asn Thr Tyr Lys Thr
    210                 215                 220
Leu Glu Leu Glu Ile Ala Glu Ser Asp Val Lys Val Lys Ala Ala Lys
225                 230                 235                 240
Asp Ala Ala Asp Lys Met Ile Asp Glu Ala Lys Lys Arg Glu Glu Glu
                245                 250                 255
```

```
Ala Lys Thr Lys Phe Asn Thr Val Arg Ala Met Val Val Lys Glu Ala
            260                 265                 270

Glu Leu Glu Leu Val Lys Glu Glu Ala Asn Glu Ser Arg Asn Glu Glu
            275                 280                 285

Lys Ile Lys Gln Ala Lys Glu Lys Val Glu Ser Lys Lys Ala Glu Ala
            290                 295                 300

Thr Arg Leu Glu Lys Ile Lys Thr Asp Arg Lys Lys Ala Glu Glu Pro
305                 310                 315                 320

Glu Pro Glu Gln Leu Ala Glu Thr Lys Lys Ser Glu Glu Ala Lys
            325                 330                 335

Gln Lys Ala Pro Glu Leu Thr Lys Lys Leu Glu Glu Ala Lys Arg Lys
            340                 345                 350

Ala Glu Glu Ser Glu Lys Lys Ala Glu Ala Lys Gln Lys Val Asp
            355                 360                 365

Ala Glu Glu Tyr Ala Leu Glu Ala Lys Ile Ala Glu Leu Glu Tyr Glu
            370                 375                 380

Val Gln Arg Leu Glu Lys Glu Leu Lys Glu Ile Asp Glu Glu Ala Lys
385                 390                 395                 400

Ala Lys Leu Glu Glu Ala Glu Lys Lys Ala Thr Glu Ala Lys Gln Lys
            405                 410                 415

Val Asp Ala Glu Glu Val Ala Pro Gln Ala Lys Ile Ala Glu Leu Glu
            420                 425                 430

Asn Gln Val His Arg Leu Glu Gln Glu Leu Lys Glu Ile Asp Glu Ser
            435                 440                 445

Asp Ser Glu Asp Tyr Leu Lys Glu Gly Leu Arg Ala Pro Leu Gln Ser
450                 455                 460

Lys Leu Asp Thr Lys Lys Ala Lys Leu Ser Lys Leu Glu Glu Leu Ser
465                 470                 475                 480

Asp Lys Ile Asp Glu Leu Asp Ala Glu Ile Ala Lys Leu Glu Val Gln
            485                 490                 495

Leu Ser Glu Ser Glu Asp Tyr Ala Lys Glu Gly Phe Arg Ala Pro Leu
            500                 505                 510

Gln Ser Lys Leu Asp Ala Lys Lys Ala Lys Leu Ser Lys Leu Glu Glu
            515                 520                 525

Leu Ser Asp Lys Ile Asp Glu Leu Asp Ala Glu Ile Ala Lys Leu Glu
            530                 535                 540

Asp Gln Leu Lys Asp Ala Glu Gly Asn Asn Val Glu Ala Tyr Phe
545                 550                 555                 560

Lys Glu Gly Leu Glu Lys Thr Thr Ala Glu Lys Lys Ala Glu Leu Glu
            565                 570                 575

Lys Ala Glu Ala Asp Leu Lys Lys Ala Val Asp Glu Pro Glu Thr Pro
            580                 585                 590

Ala Pro Ala Pro Gln Lys Ala Glu Glu Asn Asn Val Glu Asp
            595                 600                 605

Tyr Phe Lys Glu Gly Leu Glu Lys Thr Ile Ala Ala Lys Lys Ala Glu
            610                 615                 620

Leu Glu Lys Thr Glu Ala Asp Leu Lys Lys Ala Val Asn Glu Pro Glu
625                 630                 635                 640

Lys Pro Ala Pro Ala Pro Glu Pro Ala Pro Glu Lys Pro Ala
            645                 650                 655

Glu Lys Pro Ala Pro Ala Pro Glu Lys Pro Ala Pro Ala Pro Glu Lys
            660                 665                 670
```

```
Pro Ala Pro Ala Pro Glu Lys Pro Ala Pro Ala Thr Pro Ala Pro Glu
            675                 680                 685
Ala Pro Ala Glu Gln Pro Lys Pro Ala Pro Ala Pro Gln Pro Ala Pro
        690                 695                 700
Ala Pro Lys Pro Glu Lys Pro Ala Glu Gln Pro Lys Pro Glu Lys Thr
705                 710                 715                 720
Asp Asp Gln Gln Ala Glu Glu Asp Tyr Ala Arg Arg Pro Glu Lys Pro
                725                 730                 735
Ala Pro Ala Pro Glu Lys Pro Ala Pro Thr Pro Glu Thr Pro Lys Thr
            740                 745                 750
Gly Trp Lys Gln Glu Asn Gly Met Trp Tyr Phe Tyr Asn Thr Asp Gly
            755                 760                 765
Ser Met Ala Thr Gly Trp Ser Glu Glu Tyr Asn Arg Leu Thr Gln
            770                 775                 780
Gln Gln Pro Pro Lys Ala Glu Lys Pro Ala Pro Ala Pro Lys Thr Gly
785                 790                 795                 800
Trp Lys Gln Glu Asn Gly Met Trp Tyr Phe Tyr Asn Thr Asp Gly Ser
                805                 810                 815
Leu Gln Asn Asn Gly Ser Trp Tyr Tyr Leu Asn Ser Asn Gly Ala Met
            820                 825                 830
Ala Thr Gly Trp Leu Gln Asn Asn Gly Ser Trp Tyr Tyr Leu Asn Ser
            835                 840                 845
Asn Gly Ala Met Ala Thr Gly Trp Leu Gln Tyr Asn Gly Ser Trp Tyr
850                 855                 860
Tyr Leu Met Ala Thr Gly Trp Leu Gln Asn Asn Gly Ser Trp Tyr Tyr
865                 870                 875                 880
Leu Asn Ser Asn Gly Ala Met Ala Thr Gly Trp Leu Gln Tyr Asn Gly
                885                 890                 895
Ser Trp Tyr Tyr Leu Asn Ala Asn Gly Asp Met Ala Thr Gly Trp Leu
            900                 905                 910
Gln Tyr Asn Gly Ser Trp Tyr Tyr Leu Asn Ala Asn Gly Asp Met Ala
            915                 920                 925
Thr Gly Trp Phe Gln Tyr Asn Gly Ser Trp Tyr Tyr Leu Asn Ala Asn
930                 935                 940
Gly Asp Met Ala Thr Gly Trp Asn Ala Asn Gly Ala Met Ala Thr Gly
945                 950                 955                 960
Trp Ala Lys Val Asn Gly Ser Trp Tyr Tyr Leu Asn Ala Asn Gly Ala
                965                 970                 975
Met Ala Thr Gly Trp Leu Gln Tyr Asn Gly Ser Trp Tyr Tyr Leu Asn
            980                 985                 990
Ala Asn Gly Ala Met Ala Thr Gly Trp Phe Gln Tyr Asn Gly Ser Trp
        995                 1000                1005
Tyr Tyr Leu Asn Ala Asn Gly Asp Met Ala Thr Gly Trp Leu Gln Tyr
    1010                1015                1020
Asn Gly Ser Trp Tyr Tyr Leu Asn Ser Asn Gly Ala Met Val Thr Gly
1025                1030                1035                1040
Trp Leu Gln Asn Asn Gly Ser Trp Tyr Tyr Leu Ala Lys Val Asn Gly
                1045                1050                1055
Ser Trp Tyr Tyr Leu Asn Ala Asn Gly Ala Met Ala Thr Gly Trp Leu
            1060                1065                1070
Gln Tyr Asn Gly Ser Trp Tyr Tyr Leu Asn Ala Asn Gly Ala Met Ala
            1075                1080                1085
Thr Gly Trp Ala Lys Val Asn Gly Ser Trp Tyr Tyr Leu Asn Ala Asn
```

-continued

```
        1090                1095                1100
Gly Ser Met Ala Thr Asp Trp Val Lys Asp Gly Asp Thr Trp Tyr Tyr
1105                1110                1115                1120

Leu Glu Ala Ser Gly Ala Met Lys Ala Ser Gln Trp Phe Lys Val Ser
                    1125                1130                1135

Asp Lys Trp Tyr Tyr Val Asn Gly Ser Gly Ala Leu Ala Val Asn Asn
                1140                1145                1150

Ala Asn Gly Ala Met Ala Thr Gly Trp Val Lys Asp Gly Asp Thr Trp
                1155                1160                1165

Tyr Tyr Leu Glu Ala Ser Gly Ala Met Lys Ala Ser Gln Trp Phe Lys
    1170                1175                1180

Val Ser Asp Lys Trp Tyr Tyr Val Asn Gly Leu Gly Ala Leu Ala Val
1185                1190                1195                1200

Asn Thr Thr Val Asp Ser Tyr Arg Val Asn Ala Asn Gly Glu Trp Val
                    1205                1210                1215

Thr Thr Val Asp Gly Tyr Lys Val Asn Ala Asn Gly Glu Trp Val
                1220                1225                1230
```

(2) INFORMATION FOR SEQ ID NO:42:

(i) SEQUENCE CHARACTERISTICS:
        (A) LENGTH: 588 amino acids
        (B) TYPE: amino acid
        (C) STRANDEDNESS: single
        (D) TOPOLOGY: linear (ii) MOLECULE TYPE: amino acid (xi) SEQUENCE DESCRIPTION: SEQ ID NO:42:

```
Glu Gly Val Arg Ser Gly Asn Asn Leu Thr Val Thr Ser Ser Gly Gln
1               5                   10                  15

Asp Ile Ser Lys Lys Tyr Ala Asp Glu Val Glu Ser His Leu Glu Ser
            20                  25                  30

Ile Leu Lys Asp Val Lys Lys Asn Leu Lys Lys Val Gln His Thr Gln
        35                  40                  45

Asn Val Gly Leu Ile Thr Lys Leu Ser Glu Ile Lys Lys Lys Tyr Leu
50                  55                  60

Tyr Asp Leu Lys Val Asn Val Leu Ser Glu Ala Glu Leu Thr Ser Lys
65                  70                  75                  80

Thr Lys Glu Thr Lys Glu Lys Leu Thr Ala Thr Phe Glu Gln Phe Lys
                85                  90                  95

Lys Asp Thr Leu Pro Thr Glu Pro Glu Lys Lys Val Ala Glu Ala Gln
            100                 105                 110

Lys Lys Val Glu Glu Ala Lys Lys Ala Glu Asp Gln Lys Glu Lys
        115                 120                 125

Asp Arg Arg Asn Tyr Pro Thr Ile Thr Tyr Lys Thr Leu Glu Leu Glu
    130                 135                 140

Ile Ala Glu Ser Asp Val Glu Val Lys Lys Ala Glu Leu Glu Leu Val
145                 150                 155                 160

Lys Val Lys Ala Lys Glu Ser Gln Asp Glu Glu Lys Ile Lys Gln Ala
                165                 170                 175

Glu Ala Glu Val Glu Ser Lys Gln Ala Glu Ala Thr Arg Leu Lys Lys
            180                 185                 190

Ile Lys Thr Asp Arg Glu Glu Ala Lys Arg Lys Ala Asp Ala Lys Leu
        195                 200                 205

Lys Glu Ala Val Glu Lys Asn Val Ala Thr Ser Glu Gln Asp Lys Pro
```

```
                210                 215                 220
Lys Arg Arg Ala Lys Arg Gly Val Ser Gly Glu Leu Ala Thr Pro Asp
225                 230                 235                 240

Lys Lys Glu Asn Asp Ala Lys Ser Ser Asp Ser Ser Val Gly Glu Thr
                245                 250                 255

Leu Pro Ser Pro Ser Leu Asn Met Ala Asn Glu Ser Gln Thr Glu His
                260                 265                 270

Arg Lys Asp Val Asp Glu Tyr Ile Lys Lys Met Leu Ser Glu Ile Gln
                275                 280                 285

Leu Asp Arg Arg Lys His Thr Gln Asn Val Asn Leu Asn Ile Lys Leu
        290                 295                 300

Ser Ala Ile Lys Thr Lys Tyr Leu Tyr Glu Leu Ser Val Leu Lys Glu
305                 310                 315                 320

Asn Ser Lys Lys Glu Glu Leu Thr Ser Lys Thr Lys Ala Glu Leu Thr
                325                 330                 335

Ala Ala Phe Glu Gln Phe Lys Lys Asp Thr Leu Lys Pro Glu Lys Lys
                340                 345                 350

Val Ala Glu Ala Glu Lys Lys Val Glu Glu Ala Lys Lys Lys Ala Lys
                355                 360                 365

Asp Gln Lys Glu Glu Asp Arg Arg Asn Tyr Pro Thr Asn Thr Tyr Lys
        370                 375                 380

Thr Leu Glu Leu Glu Ile Ala Glu Ser Asp Val Lys Val Lys Glu Ala
385                 390                 395                 400

Glu Leu Glu Leu Val Lys Glu Glu Ala Asn Glu Ser Arg Asn Glu Glu
                405                 410                 415

Lys Ile Lys Gln Ala Lys Glu Lys Val Glu Ser Lys Lys Ala Glu Ala
                420                 425                 430

Thr Arg Leu Glu Lys Ile Lys Thr Asp Arg Lys Lys Ala Glu Glu Glu
                435                 440                 445

Ala Lys Arg Lys Ala Glu Glu Ser Glu Lys Lys Ala Ala Glu Ala Lys
        450                 455                 460

Gln Lys Val Asp Ala Glu Tyr Ala Leu Glu Ala Lys Ile Ala Glu
465                 470                 475                 480

Leu Glu Tyr Glu Val Gln Arg Leu Leu Lys Glu Leu Lys Glu Ile Asp
                485                 490                 495

Glu Ser Asp Ser Glu Asp Tyr Leu Lys Glu Gly Leu Arg Ala Pro Leu
                500                 505                 510

Gln Ser Lys Leu Asp Thr Lys Ala Lys Leu Ser Lys Leu Glu Glu
        515                 520                 525

Leu Ser Asp Lys Ile Asp Glu Leu Asp Ala Glu Ile Ala Lys Leu Glu
530                 535                 540

Val Gln Leu Lys Asp Ala Glu Gly Asn Asn Val Glu Ala Tyr Phe
545                 550                 555                 560

Lys Glu Gly Leu Glu Lys Thr Thr Ala Glu Lys Lys Ala Glu Leu Glu
                565                 570                 575

Lys Ala Glu Ala Asp Leu Lys Lys Ala Val Asp Glu
        580                 585
```

(2) INFORMATION FOR SEQ ID NO:43:

(i) SEQUENCE CHARACTERISTICS:
        (A) LENGTH: 1296 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

| | | | | | |
|---|---|---|---|---|---|
| CCAAGCTATT | AGGTGACACT | ATAGAATACT | CAAGCTATGC | ATCAAGCTTA TGCTTGTCAA | 60 |
| TAATCACAAA | TATGTAGATC | ATATCTTGTT | TAGGACAGTA | AAACATCCTA ATTACTTTTT | 120 |
| AAATATTCTT | CCTGAGTTGA | TTGGCTTGAC | CTTGTTGAGT | CATGCTTATG TGACTTTTGT | 180 |
| TTTAGTTTTT | CCAGTTTATG | CAGTTATTTT | GTATCGACGA | ATAGCTGAAG AGGAAAAGCT | 240 |
| ATTACATGAA | GTTATAATCC | CAAATGGAAG | CATAAAGAGA | TAAATACAAA ATTCGATTTA | 300 |
| TATACAGTTC | ATATTGAAGT | AATATAGTAA | GGTTAAAGAA | AAAATATAGA AGGAAATAAA | 360 |
| CATGTTTGCA | TCAAAAAGCG | AAAGAAAAGT | ACATTATTCA | ATTCGTAAAT TTAGTATTGG | 420 |
| AGTACTAGTG | TAGCTGTTGC | CAGTCTTGTT | ATGGAAGTG | TGGTTCATGC ACCAGAAAAC | 480 |
| GAGGAAGTAC | CCAAGCAGCC | CTTCTTCTAA | TATGGCAAAG | ACAGAACATA GGAAAGCGCT | 540 |
| AAACAGTCGT | CGATGAATAT | ATAGAAAAAA | TGTTGAGGGA | GATTCAACTA GATAGAAGAA | 600 |
| AACATACCCA | AATGTCGCC | TTAAACATAA | AGTTGAGCGC | AATTAAACGA AGTATTTGCG | 660 |
| TGAATTAATG | TTTAGAAGAG | AAGTCGAAAT | GAGTTGCCGT | CAGAAATAAA AGCGAAGTTA | 720 |
| GACGCCGCTT | TTGAAAGTTT | AAAAAAGATA | CATTGAAACC | AGGAGAAAAG GTAGCGAAGC | 780 |
| TAAGAAGAAG | TTGAAGAAGC | TAAGAAAAAG | CCAGGATCAA | AAGAAGAAG ATCGCGTAAC | 840 |
| TACCCAACCA | ATACTTCAAA | ACGCTTGACC | TTGAAATTGC | TGAGTCGATG TGAAAGTTAA | 900 |
| AGAAGCGGAG | CTTGAACTAG | TAAAGAGGAA | GCTGAACTCG | AGACGAGGAA AAAATTAAGC | 960 |
| AAGCAAAAGC | GAAAGTTGAG | AGTAAAAAAG | CTGAGGCTAC | AAGGTTAGAA AACATCAAGA | 1020 |
| CAGATGTAAA | AAAGCAGAAG | AAGAAGTAAA | CGAAAAGCAG | CAGAAGAAGA TAAAGTTAAA | 1080 |
| GAAAAACCAG | CTGAACAACC | ACAACCAGCG | CCGGTACTCA | ACCAGAAAAA CCAGCTCCAA | 1140 |
| AACCAGAGAA | GCCAGCTGAA | CAACCAAAAG | CAGAAAAAAC | AGATGATCAA CAAGCTGAAG | 1200 |
| AAGACTATGC | TCGTAGATCA | GAAGAAGAAT | ATAATCGCTT | GATCAACAGC AACCGCCAAA | 1260 |
| AACTGAAAAA | CCAGCACAAC | CATTACTCCA | AAAACA | | 1296 |

(2) INFORMATION FOR SEQ ID NO:44:

(i) SEQUENCE CHARACTERISTICS:
        (A) LENGTH: 908 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
Ala Ala Ala Ala Ala Gly Cys Thr Ala Ala Cys Thr Ala Thr Cys
1               5                   10                  15

Ala Ala Ala Ala Cys Thr Thr Gly Ala Ala Gly Ala Gly Thr Thr Ala
            20                  25                  30

Ala Gly Thr Gly Ala Thr Ala Ala Gly Ala Thr Gly Ala Thr Gly
        35                  40                  45

Ala Gly Ala Ala Ala Ala Cys Gly Cys Thr Thr Gly Ala Cys Cys Thr
    50                  55                  60

Thr Gly Ala Ala Ala Thr Thr Gly Cys Thr Gly Ala Gly Thr Tyr Cys
65                  70                  75                  80

Gly Ala Thr Gly Thr Gly Ala Ala Ala Gly Thr Thr Ala Ala Ala Gly
                85                  90                  95
```

-continued

```
Ala Ala Thr Thr Ala Gly Ala Cys Gly Cys Thr Gly Ala Ala Ala Thr
            100                 105                 110
Thr Gly Cys Ala Ala Ala Ala Cys Thr Thr Gly Ala Ala Gly Ala Thr
        115                 120                 125

Cys Ala Ala Cys Thr Thr Ala Ala Ala Gly Cys Thr Gly Cys Thr Gly
    130                 135                 140

Ala Ala Gly Ala Gly Cys Gly Gly Ala Gly Cys Thr Thr Gly Ala Ala
145                 150                 155                 160

Cys Thr Ala Gly Thr Ala Ala Ala Arg Gly Ala Gly Gly Ala Ala Gly
                165                 170                 175
Cys Thr Met Met Arg Gly Ala Ala Tyr Cys Thr Cys Gly Ala Gly Ala
            180                 185                 190

Cys Gly Ala Gly Gly Ala Ala Ala Ala Cys Ala Ala Thr Ala Ala Thr
        195                 200                 205

Gly Thr Ala Gly Ala Ala Gly Ala Cys Thr Ala Cys Thr Thr Thr Ala
    210                 215                 220
Ala Ala Gly Ala Ala Gly Gly Thr Thr Thr Ala Gly Ala Gly Ala Ala
225                 230                 235                 240

Ala Ala Cys Thr Ala Thr Thr Gly Ala Ala Ala Ala Ala Thr Thr Ala
                245                 250                 255

Ala Gly Cys Ala Ala Gly Cys Ala Ala Ala Ala Gly Cys Gly Ala Ala
            260                 265                 270
Ala Gly Thr Thr Gly Ala Gly Ala Gly Cys Thr Gly Cys Thr Ala Ala
        275                 280                 285

Ala Ala Ala Ala Gly Cys Thr Gly Ala Ala Thr Thr Ala Gly Ala Ala
    290                 295                 300

Ala Ala Ala Ala Cys Thr Gly Ala Ala Gly Cys Thr Gly Ala Cys Cys
305                 310                 315                 320

Thr Thr Thr Ala Ala Ala Ala Ala Ala Gly Cys Thr Gly Ala Gly Gly
                325                 330                 335

Cys Thr Ala Cys Ala Ala Gly Gly Thr Thr Ala Gly Ala Ala Ala Ala
            340                 345                 350
Cys Ala Thr Cys Ala Ala Gly Ala Cys Ala Gly Ala Thr Asn Gly Thr
        355                 360                 365

Ala Ala Gly Ala Ala Ala Gly Cys Ala Gly Thr Thr Ala Ala Thr Gly
    370                 375                 380

Ala Gly Cys Cys Ala Gly Ala Ala Ala Ala Ala Cys Cys Ala Gly Cys
385                 390                 395                 400
Thr Cys Cys Ala Gly Cys Thr Cys Cys Ala Gly Ala Ala Ala Cys Thr
                405                 410                 415

Cys Cys Ala Ala Ala Ala Ala Ala Gly Cys Ala Gly Ala Ala Gly Ala
            420                 425                 430
Ala Gly Ala Ala Gly Asn Thr Ala Ala Ala Cys Gly Ala Ala Ala Ala
        435                 440                 445

Gly Cys Ala Gly Cys Ala Gly Ala Ala Gly Ala Ala Gly Ala Thr Ala
    450                 455                 460

Ala Ala Gly Cys Cys Cys Cys Ala Gly Ala Ala Gly Cys Ala Cys Cys
465                 470                 475                 480

Ala Gly Cys Thr Gly Ala Ala Cys Ala Ala Cys Cys Ala Ala Ala Ala
                485                 490                 495

Cys Cys Ala Gly Cys Gly Cys Cys Gly Gly Cys Thr Cys Cys Thr Cys
            500                 505                 510
```

-continued

```
Ala Ala Cys Ala Gly Thr Thr Ala Ala Ala Gly Ala Ala Ala Ala Ala
        515                 520                 525

Cys Cys Ala Gly Cys Thr Gly Ala Ala Cys Ala Ala Cys Cys Ala Cys
    530                 535                 540

Ala Ala Cys Cys Ala Gly Cys Gly Cys Cys Gly Gly Asn Thr Ala Cys
545                 550                 555                 560

Thr Cys Ala Ala Cys Cys Ala Gly Cys Thr Cys Cys Cys Gly Cys Ala
                565                 570                 575

Cys Cys Ala Ala Ala Ala Cys Cys Ala Gly Ala Gly Ala Ala Gly Cys
            580                 585                 590

Cys Ala Gly Cys Thr Gly Ala Ala Cys Ala Ala Cys Cys Ala Ala Ala
        595                 600                 605

Ala Cys Cys Ala Cys Ala Gly Ala Ala Ala Ala Ala Cys Cys Ala Gly
    610                 615                 620

Cys Thr Cys Cys Ala Ala Ala Ala Cys Cys Ala Gly Ala Gly Ala Ala
625                 630                 635                 640

Gly Cys Cys Ala Gly Cys Thr Gly Ala Ala Cys Ala Ala Cys Cys Ala
                645                 650                 655

Ala Ala Ala Gly Cys Ala Gly Ala Ala Ala Ala Ala Ala Cys Ala Gly
            660                 665                 670

Ala Thr Gly Ala Thr Cys Ala Ala Cys Ala Ala Gly Cys Thr Gly Ala
        675                 680                 685

Ala Gly Ala Ala Gly Ala Cys Thr Ala Thr Gly Cys Thr Cys Gly Thr
    690                 695                 700

Ala Gly Ala Thr Cys Ala Gly Ala Gly Ala Ala Ala Ala Ala Ala Cys
705                 710                 715                 720

Ala Gly Ala Thr Gly Ala Thr Cys Ala Ala Cys Ala Ala Gly Cys Thr
                725                 730                 735

Gly Ala Ala Gly Ala Ala Gly Ala Cys Thr Ala Thr Gly Cys Thr Cys
            740                 745                 750

Gly Thr Ala Gly Ala Thr Cys Ala Gly Ala Ala Gly Ala Ala Gly Ala
        755                 760                 765

Ala Thr Ala Thr Ala Ala Thr Cys Gly Cys Thr Thr Gly Ala Cys Thr
    770                 775                 780

Cys Ala Ala Cys Ala Gly Cys Ala Ala Cys Cys Gly Cys Cys Ala Ala
785                 790                 795                 800

Ala Ala Gly Cys Thr Gly Ala Ala Ala Ala Ala Cys Ala Gly Ala Ala
                805                 810                 815

Gly Ala Ala Thr Ala Thr Ala Ala Thr Cys Gly Cys Thr Thr Gly Ala
            820                 825                 830

Asn Thr Cys Ala Ala Cys Ala Gly Cys Ala Ala Cys Cys Gly Cys Cys
        835                 840                 845

Ala Ala Ala Ala Ala Cys Thr Gly Ala Ala Ala Ala Ala Cys Cys Ala
    850                 855                 860

Gly Cys Thr Cys Cys Thr Gly Cys Ala Cys Cys Ala Ala Ala Ala Ala
865                 870                 875                 880

Cys Ala Cys Ala Gly Cys Ala Cys Ala Ala Cys Cys Ala Thr Asn Thr
                885                 890                 895

Ala Cys Thr Cys Cys Ala Ala Ala Ala Ala Cys Ala
            900                 905
```

(2) INFORMATION FOR SEQ ID NO:45:

(i) SEQUENCE CHARACTERISTICS:

(A) LENGTH: 2059 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:45:

| | | | | | |
|---|---|---|---|---|---|
| AAGCTTATGC | TTGTCAATAA | TCACAAATAT | GTAGATCATA | TCTTGTTTAG | AAGCTTATGC | 60 |
| TTGTCAATAA | TCACAAATAT | GTAGATCATA | TCTTGTTTAG | GACAGTAAAA | CATCCTAATT | 120 |
| ACTTTTTAAA | TATTTTACCT | GAGTTGATTG | GACAGTAAAA | CATCCTAATT | ACTTTTTAAA | 180 |
| TATTCTTCCT | GAGTTGATTG | GCTTGACCTT | GTTGAGTCAT | GCCTATATGA | CTTTTGTTTT | 240 |
| AGTTTTTCCA | GCTTGACCTT | GTTGAGTCAT | GCTTATGTGA | CTTTTGTTTT | AGTTTTTCCA | 300 |
| GTTTATGCAG | TTATTTTGTA | TCGACGAATA | GCTGAAGAGG | AAAAGTTATT | GTTTATGCAG | 360 |
| TTATTTTGTA | TCGACGAATA | GCTGAAGAGG | AAAAGCTATT | ACATGAAGTT | ATAATCCCAA | 420 |
| ATGGAAGCAT | AAAGAGATAA | ATACAAAATT | ACATGAAGTT | ATAATCCCAA | ATGGAAGCAT | 480 |
| AAAGAGATAA | ATACAAAATT | CGATTTATAT | ACAGTTCATA | TTGAAGTGAT | ATAGTAAGGT | 540 |
| TAAAGAAAAA | CGATTTATAT | ACAGTTCATA | TTGAAGTAAT | ATAGTAAGGT | TAAAGAAAAA | 600 |
| ATATAGAAGG | AAATAAACAT | GTTTGCATCA | AAAAGCGAAA | GAAAAGTACA | ATATAGAAGG | 660 |
| AAATAAACAT | GTTTGCATCA | AAAAGCGAAA | GAAAAGTACA | TTATTCAATT | CGTAAATTTA | 720 |
| GTATTGGAGT | AGCTAGTGTA | GCTGTTGCCA | TTATTCAATT | CGTAAATTTA | GTATTGGAGT | 780 |
| ACTAGTGTAG | CTGTTGCCAG | CTTGTTCTTA | GGAGGAGTAG | TCCATGCAGA | AGGGGTTAGA | 840 |
| AGTGGGAATG | TCTTGTTATG | GGAAGTGTGG | TTCATGCACC | AGAAAACGAG | GAAGAACCTC | 900 |
| ACGGTTACAT | CTAGTGGGCA | AGATATATCG | AAGAAGTATG | TACCCAAGCA | GCCCTTCTTC | 960 |
| TAATATGGCA | AAGACAGAAC | ATAGGAAAGC | TGATGAAGTC | GAGTCGCATC | TAGAAAGTAT | 1020 |
| ATTGAAGGAT | GTCCGCTAAA | CAGTCGTCGA | TGAATATATA | GAAAAAATGT | TGAGGGAGAT | 1080 |
| TAAAAAAAAT | TTGAAAAAAG | TTCAACATAC | CCAAAATGTC | GGCTTAATTA | CCAACTAGAT | 1140 |
| AGAAGAAAAC | ATACCCAAAA | TGTCGCCTTA | AACATAAAGT | TGAGCGAAAT | TAAAAAGAAG | 1200 |
| TATTTGTATG | ACTTAAAAGT | TAAAAGTTGA | GCGCAATTAA | ACGAAGTATT | TGCGTGAATT | 1260 |
| AATGTTTAGA | TGTTTTATCG | GAAGCTGAGT | TGACGTCAAA | AACAAAGAA | ACAAAAGAAA | 1320 |
| AGAGAAGTCG | AAATGAGTTG | CCGTCAGAAA | TAAAAGCGAA | GTTAACCGCA | ACTTTTGAGC | 1380 |
| AGTTTAAAAA | AGATACATTA | CCAACAGAAA | GTTAGACGCC | GCTTTTGAAA | GTTTAAAAAA | 1440 |
| GATACATTGA | AACCAGAAAA | AAAGGTAGCA | GAAGCTCAGA | AGAAGGTTGA | AGAAGCTAAG | 1500 |
| AACCAGGAGA | AAAGGTAGCG | AAGCTAAGAA | GAAGTTGAAG | AAGCTAAGAA | AAAAGCCGAG | 1560 |
| GATCAAAAAG | AAAAAGATCG | CCGTAACTAC | CCAACCATTA | AAAGCCAGGA | TCAAAAAGAA | 1620 |
| GAAGATCGCG | TAACTACCCA | ACCAATACTT | ACAAAACGCT | TGAACTTGAA | ATTGCTGAGT | 1680 |
| CCGATGTGGA | AGTTAAACTT | CAAAACGCTT | GACCTTGAAA | TTGCTGAGTC | GATGTGAAAG | 1740 |
| TTAAAAAAGC | GGAGCTTGAA | CTAGTAAAAG | TGAAAGCTAA | GGAATCTCAA | GACGAGAAGC | 1800 |
| GGAGCTTGAA | CTAGTAAAGA | GGAAGCTGAA | CTCGAGACGA | GGAAAAAATT | AAGCAAGCAG | 1860 |
| AAGCGGAAGT | TGAGAGTAAA | CAAGCTGAGA | GGAAAAAATT | AAGCAAGCAA | AAGCGAAAGT | 1920 |
| TGAGAGTAAA | AAAGCTGAGG | CTACAAGGTT | AAAAAAAATC | AAGACAGATC | GTGAAGAGCT | 1980 |
| ACAAGGTTAG | AAAACATCAA | GACAGATGTA | AAAAAGCAGA | GAAGAAGCT | AAACGAAAAG | 2040 |
| CAGAGTAAAC | GAAAAGCAG | | | | | 2059 |

(2) INFORMATION FOR SEQ ID NO:46:

(i) SEQUENCE CHARACTERISTICS:
        (A) LENGTH: 605 amino acids
        (B) TYPE: amino acid
        (C) STRANDEDNESS: single
        (D) TOPOLOGY: linear (ii) MOLECULE TYPE: amino acid (xi) SEQUENCE DESCRIPTION: SEQ ID NO:46:

```
Ser Gln Thr Glu His Arg Lys Asp Val Asp Glu Tyr Ile Lys Lys Met
  1               5                  10                  15

Leu Ser Glu Ile Gln Leu Asp Arg Arg Lys His Thr Gln Asn Val Asn
             20                  25                  30

Leu Asn Ile Lys Leu Ser Ala Ile Lys Thr Lys Tyr Leu Tyr Ala Lys
         35                  40                  45

Thr Glu His Arg Lys Ala Ala Lys Xaa Val Val Asp Glu Tyr Ile Glu
     50                  55                  60

Lys Met Leu Arg Glu Ile Gln Leu Asp Arg Arg Lys His Thr Gln Asn
 65                  70                  75                  80

Val Ala Leu Asn Ile Lys Leu Ser Ala Ile Xaa Thr Lys Tyr Leu Arg
                 85                  90                  95

Glu Leu Ser Val Leu Lys Glu Asn Ser Lys Lys Glu Glu Leu Thr Ser
             100                 105                 110

Lys Thr Lys Ala Glu Leu Thr Ala Ala Phe Glu Gln Phe Lys Lys Asp
         115                 120                 125

Thr Leu Lys Pro Glu Lys Lys Val Ala Glu Ala Glu Lys Lys Val Glu
     130                 135                 140

Glu Ala Glu Leu Xaa Val Xaa Glu Gly Lys Ser Xaa Xaa Glu Leu Pro
145                 150                 155                 160

Ser Glu Ile Lys Ala Lys Leu Asp Ala Ala Phe Xaa Lys Phe Lys Lys
                 165                 170                 175

Asp Thr Leu Lys Pro Gly Glu Lys Val Ala Glu Ala Lys Lys Xaa Val
             180                 185                 190

Glu Glu Ala Lys Lys Lys Ala Lys Asp Gln Lys Glu Glu Asp Arg Arg
         195                 200                 205

Asn Tyr Pro Thr Asn Thr Tyr Lys Thr Leu Glu Leu Glu Ile Ala Glu
     210                 215                 220

Ser Asp Val Lys Val Lys Glu Ala Glu Leu Glu Leu Val Lys Glu Glu
225                 230                 235                 240

Ala Asn Glu Ser Arg Lys Xaa Lys Ala Xaa Asp Gln Lys Glu Glu Asp
                 245                 250                 255

Arg Arg Asn Tyr Pro Thr Asn Thr Xaa Lys Thr Leu Asp Leu Glu Ile
             260                 265                 270

Ala Glu Xaa Asp Val Lys Val Lys Glu Ala Glu Leu Glu Leu Val Lys
         275                 280                 285

Glu Glu Ala Xaa Glu Xaa Arg Asn Glu Glu Lys Ile Lys Gln Ala Lys
     290                 295                 300

Glu Lys Val Glu Ser Lys Lys Ala Glu Ala Thr Arg Leu Glu Lys Ile
305                 310                 315                 320

Lys Thr Asp Arg Lys Lys Ala Glu Glu Ala Lys Arg Lys Ala Glu
                 325                 330                 335

Glu Ser Glu Lys Lys Ala Ala Glu Ala Asp Glu Lys Ile Lys Gln
             340                 345                 350
```

```
Ala Lys Ala Lys Val Glu Ser Lys Lys Ala Glu Ala Thr Arg Leu Glu
            355                 360                 365

Asn Ile Lys Thr Asp Xaa Lys Lys Ala Glu Glu Xaa Lys Arg Lys
        370                 375                 380

Ala Ala Glu Glu Asp Lys Ser Lys Leu Asp Thr Lys Lys Ala Lys Leu
385                 390                 395                 400

Ser Lys Leu Glu Glu Leu Ser Asp Lys Ile Asp Glu Leu Asp Ala Glu
                405                 410                 415

Ile Ala Lys Leu Glu Val Gln Leu Lys Asp Ala Glu Gly Asn Asn Asn
                420                 425                 430

Val Glu Ala Tyr Phe Lys Glu Gly Val Lys Glu Lys Pro Ala Glu Gln
            435                 440                 445

Leu Glu Lys Thr Thr Ala Glu Lys Lys Ala Glu Leu Glu Lys Ala Glu
    450                 455                 460

Ala Asp Leu Lys Lys Ala Val Asp Glu Pro Glu Thr Pro Ala Pro Ala
465                 470                 475                 480

Pro Gln Pro Ala Pro Ala Pro Glu Lys Pro Ala Glu Lys Pro Ala Pro
                485                 490                 495

Ala Pro Pro Gln Pro Ala Pro Xaa Thr Gln Pro Glu Lys Pro Ala Pro
                500                 505                 510

Lys Pro Glu Lys Pro Ala Glu Gln Pro Lys Ala Glu Lys Glu Lys Pro
            515                 520                 525

Ala Pro Ala Pro Glu Lys Pro Ala Pro Ala Pro Glu Lys Pro Ala Pro
            530                 535                 540

Ala Pro Glu Lys Pro Ala Pro Ala Pro Glu Lys Pro Ala Pro Thr Pro
545                 550                 555                 560

Glu Thr Pro Lys Thr Thr Asp Asp Gln Gln Ala Glu Glu Asp Tyr Ala
                565                 570                 575

Arg Arg Ser Glu Glu Gly Tyr Asn Arg Leu Xaa Gln Gln Gln Pro Pro
                580                 585                 590

Lys Thr Glu Lys Pro Ala Gln Pro Xaa Thr Pro Lys Thr
            595                 600                 605

(2) INFORMATION FOR SEQ ID NO:47:

(i) SEQUENCE CHARACTERISTICS:
        (A) LENGTH: 623 amino acids
        (B) TYPE: amino acid
        (C) STRANDEDNESS: single
        (D) TOPOLOGY: linear (ii) MOLECULE TYPE: amino acid (xi) SEQUENCE DESCRIPTION: SEQ ID NO:47:

Ala Lys Lys Asp Ala Lys Asn Ala Lys Lys Ala Val Glu Asp Ala Gln
1               5                   10                  15

Lys Ala Leu Asp Asp Ala Lys Ala Ala Gln Lys Lys Tyr Asp Glu Asp
                20                  25                  30

Gln Lys Lys Thr Glu Glu Lys Ala Ala Leu Glu Lys Ala Ala Ser Glu
            35                  40                  45

Glu Met Ala Lys Thr Glu His Arg Lys Ala Ala Lys Xaa Val Val Asp
    50                  55                  60

Glu Tyr Ile Glu Lys Met Leu Arg Glu Ile Gln Leu Asp Arg Arg Lys
65              70                  75                  80

His Thr Gln Asn Val Ala Leu Asn Ile Lys Leu Ser Ala Ile Xaa Asp
                85                  90                  95
```

-continued

```
Lys Ala Val Ala Ala Val Gln Gln Ala Tyr Leu Ala Tyr Gln Gln Ala
                100                 105                 110
Thr Asp Lys Ala Ala Lys Asp Ala Ala Asp Lys Met Ile Asp Glu Ala
            115                 120                 125
Lys Lys Arg Glu Glu Glu Ala Lys Thr Lys Phe Asn Thr Val Arg Ala
        130                 135                 140
Met Thr Lys Tyr Leu Arg Glu Leu Xaa Val Xaa Glu Glu Lys Ser Xaa
145                 150                 155                 160
Xaa Glu Leu Pro Ser Glu Ile Lys Ala Lys Leu Asp Ala Ala Phe Xaa
                165                 170                 175
Lys Phe Lys Lys Asp Val Val Pro Glu Pro Glu Gln Leu Ala Glu Thr
            180                 185                 190
Lys Lys Lys Ser Glu Glu Ala Lys Gln Lys Ala Pro Glu Leu Thr Lys
        195                 200                 205
Lys Leu Glu Glu Ala Lys Ala Lys Leu Glu Glu Ala Glu Lys Lys Ala
        210                 215                 220
Thr Glu Ala Lys Gln Lys Val Thr Leu Lys Pro Gly Glu Lys Val Ala
225                 230                 235                 240
Glu Ala Lys Lys Xaa Val Glu Ala Lys Xaa Lys Ala Xaa Asp Gln
                245                 250                 255
Lys Glu Glu Asp Arg Arg Asn Tyr Pro Thr Asn Thr Xaa Lys Thr Leu
            260                 265                 270
Asp Ala Glu Glu Val Ala Pro Gln Ala Lys Ile Ala Glu Leu Glu Asn
        275                 280                 285
Gln Val His Arg Leu Glu Gln Glu Leu Lys Glu Ile Asp Glu Ser Glu
        290                 295                 300
Ser Glu Asp Tyr Ala Lys Glu Gly Phe Arg Ala Pro Leu Gln Ser Lys
305                 310                 315                 320
Leu Asp Asp Leu Glu Thr Ala Glu Xaa Asp Val Lys Val Lys Glu Ala
                325                 330                 335
Glu Leu Glu Leu Val Lys Glu Glu Ala Xaa Glu Xaa Arg Asp Glu Glu
            340                 345                 350
Lys Ile Lys Gln Ala Lys Ala Lys Val Glu Ala Lys Lys Ala Lys Leu
        355                 360                 365
Ser Lys Leu Glu Glu Leu Ser Asp Lys Ile Asp Glu Leu Asp Ala Glu
        370                 375                 380
Ile Ala Lys Leu Glu Asp Gln Leu Lys Ala Ala Glu Glu Asn Asn Asn
385                 390                 395                 400
Val Glu Asp Tyr Phe Lys Glu Gly Leu Glu Lys Thr Ser Lys Lys Ala
                405                 410                 415
Glu Ala Thr Arg Leu Glu Asn Ile Ile Ala Ala Lys Lys Ala Glu Leu
            420                 425                 430
Glu Lys Thr Glu Ala Asp Leu Lys Lys Ala Val Asn Glu Pro Glu Lys
        435                 440                 445
Pro Ala Pro Ala Pro Glu Thr Pro Ala Pro Glu Ala Pro Ala Glu Gln
        450                 455                 460
Pro Lys Pro Ala Pro Ala Pro Gln Pro Ala Lys Thr Asp Xaa Lys Lys
465                 470                 475                 480
Ala Glu Glu Glu Xaa Lys Arg Lys Ala Ala Glu Glu Asp Lys Val Lys
                485                 490                 495
Glu Lys Pro Ala Glu Gln Pro Gln Pro Ala Pro Xaa Thr Gln Pro Glu
            500                 505                 510
```

-continued

```
Pro Ala Pro Lys Pro Glu Lys Pro Ala Glu Gln Pro Lys Pro Glu Lys
        515                 520                 525

Thr Asp Asp Gln Gln Ala Glu Glu Asp Tyr Ala Arg Arg Ser Glu Glu
        530                 535                 540

Glu Tyr Asn Arg Leu Thr Gln Gln Gln Pro Pro Lys Ala Glu Lys Pro
545                 550                 555                 560

Ala Lys Pro Ala Pro Lys Pro Glu Lys Pro Ala Glu Gln Pro Lys Ala
            565                 570                 575

Glu Lys Thr Ile Asp Gln Gln Ala Glu Glu Tyr Ala Arg Arg Ser
                580                 585                 590

Glu Glu Glu Tyr Asn Arg Leu Xaa Gln Gln Gln Pro Pro Lys Thr Glu
        595                 600                 605

Lys Pro Ala Pro Ala Pro Lys Thr Gln Pro Xaa Thr Pro Lys Thr
    610                 615                 620
```

PNEUMOCOCCAL SURFACE PROTEINS AND USES THEREOF

RELATED APPLICATIONS

This application is a continuation-in-part ("CIP"): of application Ser. No. 08/529,055, filed Sep. 15, 1995, Reference is also made to applications Ser. No. 08/093,907, filed May 29, 1992, Ser. No. 07/884,918, filed Jul. 5, 1994 (corresponding to PCT/US93/05191); of application Ser. No. 08/482,981, filed Jun. 7, 1995; of application Ser. No. 08/458,399, filed Jun. 2, 1995; of application Ser. No. 08/446,201, filed May 19, 1995 (as a CIP of U.S. Ser. No. 08/246,636); of application Ser. No. 08/246,636, filed May 20, 1994 (as a CIP of U.S. Ser. No. 08/048,896, filed Apr. 20, 1993 as a CIP of U.S. Ser. No. 07/835,698, filed Feb. 12, 1992 as a CIP of U.S. Ser. No. 07/656,773); of application Ser. No. 08/319,795, filed Oct. 7, 1994 (as a CIP of U.S. Ser. No. 08/246,636); of application Ser. No. 08/072,070, filed Jun. 3, 1993; of application Ser. No. 07/656,773, filed Feb. 15, 1991 (U.S. Ser. Nos. 656,773 and 835,698 corresponding to Int'l application WO 92/1448); and, each of these applications, as well as each application, document or reference cited in these applications, is hereby incorporated herein by reference. Documents or references are also cited in the following text, either in a Reference List appended to certain Examples, or before the claims, or in the text itself; and, each of these documents or references is hereby expressly incorporated herein by reference.

FIELD OF THE INVENTION

This invention relates to pneumococcal genes, portions thereof, expression products therefrom and uses of such genes, portions and products; especially to genes of *Streptococcus pneumoniae*, e.g., the gene encoding pneumococcal surface protein A (PspA) (said gene being "pspA"), pspA-like genes, pneumococcal surface protein C (PspC) (said gene being "pspC"), portions of such genes, expression products therefrom, and the uses of such genes, portions thereof and expression products therefrom. Such uses include uses of the genes and portions thereof for obtaining expression products by recombinant techniques, as well as for detecting the presence of Streptococcus pneumoniae or strains thereof by detecting DNA thereof by hybridization or amplification (e.g., PCR) and hybridization techniques (e.g., obtaining DNA-containing sample, contacting same with genes or fragment under PCR, amplification and/or hybridization conditions, and detecting presence of or isolating hybrid or amplified product). The expression product uses include use in preparing antigenic, immunological or vaccine compositions, for eliciting antibodies, an immunological response (other than or additional to antibodies) or a protective response (including antibody or other immunological response by administering composition to a suitable host); or, the expression product can be for use in detecting the presence of Streptococcus pneumoniae by detecting antibodies to Streptococcus pneumoniae protein(s) or antibodies to a portion thereof in a host, e.g., by obtaining an antibody-containing sample from a relevant host, contacting the sample with expression product and detecting binding (for instance by having the product labeled); and, the antibodies generated by the aforementioned compositions are useful in diagnostic or detection kits or assays. Thus, the invention relates to varied compositions of matter and methods for use thereof.

BACKGROUND OF THE INVENTION

*Streptococcus pneumoniae* is an important cause of otitis media, meningitis, bacteremia and pneumonia. Despite the use of antibiotics and vaccines, the prevalence of pneumococcal infections has declined little over the last twenty-five years.

It is generally accepted that immunity to *Streptococcus pneumoniae* can be mediated by specific antibodies against the polysaccharide capsule of the pneumococcus. However, neonates and young children fail to make an immune response against polysaccharide antigens and can have repeated infections involving the same capsular serotype.

One approach to immunizing infants against a number of encapsulated bacteria is to conjugate the capsular polysaccharide antigens to protein to make them immunogenic. This approach has been successful, for example, with *Haemophilus influenzae* b (see U.S. Pat. No. 4,496,538 to Gordon and U.S. Pat. No. 4,673,574 to Anderson). However, there are over eighty known capsular serotypes of *S. pneumoniae* of which twenty-three account for most of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all adequately immunogenic, even in adults.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

McDaniel et al. (I), J. Exp. Med. 160:386–397, 1984, relates to the production of hybridoma antibodies that recognize cell surface polypeptide(s) on *S. pneumoniae* and protection of mice from infection with certain strains of encapsulated pneumococci by such antibodies. This surface protein antigen has been termed "pneumococcal surface protein A" or PspA for short.

McDaniel et al. (II), Microbial Pathogenesis 1:519–531, 1986, relates to studies on the characterization of the PspA. Considerable diversity in the PspA molecule in different strains was found, as were differences in the epitopes recognized by different antibodies.

McDaniel et al. (III), J. Exp. Med. 165:381–394, 1987, relates to immunization of X-linked immunodeficient (XID) mice with non-encapsulated pneumococci expressing PspA, but not isogenic pneumococci lacking PspA, which protects mice from subsequent fatal infection with pneumococci.

McDaniel et al. (IV), Infect. Immun., 59:222–228, 1991, relates to immunization of mice with a recombinant full length fragment of PspA. that is able to elicit protection against pneumococcal strains of capsular types 6A and 3.

Crain et al, Infect.Immun., 56:3293–3299, 1990, relates to a rabbit antiserum that detects PspA in 100% (n=95) of clinical and laboratory isolates of strains of *S. pneumoniae*. When reacted with seven monoclonal antibodies to PspA, fifty-seven *S. pneumoniae* isolates exhibited thirty-one different patterns of reactivity.

The PspA protein type is independent of capsular type. it would seem that genetic mutation or exchange in the environment has allowed for the development of a large pool of strains which are highly diverse with respect to capsule, PspA, and possibly other molecules with variable structures. Variability of PspA's from different strains also is evident in their molecular weights, which range from 67 to 99 kD. The observed differences are stably inherited and are not the result of protein degradation.

Immunization with a partially purified PspA from a recombinant λ gt11 clone, elicited protection against challenge with several *S. pneumoniae* strains representing different capsular and PspA types, as described in McDaniel et al. (IV), Infect. Immun. 59:222–228, 1991. Although clones expressing PspA were constructed according to that paper, the product was insoluble and isolation from cell fragments following lysis was not possible.

While the protein is variable in structure between different pneumococcal strains, numerous cross-reactions exist between all PspA's, suggesting that sufficient common epitopes may be present to allow a single PspA or at least a small number of PspA's to elicit protection against a large number of *S. pneumoniae* strains.

In addition to the published literature specifically referred to above, the inventors, in conjunction with co-workers, have published further details concerning PspA's, as follows:

1. Abstracts of 89th Annual Meeting of the American Society for Microbiology, p. 125, item D-257, May 1989;
2. Abstracts of 90th Annual Meeting of the American Society for Microbiology, p. 98, item D-106, May 1990;
3. Abstracts of 3rd International ASM Conference on Streptococcal Genetics, p. 11, item 12, June 1990;
4. Talkington et al, Infect. Immun. 59:1285–1289, 1991;
5. Yother et al (I), J. Bacteriol. 174:601–609, 1992; and
6. Yother et al (II), J. Bacteriol. 174:610–618, 1992.
7. McDaniel et al (V), Microbiol. Pathogenesis, 13:261–268.

It would be useful to provide PspA or fragments thereof in compositions, including PspA's or fragments from varying strains in such compositions, to provide antigenic, immunological or vaccine compositions; and, it is even further useful to show that the various strains can be grouped or typed, thereby providing a basis for cross-reactivities of PspA's or fragments thereof, and thus providing a means for determining which strains to represent in such compositions (as well as how to test for, detect or diagnose one strain from another).

Further, it would be advantageous to provide a pspA-like gene or a pspC gene in certain strains, as well as primers (oligonucleotides) for identification of such a gene, as well as of conserved regions in that gene and in pspA; for instance, for detecting, determining, isolating, or diagnosing strains of *S. pneumonia*. These uses and advantages, it is believed, have not heretofore been provided in the art.

OBJECTS AND SUMMARY OF THE INVENTION

The invention provides an isolated amino acid molecule comprising residues 1 to 115, 1 to 260, 192 to 588, 192 to 299, or residues 192 to 260 of pneumococcal surface protein A of *Streptococcus pneumoniae*.

The invention further provides an isolated DNA molecule comprising a fragment of a pneumococcal surface protein A gene of *Streptococcus pneumoniae* encoding the isolated amino acid molecule.

The invention also provides PCR primers or hybridization probes comprising the isolated DNA molecule.

The invention additionally provides an antigenic, vaccine or immunological composition comprising the amino acid molecule.

The invention includes an isolated DNA molecule comprising nucleotides 1 to 26, 1967 to 1990, 161 to 187, 1093 to 1117, or 1312 to 1331 or 1333 to 1355 of a pneumococcal surface protein A gene of *Streptococcus pneumoniae*. The DNA molecule can be used as a PCR primer or hybridization probe; and therefore the invention comprehends a PCR primer or hybridization probe comprising the isolated DNA molecule.

The invention also includes an isolated DNA molecule comprising a fragment having homology with a portion of a pneumococcal surface protein A gene of *Streptococcus pneumoniae*. The DNA preferably is the following (which include the portion having homology and restriction sites, and selection of other restriction sites or sequences for such DNA is within the ambit of the skilled artisan from this disclosure):

CCGGATCCAGCTCCTGCACCAAAAAC SEQ ID NO:1;
GCGCGTCGACGGCTTAAACCCATTCACCATTGG SEQ ID NO:2;
CCGGATCCTGAGCCAGAGCAGTTGGCTG SEQ ID NO:3;
CCGGATCCGCTCAAAGAGATTGATGAGTCTG SEQ ID NO:4;
GCGGATCCCGTAGCCAGTCAGTCTAAAGCTG SEQ ID NO:5;
CTGAGTCGACTGGAGTTTCTGGAGCTGGAGC SEQ ID NO:6;
CCGGATCCAGCTCCAGCTCCAGAAACTCCAG SEQ ID NO:7;
GCGGATCCTTGACCAATATTTACGGAGGAGGC SEQ ID NO:8;
GTTTTTGGTGCAGGAGCTGG SEQ ID NO:9;
GCTATGGGCTACAGGTTG SEQ ID NO:10;
CCACCTGTAGCCATAGC SEQ ID NO:11;
CCGCATCCAGCGTGCCTATCTTAGGGGCTGGTT SEQ ID NO:12; and
GCAAGCTTATGATATAGAAATTTGTAAC SEQ ID NO:13

(thus, the invention broadly comprehends DNA homologous to portions of pspA; preferably further including restriction sequences)

These DNA molecules can be used as PCR primers or probes; and thus, the invention comprehends a primer or probe comprising and of these molecules.

The invention further still provides PCR probe(s) which distinguishes between pspA and pspA-like nucleotide sequence, as well as PCR probe(s) which hybridizes to both pspA and pspA-like nucleotide sequences.

Additionally, the invention includes a PspA extract prepared by a process comprising: growing pneumococci in a first medium containing choline chloride, eluting live pneumococci with a choline chloride containing salt solution, and growing the pneumococci in a second medium containing an alkanolamine and substantially no choline; as well as a PspA extract prepared by that process and further comprising purifying PspA by isolation on a choline-Sepharose affinity column. These processes are also included in the invention.

An immunological composition comprising these extracts is comprehended by the invention, as well as an immunological composition comprising the full length PspA.

A method for enhancing the immunogenicity of a PspA-containing immunological composition comprising, in said composition, the C-terminal portion of PspA, is additionally comprehended, as well.

An immunological composition comprising at least two PspAs. The latter immunological composition can have the PspAs from different groups or families; the groups or families can be based on RFLP or sequence studies (see, e.g., FIG. 13).

Further, the invention provides an isolated amino acid molecule comprising pneumococcal surface protein C, PspC, of *Streptococcus pneumoniae* having an alpha-helical, proline rich and repeat regions, an isolated DNA molecule comprising a pneumcoccal surface protein C gene encoding the aforementioned PspC, and primers and hybrization probes consisting essentially of the isolated DNA molecule.

Still further, an isolated amino acid molecule comprising pneumococcal surface protein C, PspC, of *Streptococcus pneumoniae* is provided, having an alpha-helical, proline rich and repeat regions, having substantial homology with a protection eliciting region of PspA, and an isolated DNA molecule comprising a pneumoccal surface protein C gene encoding the aforementioned PspC, and primers and hybridization probes consisting essentially of the isolated DNA molecule are provided by the present invention.

Additionally, the present invention provides immunological compositions comprising PspC.

These and other embodiments are disclosed or are obvious from the following detailed description.

BRIEF DESCRIPTION OF THE FIGURES

FIGS. 1A and 1B show: Evaluation of digested plasmid constructs. FIG. 1A: 1% agarose gel electrophoresis of plasmids isolated from transformed *E. coli* BL21(DE3) strains stained with ethidium bromide. Lane 1: 1 kb DNA ladder (sizes noted in kb), lane 2: pRCT125; lane 3: Pro105, lane 4: DBL5 pspA insert, lane 5: pPRCT113, lane 6: BG9739 pspA insert, lane 7: 8: pRCT117, and lane of: L81905 psPA insert. FIG. 1B: Corresponding Southern blot of gel in FIG. 1A probed with full-length Rx1 pspA and hybridization detected as described in Example 1. The arrow indicates the 1.2 kb psnA digested inserts from plasmid constructs and the PCR-amplified psPA fragments from the pneumococcal donor strains used in cloning.

Figures 5A, 5B:
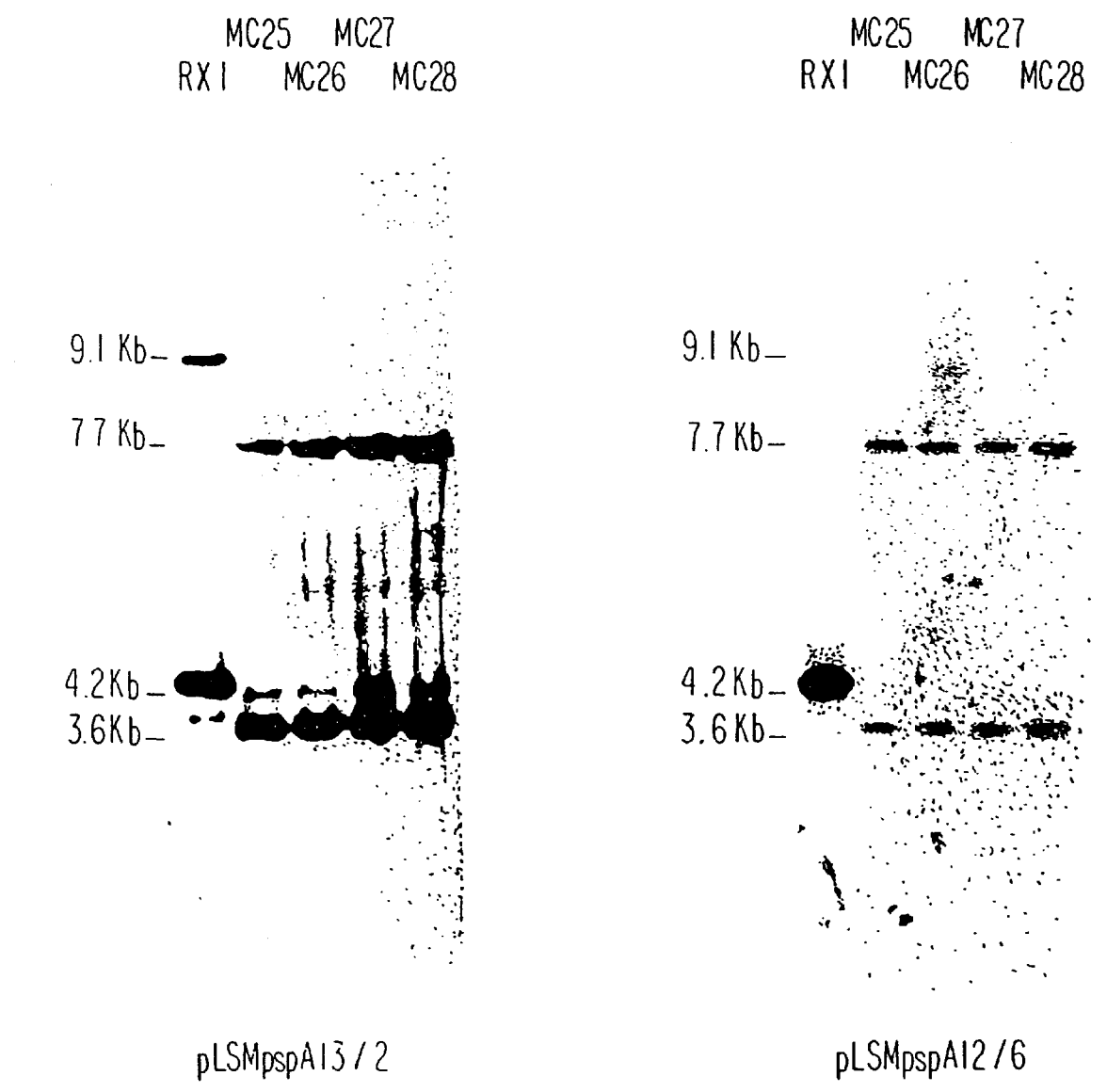

FIG. 5 (FIGS. 5A and 5B) shows: Southern blot of Hind III digest of MC25–MC28 chromosomal DNA developed at a stringency greater than 95 percent. A digest of Rx1 DNA was used as a comparison. The blot was probed with LSMpspA13/2, a full length Rx1 probe (FIG. 5) and LSMpspA12/6 a 5' probe of Rx1 pspA (FIG. 5). The same concentration of Rx1 DNA was used in both panels, but the concentrations of MC25–MC28 DNA in FIG. 5B were half that used in FIG. 5A to avoid detection of partial digests.

FIG. 13 (SEQ ID NOS:32,33,34) shows: Sequence primarily in the N-terminal half of PspA.

FIGS. 15C and 15D (SEQ ID NOS:35 and 36) show: the nucleotide sequences of primers LSM13, LSM2, LSM12 and LSM6, and that of probes LSMpspA13/2 and LSMpspA12/6.

FIG. 19 shows: the nucleotide sequences of SKH2, LSM13, N192 and C588.

FIG. 21 (SEQ ID NOS:39 and 40) shows: the amino acid and nucleotide sequence of PspC, wherein the putative −10 and −35 regions are underlined, and the ribosomal binding site is in lower case.

FIG. 22 (SEQ ID NO:41) shows: the Bestfit analysis of PspA and PspC; percent identity is 69% and percent similarity is 77%; amino acids of PspA are one the bottom line (1–588) and amino acids of PspC are on the top line (249–891), and a dashed line indicated identity.

FIG. 23 (SEQ ID NO:42) shows: the coiled coil motif of the alpha- helix of PspC; amino acids that are not in the coiled coil motif are in the right column.

FIG. 25 (SEQ ID NO:43) shows: the sequence of the alpha helical and proline regions of LXS532 (PspC.D39).

FIG. 26 (SEQ ID NO:44) shows: a comparison of nucleotides of pspA.Rx1 to pspC.D39.

FIG. 27 (SEQ ID NO:45) shows: a BESTFIT analysis of pspC.EF6797 and pspC.D39.

FIG. 28 (SEQ ID NO:46) shows: the amino acid comparison of PspC of EF6797 and D39.

FIG. 29 (SEQ ID NO:47) shows: the amino acid comparison of PspC.D39 and PspA.Rx1.

DETAILED DESCRIPTION

Figure 2:
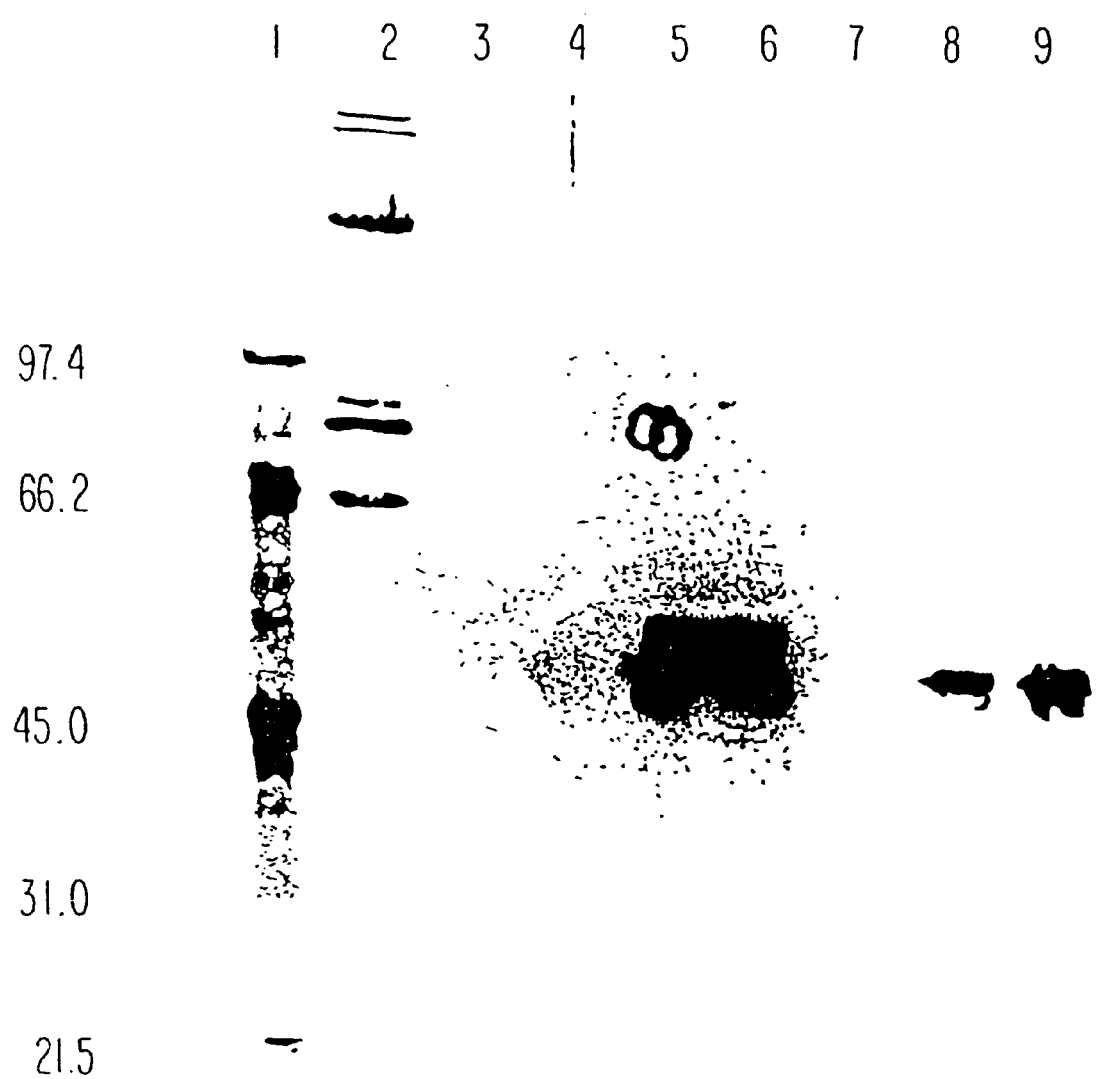
FIG. 2 shows: Evaluation of strain RCT105 cell fractions containing truncated DBL5 PspA. Proteins from *E. coli* cell fractions were resolved by 10% SDS-PAGE, transferred to NC, and probed with MAb XiR278. Lane 1: molecular weight markers (noted in kDa), lane 2: full-length, native DBL5 PspA, lane 3: uninduced cells, lanes 4–6: induced cells; 1 hr, 2 hr, and 3 hr of IPTG induction respectively, lane 7: periplasmic proteins, lane 8: cytoplasmic proteins, and lane 9: insoluble cell wall/membrane material.

Knowledge of and familiarity with the applications incorporated herein by reference is assumed; and, those applications disclose the sequence of pspA as well as certain portions thereof, and PspA and compositions containing PspA.

As discussed above and in the following Examples, the invention relates to truncated PspA, e.g., PspA C-terminal to position 192 such as a.a. 192–588 ("BC100") 192–299 and 192–260 of PspA eliciting cross-protection, as well as to DNA encoding such truncated PspA (which amplify the coding for these amino acid regions homologous to most PspAs).

The invention further relates to a pspA-like gene, or a pspC gene and portions thereof (e.g., probes, primers) which can hybridize thereto and/or amplify that gene, as well as to DNA molecules which hybridize to pspA, so that one can, by hybridization assay and/or amplification, ascertain the presence of a particular pneumococcal strain; and, the invention provides that a PspC can be produced by the pspA-like or pspC sequence (which PspC can be used like PspA).

Indeed, the invention further relates to oligonucleotide probes and/or primers which react with pspA and/or pspC of many, if not all, strains, so as to permit identification, detection or diagnosis of any pneumococcal strain, as well as to expression products of such probes and/or primers, which can provide cross-reactive epitopes of interest.

The repeat region of pspA and/or pspC is highly conserved such that the present invention provides oligonucleotide probes or primers to this region reactive with most, if not all strains, thereby providing diagnostic assays and a means for identifying epitopes of interest.

The invention demonstrates that the pspC gene is homologous to the pspA gene in the leader sequence, first portion of the proline-rich region and in the repeat region; but, these genes differ in the second portion of their proline-rich regions and at the very 3' end of the gene encoding the 17 amino acid tail of PspA. The product of the pspC gene is expected to lack a C-terminal tail, suggesting different anchoring than PspA. Drug interference with functions such as surface binding of the coding for repeat regions of pspA and the pspC genes, or with the repeat regions of the expression products, is therefore a target for intervention of pneumococcal infection.

Further still, the invention provides evidence of additional pspA homologous sequences, in addition to pspA and the pspC sequence. The invention, as mentioned above, includes oligonucleotide probes or primers which distinguish between pspA and the pspC sequence, e.g., LSM1 and LSM2, useful for diagnostic detecting, or isolating purposes; and LSM1 and LSM10 or LSM1 and LSM7 which amplify a portion of the pspC gene, particularly the portion of that gene which encodes an antigenic, immunological or protective protein.

The invention further relates to a method for the isolation of native PspA by growth of pneumococci medium containing high concentrations of(about 0.9% to about 1.4%, preferably 1.2%) choline chloride, elution of live pneumococci with a salt solution containing choline chloride, e.g., about 1% about 3%, preferably 2% choline chloride, and growth of pneumococci in medium in which the choline in the medium has been almost or substantially completely replaced with a lower alkanolamine, e.g., $C_1$–$C_6$, preferably $C_2$ alkanolamine, i.e., preferably $C_2$ alkanolamine, i.e., preferably ethanolamine (e.g., 0.0000005% to 0.0000015%, preferably 0.000001% choline chloride plus 0.02% to 0.04% alkanolamine (ethanolamine), preferably 0.03%). PspA from such pneumococci is then preferably isolated from a choline-sepharose affinity column, thereby providing highly purified PspA. Such isolated and/or purified PspA is highly immunogenic and is useful in antigenic, immunological or vaccine composition.

Indeed, the growth media of the pneumococci grown in the presence of the alkanolamine (rather than choline) contains PspA and is itself highly immunogenic and therefore useful as an antigenic, immunological or vaccine composition; and, is rather inexpensive to produce. Per microgram of PspA, the PspA in the alkanolamine medium is much more protective than PspA isolated by other means, e.g., from extracts. Perhaps, without wishing to necessarily be bound by any one particular theory, there is a synergistic effect upon PspA by the other components present prior to isolation, or simply PspA is more protective (more antigenic) prior to isolation and/or purification (implying a possibility of some loss of activity from the step of isolation and/or purification).

The invention further relates to the N-terminal 115 amino acids of PspA, which is useful for compositions comprising an epitope of interest, immunological or vaccine compositions, as well as the DNA coding therefor, which is useful in preparing these N-terminal amino acids by recombination, or for use as probes and/or primers for hybridization and/or amplification for identification, detection or diagnosis purposes.

The invention further demonstrates that there is a grouping among the pspA RFLP families. This provides a method of identifying families of different PspAs based on RFLP pattern of pspAs, as well as a means for obtaining diversity of PspAs in an antigenic, immunological or vaccine composition; and, a method of characterizing clonotypes of pspA based on RFLP patterns of PspA. And, the invention thus provides oligonucleotides which permit amplification of most, e.g., a majority, if not all of *S. pneumoniae* and thereby permit RFLP analysis of a majority, if not all, *S. pneumoniae*.

The invention also provides PspC, having an approximate molecular weight of 105 kD, with an estimated pI of 6.09, and comprising an alpha-helical region, followed by a proline-rich domain and repeat region. A major cross-protective region of PspA comprises the C-terminal third of the alpha-helical region (between residues 192 and 260 of PspA), which region accounts for the binding of 4 of 5 cross-protective MAb, and PspA fragments comprising this region can elicit cross-protective immunity in mice. Homology between PspC and PspA begins at amino acid 148 of PspA, thus including the region from 192 to 299, and including the entire PspC sequence C-terminal of amino acid 486. Due to the substantial sequence homology between PspA and PspC in a region comprising the epitopes of interest, known to be protection eliciting, PspC is likely to comprise epitopes of interest similar to those found in PspA. Antibodies specific for this region of PspA, i.e., between amino acids 148 and 299, should cross-react with PspC, and thus afford protection by reacting with PspC and PspA. Similarly, immunization with PspC would be expected to elicit antibodies cross-protective against PspA.

An epitope of interest is an antigen or immunogen or immunologically active fragment thereof from a pathogen or toxin of veterinary or human interest.

The present invention provides an immunogenic, Immunological or vaccine composition containing the pneumococcal epitope of interest, and a pharmaceutically acceptable carrier or diluent. An immunological composition containing the pneumococcal epitope of interest, elicits an immunological response—local or systemic. The response can, but need not be, protective. Am immunogenic composition containing the pneumococcal epitope of interest, likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method of inducing an immunological response in a host mammal comprising administering to the host an immunogenic, immunological or vaccine composition comprising the pneumococcal epitope of interest, and a pharmaceutically acceptable carrier or diluent.

The DNA encoding the pneumococcal epitope of interest can be DNA which codes for full length PspA, PspC, or fragments thereof. A sequence which codes for a fragment of PspA or PspC can encode that portion of PspA or PspC which contains an epitope of interest, such as a protection-eliciting epitope of the protein.

Regions of PspA and PspC have been identified from the Rx1 strain of *S. pneumoniae* which not only contain protection-eliciting epitopes, but are also sufficiently cross-reactive with other PspAs from other *S. pneumoniae* strains so as to be suitable candidates for the region of PspA to be incorporated into a vaccine, immunological or immunogenic composition. Epitopic regions of PspA include residues 1 to 115, 1 to 314, 192 to 260 and 192 to 588. DNA encoding fragments of PspA can comprise DNA which codes for the aforementioned epitopic regions of PspA; or it can comprise DNA encoding overlapping fragments of PspA, e.g., fragment 192 to 588 includes 192 to 260, and fragment 1 to 314 includes 1 to 115 and 192 to 260.

As to epitopes of interest, one skilled in the art can determine an epitope of immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology,* 1988.

As to size, the skilled artisan can maximize the size 6f the protein encoded by the DNA sequence to be inserted into the viral vector (keeping in mind the packaging limitations of the vector). To minimize the DNA inserted while maximizing the size of the protein expressed, the DNA sequence can exclude introns (regions of a gene which are transcribed but which are subsequently excised from the primary RNA transcript).

At a minimum, the DNA sequence can code for a peptide at least 8 or 9 amino acids long. This is the minimum length that a peptide needs to be in order to stimulate a CD4+ T cell response (which recognizes virus infected cells or cancerous cells). A minimum peptide length of 13 to 25 amino acids is useful to stimulate a CD8+ T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), a longer peptide is preferred.

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides completed with MHC molecules. The method is less effective for determining B-cell epitopes" since B cell epitopes are often not linear amino acid sequence but rather result from the tertiary structure of the folded three dimensional protein. Janis Kuby, *Immunology,* (1992) pp. 79–80.

Another method for determining an epitope of interest is to choose the regions of the protein that are hydrophilic. Hydrophilic residues are often on the surface of the protein and therefore often the regions of the protein which are accessible to the antibody. Janis Kuby, *Immunology,* (1992) P. 81.

Yet another method for determining an epitope of interest is to perform an X-ray cyrstallographic analysis of the antigen (full length)-antibody complex. Janis Kuby, *Immunology,* (1992) p. 80.

Still another method for choosing an epitope of interest which can generate a T cell response is to identify from the protein sequence potential HLA anchor binding motifs which are peptide sequences which are known to be likely to bind to the MHC molecule.

The peptide which is a putative epitope, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurance of the peptide sequence in other vital cells.

An immune response is generated, in general, as follows: T cells recognize proteins only when the protein has been cleaved into smaller peptides and is presented in a complex called the "major histocompatability complex MHC" located on another cell's surface. There are two classes of MHC complexes—class I and class II, and each class is made up of many different alleles. Different patients have different types of MHC complex alleles; they are said to have a 'different HLA type'.

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD4 on their surface, bind to the MHC class I cells and secrete lymphokines. The lymphokines stimulate a response; cells arrive and kill the viral infected cell.

Class II MHC complexes are found only on antigen-presenting cells and are used to present peptides from circulating pathogens which have been endocytosed by the antigen-presenting cells. T cells which have a protein called CD8 bind to the MHC class II cells and kill the cell by exocytosis of lytic granules.

Some guidelines in determining whether a protein is an epitopes of interest which will stimulate a T cell response, include: Peptide length—the peptide should be at least 8 or 9 amino acids long to fit into the MHC class I complex and at least 13–25 amino acids long to fit into a class II MHC complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al, *Specific Binding of Leukemia Oncogene Fusion Protein Peptides to HLA Class I Molecules,* Blood 85:2680–2684; Englehard, VH, *Structure of peptides associated with class I and class II MHC molecules* Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are prestnted on the cell surface in association with class I or class II MHC molecules.

Further, the skilled artisan can ascertain an epitope of interest by comparing the protein sequence with sequences listed in the protein data base. Regions of the protein which share little or no homology are better choices for being an epitope of that protein and are therefore useful in a vaccine or immunological composition. Regions which share great homology with widely found sequences present in vital cells should be avoided.

Even further, another method is simply to generate or express portions of a protein of interest, generate monoclonal antibodies to those portions of the protein of interest, and then ascertain whether those antibodies inhibit growth in vitro of the pathogen from which the from which the protein was derived. The skilled artisan can use the other guidelines set forth in this disclosure and in the art for generating or expressing portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophilic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

Further, the invention demonstrates that more than one serologically complementary PspA molecule can be in an antigenic, immunological or vaccine composition, so as to elicit better response, e.g., protection, for instance, against a variety of strains of pneumococci; and, the invention provides a system of selecting PspAs for a multivalent composition which includes cross-protection evaluation so as to provide a maximally efficacious composition.

The determination of the amount of antigen, e.g., PspA or truncated portion thereof and optional adjuvant in the inventive compositions and the preparation of those compositions can be in accordance with standard techniques well known to those skilled in the pharmaceutical or veterinary arts. In particular, the amount of antigen and adjuvant in the inventive compositions and the dosages administered are determined by techniques well known to those skilled in the medical or veterinary arts taking into consideration such factors as the particular antigen, the adjuvant (if present), the age, sex, weight, species and condition of the particular patient, and the route of administration. For instance, dosages of particular PspA antigens for suitable hosts in which an immunological response is desired, can be readily ascertained by those skilled in the art from this disclosure (see, e.g., the Examples), as is the amount of any adjuvant typically administered therewith. Thus, the skilled artisan can readily determine the amount of antigen and optional adjuvant in compositions and to be administered in methods of the invention. Typically, an adjuvant is commonly used as 0.001 to 50 wt % solution in phosphate buffered saline, and the antigen is present on the order of micrograms to milligrams, such as about 0.0001 to about 5 wt %, preferably about 0.0001 to about 1 wt %, most preferably about 0.0001 to about 0.05 wt % (see, e.g., Examples below or in applications cited herein).

Typically, however, the antigen is present in an amount on the order of micrograms to milligrams, or, about 0.001 to about 20 wt %, preferably about 0.01 to about 10 wt %, and most preferably about 0.05 to about 5 wt % (see, e.g., Examples below).

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations can be ascertained without undue experimentation.

Examples of compositions of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by-means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, Gin be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form [e.g., whether the composition is to be formulated into a solution, a suspension, gel or another liquid form], or solid dosage form [e.g., whether the composition is to be formulated into a pill, tablet, capsule, caplet, time release form or liquid-filled form].

Solutions, suspensions and gels, normally contain a major amount of water (preferably purified water) in addition to the antigen, lipoprotein and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the PspA antigen and optional adjuvant. This will present no problem to those skilled in chemical and pharmaceutical principles, or problems can be readily avoided by inference to standard texts or by simple experiments (not involving undue experimentation), from this disclosure and the documents cited herein.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other mammals can be determined without undue experimentation by the skilled artisan, from this disclosure, the documents cited herein, the Examples below (e.g., from the Examples involving mice).

Suitable regimes for initial administration and booster doses or for sequential administrations also are variable, may include an initial administration followed by subsequent administrations; but nonetheless, may be ascertained by the skilled artisan, from this disclosure, the documents cited herein, and the Examples below.

PCR techniques for amplifying sample DNA for diagnostic detection or assay methods are known from the art cited herein and the documents cited herein (see Examples), as are hybridization techniques for such methods. And, without undue experimentation, the skilled artisan can use gene products and antibodies therefrom in diagnostic, detection or assay methods by procedures known in the art.

The following Examples are provided for illustration and are not to be considered a limitation of the invention.

EXAMPLES

Example 1

Truncated *Streptococcus pneumoniae* PspA Molecules Elicit Cross-Protective Immunity Against Pneumococcal Challenge Since the isolation of *S. pneumoniae* from human saliva in 1881 and its subsequent connection with lobar pneumonia two years later, human disease resulting from pneumococcal infection has been associated with a significant degree of morbidity and mortality. A recent survey of urgently needed vaccines in the developing and developed world places an improved pneumococcal vaccine among the top three vaccine priorities of industrialized countries. The currently licensed vaccine is a 23-valent composition of pneumococcal capsular polysaccharides that is only about 60% effective in the elderly and due to poor efficacy is not recommended for use in children below two years of age. Furthermore the growing frequency of multi-drug resistant strains of *S. pneumoniae* being isolated accentuates the need for a more effective vaccine to prevent pneumococcal infections.

The immunogenic nature of proteins makes them prime targets for new vaccine strategies. Pneumococcal molecules being investigated as potential protein vaccine candidates include pneumolysin, neuraminidase, autolysin and PspA. All of these proteins are capable of eliciting immunity in mice resulting in extension of life and protection against death with challenge doses near the $LD_{50}$. PspA is unique among these macromolecules in that is can elicit antibodies in animals that protect against inoculums 100-fold greater than the $LD_{50}$.

PspA is a surface-exposed protein with an apparent molecular weight of 67–99 kDa that is expressed by all clinically relevant *S. pneumoniae* strains examined to date. Though PspAs from different pneumococcal strains are serologically variable, many PspA antibodies exhibit cross-reactivities with PspAs from unrelated strains. Upon active immunization with PspA, mice generate PspA antibodies that protect against subsequent challenge with diverse strains of *S. pneumoniae*. The immunogenic and protection-eliciting properties of PspA suggest that it may be a good candidate molecule for a protein-based pneumococcal vaccine.

Four distinct domains of PspA have been identified based on DNA sequence. They include a N-terminal highly charged alpha-helical region, a proline-rich 82 amino acid stretch, a C-terminal repeat segment comprised of ten 20-amino acid repeat sequences, and a 17-amino acid tail. A panel of MAbs to Rx1 PspA have been produced and the binding sites of nine of these Mabs were recently localized within the Rx1 pspA sequence in the alpha-helical region. Five of the Rx1 Mabs were protective in mice infected with a virulent pneumococcal strain, WU2. Four of these five protective antibodies were mapped to the distal third (amino acids 192–260) of the alpha-helical domain of Rx1 PspA.

Truncated PspAs containing amino acids 192–588 or 192–299, from pneumococcal strain Rx1 were cloned and the recombinant proteins expressed and evaluated for their ability to elicit protection against subsequent challenge with *S. pneumoniae* WU2. As with full-length Rx1 PspA, both truncated PspAs containing the distal alpha-helical region protected mice against fatal WU2 pneumococcal infection. However, the recombinant PspA fragment extending from amino acid 192 to 588 was more immunogenic than the smaller fragment, probably due to its larger size. In addition, the protection elicited by the amino acid fragment 192–588 of Rx1 was comparable to that elicited by full-length Rx1 PspA. Therefore, cross-protective epitopes of other PspAs were also sought in the C-terminal two-thirds of the molecule. As discussed below, PspAs homologous to amino acids 192–588 of strain Rx1 were amplified by PCR, cloned, and expressed in *E. coli*. Then three recombinant PspAs, from capsule type 4 and 5 strains, were evaluated for their ability to confer cross-protection against challenge strains of variant capsular types. The data demonstrate that the truncated PspAs from capsular type 4 and 5 strains collectively protect against or early death caused by challenge with capsular type 4 and 5 parental strains as well as type 3, 6A, and 6B *S. pneumoniae*.

Bacterial strains and culture conditions. All pneumococci were from the culture collection of this laboratory, and have been described (Yother, J. et al., Infect. Immun. 1982; 36: 184–188; Briles, D. E., et al., Infect. Immun. 1992; 60: 111–116; McDaniel, L. S., et al., Microb. Pathog. 1992; 13: 261–269; and McDaniel, L. S, et al., In: Ferretti, J. J. et al., eds. *Genetics of streptococci, enterococci, and lactococci*. 1995; 283–286), with the exception of clinical isolates TJ0893, 0922134 and BG8740. Pneumococcal strains TJ0893 and 0922134 were recovered from the blood of a 43-year old male and an elderly female, respectively. *S. pneumoniae* BG8743 is a blood isolate from an 8-month old infant. Strains employed in this study included capsular type 3 (A66.3, EF10197, WU2), type 4 (BG9739, EF3296, EF5668, L81905), type 5 (DBL5), type 6A (DBL6A, EF6796), type 6B (BG7322, BG9163, DBL1), type 14 TJ0893), type 19 (BG8090), and type 23 (0922134, BG8743). In addition, strain WG44.1, which expresses no detectable PspA, was employed in PspA-specific antibody analysis. All chemicals were purchased from Fisher scientific, Fair Lawn, N.J. unless indicate otherwise.

S. pneumoniae were grown in Todd Hewitt broth (Difco, Detroit, Mich.) supplemented with 5% yeast extract (Difco). Mid-exponential phase cultures were used for seeding inocula in Lactated Ringer's (Abbott laboratories, North Chicago, Ill.) for challenge studies. For pneumococcal strains used in challenge studies, inocula ranged from 2.8 to 3.8 $\log_{10}$ CFU (verified by dilution plating on blood agar). Plates were incubated overnight in a candle jar at 37° C.

E. coil DH1 and BL21(DE3) were cultured in LB medium (1% Bacto-tryptone (Difco), 0.5% Bacto Yeast (Difco), 0.5% NaCl, 0.1% dextrose). For the preparation of cell lysates, recombinant E. coil were grown in minimal E medium supplemented with 0.05 M thiamine, 0.2% glucose, 0.1% casamino acids (Difco), and 50 mg/ml kanamycin. Permanent bacterial stocks were stored at −80° C. in growth medium containing 10% glycerol.

Construction of plasmid-based strains. pET-9a (Novagen, Madison, Wis.) was used for cloning truncated pspA genes from fourteen S. pneumoniae strains: DBL5, DBL6A, WU2, &9739, EF5668, L81905, 0922134, BG8090, BG8743, BG9163, DBL1, EF3296, EF6796, and EF10197 (Table 1). pspA gene fragments, from fifteen strains, were amplified by PCR using two primers provided by Connaught Laboratories, Swiftwater, Pennsylvania Primer N192(SEQ ID NO:14)-5'GGAAGGCCATATGCTCAAAGAGAT TGATGAGTCT3' and primer C588 (SEQ ID NO:15)-5'CCAAGGATCCTTAAACCCATTCACCATTGGC3' were engineered with NdeI and BamHI restriction endonuclease sites, respectively. PCR-amplified gene products were digested with BamHI and NdeI, and ligated to linearized pET-9a digested likewise and further treated with bacterial alkaline phosphatase United States Bio-chemical Corporation, Cleveland, Ohio) to prevent recircularization of the cut plasmid. Clones were first established in E. coli BL21(DE3) which contained a chromosomal copy of the T7 RNA polymerase gene under the control of an inducible lacUV5 promoter.

E. coli DH1 cells were transformed by the method of Hanahan (Hanahan, D. J. Mol. Biol. 1983; 166: 557–580). Stable transformants were identified by screening on LB-kanamycin plates. Plasmid constructs, isolated from each of these strains, were electroporated (Electro Cell Manipulator 600, BTX Electroporation System, San Diego, Calif.) into E. coli BL21(DE3) and their respective strain designations are listed in Table 1. The pET-9a vector alone was introduced into E. coli BL21(DES) by electroporation to yield strain RCT125 (Table 2). All plasmid constructs and PCR-amplified pspA gene fragments were evaluated by agarose gel electrophoresis (with 1 kb DNA ladder, Gibco BRL, Gaithersburg, Md.). Next, Southern analysis was performed using LMpspA1, a previously described full-length pspA probe (McDaniel. L. S. et al., Microb. Pathog. 1992; 13: 261–269) random primed labeled with digoxigenin-11-dUTP (Genius System, Boehringer Mannheim, Indianapolis, Ind.). Hybridization was detected with chemiluminescent sheets according to the manufacturer's instructions (Schleicher & Schuell, Keene, N.H.).

Cell fractionation of recombinant E. coli strains. Multiple cell fractions from transformed E. coli were evaluated for the expression of truncated PspA molecules. Single colonies were inoculated into 3 ml LB cultures containing kanamycin and grown overnight at 37° C. Next, an 80 ml LB culture, inoculated with 1:100 dilution of the overnight culture, was grown at 37° C. to mid-exponential phase ($A_{600}$ of ca. 0.5) and a 1 ml sample was harvested and resuspended (uninduced cells) prior to induction with isopropylthiogalactoside (IPTG, 0.3 mM final concentration). Following 1, 2, and 3 hr of induction, 0.5 ml of cells were centrifuges, resuspended, and labeled induced cells. The remaining culture was divided into two aliquots, centrifuged (4000× g, 10 min, DuPont Sorvall RC 5B Plus), and the supernatant discarded. One pellet was resuspended in 5 ml of 20 mM Tris-HCl ph 7.4 200 mM NaCl, 1 mM (ethylenedinitrilo)-tetraacetic acid disodium salt (EDTA) and frozen at −20° C. overnight. Cells were thawed at 65° C. for 30 min, placed on ice, and sonicated for vive 10-sec pulses (0.4 relative output, Fisher Sonic Dismembrator, Dynatech Laboratories, Inc. Chantilly, Va.). Next, the material was centrifuged (9000× g, 20 min) and the supernatant was designated the crude extract-cytoplasmic fraction. The pellet was resuspended in Tris-NaCl-EDTA buffer and labeled the insoluble cell well and membrane fraction. The other pellet, from the divided induced culture, was resuspended in 10 ml of 30 mM Tris-HCl pH 8.0 containing 20% sucrose and 1 mM EDTA and incubated at room temperature for 10 min with agitation. Cells were then centrifuged, the supernatant removed, and the pellet resuspended in 5 mM $MgSO_4$ (10 ml, 10 min, shaking 4° C. bath). This material was centrifuged and the supernatant was designated osmotic shock-periplasmic fraction. Cell fractions were evaluated by SDS-PAGE and immunoblot analysis.

MAbs to PspA. PspA-specific monoclonal antibodies (MAbs) XiR278 and 1A4 were used as previously described (Crain, M. J. et al., 1990, Infect. Immun.; 58: 3293-3299). MAb P50-92D9 was produced by immunization with DBL5 PspA. The PspA-specificity of MAb P50-92D9 was confirmed by Western Analysis by its reactivity with native PspAs from S. pneumoniae DBL5, BG9739, EF5668, and L81095 and its failure to recognize the PspA-control strain WG44.1.

SDS-PAGE and immunoblot analysis. E. Coli cell fractions containing recombinant PspA proteins and biotinylated molecular weight markers (low range, Bio-Rad, Richmond, Calif.) were separated by sodium dodecyl sulfate-polyacrylamide (10%; Bethesda Research Laboratories, Gaithersburg, Md.) gel electrophoresis (SDS-PAGE) by the method of Laemmli (Laemmli, U.K. Nature 1970; 227: 680–685). Samples were first boiled for 5 min in sample buffer containing 60 mM Tris pH 6.8, 1% 2-B-mercaptoethanol (Sigma, St. Louis, Mo.), 1% SDS, 10% glycerol, and 0.01% bromophenol blue. Gels were subsequently transferred (1 hr, 100 volts) to nitrocellulose (0.45 mM pores, Millipore, Bedford, Mass.) as per the method of Towbin et al. Blots were blocked with 3% casein, 0.05% Tween 20 in 10 mM Tris, 0.1 M NaCl, pH 7.4 for 30 min prior to incubating with PspA-specific monoclonal antibodies diluted in PBST for 1 hr at 25° C. Next, the blot was washed 3 times with PBST before incubating with alkaline phosphatase-labeled goat anti-mouse immunoglobulin (Southern Biotechnology Associates, Inc., Birmingham, Ala.) for 1 hr at 25° C. Washes were performed as before and blots was developed with 0.5 mg/ml 5-bromo-4-chloro-3-indolyl phosphate and 0.01% nitro blue tetrazolium (Sigma) first dissolved in 150 μl of dimethyl sulfoxide and then diluted in 1.5 M Tris-HCl pH 8.8. Dot blots were analyzed similarly. Lysate samples (2 μl) were spotted on nitrocellulose filters (Millipore), allowed to dry, blocked, and detected as just described.

Preparation of cell lysates containing recombinant PspA proteins. Transformed E. coli strains RCT105, RCT113, RCT117, and RCT125 (Table 2) were grown in mid-exponential phase in minimal E medium before IPTG induction (2 mM final concentration, 2 hours, 37° C.). Cultures were harvested by centrifugation (10 min at 9000× g), resuspended in Tris-acetate pH 6.9, and frozen at −80° C. overnight. Samples were thawed at 65° C. for 30 min, cooled on ice, and sonicated. Next the samples were treated with 0.2 mM AEBSF (Calbiochem, La Jolla, Calif.) at 37° C. for 30 min and finally centrifuged to remove cell wall and membrane components. Dot blot analysis was performed using PspA-specific MAbs to validate the presence of recombinant, truncated PspA molecules in the lysates prior to their use as immunogens in mice. Unused lysate material was stored at −20° C. until subsequent immunizations were performed.

Mouse immunization and challenge. CBA/CAHN-XID/J mice (Jackson Laboratories, Bar Harbor, Me.), 6–12 weeks old, were employed for protection studies. These mice carry a X-linked immunodeficiency that prevents them from generating antibody to polysaccharide components, thus making them extremely susceptible to pneumococcal infection. Animals were immunized subcutaneously with cell lysates from E coli recombinant strains RCT105, RCT113, RCT117, and RCT125 (Table 2) in complete Freund's adjuvant for primary immunizations. Secondary injections were administered in incomplete adjuvant and subsequent boosts in dH$_2$O. Immunized and nonimmunized mice (groups of 2 to 5 animals) were challenged with S. pneumoniae strains A66.3, BG7322, DBL6A, WU2, DBL5, BG9739, and L81905 intravenously (tail vein) to induce pneumococcal sepsis. Infected animals were monitored for 21 days and mice that survived the 3-week evaluation period were designated protected against death and scored as surviving 22 days for statistical analysis. Protection that resulted in extension of life was calculated as a comparison between mean number of days to death for immunized versus pooled control mice (nonimmunized and RCT125 sham-immunized; total of 6–7 animals).

Determination of PspA serum levels. Mice were bled retro-orbitally following the secondary boost and again prior to challenge. Representative mouse titers were evaluated by enzyme-linked immunosorbent assay (ELISA) using native, parental PspAs isolated from pneumococcal strains DBL5, BG9739, and L81905. PspAs were immobilized on microtiter plates by incubating in 0.5 NaHCO$_3$, 0.5 M Na$_2$CO$_3$pH9.5 at 4° C. overnight. Alkaline phosphatase-labeled goat anti-mouse immunoglobulin (Southern Biotechnology Associates, Inc.) was used to detect mouse serum antibodies. Color development was with p-nitrophenyl phosphate (Sigma, 1 mg/ml) in 0.5 m MgCL$_2$ pH 9.8 with 10% diethanolamine and absorbance was read at 405 nm after a 30 min incubation. Reciprocal titers were calculated as the last dilution of antibody that registered an optical density value of 0.1. Sera from individual mice within a particular immunogen group were evaluated separately and then the respective titers from four mice per group were combined to obtain titer range (Table 3).

Statistics. The one-tailed Fisher exact and two sample rank tests were used to evaluate protection against death and extension of life in the mouse model.

Cloning of truncated pspA genes. Using primers N192 and C588, truncated pspA genes from fifteen diverse pneumococcal strains representing eight different capsular types (Table 1) were amplified by PCR. Even though variability exists in pspA genes from different strain, this result demonstrates that sufficient conservation exists between variant pspA genes to allow sequence amplification in all strains examined to date. Successful pspA PCR-amplification extended to all capsule types evaluated.

Fourteen of the amplified pspA genes were cloned and three clones containing truncated PspA molecules from pneumococcal strains DBL5, BG9739, and L81905 were further studies (Table 2). To verify the constructions, plasmids from recombinant E. coli strains (RCT105, RCT113, RCT117, and RCT125 (Table 2) were isolated, digested with NdeI and BAMHI restriction endonucleases, and electrophoresed in 1% agarose side-by-side with the PCR products used in their respective constructions (FIG. 1A). The digestion reaction was complete for pRCT105, wile pRCT113 and pRCT117 digestions were incomplete (lanes 5 and 7, respectively). This gel was denatured and DNA transferred to nylon for Southern analysis. FIG. 1B depicts the corresponding Southern blot probed with full-length Rx1pspA DNA. Lane 1 contains pRCT125, digested vector alone, which does not react with the pneumococcal DNA-specific probe, as expected. The pspA-specific probe hybridized with the PCR products and the digested plasmid inserts (see arrow, FIG. 1B) as well as the partially undigested pRCT113 and pRCT117 (lane 5 and 7), confirming successful cloning of DBL5, BG9739, and L81905 pspA DNA. Constructions were similarly confirmed with the eleven additional recombinant strains containing truncated pspA genes from S. pneumoniae strains of different capsular and PspA types.

Expression of recombinant PspA in E. coli B121(De3). Transformed E. coli strains RCT105, RCT113, RCT117, and RCT125 were cultured to mid-exponential phase prior to the addition of IPTG to induce expression of the cloned, truncated pspA gene in each strain. A cell fractionation experiment was performed to identify the location of recombinant PspA proteins in transformed E. coli strains. Samples representing uninduced cells, included cells (1 hr, 2 hr, and 3 hr time intervals), the periplasmic fraction, the cytoplasmic fraction, and insoluble cell wall/membrane material were resolved by SDS-PAGE. Proteins were then transformed to nitrocellulose and Western analysis was performed using monoclonal antibodies specific for PspA epitopes.

FIG. 2 reveals that both the cytoplasmic (lane 8) and the insoluble matter fractions (lane 9), from recombinant strain RCT 105, contain a protein of approximately 53.7 kDa that is recognized by MAb XiR278 that is not seen in the uninduced cell sample (lane 3). This protein increases in quantity in direct correlation with the length of IPTG induction (lanes 4–6; 1 hr, 2 hr, and 3 hr respectively). No truncated RCT105 PspA was found in the periplasmics fraction (lane 7), which was expected since the pET-9a vector lacks a signal sequence that would be necessary for directing proteins to the periplasm. The observed molecular weight (ca. 53.5 kDa) is larger than the predicted molecular weight for the 1.2 kb DBL5pspA gene product (43.6 kDa; FIG. 1A, lane 4). Like full-length Rx1 PspA, the observed and predicted molecular weights for truncated PspAs do not agree precisely. In addition, immunoblot analysis was performed for recombinant E. coli strains RCT113, and RCT117 (using MAbs 1A4 and P50-92D, respectively) and similar results were obtained, while no cell fractions from control strain RCT125 were recognized by MAb XiR278.

Evaluating the protective capacity of recombinant, truncated PspAs. The truncated PspA proteins from strains RCT113, RCT117, and RCT105 were expressed and analyzed for their ability to generate cross-protection against a battery of seven S. pneumoniae strains. Control mice (nonimmunized and RCT125 sham-immunized) and recombinant PspA-immunized mice were challenged with mouse-virulent strains A66.3, BG7322, DBL6A, WU2, DBL5, BG9739, and L81905. Table 3 presents the day of death for each infected mouse.

Immunization with truncated PspA from RCT113, RCT117, and RCT105 conferred protection against death for all mice challenged with capsular type 3 strains (A66.3 and WU2 (Table 3). The three truncated PspAs also provided significant protection against death with DBL6A, and BG7322 pneumococci (capsular types 6A and 6B, respectively). In addition, immunization with recombinant RCT113 PspA extended days to death in mice challenged with strains DBL5, BG9739, and L81905, while RCT117 PspA prolonged the lives of mice inoculated with BG9739 pneumococci (Table 3). Truncated BG9739 PspA elicited protection against all challenge strains (100%) evaluated in this study, while recombinant L81905 and DBL5 truncated PspAs conferred protection against death with 71% and 57% of S. pneumoniae challenge strains, respectively.

Anti-PspA antibody titers elicited by the three immunogens vary over approximately a 10-fold range (Table 3). The lowest antibody levels were elicited by RCT105 and this truncated PspA also elicited protection against the fewest number of challenge strains. RCT113 and RCT117 elicited three and nine time as much anti-PspA antibody, respectively. As expected, no antibody to PspA was detected in nonimmunized mice nor was specific-PspA antibody measured in mice immunized with the vector-only control strain (RCT125).

In summary, immunization with RCT113 and RCT117 PspAs protected mice against fatal challenge with capsular type 3 and 6A strains and extended life for mice inoculated with type 4, 5, and 6B pneumococci. RCT105 PspA immunization protected against fatal infection with capsular type 3 and 6B strains and prolonged time to death for type 6A S. pneumoniae but offered not protection against type 4 and 5 strains. These data demonstrate that truncated PspAs from capsular type 4 and 5 pneumococci collectively protect mice and ergo other hosts, such as humans, against or delay death caused by each of the seven challenge strains. In general, however, more complete protection was observed against strains of capsular type 3, 6A, and 6B than against type 4 and 5 S. pneumoniae.

PspA has been shown to be a protection-eliciting molecule of S. pneumoniae. Immunization with PspA has also been shown to be cross-protective, although eliciting more complete protection against certain strains than others. Thus, it is possible that a broadly protective PspA vaccine might need to contain PspAs of more than one pneumococcal strain. The distal third of the alpha-helical region of PspA has been identified as a major protective region of PspA. Moreover, this region is presented in a very antigenic form when expressed with the intact C-terminal half of the molecule. In this Example, the ability to use truncated PspA proteins homologous to the region of Rx1 PspA extending from amino acid residue 192 to the C-terminus at residue 588 is demonstrated.

The C-terminal two-thirds of PspA was cloned from fourteen strains by PCR amplification of a gene fragment of the appropriate size (1.2 kb) which hybridized with full-length Rx1 pspA. Successful PCR amplification extended to all capsule types analyzed. Thus, the C-terminal two-third of PspA may be amplified from many, if not all, pneumococcal capsule types with Rx1 pspA-specific primers. This technique is thus applicable to the development of antigenic immunological or vaccine compositions containing multiple PspA or fragments thereof.

Of these clones, three truncated PspA proteins were expressed and evaluated in mouse immunization studies to determine their ability to cross-protect against challenge with a variety of pneumococcal capsular types. All three recombinant PspAs elicited antibody reactive with their respective donor PspA and all three elicited protection against pneumococcal infection. Of the two truncated PspA proteins that elicited the highest antibody responses, 100% and 71% of the challenge strains were protected. RCT105 PspA, which elicited the lowest titers of PspA-specific antibody, yielded protection against 57% of S. pneumoniae strains evaluated. With all truncated PspAs, significant levels of protection were observed in four of the seven challenge strains. In fact, in all instances except for on (RCT105-immunized mice challenged with strain BG9739) the trend was for truncated PspA-immunization to elicit protection against pneumococcal challenge. These results demonstrate that truncated Rx1 PspA (amino acids 192×588) cross-protects mice against fatal S. pneumoniae WU2 challenge. More importantly, these data show that the homologous regions of diverse PspAs demonstrate comparable cross-protective abilities.

Strains of capsular type 4 and 5 were more difficult to protect against than were type 3, 6A and 6B pneumococcal strains. Serological differences in PspAs might affect cross-protection in some cases. Yet the difficulty in protecting against the type 4 and 5 strains used herein could not be explained on this basis, since the truncated PspA immunogens were cloned from the same three type 4 and 5 strains used for challenge. Both PspAs from the type 4 strains delayed death caused by one or both type 4 challenge strains but neither could prevent death caused by either type 4 pneumococcal strain. Moreover, the truncated PspA from the type 5 strain DBL5 elicited protection against death or delayed death with strains of capsular types 3, 6A and 6B but failed to protect against infection with its donor strain or either type 4 challenge strain.

There may be several reasons why the truncated PspAs from capsular type 4 and type 5 strains failed to protect against death even with their homologous donor S. pneumoniae strains. One possibility is that the type 4 and 5 strains chosen for study are especially virulent in the XID mouse model. XID mice fail to make antibodies to polysaccharides and are therefore extremely susceptible to pneumococcal infection with less than 100 CFU of most strains, including those of capsular type 3, 4, 5, 6A, and 6a. The increased mouse virulence of types 4 and 5 is apparent from the fact that in immunologically normal mice these strains have lower $LD_{50}$s and/or are more consistently fatal than strains of capsular types 3, 6A, or 6B.

Another possibility is that epitopes critical to protection-eliciting capacity with capsular type 4 and 5 strains are not present in the C-terminal two-thirds of PspA (amino acids 192–588), the truncated fragments used for immunization. The critical epitopes for these strains may be located in the N-terminal two thirds of the alpha-helical region of their PspA molecules. Finally, it is also possible that PspA may be less exposed on some S. pneumoniae strains than others. Strain Rx1 PspA amino acid sequence does not contain the cell wall attachment motif LPXTGX described by Schneewind et al. found in many gram-positive bacteria. Rather, PspA has a novel anchoring mechanism that is mediated by choline interactions between pneumococcal membrane-associated lipoteichoic acid and the repeat region in the C-terminus of the molecule. Electron micrographic examination has confirmed the localization of PspA on the pneumococcal surface and PspA-specific MAb data supports the accessibility of surface-exposed PspA. However, it is not known whether S. pneumoniae strains differ substantially in the degree to which different PspA regions are exposed to the surrounding environment. Nor is it known if the quantity of PspA expressed on the bacterial cell surface differs widely between strains.

TABLE 1 pspA recombinant strains categorized by pneumococcal capsular type.

| Capsular Type | Parent Strains | Respective Recombinant Strains |
|---|---|---|
| 3 | WU2, EF10197 | RCT111, RCT137 |
| 4 | BG9739, EF5668 | RCT113, RCT115 |
|   | L81905, EF3296 | RCT117, RCT133 |
| 5 | DBL5 | RCT105 |
| 6A | DBL6A, EF6796 | RCT109, RCT135 |
| 6B | BG9163, DBL1 | RCT129, RCT131 |
| 14 | TJO893 | none* |
| 19 | BG8090 | RCT121 |
| 23 | 0922134, BG8743 | RCT119, RCT123 |

*Truncated pspA amplified recently, not yet cloned

TABLE 2

Description of recombinant strains used in evaluating the protection-eliciting capacity of truncated PspAs in mice.

| Recombinant Strain | Description | Capsule Type of Parent PspA |
|---|---|---|
| RCT 105 | BL21(DE3) E. coli with pET-9a: DBL5 | 5 |
| RCT 113 | BL21(DE3) E. coli with pET-9a: BG9739 | 4 |
| RCT 117 | BL21(DE3) E. coli with pET-9a: L81905 | 4 |
| RCT 125 | BL21(DE3) E. coli with pET-9a (vector only) |   | sheep blood at 37° C. under reduced oxygen tension. *E. coli* strains were grown in Luria-Bertani medium or minimal E medium. Bacteria were stored at −80° C. in growth medium supplemented with 10% glycerol. *E. coil* were transformed by the methods of Hanahan (Hanahan, D. J. Mol. Biol. 1983; 166: 557). Ampicillin (Ap) was used at a concentration of 100 μg/ml for *E. Coli*.

Construction of pIN-III-ompA3 and pMAL-based *E. Coli* strains. Recombinant plasmids pBC100 and pBAR416 that express and secrete pspA fragments from *E. Coli* were constructed with pIN-III-ompA3 as previously described (McDaniel, L. S. et al., Microb. Pathog. 1994; 17: 323).

The pMAL-p2 vector (New England Biolabs, Protein Fusion & Purification System, catalog #800) was used for cloning pspA gene fragments to amino acids 192–299 from strain Rx1 and from 7 other *S. pneumoniae* strains: R36A, D39, A66, BF9739, DBL5, DBL6A, and LM100. Amplification of the pspA gene fragments was done by the polymerase chain reaction (PCR) as described previously (McDaniel, L. S. et al., Microb. Pathog. 1994; 17: 323) using primers 5'CCGGATCCGCTCAAAGAGATTGATG AGTCTG3'[LSM4](SEQ ID NO:16) and 5'CTG AGTCGACTGAGTTTCTGGAGCTGGAGC3'[LMS6] (SEQ ID NO:17) made with BamHI and SalI restriction endonuclease sites, respectively. Primers were based on the sequence of Rx1 PspA. PCR products and the pMAL vector were digested with BAMHI and SalI, and ligated together. clones were transformed into *E. Coli* DH5α by the methods of Hanahan. Stable transformants were selected on LB plates containing 100 μg/ml Ap. These clones were screened on LB plates containing 0.1 mM IPTG, 80 μg/ml X-gal and 100

TABLE 3

Evaluation of the protection elicited by truncated *S. pneumoniae* PspA molecules in mice by days to death post-challenge*.

| | | Challenge Strain [capsular type] ($log_{10}$ dose in CFU) | | | | | | |
|---|---|---|---|---|---|---|---|---|
| Immunizing recombinant PspA/ PspA donor strain | Reciprocal anti-PspA titer† | A66.3 [type 3] (2.78) | WU2 [type 3] (3.57) | DBL6A [type 6A] (3.24) | BG7322 [type 6B] (3.11) | DBL5 [type 5] (3.81) | BG9739 [type 4] (3.56) | L81905 [type 4] (3.62) |
| RCT113/BG9739 | 5590–50,300 | 4x > 21‡ | 4x > 21 § | 15, 3x > 21‡ | 12, 13, 16, > 21‡ | 3, 3, 4, 5§ | 5, 5, 5, 7§ | 5, 6, 8, 8‡ |
| RCT117/L81905 | 5590–150,900 | 4x > 21‡ | 4x > 21§ | 7, 16, 2x > 21‡ | 10, 12, 13, > 21§ | 3, 3, 4, 4¶ | 4, 5, 13, > 21§ | 3, 4, 6, 8 |
| RCT105/DBL5 | 1860–16,770 | 4x > 21‡ | 4x > 21§ | 8, 10, 13, 21‡ | 4x > 21‡ | 2, 2, 2, > 21 | 2, 2, 2, 4 | 4, 5, 5, 5 |
| RCT125/vector only | 20–620 | 3, 6, 6, > 21 | −2, 3, 3, > 21 | 3, 6, 6, 6 | 7, 8, 8, 14 | 2, 2, 2, 2 | 2, 2, 3, 4, 5 | 2, 3, 5, 5 |
| none | 0 | 2, 2, 2 | 2, 3 | 3, 3, 4 | 6, 7, 9 | 2, 5 | 3, 5 | 2, 5 |

*Animals surviving the 3-week evaluation period were sacrificed and days to death recorded as >21 days. For statistical analysis, P values were calculated at 22 days for these fully protected mice.
†Range of four sera per group of mice; titers measured against native donor PspAs
‡$P \leq 0.012$
§$P \leq 0.035$
¶$P \leq 0.057$
Note: One-tailed Fisher exact and two sample rank tests were used for statistical analysis.

Example 2
Localization of protection-eliciting epitopes and PspA of *S. pneumoniae*

This Example, the ability of PspA epitopes on two PspA fragments (amino acids 192–588 and 192–299) to elicit cross-protection against a panel of diverse pneumococci is demonstrated. Also, this Example identifies regions homologous to amino acids 192–299 of Rx1 in 15 other diverse pneumococcal strains. The DNA encoding these regions was then amplified and cloned. The recombinant PspA fragments expressed were evaluated for their ability to elicit cross-protection against a panel of virulent pneumococci.

Bacterial strains and media conditions. *S. pneumoniae* strains were grown in Todd Hewitt broth with 0.5% yeast extract (THY) (both from Difco Laboratories, Detroit, Michigan) at 37° C. or on blood agar plates containing 3%

μg/ml Ap and replica LB plates with 100 μg/ml Ap according to the manufacturer's instructions. The strain designations for these constructs are listed in Table 6. Positive clones were evaluated for the correct pspA gene fragment by agarose gel electrophoresis following plasmid isolation by the methods of Birnboim and Doly (Birnboim, H. C. et al., Nucl. Acids Res. 1979, 7: 1513). Southern analysis was done as previously described using a full-length pspA probe (McDaniel, L. S. et al., Microb. Pathog. 1994; 17: 323), randomly primed labeled with digoxigenin-11-dUTP (Genius System, Boehdinger Mannheim, Indianapolis, Ind.) and detected by chemiluminescence.

Expression of recombinant PspA protein fragments. For induction of expression of strains BC100 and BAR416, bacteria were grown to an optical density of approximately 0.6 at 660 nm at 37° C. in minimal media, and IPTG was added to a final concentration of 2 mM. The cells were incubated for an additional 2 hours at 37° C., harvested, and the periplasmic contents released by osmotic shock. For strains BAR36A, BAR39, BAR66, BAR5668, BAR9739, BARL5, BAR6A and BAR100, bacteria were grown and induced as above except LB media +10 mM. glucose was the culture medium. Proteins from these strains were purified the an amylose resin column according to the manufacturer's instructions (New England Biolabs, Protein Fusion & Purification System, Catalog #800). Briefly, amylose resin was poured into a 10 mL column and washed with column buffer. The diluted osmotic shock extract was loaded at a flow rate of approximately 1 mL/minute. The column was then washed again with column buffer and the fusion protein eluted off the column with column buffer containing 10 mM maltose. Lysates were stored at −20° C. until further use.

Characterization of truncated PspA proteins used for immunization. The truncated PspA molecules, controls and molecular weight markers (Bio-Rad, Richmond, Calif.) were electrophoresed in a 10% sodium dodecyl (SDS)—polyacrylamide gel and electroblotted onto nitrocellulose. Rabbit polyclonal anti-PspA serum and rabbit antimaltose binding protein were used as the primary antibodies to probe the blots.

A direct binding ELISA procedure was used to quantitatively confirm reactivities observed by immunoblotting. For all protein extracts, osmotic shock preparations were diluted to a concentration of 3 $\mu$g/ml in phosphate buffered saline (PBS), and 100 $\mu$l was added to the wells of Immulon 4 microtitration plates (Dynatech Laboratories, Inc., Chantilly, Va.). After blocking with 1.5% bovine serum albumin in PBS, unfractionated tissue culture supernates of individual MAbs were titered in duplicated by three-fold serial dilution through seven wells and developed using an alkaline phosphatase-labeled goat anti-mouse immunoglobulin secondary antibody (Southern Biotech Associates, Birmingham, Ala.) and alkalinephosphatase substrate (Sigma, St. Louis, Mo.). The plates were read at 405 nm in a Dynatech plate reader after 25 minutes, and the 30% end point was calculated for each antibody with each preparation.

Immunization and Protection Assays. Six to nine week old CBA/CAHN-XID/J (CBA/N) mice were obtained from the Jackson Laboratory, Bar Harbor, Me. CBA/N mice carry an X-linked immunodeficiency trait, which renders them relatively unable to respond to polysaccharide antigens, but they do respond with normal levels of antibodies against protein antigens. Because of the absence of antibodies reactive with the phosphocholine determinant of C-polysaccharide in their serum, the mice are highly susceptible to pneumococcal infection. Mice immunized with the BC100 fragment were injected inguinally with antigen emulsified in CFA, giving an approximate dose of 3 $\mu$g of protein per mouse. Fourteen days later the mice were boosted intraperitoneally with 3 $\mu$g of antigen diluted in Ringer's lactate without adjuvant. Control mice were immunized following the same protocol with diluent and adjuvant, but no antigen. Mice immunized with the BAR416 fragment were injected with 0.2 ml at two sites in the sublingual area with antigen emulsified in CFA. The mice were boosted inguinally fourteen days later with antigen emulsified in IFA and were boosted a second time fourteen days later intraperioneally with 0.2 ml of antigen diluted in Ringer's lactate without adjuvant.

Mice that were immunized with the homologues of Rx1 BAR416 were immunized as described above. The control animals followed the same immunization protocol but received maltose binding protein (MBP) diluted 1:1 in CFA for their immunization and were also boosted with MBP.

Serum analysis. Mice were retro-orbitally bled with a 75 $\mu$l heparinized microhematocrit capillary tube (Fisher Scientific) before the first immunization and then once approximately 2 hours before challenge with virulent pneumococci. The serum was analyzed for the presence of antibodies to PspA by an enzyme-linked immunosorbent assay (ELISA) using native full-length R36A PspA as coating antigen as previously described (McDaniel, L. S. Microb. Pathog. 1994; 17: 323).

Intravenous infection of mice. Pneumococcal cultures were grown to late log phase in THY. Pneumococci were diluted to 104 CFU based on the optical density at 420 nm into lactated Ringer's solution. Seven days following the last boost injection for each group, diluted pneumococci were injected intravenously (tail vein) in a volume of 0.2 ml and plated on blood agar plates to confirm the numbers of CFU per milliliter. The final challenge dose was approximately 50–100 times the $LD_{50}$ of each pneumococcal strain listed in Tables 4–6. The survival of the mice was followed for 21 days. Animals remaining alive after 21 days were considered to have survived the challenge.

Statistical analysis. Statistical significance of differences in days to death was calculated with the Wilcoxon two-sample rank test. Statistical significance of survival versus death was made using the Fisher exact test. In each case, groups of mice immunized with PspA containing preparations were compared to unimmunized controls, or controls immunized with preparations lacking PspA. One-tailed, rather than two-tailed, calculations were used since immunization with PspA or fragments of PspA has never been observed to cause a statistically significant decrease in resistance to infection.

Cloning into pMAL vector. Using primers based on the sequence of Rx1 PspA, LSM4 and LSM6, pspA gene fragments were amplified by PCR from fifteen out of fifteen pneumococcal strains examined. Seven of the eleven gene fragments were cloned into pMAL-p2 and transformed into E. coil (Table 6). The correct insert for each new clone was verified by agarose gel electrophoresis and Southern hybridization analysis. Plasmids from recombinant E. coli strains BAR36A, BAR39, BAR66, BAR9739, BARL5, BAR6A and BAR100 were isolated, digested with BamHI and SalI restriction endonucleases and electrophoresed on a 0.7% TBE agarose gel. The gel was then denatured and the DNA transferred to a nylon membrane for southern hybridization. The blot was probed with full-length Rx1 pspA DNA at high stringency conditions. The cloning of R36A, D39, A66, BG9739, DBL5, DBL6A and LM100 pspA DNA into pMal-p2 was confirmed by the recognition of all BamHI and SalI digested DNA inserts by the Rx1 probe.

Expression and conformation of truncated recombinant proteins. The transformed E. coli strains BAR36A, BAR39, BAR66, BAR9739, BARL5, BAR6A and BAR100 were grown in LB media supplemented with 10 mM glucose and induced with 2 mM IPTG for expression of the truncated PspA protein fused with maltose binding protein. Transformed E. coli strains BC100 and BAR416, which express PspA fragments fused to the OmpA leader sequence in the pIN-III-ompA3 vector, were grown in minimal medium and induced with 2 mM IPTG for expression. Both vectors, pIN-III-ompA3 and pMal-p2, are vectors in which fusion proteins are exported to the periplasmic space. Therefore, an osmotic shock extract from the pMal-p2 containing bacteria was then run over an amylose column for purification and resolved by SDS-PAGE western blotting. The western blot of the protein extracts from BAR36A, BAR39, BAR66, BAR9739, BARL5, BAR6A and BAR100 were recognized by a rabbit polyclonal antibody made to strain BC100 PspA. The apparent $M_r$ of full-length PspA from WU2 is 91.5 kD. The $M_r$ of maltose binding protein is 42 kD and the expected $M^r$ for the PspA portion of the fusion is 12 kD. All extracts exhibited molecular weights that ranged from 54 to 80 kD. This range of molecular weights can be attributed to the variability of pspA among different pneumococcal strains. An ELISA, with plates coated with the various cloned fragments quantitatively confirmed the reactivities that were observed in the western blots with all protein extracts.

Protection and cross-protection against fatal pneumococcal infection elicited by cloned PspA fragments. CBA/N mice were immunized with the truncated PspA fragment encoded by pBC100, which is composed of amino acids 192 to 588 of Rx1 PspA, and challenged with 13 different S. pneumoniae strains representing 7 different capsular types (Table 4). With all 13 strains, the immunization resulted in protection from death or an extended time to death. With 10 of the strains the difference was statistically significant. With strains of capsular types 3, 6A, and 6B, all immunized mice were protected against death.

Although there were fewer survivors in the case of capsular types 2, 4, and 5, the immunization with BC100 resulted in significant increases in times to death.

The BC100 immunization studies made it clear that epitopes C-terminal to residue 192 could elicit cross-protection. The BAR416 fragment, which includes amino acids 192–299, could elicit protection from fatal infection with a single challenge strain WU2. This Example shows the ability of BAR416 immunization to protect against the 6 strains that had been best protected against by immunization with BC100. Immunization with the BAR416 construct resulted in increased time to death for all 6 challenge strains examined (Table 5). BAR416 provided significant protection against death with WU2, A66, BG7322 and EF6796 pneumococci (capsular types 3, 3, 6B and 6A respectively). It also prolonged the lives of mice challenged with ATCC6303 and DBL6A pneumococci (capsular types 3 and 6A respectively). Serum from mice immunized with the BAR416 fragment yielded a geometric mean reciprocal anti-PspA ELISA titer to full-length Rx1 PspA of 750. Mice immunized with BC100 had geometric mean reciprocal titers of close to 2000, while non-immunized mice had anti-PspA titers of <10.

The above data indicates that the BAR416 fragment from Rx1 elicits adequate cross-reactive immunity to protect against diverse pneumococci and suggests that this region must be serologically conserved among PspAs. This hypothesis was confirmed by immunized with recombinant BAR416 homologous regions from the 7 different clones and then challenging with strain WU2 (Table 6). All 7 immunogens elicited significant protection. PspA fragments from capsular types 2 and 22 and the rough R36A strain elicited complete protection against death with all challenged mice. All of the other immunogens were able to extend the time to death of all the mice with the median days to death being 21 days or >21 days. Serum from mice immunized with the BAR416 homologous fragments had anti-PspA reciprocal titers that ranged from 260 to 75,800 with an average of 5700 while control animals immunized with only maltose binding protein had anti-PspA reciprocal titers of <10.

Antibody reactivities. All of the above immunization studies attest to the cross-reactivity of epitopes encoded by amino acids from position 192–299. This region includes the C-terminal third of the α-helical region and the first amino acids of the proline rich region. Other evidence that epitopes within this region are cross-reactive among different PspAs comes form the cross-reactivity of a panel of nine MAbs all of which were made by immunization with Rx1 PspA. The epitopes of four of the antibodies in the panel reacted with epitopes mapping between amino acids 192–260. The epitopes of the other five MAbs in the panel map between amino acids 1 and 115 (McDaniel, L. S., et al., Microb. Pathog. 1994; 17: 323). Each of these 9 MAbs were tested for its ability to react with 8 different PspAs in addition to Rx1. The 5 MAbs whose epitopes were located within the first 115 amino acids, reacted on average with only 1 other PspA. Three of the 5 in fact, did not react with any of the other 8 PspAs. In contrast the MAbs whose epitopes map between 192 and 260 amino acids each cross-reacted with an average of 4 of the 8 non-Rx1 PspAs, and all of them reacted with at least two non-Rx1 PspAs. Thus, based on this limited section of individual epitopes, it would appear that epitopes in the region from 192–260 amino acids are generally much more cross-reactive than epitopes in the region from 1–115 amino acids.

The BC100 fragment of Rx1 PspaA can elicit protection against the encapsulated type 3 strain WU2. Although the PspAs of the two strains can be distinguished serologically they are also cross-reactive (Crain, M. J., et al., Infect. Immun. 1990; 58: 3293). The earlier finding made it clear that epitopes cross-protective between Rx1 and WU2 PspAs exist. The importance of cross-reactions in the region C-terminal to residue 192 is demonstrated in this Example where 13 mouse virulent challenge strains have been used to elicit detectable protection against all of them. The first indication that epitopes C-terminal to position 192 might be able to elicit cross-protection came from our earlier study where we showed the MAbs Xi64, XiR278, XiR1323, and XiR1325, whose epitopes mapped between amino acids 192 and 260 of strain Rx1 PspA, could protect against infection with WU2. Moreover, immunization with PspA fragments from 192–588 and 192–299 were able to elicit protection against infection against WU2. This Example shows that the BC100 Rx1 fragment (192–588) elicits significant protection against each of 13 different mouse virulent pneumococci, thereby firmly establishing the ability of epitopes C-terminal to position 192 to elicit a protective response. The observation that a fusion protein containing amino acids 192–299 fused C-terminal to maltose binding protein could also elicit cross-protection, permits the conclusion that epitopes in this 107 amino acid region of PspA are sufficient to elicit significant cross-protection against a number of different Strains.

Evidence that a comparable region of other PspAs is also able to elicit cross-protection cam from the studies where sequences homologous to the 192–299 region of Rx1 PspA were made from 5 other PspAs. All 5 of these fragments elicited significant protection against challenge with strain WU2. These a provide some suggestion for serologic differences in cross-protection elicited by the 192–299 region.

Based on present evidence, without wishing to be bound by any one particular theory, it is submitted that the PspAs in strains D39, Rx1 and R36A are identical. All of the 9 mice immunized with the 192–299 fragments from R36A and D39 survived challenge with WU2. Only LM100, one of the non-R36A/D39 PspAs, protected as high a percentage of mice from WU2. The difference in survival elicited by the R36A/D39 PspAs and the non-Rx1 related PspAs was statistically significant.

The data does indicate however, that all of the differences in protection against different strains are not due to differences in serologic cross-reactivity. BC100, which is made from Rx1, protected against death in 100% of the mice challenged with 7 different strains of *S. pneumonia*, but only delayed death with strain D39, which is thought to have the same PspA as strain Rx1. Thus, some of the differences in cross-protection are undoubtedly related to factors other than PspA cross-reactivity. Whether such factors are related to differences in virulence of the different strains in the hypersuceptible Xid mouse, or differences in requirements for epitopes N-terminal to amino acid 192, or difference in the role of PspA in different strains is not yet known.

These results suggest that a vaccine containing only the recombinant PspA fragments homologous with Rx1 amino acids 192–299 is effective against pneumococcal infection. Moreover, the results demonstrate that utility of PspA a.a. 192–299, a.a. 192–260 and DNA coding therefor, e.g. primers N192 or 588 (variants of LSM4 and LSM2) as useful for detecting the presence of pneumococciae by detecting presence of that which binds to the amino acid or to the DNA, or which is amplified by the DNA, e.g., by using that DNA as a hybridization probe, or as a PCR primer, or by using the amino acids in antibody-binding kits, assays or tests; and, the results demonstrate that a.a. 192–299 and a.a. 192–260 can be used to elicit antibodies for use in antibody-binding kits assays or tests.

TABLE 6

Protection of mice against *S. pneumoniae* WU2 by immunization with BAR416 Analogs of 7 PspAs

| Immunogen | Parent Strain | Capsule type | PspA type | # alive/ total # | % Survival | Median days alive | P. value* vs. MBP |
|---|---|---|---|---|---|---|---|
| BAR36A | R36A | — | 25 | 4/4 | 100% | >21 | 0.002 |
| BAR39 | D39 | 2 | 25 | 5/5 | 100% | >21 | 0.0008 |
| BAR66 | A66 | 3 | 13 | 7/8 | 88% | >21 | <0.0001 |
| BAR9739 | BG9739 | 4 | 26 | 5/8 | 63% | >21 | 0.0002 |
| BARL5 | DBL5 | 5 | 33 | 4/8 | 50% | 21 | 0.03 |
| BAR6A | DBL6A | 6A | 19 | 3/5 | 60% | >21 | 0.05 |
| BAR100 | LM100 | 22 | ND | 5/5 | 100% | >21 | 0.0008 |
| MBP | — | — | — | 0/8 | 0% | 2 | — |

*P values were based on comparison of days alive by a one-tailed Wilcoxon 2 sample-rank test
Note, the PspA fragments used for immunization were cloned from products amplified with primers LSM4 and LSM6. In addition to the strains listed above, PCR reactions with LSM4 and LSM6 amplified products of the appropriate size from strains BG9163, WU2, L81905, EF6796, EF5668, BG7376, BG7322, and BG5-8A.

TABLE 4

Protection of mice by immunization with BC100 from Rx1 PspA

| Challenge Strain* | Capsule type | PspA type | BC100 Immunogen # alive/ # dead | % Survival | Median days alive | Controls # alive/ # dead | % Survival | Median days alive | P Value[§] |
|---|---|---|---|---|---|---|---|---|---|
| D39 | 2 | 25 | 0/5 | 0% | 5 | 0/3 | 0% | 2 | 0.02 |
| WU2 | 3 | 1 | 4/0 | 100% | >21 | 0/3 | 0% | 3 | 0.002 |
| ATCC6303 | 3 | 7 | 5/0 | 100% | >21 | 0/5 | 0% | 7 | 0.004 |
| A66 | 3 | 13 | 4/0 | 100% | >21 | 0/3 | 0% | 1 | 0.03 |
| EF10197 | 3 | 18 | 5/0 | 100% | >21 | 0/3 | 0% | 2 | 0.02 |
| EF5668 | 4 | 12 | 1/3 | 25% | 9 | 0/3 | 0% | 4 | N.S. |
| EF3296 | 4 | 20 | 1/3 | 25% | 5 | 0/3 | 0% | 3 | N.S. |
| L81905 | 4 | 23 | 1/4 | 20% | 4 | 0/6 | 0% | 2 | 0.02 |
| BG9739 | 4 | 26 | 0/4 | 0% | 6.5 | 0/3 | 0% | 2 | N.S. |
| DBL5 | 5 | 33 | 0/5 | 0% | 5 | 0/3 | 0% | 2 | 0.02 |
| BG7322 | 6 | 24 | 4/0 | 100% | >21 | 1/2 | 33.3% | 6 | 0.03 |
| EE6796 | 6A | 1 | 4/0 | 100% | >21 | 0/3 | 0% | 1 | 0.03 |
| DBL6A | 6A | 19 | 5/0 | 100% | >21 | 0/3 | 0% | 7 | 0.03 |

*Mice were challenged with approximately $10^3$ CFU/mL of each strain
[§]P values were based on comparison of days alive by a one-tailed Wilcoxon 2 sample-rank test

TABLE 5

Protection of mice by immunization with BAR416 from Rx1 PspA

| Challenge Strain | Capsule type | PspA type | BAR416 Immunogen # alive/ # dead | % Survival | Median days alive | Controls # alive/ # dead | % Survival | Median days alive | P Value[§] |
|---|---|---|---|---|---|---|---|---|---|
| WU2 | 3 | 1 | 4/1 | 80% | >21 | 0/3 | 0% | 1 | 0.002 |
| ATCC6303 | 3 | 7 | 2/3 | 40% | 13 | 1/4 | 20% | 4 | 0.048 |
| A66 | 3 | 13 | 5/0 | 100% | >21 | 0/5 | 0% | 2 | 0.004 |
| BG7322 | 6 | 24 | 3/2 | 60% | >21 | 0/4 | 0% | 7 | 0.02 |
| EF6796 | 6A | 1 | 3/2 | 60% | >21 | 0/5 | 0% | 5 | 0.004 |
| DBL6A | 6A | 19 | 0/5 | 0% | 7 | 0/5 | 0% | 2 | 0.008 |

Note, mice were challenged with about $10^3$ CFU of each strain
[§]P values were based on comparison of days alive by a one-tailed Wilcoxon 2 sample-rank test

TABLE 7

Reactivity of MAbs with PspAs of Different Pneumococci

| Donor of test PspA | | | MAb mapping to 1-115 amino acids | | | | | MAb mapping to 192-260 amino acids | | | |
|---|---|---|---|---|---|---|---|---|---|---|---|
| Strain | Capsule Type | PspA Type | Xi126 IgG2b | XiR1224 IgM | XiR1526 IgG2b | XiR35 IgG2a | XiR16 IgG2a | XiR1323 IgM | X164 IgM | XiR278 IgG1 | XiR1325 IgG2a |
| Rx1 | rough | 25 | ++ | ++ | ++ | ++ | ++ | ++ | ++ | ++ | ++ |
| ATCC101813 | 3 | 3 | ++ | − | − | − | − | ++ | ++ | ++ | ++ |
| EF10197 | 3 | 18 | − | − | − | − | − | − | − | ++ | +/− |
| BG9739 | 4 | 26 | − | − | − | − | − | ++ | − | + | ++ |
| L81905 | 4 | 23 | − | − | − | − | − | − | − | − | − |
| BG-5-8A | 6A | 0 | +/− | + | − | − | − | + | − | + | − |
| BG9163 | 6B | 21 | − | − | − | − | − | − | − | + | − |
| LM100 | 22 | N.D. | +/− | − | − | − | − | − | − | − | − |
| WU2 | 3 | 1 | ++ | − | − | − | − | ++ | ++ | ++ | ++ |

Note, immunoblot analysis was carried out with the nine MAbs from this study against a panel of nine different pneumococcal strains. Rx1 served as a positive control.
The results are presented as ++ (strong reaction),
+ (weak, but clearly positive reaction),
+/− (difficult to detect),
and − (no reaction).
The PspA of all strains gave a positive reaction with rabbit antiserum against PspA.
N.D. means not determined. Mapping of epitopes was to fragments of strain Rx1 PspA

Example 3
Isolation of PspA and Truncated Forms Thereof, and Immunization Thereby PspA is attached to the pneumococcal surface through a choline binding site on PspA. This allows for successful procedures for the isolation of FL-PspA. PspA can be released from the surface of pneumococci by elution with 2 percent choline chloride (CC), or by growth in a chemically defined medium (CDM) containing 1.2 percent CC (CDM-CC) or medium in which the choline had been replaced by ethanolamine (CDM-ET). Since CDM-ET supernatants lack high concentrations of choline, the PspA released into them can be adsorbed to a choline (or choline analog) column and isolated by elution from the column with 2 percent choline chloride (CC).

This Example describes the ability to obtain PspA by these procedures, and the ability of PspA obtained by these procedures to elicit protection in mice against otherwise fatal pneumococcal sepsis. Native PspA from strains R36A, RX1, and WU2 was used because these strains have been used previously in studies of the ability of PspA to elicit protective immunity (see, e.g., Examples infra and supra). The first MAbs to PspA were made against PspA from strain R36A and the first cloned fragments of PspA and PspA mutants came from strain Rx1. Strain Rx1 was derived from strain R36A, which was in turn derived from the encapsulated type 2strain, D39. PspAs from these three strains appears to be indentical based on serologic and molecular weight analysis. Molecular studies have shown no differences in the pspA genes of strains D39, Rx1, and R36A. The third strain that provided PspA in this Example is the mouse virulent capsular type 3 strain WU2. Its PspA is highly cross-reactive with that from R36A and Rx1, and immunization with Rx1 and D39 PspA can protect against otherwise fatal infections with strain WU2.

S. pneumoniae

Strains of S. pneumoniae used in this study have been described previously (Table 8). Bacteria were grown in either Todd-Hewitt broth with 0.5 percent yeast extract (THY), or a chemically defined medium (CDM) described previously 32, 43. Serial passage of stock cultures was avoided. Strains were maintained frozen in THY +20 percent glycerol and cultured from a scraping of the frozen culture.

Recovery of PspA from pneumococci

PspA is not found in the medium of growing pneumococci unless they have reached stationary phase and autolysis has commenced[36]. To release PspA from pneumococci three procedures were used. In one approach were grow pneumococci in 100 ml of THY and collect the cells by centrifugation at mid-log phase. The pellet was washed three times in lactated Ringer's solution (Abbot Lab. North Chicago, Ill.), suspended in a small volume of 2 percent choline chloride in phosphate buffered saline (PBS) (pH 7.0), incubated for 10 minutes at room temperature, and centrifuged to remove the whole pneumococci. From immunoblots with anti-PspA MAb Xi126[48] at serial dilutions of the original culture, the suspended pellet, and the supernatant, it was evident that this procedure released about half of the PspA originally present on the pneumococci. Analysis of silver stained polyacrylamide gels showed this supernatant to contain proteins in addition to PspA[36].

The CDM used in the remaining two procedures was modified from that of Van der Rijn[43]. For normal growth it contained 0.03% CC. To cause PspA to be released during bacterial growth, the pneumococci were grown in CDM containing 1.2 percent choline chloride (CDM-CC), or in CDM containing 0.03 percent ethanolamine and only 0.000, 001 percent choline (CDM-ET). In media lacking a normal concentration of choline the F-antigen and C-polysaccharide contain phosphoethanolamine rather than phosphocholine[49]. In CDM-CC and CDM-ET, PspA is released from the pneumococcal surface because of its inability to bind to the cholines in the lipoteichoic acids[36]. In addition to releasing PspA from the pneumococcal surface, growth in CDM-CC or CDM-ET facilitates PspA isolation by its other effects on the cell wall. In these media pneumococci do not autolyse[49], thus permitting them to be grown into stationary phase to maximize the yield of PspA. In these media septation does not occur and the pneumococci grow in long chains[36,49]. As the pneumococci reach stationary phase they dim, cease making PspA, and rapidly settle out. Preliminary studies, using serial dilution dot blots to quantitate PspA, indicated that the production of PspA ceases at about the time the pneumococci begin to settle out, with the formation of visible strands of the condensed pneumococcal chains. When the pneumococci began to settle out, the medium was recovered by centrifugation at 2900× g for 20 minutes, and filtered with a low protein-binding filter (0.45µ Nalgene Tissue Culture Filter # 158-0045).

For growth in CDM-CC or CDM-ET, the pneumococci were first adapted to the defined medium and then, in the case of CDM-ET, to very low choline concentrations. To do this, strains were first inoculated into 1 part of THY and 9 parts of CDM medium containing 0.03 percent choline and 0.03 percent ethanolamine. After two subsequent subcultures in CDM containing 0.03 percent choline and 0.03 percent ethanolamine (0.1 ml of culture +0.9 ml of prewarmed fresh medium), the culture was used to inoculate CDM with only 0.003 percent choline (and 0.03 percent ethanolamine). These steps was repeated until the strain would grow in CDM-ET containing 0.000,001 percent choline and 0.03 percent ethanolamine. It was critical that cultures be passed while in exponential growth phase (at about $10^7$ CFU/ml). Even trace contamination of the medium by exogenous choline resulted in the failure of the PspA to be released from the pneumococcal surface[36]. Thus, disposable plastic ware was used for the preparation of CDM-ET media and for growth of cultures. Once a strain was adapted to CDM-ET it was frozen in 80 percent CDM-ET and 20 percent glycerol at −80° C. When grown subsequently the strain was inoculated directly into the CDM-ET.

Isolation of native (full-length) PspA

PspA was isolated from the medium of cells grown in CDM-ET using choline-Sepharose prepared by conjugating choline to epoxy-activated Sepharose[50]. A separate column was used for media from different strains to avoid cross-contamination of their different PspAs. For isolation of PspA from clarified CDM-ET, we used a 0.6 ml bed volume of choline-Sepharose. The column bed was about 0.5 cm high and 1.4 cm in diameter. The flow rate during loading and washing was approximately 3 ml/min. After loading 300 ml CDM-ET supernatant, the column was washed 10 times with 3 ml volumes of 50 mM Tris acetate buffer, pH 6.9 containing 0.25 M NaCl (TAB). The washed column was eluted with sequential 3 ml volumes of 2 percent CC in TAB. Protein eluted from the column was measured (Bio-Rad protein assay, Bio-Rad, Hercules, Calif.). The column was monitored by quantitative dot blot. The loading material, washes, and the eluted material were dot blotted (1 µl) as undiluted, ¼, ¹⁄₁₆, ¹⁄₆₄, ¹⁄₂₅₆, and ¹⁄₁₀₂₄ on nitrocellulose. The membranes were then blocked with 1 percent BSA in PBS, incubated for 1 hr with PspA-specific MAbs Xi126 or XiR278, and developed with biotinylated goat-anti-mouse Ig, alkaline phosphatase conjugated streptavidin (Southern Biotechnology Associates Inc. Birmingham, Ala.), and nitrobluetetrazolium substrate with 5-bromo 4-chloro-3-indoyl phosphate p-toluidine salt (Fisher Scientific, Norcross Ga.)[17]. The purity of eluted PspA was assessed by silver-stained (silver stain kit, Bio Rad, Hercules, Calif.) SDS-PAGE gels run as described previously[32]. Immunoblots of SDS-PAGE gels were developed with MAbs Xi126 and XiR278[17].

Isolation of 29 kDa PspA

The 29 kDa fragment comprising the N-terminal 260 amino acids of PspA was produced in DH1 E. Coli from pJY4306[31,37]. An overnight culture of JY4306 was grown in 100 ml of Luria Broth (LB) containing 50 µg/ml ampicillin. The culture was grown at 37° C. in a shaker at 225 rpm. This culture was used to inoculate 6 one liter cultures that were grown under the same conditions. When the culture O.D. at 600 nm reached 0.7, 12 grams of cells, as a wet paste, were harvested at 4° C. at 12,000× g. The pellet was washed in 10 volumes of 25 mM Tris pH 7.7 at 0° C. and suspended in 600 ml of 20% sucrose, 25 mM Tris pH 7.7 with 10 mM ethylenediamine tetraacetic acid (EDTA) for 10 minutes. The cells were pelleted by centrifugation (8000× g) and rapidly suspended in 900 ml of 1 percent sucrose with 1 mM Pefabloc SC hydrochloride (Boehringer Mannheim Corp., Indianapolis, Ind.) at 0° C. The suspension was pelleted at 8000× g at 4° C. for 15 minutes and the PspA-containing supernatant (periplasmic extract) 51 recovered. The recombinant PspA was precipitated from the periplasmic extract by 70 percent saturated ammonium sulfate overnight at 4° C. The precipitated material was collected by centrifugation at 12,000× g at 4° C. for 30 minutes. The precipitated protein was resuspended in 35 ml of 20 mM histidine 1 percent sucrose at pH 6.6 (HSB). Insoluble materials were removed at 1,000× g at 4° C. for 10 minutes. The clarified material was dialyzed versus HSB, passed through a 0.2 µm filter and further purified on a 1 ml MonoQ HR 515 column (Pharmacia Biotech, Inc., Piscataway, N.J.) equilibrated with HSB. The clarified material was loaded on the column at 1 ml/min, and the column was washed with 10 column volumes of HSB. The column was then eluted with a gradient change to 5 mM NaCl per minute at a flow rate of 1 ml/min. As detected by immuno blot with Xi126, SDS-PAGE and absorbance, PspA eluted as a single peak at approximately 0.27 to 0.30 M NaCl. By SDS-PAGE the material was approximately 90 percent pure. The yield from 6 liters of culture was 2 mg (Bio-Rad protein assay) of recombinant PspA.

Growth of pneumococci for challenge

Mice were challenged with log-phase pneumococci grown in THY. For challenge, the pneumococci were diluted directly into lactated Ringer's without prior washing or centrifugation. To inject the desired numbers of pneumococci, their concentration in lactated Ringer's solution was adjusted to an O.D. of about 0.2 at 420 nM (LKB Ultrospec III spectrophotometer). The number of pneumococci present was calculated at $5 \times 10^8$ CFU per ml/O.D. and confirmed by colony counts (on blood agar) of serial dilutions of the inoculum.

Immunization, challenge, and bleeding of mice

CBA/CAHN/XID/J (CBA/N) and BALB/cByJ (BALB/c) mice were purchased from Jackson Laboratory Bar Harbor, Me. Mice were given two injections two weeks apart and challenged i.v. two weeks later. Injections without CFA were given intrapertioneally in a 0.1 ml of Ringers. Where indicated, the first injection was given in complete Freund's adjuvant (CFA) consisting of approximately a 1:1 emulsion of antigen solution and CFA oil (Difco, Detroit Miss.). Antigen in CFA was injected inguinally in 0.2 ml divided between the two hind legs. All mice were boosted i.p. without adjuvant. When mice were injected with media supernatants or 2 percent choline chloride eluates of whole bacteria, the amounts of material injected were expressed as the volume of media from which the injected material was derived. For example, if the clarified medium from pneumococci grown in CDM-CC or CDM-ET was used for immunization without dilution or concentration, the dose was described as 100 µl. If the material was first diluted ¹⁄₁₀, or concentrated 10 fold, the dose was referred to as 10 or 1000 µl respectively.

ELISA for antibodies to PspA

Specific modifications of previously reported ELISA conditions 17, are described. Microtitration plates (Nunc Maxisorp, P. G. C. Scientific, Gaithersburg Md.) were coated with undiluted supernatants of Rx1 and WG44.1 pneumococci grown in CDM-ET or 1 percent BSA in PBS.

Mice were bled retro-orbitally (75 μl) in a heparanized capillary tube (Fisher Scientific, Fair Lawn, N.J.) The blood was immediately diluted in 0.5 ml of one percent bovine serum albumin in PBS. The dilution of the resultant sera was 1/15 based on an average hematocrit of 47 percent. The sera were diluted in 7 three fold dilution in microtitration wells starting at 1/45. Mab Xi126 was used as a positive control. The maximum reproducible O.D. observed with Xi126 was defined as "maximum O.D." The O.D. observed in the absence of immune sera or MAb was defined as "minimum O.D." Antibody titers were defined as the dilution that gives 33 percent of maximum O.D. The binding to the Rx1 CDM-ET coated plates was shown to be PspA-specific, since in no case did we observe $\geq 33$ percent of maximum binding of immune sera or Xi126 on plates coated with WG44.1 CDM-ET or BSA.

Statistical analysis. Unless otherwise indicated P values refer to comparisons using the Wilcoxin two-sample rank test to compare the numbers of days to death in different groups. Mice alive at 21 days were assigned a value of 22 for the sake of calculation. P values of >0.05 have been regarded as not significant. Since we have never observed immunization with PspA or other antigens to make pneumococci more susceptible to infection the P values have been calculated as single tailed tests. To determine what the P value would have been if a two tailed test had been used the values given should be multiplied by two. In some cases P values were given for comparisons of alive versus dead. These were always calculated using the Fisher exact test. All statistical calculations were carried out on a Macintosh computer using InStat (San Diego, Calif.). PspA is the major protection-eliciting component released from pneumococci grown in CDM-ET or CDM-CC, or released from conventionally grown pneumococci by elution with 2% CC.

PspA-containing preparations from pneumococci were able to protect mice from fatal sepsis following i.v. challenge with $3 \times 10^3$ (100× LD50) capsular type 3 *S. pneumoniae* (Table 9). Comparable preparations from the strains unable to make PspA (WG44.1 and JY1119), or unable to make full length PspA (LM34 and JY2141) were unable to elicit protection. Regardless of the method of isolation the minimum protective dose was derived from pneumococci grown in from 10–30 μl of medium. We also observed 9 that supernatants of log phase pneumococci grown in normal THY or CDM media could not elicit protection (data not shown). This finding is consistent with earlier studies[36,37] indicating the PspA is not normally released in quantity into the medium of growing pneumococci.

Isolated PspA can elicit protection against fatal infection

Although PspA was necessary for these preparations to elicit protection it was possible that it did not act alone. Mice were thus, immunized with purified FL-PspA to address this question.

Isolation of FL-PspA from CDM-ET growth medium. We isolated the FL-PspA from CDM-ET rather than from CDM-CC medium or a 2 percent choline chloride elution of live cells, because the high levels of choline present in the latter solutions prevents adsorption of the PspA to the choline residues on the choline-Sepharose column. PspA for immunization was isolated from strain R36A, as the strain is non-encapsulated and the isolated PspA could not be contaminated with capsular polysaccharide. As a control we have conducted make isolations from WG44.1 since this strain has an inactivated pspA gene and produces no PspA. The results shown in Table 10 are typical of isolations from 300 ml of CDM-ET medium from R36A grown pneumococci. We isolated 84 μg of PspA from 300 ml of medium, or about 280 μg/liter. Based on the dot blot results this appears to be about 75% of the PspA in the original medium; and that CDM-ET from R36A cultures contains about 400 μg/liter of PspA, or about 0.4 μg/ml.

Figure 3:
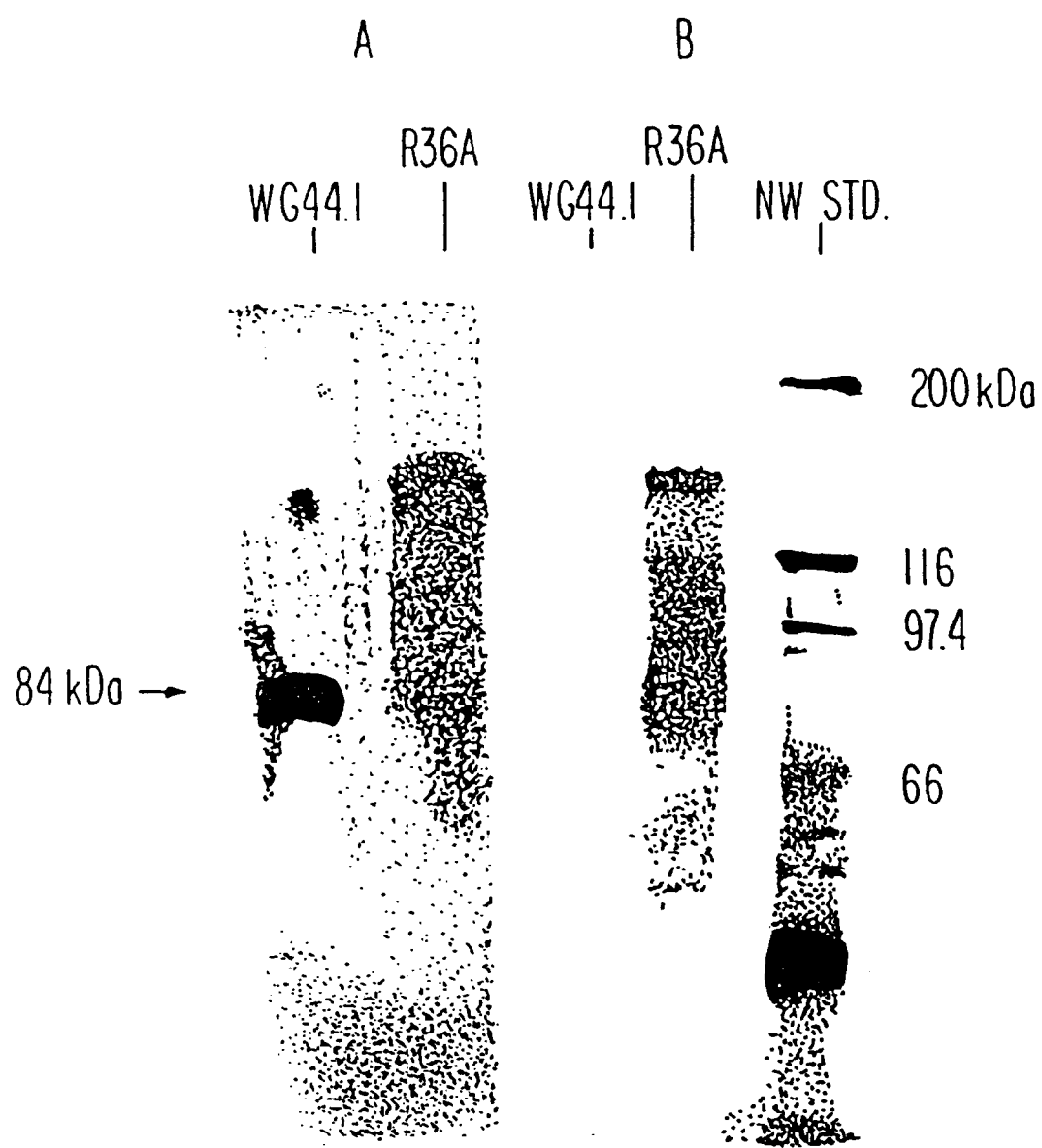
FIG. 3 shows: SDS-PAGE of R36A PspA (80 ng) column isolated from CDM-ET and an equal volume of an equivalent WG44.1 prep. Identical gels are shown stained with Bio-Rad silver kit (A) or immunoblotted with PspA MAb XiR278(B). The PspA isolated from R36A shows the characteristic monomer (84 kDa) and dimer bands.

No serologically detectable PspA was seen in the CDM-ET from WG44.1 cultures. More significantly there was undetectable protein recovered from the choline-Sepharose column after adsorption of CDM-ET from a WG44.1 culture, indicating that PspA is the only protein that could be isolated by this procedure. Moreover by silver stained SDS PAGE gel the PspA isolated from R36A appeared to be homogenous (FIG. 3). Although autolysin can also be isolated on choline-Sepharose[20,50], we did not expect it to be isolated by this procedure since autolysin is not released from pneumococci grown in choline deficient medium[36]. The immunologic purity of the isolated PspA was emphasized by the fact that immunization with it did not elicit any antibodies detectable on plates coated with CDM-ET supernatants of WG44.1.

Loading more than 300 ml on the 0.6 ml bed volume column did not result in an increased yield, which suggested that the column capacity had been reached. However, increasing the depth of the choline-Sepharose bed to greater than 0.5 cm, decreased the amount of PspA eluted from the column, presumably because of non-specific trapping of aggregates in the column matrix. The elution buffer contains 50 mM Tris acetate 0.25 M NaCl and 2% choline chloride. Elution without added NaCl or with IM NaCl resulted in lower yields. Elution with less than 1% CC also reduced yields.

Immunization of mice with purified R36A PspA. For immunization we used only the first 3 ml fraction of the R36A column. Mice were immunized with two injections of 1, 0.1, or 0.01 μg of R36A PspA, spaced two weeks apart. As controls, some mice were inoculated with a comparable dilutions of the first 3 ml fraction from the WG44.1 column. Purified FL-PspA elicited antibody to PspA at all doses regardless of whether CFA was used as an adjuvant (Table 11). In the absence of CFA the highest levels of antibody were seen with the 1 μg do of PspA. In the presence of CFA, however, the 0.1 μg dose was as immunogenic as the 1 μg dose.

To test the ability of the different doses of PspA to elicit protection against challenge we infected the immunized mice with two capsular type 3 strains, WU2 and A66. Although both of these strains are able to kill highly susceptible CBA/N XID mice at challenge doses of less than $10^2$, the A66 strain is several logs more virulent when BALB/c mice are used[47,52]. The difference in virulence of A66 and WU2, was partially compensated for by challenging the immunized CBA/N mice with lower doses of strain A66 than WU2.

After immunization of CBA/N mice with 1 and 0.1 μg doses of PspA we observed protection against WU2 challenge regardless of whether or not CFA was used as an adjuvant (Table 4). At the lowest dose, 0.01 μg PspA, most of the mice immunized with PspA +CFA lived whereas most immunized with PspA alone did not; however, the difference was not statistically significant. When immunized mice were challenged with the more virulent strain A66[47,53], survivors were only observed among mice immunized with the 1 and 0.1 μg doses. There was slightly, more protection against fatal A66 infection among mice immunized with CFA than without, but the difference was not statistically significant. When the two sample rank test was used to analyze the time to death of mice infected with A66 we observed a statistically significant delay in the time to death in each immunized group as compared to the pooled controls.

The 29 kDa N-terminal fragment of PspA can elicit protection against infection when injected with CFA We have compared the immunogenicity, with and without CFA, of an isolated 29 kDa fragment composed of the first 260 amino acids of PspA. Unlike the case with FL-PspA, adjuvant was required for the 29 kDa fragment to elicit a protective response. This was observed even though the immunizing doses of the 29 kDa antigen used were 10 and 30 $\mu$g/mouse, or about 100 and 300 times the minimum dose of FL-PspA that can elicits protection in the absence of adjuvant.

Injection with CFA revealed the presence of additional protection eliciting antigen(s) in CDM-CC, and CDM-ET growth medium but not in the 2 percent choline chloride eluates of live cells The observation that Freund's adjuvant could have such a major effect on the immunogenicity of the 29 kDa fragment (Table 12), prompted us to reexamine the immunogens described in Table 2 to determine if immunization with adjuvant might enhance protection elicited by PspA-containing preparations or provide evidence for protection eliciting antigens in addition to PspA. By using CFA with the primary injection, the dose of PspA-containing growth medium (CDM-CC and CDM-ET) required to elicit protection was reduced from 10–30 $\mu$l (Table 9) down to 1 to 3 $\mu$l (Table). When CFA was used as an adjuvant with CDM-CC and CDM-ET from PspA$^-$ strains WG44.1 and JY1119 we were able to elicit protective immune responses if material from $\geq$100$\mu$l or more of media were injected. Thus, although there were apparently some protection eliciting components other than PspA in CDC-CC and CDM-ET growth media, PspA remained the major protection eliciting component even in the presence of adjuvant.

One of the media used for injection was CDM-ET in which JY2141 had been grown. This medium elicited protection against WU2 challenge even when injected at doses as low as 1 $\mu$l. It should be noted that although this strain does not make full-length PspA, it secretes a truncated molecule comprising the first 115 amino acids of PspA into the growth medium. Thus, unlike CDM-ET from WG44.1 and JY1119, CDM-ET from JY2141 has the potential to elicit PspA-specific immunity. In contrast to these results, the material eluted from JY2 141 with 2 percent CC was relatively non-immunogenic even when emulsified with CFA. This result is consistent with the fact that the 115 amino acid N-terminal PspA fragment of JY2141 is not surface attached[37], and would be expected to be washed away prior to the elution with 2 percent CC.

Extension of studies to BALB/c mice and i.p. challenge route

The studies above all involve i.v. challenge of CBA/N mice expressing with the XID genetic defect. The i.v. route, used in the present studies provides a relevant model for bacteremia and sepsis, but pneumococci have higher LD$_{50}$s when injected i.v. than i.p. CBA/N mice are hypersusceptible to pneumococcal infection because of the XID defect. This genetic defect prevents them from having circulating naturally occurring antibody to phosphocholine. The absence of these antibodies has been shown to make XID mice several logs more susceptible to pneumococci than isogenic mice lacking the immune detect From the data in Table 14 it is clear, however, that immunization with PspA can protect against infection in mice lacking the XID defect even when the challenge is by the i.p. route. Thus, there is no reason to suspect that the results presented are necessarily dependent on the use of the CBA/N ED mouse or the i.v. route.

PspA Is highly immunogenic

These studies provide the first quantitative data on the amount of purified FL-PspA that is required to elicit protective immunity in mice. The isolated PspA for these studies was obtained by taking advantage of the fact that the C-terminal half of PspA binds to cell surface choline[36]. The isolated FL-PspA was found to be highly immunogenic in the mouse. Only two injections of 100 ng of PspA in the absence of adjuvant were required to elicit protection against otherwise fatal sepsis with greater than 100 LD$_{50}$ of capsular type 3 S. pneumoniae. When the first injection was given with adjuvant, doses as small as 10 ng could elicit protective response. The potent immunogenicity of PspA, and the ability to isolate it on choline-Sehparose columns provides a demonstration for the possible use of PspA as a vaccine in humans.

A large body of published[17,29,37] as well as unpublished evidence indicates that the major protection eliciting epitopes of PspA are located in the $\alpha$-helical (N-terminal) half of the molecule. From the present studies, it is clear that immunization with N-terminal fragments containing the first 1 15 or 260 of the 288 amino acid $\alpha$-helical region are able to elicit protection when given with CFA. However, these fragment were not able to elicit protective responses without CFA. In the case of the both the 115 and 260 amino acid fragments, even immunization at 100 times the minimum dose that is immunogenic for FL-PspA failed to elicit a protective response. This result is consistent with previous results showing that a fragment composed of the N-terminal 245 amino acids[31,37] could elicit protection against otherwise fatal pneumococcal infection of mice when the immunization was given with CFA[32]. In that study no immunization without CFA was attempted. Even though the C-terminal half of PspA may not contain major protection-eliciting epitopes it appears to contain sequence important in the immunogenicity of the molecule as a whole, since the full length molecule elicited much greater protection than the N-terminal fragments' The effect of the C terminal half on antigenicity may be in part that it doubles the size of the immunogen. Molecules containing the C-terminal half of PspA may also be especially immunogenic because they exhibit more extensive aggregation than is seen with fragments expressing only the $\alpha$-helical region[38], Protein aggregates are known to generally be more antigenic and less tolerogenic than individual free molecules[54].

PspA Is the major protection ting component of our pneumococcal extracts

Evidence that PspA is the major protection eliciting component of the CDM-ET, CDM-CC growth media and the two percent CC eluates was dependent on the use of mutant pneumococci that lacked the ability to produce FL-PspA. More than one pspA mutant strain was used to insure that the failure to elicit protection in the absence of FL-PspA was not a spurious result of non-PspA mutation blocking the production of some other antigen. Strains WG44.1 and JY1119 contain identical deletions that include the 5' end of the pspA genes and extend about 3 kb upstream of pspA[37]. WG44.1 is a mutant of the non-encapsulated strain Rx1 and JY1119 was made by transforming capsular type 3 strain WU2 with the WG44.1 pspA mutation. In no case were preparations from WG44.1 and JY1119 as efficient at eliciting protection as those from the PspA$^+$ strains. To rule out the possibility that protection elicited by preparations from the PspA$^+$ strains was elicited by some non-PspA molecule also encoded by a 3 kb deletion linked to the mutant pspA genes of WG44.1 and JY1119, we also used strains JY2141 and LM34[26,37]. In these strains the Rx1 pspA gene has been insertionally inactivated causing the production of N-terminal fragments of 115 and 245 amino acids respectively. These strains have no other known mutations. Although Rx1 and R36A are closely related non-encapsulated strains, some of the studies included Rx1 as the PspA+ control since it is the isogenic partner to WG44.1, LM34, and JY2141. The N-terminal fragments produced by JY2141 and LM34 lack the surface anchor and are secreted into the medium 36 Two percent CC eluates of JY2141 were non-protection eliciting even in the presence of adjuvant. In the absence of adjuvant, CDM-ET from JY2141 was not protection-eliciting. LM34 was tested without CFA in only 3 mice, but gave results consistent with those obtained with JY2141.

Anticapsular antibodies are known to be protective against pneumococcal infection[5,19]. However, in these studies it is unlikely that they account for any of the protection we attributed to PspA. Our challenge strain bore the type 3 capsular polysaccharide and our primary source of PspA was strain R36A, which is a spontaneous non-encapsulated mutant of a capsular type 2 strain[39,41]. The R36A strain has been recently demonstrated to lack detectable type 3 capsule on the surface or in its cytoplasm[55]. Furthermore, the CBA/N mice used in most of the studies are unable to make antibody responses to capsular type 3 polysaccharide[56].

Non-PspA protection eliciting components

The observation that CDM-CC and CDM-ET supernatants of WG44.1 could elicit protection when injected in large amounts with adjuvant, suggested that these supernatants contained at least trace amounts of non-PspA protection eliciting molecules. In the case of preparations containing PspA eluted from the surface of live washed pneumococci with 2 percent CC, there was no evidence for any protection eliciting components other than PspA, presumably because the protection-eliciting non-PspA proteins released into the media were removed by the previous washing step. The identity of the protection eliciting molecules in the WG44.1 supernatant are unknown. In this regard, it is of interest that unlike R36A, strain Rx1 has been shown to contain a very small amount of cytoplasmic type 3 polysaccharide (but totally lacks surface type 3 polysaccharide[55]). This difference from Rx1 apparently came about through genetic manipulations in the construction of Rx1 from R36A[39,41]. Thus, preparations made from Rx1 or from its daughter strains WG44.1, LM34, or JY2141 could potentially contain small amounts of capsular polysaccharide. For a number of reasons however, it seems very unlikely that the non-PspA protection-eliciting material identified in these studies was type 3 capsular polysaccharide (expressed by the WU2 challenge strain: 1) growth of these strains was either in CDM-CC or CDM-ET, each of which prevent autolysin activity and lysis[57] that would be required to release the small amount of type 3 polysaccharide from the cytoplasm of the Rx1 family of strains; 2) CBA/N mice made protective responses to the non-PspA antigens, but express the XID immune response deficiency which permits responses to proteins, but blocks antibody to most polysaccharides[46], including type 3 capsular polysaccharide[56]; and 3) immunogenicity of the non-PspA component required CFA, an adjuvant known to stimulate T-dependent (protein) rather than T-independent (polysaccharide) antibody responses.

A number of non-PspA protection eliciting pneumococcal proteins have been identified: pneumolysin, autolysin, neuraminidase, and PsaA which are 52, 36.5, 107 and 37 kDa respectively[21,58,59,60]. The non-PspA protection eliciting components reported here could be composed of a mixture of these and/or other non-identified proteins. Attempts to identify lambda clones producing non-PspA protection eliciting proteins as efficacious as PspA have not been successful[25].

Isolation of PspA

The protective capacity of the CDM-CC, CDM-ET and material eluted from live cells with 2% CC were similar in terms of the volume of the original culture from which the injected dose was derived. The major advantage of eluting the PspA from the surface of pneumococci with 2 percent CC is that the pneumococci may be grown in any standard growth medium, and do not have to be first adapted to a defined medium. Moreover, concentration of PspA can be accomplished by centrifugation of the pneumococci prior to the elution of the PspA. An advantage of using either CDM-CC and CDM-ET media was that these media prevented lysis and pneumococci could be grown into stationary phase without contaminating the preparations with cytoplasmic contents and membrane and wall components. A particular advantage of CDM-ET growth medium is that since it lacks high concentrations of choline the PspA contained in it can be adsorbed directly to a choline-Sepharose column for affinity purification.

One liter of CDM-ET growth medium contains about 400 µg of PspA, and we were able to isolate about ¾ of it to very high purity. At 0.1 µg/dose, a liter of CDM-ET contains enough PspA to immunize about 4,000 mice; or possibly 40–400 humans. Our present batch size for a single column run is only 300 ml of CDM-ET. This could presumably be increased by increasing the amount of the adsorbent surface by increasing the diameter of the column. Using our present running buffer we have found that a choline-Sepharose resin depth of 0.5 cm was optimal; increases beyond 0.5 cm caused the overall yield to decrease rather than increase, even in the presence of larger loading volumes of R36A CDM-ET

TABLE 8

Pneumococcal Strains

| Strain | Capsule type | PspA expressed | Parent strain | Construction technique | References |
|---|---|---|---|---|---|
| D39 | 2 | full length | — | clinical isolate | 26, 44 |
| R36A | non-encapsulated | full length | D39 | non-encapsulated mutant | 23, 44, 45 |
| Rx1 | non-encapsulated | full length | R36A | derived from R36A | 26, 39, 41 |
| WG 44.1 | non-encapsulated | none | Rx1 | aberrant insertion inactivation with pKSD300 | 26, 37 |

TABLE 8-continued

Pneumococcal Strains

| Strain | Capsule type | PspA expressed | Parent strain | Construction technique | References |
|---|---|---|---|---|---|
| LM34 | non-encapsulated | aa 1-245 of Rx1[a] | Rx1 | insertional inactivation with pKSD300 | 26, 37, 42 |
| JY2141 | non-encapsulated | aa 1-115 of Rx1[a] | Rx1 | insertional inactivation with pJY4208 | 37 |
| WU2 | 3 | full length | — | clinical isolate | 25, 46 |
| JY1119 | 3 | none | WU2 | transformation with WG44.1 DNA | 37 |
| A66 | 3 | full length | — | clinical isolate | 44, 47 |

[a]LM34 and LY2141 express fragments containing the first 245 and first 115 amino acids of Rx1 PspA respectively.

TABLE 9

PspA is the major protection-eliciting component in antigen preparations made by three different methods

| Preparation | Strain (PspA status) | Dose as volume of media in μl[a] | Median Days Alive | Alive: Dead | P versus controls[b] |
|---|---|---|---|---|---|
| 2% CC eluate from live cells | R36A (PspA+) | 1000 | >21 | 2:0 | |
| | | 200 | >21 | 2:0 | |
| | | 20 | >21 | 2:0 | |
| | | 2 | 1.5 | 0:2 | |
| | all R36A | | >21 | 6:2 | 0.03 |
| | JY2141 (aa 1–115) | 1000 | 3, >21 | 1:1 | |
| | | 200 | 1 | 0:2 | |
| | | 20 | 1 | 0:2 | |
| CDM-CC clarified medium | Rx1 (PspA+) | 100 | >21 | 9:0 | >0.0001 |
| | | 30 | >21 | 2:1 | |
| | | 10 | 2 | 1:2 | |
| | | 3 | 2 | 0:3 | |
| | ALL | | 2, >21 | 12:6 | 0.0004 |
| | LM34 | 100 | 2, 2, >21 | 1:2 | |
| | WG44.1 (PspA−) | 100 | 2 | 0:9 | |
| | | 30 | 2 | 0:3 | |
| | | 10 | 2 | 0:3 | |
| | | 4 | 2 | 0:3 | |
| | WU2 (PspA+) | 1000 | >21 | 3:0 | 0.05 |
| | | 100 | >21 | 1:0 | |
| | ALL | | >21 | 4:0 | 0.03 |
| | JY1119 (PspA−) | 1000 | 4 | 0:3 | |
| | | CDM-CC 100 | 2 | 0:2 | |
| CDM-ET clarified medium | R36A (PspA+) | 100 | >21 | 8:0 | <0.0001 |
| | | 10 | 3, >21 | 5:5 | 0.004 |
| | | 1 | 1.5 | 3:5 | |
| | | 0.1 | 2 | 0:2 | |
| | ALL | | >21 | 16:12 | 0.006 |
| | JY2141 (aa 1–115) | 100 | 1.5 | 0:2 | |
| | | 10 | 1.5 | 0:2 | |
| | WG44.1 (PspA−) | 100 | 3 | 0:2 | |
| | | 10 | 1.5 | 0:2 | |
| None | — | | 2 | 0:14 | — |

[a]Antigen dose is given as the volume of growth media from which the 0.1 ml of injected material was derived. Each mouse was injected twice i.p. with the indicated dose diluted as necessary in lactated Ringer's injection solution.
[b]Controls used for statistical comparisons: 2% CC, all JY2141; CDM-CC Rx1, all WG44.1; CDM-CC WU2, JY1119; CDM-ET, all WG44.1 + all JY2141.

TABLE 10

Isolation of PspA from 300 ml of CDM-ET media after the growth of R36A or WG44.1 pneumococci[a]

| | R36A | | | | WG44.1 | | |
|---|---|---|---|---|---|---|---|
| fraction | μg protein/ml | total μg protein[b] | max. reciprocal dot blot[c] | total dot blot units[b,d] | μg protein per/ml | total μg protein[b] | max. reciprocal dot blot[c] |
| growth media | 13.3 | 3,990 | 4 | 1200 | 13.7 | 4,110 | <1 |
| fail-through | 13.6 | 4,080 | 1 | 300 | 13.5 | 4,050 | <1 |
| 1st wash | | | <1 | | | | <1 |
| 10th wash | | | <1 | | | | <1 |
| elution #1 | 26 | 78 | 256 | 770 | <1 | — | <1 |
| elution #2 | 2 | 6 | 16 | 48 | <1 | — | <1 |

TABLE 10-continued

Isolation of PspA from 300 ml of CDM-ET media after the growth of R36A or WG44.1 pneumococci[a]

| | R36A | | | | WG44.1 | | |
|---|---|---|---|---|---|---|---|
| fraction | µg protein/ml | total µg protein[b] | max. reciprocal dot blot[c] | total dot blot units[b,d] | µg protein per/ml | total µg protein[b] | max. reciprocal dot blot[c] |
| elution #3 | <1 | — | 4 | 12 | <1 | — | <1 |
| total eluted | | 84 | | 830 | | — | <1 |

[a]The columns were loaded with 300 ml of clarified CDM-ET medium after the growth of R36A or WG44.1. The column was washed with 10 sequential 3 ml fractions of TBA. Elution was with TBA plus 2 percent CC.
[b]Total µg protein or total dot blot units reflect the total protein in the 300 ml of the loading material or the 3 ml size of the eluted fractions.
[c]MAb XiR278 was used in the immunoblots to detect PspA in dot blots.
[d]Dot blot units were calculated as the reciprocal dot blot titer times the volume in ml.

TABLE 11

Purified full-length PspA is able to elicit protection against fatal sepsis in mice.

| Antigen | Dose[a] | Adjuvant or Diluent | Anti-PspA titer[b] (Log mean ± S.E.) | Challenge with $10^{5.1}$ WU2 | | | Challenge with $10^{4.2}$ A66 | | |
|---|---|---|---|---|---|---|---|---|---|
| | | | | Alive: Dead | Median Days Alive | P vs. pooled control[c] | Alive: Dead | Median Days Alive | P vs. pooled controls[c] |
| R36A | 1 µg | Ringer's | 3.3 ± 0.2 | 5:0 | >21 | 0.015 | 2:3 | 4 | 0.002 |
| (PspA+) | 0.1 | Ringer's | 2.6 ± 0.2 | 4:0 | >21 | 0.041 | 1:4 | 4 | 0.0032 |
| | 0.01 | Ringer's | 2.7 ± 0.2 | 1:4 | 4 | n.s. | 0:5 | 3 | 0.0058 |
| | 1 µg | CFA | 3.5 ± 0.2 | 5:0 | >21 | 0.027 | 3:2 | >21 | 0.0012 |
| | 0.1 | CFA | 3.6 ± 0.1 | 5:0 | >21 | 0.0013 | 2:3 | 4 | 0.0012 |
| | 0.01 | CFA | 3.1 ± 0.2 | 4:1 | >21 | 0.015 | 0:5 | 3 | 0.0058 |
| WG44.1 | 3600 µl | Ringer's | <1.6 | n.d. | n.d. | | 1:4 | 3 | n.s. |
| (PspA−) | 360 | Ringer's | <1.6 | n.d. | n.d. | | 0:5 | 2 | n.s. |
| | 36 | Ringer's | <1.6 | n.d. | n.d. | | 0:5 | 2 | n.s. |
| | 3600 µl | CFA | <1.6 | n.d. | n.d. | | 0:5 | 2 | n.s. |
| | 360 | CFA | <1.6 | n.d. | n.d. | | 1:4 | 2 | n.s. |
| | 36 | CFA | <1.6 | n.d. | n.d. | | 0:5 | 2 | n.s. |
| saline | — | CFA | <1.6 | 1:5 | 4 | — | n.d. | n.d. | — |
| pooled controls | | | <1.6 | 1:5 | 4 | | 2:28 | 2 | — |

[a]For comparison with the data in Table 2, it should be noted that the 1, 0.1, and 0.01 µg doses were derived from 3600, 360, and 36 µl of R36A growth media. Equivalent dilutions of the PspA− eluate from strain WG44.1 were injected as controls. The amount of the WG44.1 preparations injected is listed as 3600, 360, and 36 µl and corresponds to the volume original growth medium from which the doses of WG44, 1 was prepared.
[b]Antibody values were expressed as reciprocal ELISA tier.
[c]P values calculated by the Wilcoxon two sample rank test. By Kruskal-Wallis nonparametric ANOVA for the WU2 challenge was significant at P = 0.01, for A66 significance was at P < 0.0001.

TABLE 12

The 29 kDa N-terminal fragment of Rx1 PspA must be injected with adjuvant to elicit protection against WU2[a]

| µg 29 kDa PspA | Adjuvant or diluent | Median Days Alive | Alive:Dead | P versus none[b] |
|---|---|---|---|---|
| 30 | CFA | >21 | 3:0 | 0.0006 |
| 3 | CFA | >21 | 3:0 | |
| 30 | Ringer's | 2 | 0:3 | |
| 3 | Ringer's | 2 | 1:2 | |
| none | CFA | 2 | 0:7 | |
| none | Ringer's | 2 | 0:7 | |

[a]The 29 kDa fragment comprises the first 260 amino acids of PspA.
[b]For the calculation of P values the 30 µg and 3 µg data were pooled; mice immunized with PspA + CFA were compared to CFA controls; mice immunized with PspA + Ringer's were compared to controls immunized with Ringer's. Only the statistically significant P values are shown. The calculated P value of PspA + CFA versus CFA alone, was 0.0006 by both the Wilcoxon two sample rank test and the Fisher exact test.

TABLE 13

PspA is not the only protection eliciting molecule released from pneumococci by interference with binding to choline on the surface of pneumococci

| Preparation | Strain (PspA status) | Dose (as volume in µl) | Median Day Alive | Alive: Dead | P values[a] |
|---|---|---|---|---|---|
| | | | | | P vs. all JY2141 |
| 2% CC eluate from live cells | R36A (PspA+) | 1000 | >21 | 2:0 | |
| | | 200 | >21 | 5:0 | 0.02 |
| | | 20 | >21 | 5:0 | 0.02 |
| | | 2 | >21 | 5:0 | 0.02 |
| | | all R36A | >21 | 17:0 | 0.001 |
| | JY2141 (aa 1–115) | 1000 | >21 | 2:0 | |
| | | 200 | 1 | 0:2 | |
| | | 20 | 1 | 0:2 | |
| | | 2 | 1 | 0:2 | |
| | | all JY2141 | 1 | 2:6 | |
| | | | | | P versus pooled cont. |
| CDM-CC clarified medium + CFA | Rx1 (PspA+) | 1000 | >21 | 3:0 | 0.002 |
| | | 100 | >21 | 3:0 | 0.002 |
| | WU2 (PspA+) | 1000 | >21 | 3:0 | 0.002 |
| | | 100 | >21 | 3:0 | 0.002 |
| | | 3 | >21 | 3:0 | 0.002 |
| | WG44.1 (PspA−) | 1000 | >21 | 5:1 | <0.0001 |
| | | 100 | 2.5 | 2:4 | 0.002 |
| | JY1119 (PspA−) | 1000 | >21 | 3:0 | 0.002 |
| | | 100 | >21 | 3:0 | 0.002 |
| CDM-ET clarified medium + CFA | R36A (PspA+) | 1000 | >21 | 3:1 | 0.004 |
| | | 10 | >21 | 4:0 | 0.004 |
| | | 1 | >21 | 3:1 | 0.004 |
| | | 0.2 | 2 | 0:4 | |
| | JY2141 (aa 1–115) | 10 | >21 | 2:0 | |
| | | 1 | >21 | 2:0 | |
| | all JY2141 | — | >21 | 4:0 | 0.004 |
| | WG44.1 (PspA−) | 100 | >21 | 2:0 | |
| | | 10 | 2 | 0:2 | |
| CDM-ET only | +CFA | | 2 | 0:9 | |
| None | none | | 1.5 | 0:4 | |
| Pooled Controls[b] | | | 2 | 0:13 | |

[a] In cases where there were not statistically significant results no P value was shown.
[b] "Pooled Controls" refers to "CDM-ET only" Data and "None" data.

TABLE 14

Immunization of BALB/c mice with isolated PspA elicits protection against WU2 *S. pneumoniae*

| Antigen | | Adjuvant | Challenge | | Days to | P vs. controls |
|---|---|---|---|---|---|---|
| Source | Dose[a] | or diluent | Log CFU | Route | Death | TSR/FE[b] |
| R36A (PspA+) | 1 µg | CFA | 4 | i.p. | 2, >21, >21, >21 | 0.06/0.03 |
| WG44.1 (PspA−) | 100 µl | CFA | 4 | i.p. | 2, 3 | |
| None | — | CFA | 4 | i.p. | 2, 2, 2, 4 | |
| R36A (PspA+) | 1 µg | none | 6 | i.v. | 2, >21, >21, >21 | 0.06/0.03 |
| WG44.1 (PspA−) | 100 µl | none | 6 | i.v. | 5, 7 | |
| none | — | none | 6 | i.v. | 2, 2, 2, 3 | |
| Pooled i.v. and i.p. results | | | | i.v. or i.p. | | 0.008/0.0007 |

[a] The 1 µg dose of R36A PspA was isolated from 100 µl of CDM-ET medium. As a control mice were injected with an corresponding volume of choline-column effluent from a mock isolation of PspA from the PspA− strain WG44.1. The dose of WG44.1 material is expressed as 100 µl since this is the volume CDM-ET from which the injected column effluent was derived.
[b] P values calculated by Wilcoxon two-sample rank test, TSR, or Fisher exact, FE versus pooled controls for each group. "Pooled controls" include data obtained with by injection of "WG44.1" and "none". The i.p. and i.v. studies gave comparable results. When the data from the two studies were pooled the P values by both tests were ≦0.008. In cases where there were not statistically significant results no P value was shown.

REFERENCES

1. Anonymous. Pneumococcal polysaccharide vaccine. *MMWR* 1981, 30, 410419
2. Farley, J. J., King, J. C., Nair, P., al., e. Infasive pneumococcal disease among infected and uninfected children of mothers with immunodeficiency virus infection. *J. Pediatr.* 1994, 124, 853–858
3. Schwartz, B., Gove, S., Lob-Lovit, I., Kirkwood, B. R. Potential interactions for the prevention of childhood pneumonia in developing countries: etiology of accute lower respiratory infections among young children in developing countries. *Ped Infect. Dis.* in Press,
4. Avery, O. T., Goebel, W. F. Chemoimmunological stuides of the soluable specific substance of pneumococcus. I. The isolation and properties of the acetyl polysaccharide of pneumococcus type 1. *J. Exp. Med.* 1933, 58, 731–755
5. Austrian, R. Pneumococcal Vaccine: Development and Prospects. *Am. J. Med* 1979, 67, 547–549
6. Shapiro, E. D., Berg, A. T., Austrian, R., Schroeder, D., Parcells, V., Margolis, A., Adair, R. K., Clemmens, J. D. Protective efficacy of polyvalent pneumococcal polysaccharide vaccine. *N. Engl. J. Med* 1991, 325, 1453–1460
7. Fedson, D. S. Pneumococcal vaccination in the prevention of community-acquired pneumonia: an optimistic view of cost-effectiveness. *Sem. Resp. Infect.* 1993, 8, 285–293
8. Robbins, J. B., Austrian R., Lee, C. -J., Rastogi, S. C., Schiffinan, G., Henrichsen, J., Makela, P. H., Broome, C. V., Facklam, R. R., Tiesjema, R. H., Parke, J. C., Jr. Considerations for formulating the second-generation pneumococcal capsular polysaccharide vaccine with emphasis on the cross-reactive types within groups. *J Infect Dis* 1983, 148, 1136–1159
9. Gotschlich, E. C., Goldschneider, I., Lepow, M. L., Gold, R. *The immune response to bacterial polysaccharides in man.* Antibodies in human diagnosis and therapy. New York, Raven, 1977, 391–402.
10. Cowan, M. J., Ammann, A. J., Wara, D. W., Howie, V. M., Schultz, L., Doyle, N., Kaplan, M. Pneumococcal .polysaccharide immunization in infants and children. *Pediatrics* 1978, 62, 721–727
11. Mond, J. J., Lees, A., Snapper, C. M. T cell-independent antigens type 2. *Ann. Rev. Immunol.* 1995, 13, 655–692
12. Chiu, S. S., Greenberg, P. D., Marcy, S. M., Wong, V. K., Chang, S. J., Chiu, C. Y., Ward, J. I. Mucosal antibody responses in infants following immunization with *Haemophilus influenzae*. *Pediatric Res. Abstracts* 1994, 35, 10A
13. Kauppi, M., Eskola, J., Kathty, H. ¯H. influenzae type b (Hib) conjugate vaccines induce mucosal IgA1 and IgA2 antibody responses in infants and children. *ICAAC Abstracts* 1993, 33, 174
14. Dagen, R., Melamed, R., Abramson, O., Piglansky, L., Greenberg, D., Mendelman, P. M., Bohidar, N., TerMinassian, D., Cvanovich, N., Lov, D., Rusk, C., Donnelly, J., Yagupsky, P. Effect of heptavalent pneumococcal-OMPC conjugate vaccine on nasopharyngeal carriage when administered during the 2nd year of life. *Pediat. Res.* 1995, 37, 172A
15. Fattom, A., Vann, W. F., Szu, S. C., Sutton, A., Bryla, D., Shiffman, G., Robbins, J. B., Schneerson. R. Synthesis and physiochemical and immunological characterization of pneumomcoccus type 12F polysaccharide-diptheria toxoid conjugates. *Infect. Immun.* 1988, 56, 2292–2298
16. Kennedy, D., Derousse, C., E., A. Immunologic response of 12–18 month children to licensed pneumococcal polysaccharide vaccine primed with *Streptococcus pneumoniae* 19F conjugate faccine. ICAAC 1994, Abstract, G89
17. McDaniel, L. S., Ralph, B. A., McDaniel, D. O., Briles, D. E. Localization of protection-eliciting epitopes on PspA of *Streptococcus pneumoniae* between amono acid residues 192 and 260. *Microbial Pathogenesis* 1994, 17, 323–337
18. Langermann, S., Palaszynski, S. R., Burlein, J. E., Koenig, S., Hanson, M. S., Briles, D. E., Stover, C. K. Protective humoral response against pneumococcal infection in mice elicited by recombinant Bacille Calmette-Guerin vaccines expressing PspA. *J. Exp. Med.* 1994, 180, 2277–2286
19. Siber, G. R. Pneumococcal Disease: Prospects for a New Generation of Vaccines. *Science* 1994, 265, 1385–1387
20. Lock, R. A., Hansman, D., Paton, J. C. Comparative efficacy of autolysin and pneumolysin as immunogens protecting mice against infection by *Streptococcus pneumoniae*. *Microbial Pathogenesis* 1992, 12, 137–143
21. Sampson, J. S., O'connor, S. P., Stinson, A. R., Tharpe, J. A., Russell, H. Cloning and nucleotide sequence analysis of psaA, the *Streptococcus pneumoniae* gene encoding a 37-kilodalton protein homologus to previously reported Streptococcus sp. adhesins. *Infect. Immun.* 1994, 62, 319
22. Paton, J. C., Lock, R. A., Lee, C. -J., Li, J. P., Berry, A. M., Mitchell. Purification and inmmunogenicity of genetically obtained pneumolysin toxoids and their conjugation to *Streptococcus pneumoniae* type 19F polysaccharide. *Infect. Immun.* 1991, 59, 2297–2304
23. McDaniel, L. S., Scott, G., Kearney, J. F., Briles, D. E. Monoclonal antibodies against protease sensitive pneumococcal antigens can protect mice from fatal infection with *Streptococcus pneumoniae*. *J. Exp. Med.* 1984, 160, 386–397
24. Briles, D. E., Forman, C., Horowitz, J. C., Volanakis, J. E., Benjamin, W. H., Jr., McDaniel, L. S., Eldridge, J., Brooks, J. Antipneumococcal effects of C-reactive protein and monoclonal antibodies to pneumococcal cell wall and capsular antigens. *Infect. Immun.* 1989, 57, 1457–1464
25. McDaniel, L. S., Sheffield, J. S., Delucchi, P., Briles, D. E. PspA, a surface protein of *Streptococcus pneumoniae*, is capable of eliciting protection against pneumococci of more than one capsular type. *Infect. Immun.* 1991, 59, 222–228
26. McDaniel, L. S., Yother, J., Vijayakumar, M., McGarry, L., Guild, W. R., Briles, D. E. Use of insertional inactivation to facilitate studies of biological properties of pneumococcal surface protein A (PspA). *J. Exp. Med.* 1987, 165, 381–394
27. Yother, J., McDaniel, L. S., Crain, M. J., Talkington, D. F., Briles, D. E. Pneunococcal surface protein A: Structural analysis and biological significance In: Dunny, G. M., Cleary, P. P., McKay, L. L. ed. Genetics and Molecular Biology of Streptococci, Lactococci, and Enterococci. Washington, DC: American Society for Microbiology, 1991, 88–91
28. Waltman, W. D., II, McDaniel, L. S., Gray, B. M., Briles, D. E. Variation in the molecular weight of PspA (Pneumococcal Surface Protein A) among *Streptococcus pneumoniae*. *Microb. Pathog.* 1990, 8, 61–69
29. Cran, M. J., Waltman, W. D., II, Turner, J. S., Yother, J., Talkington, D. E., McDaniel, L. M., Gray, B. M., Briles, D. E. Pneumococcal surface protein A (PspA) is serologically highly variable and is expressed by all clinically important capsular serotypes of *Streptococcus pneumoniae*. *Infect. Immun.* 1990, 58, 3293–3299
30. McDaniel, L. S., Scott, G., Widenhofer, K., Carroll, Briles, D. E. Analysis of a surface protein of *Streptococcus pneumoniae* recognized by protective monoclonal antibodies. *Microb. Pathog.* 1986, 1, 519–531
31. Yother, I., Briles, D. E. Structural properties and evolutionary relationships of PspA, a surface protein of *Streptococcus pneumoniae*, as revealed by sequence analysis. *J. Bact.* 1992, 174, 601–609
32. Tallington, D. F., Crimmins, D. L., Voellinger, D. C., Jother, J., Briles, D. E. A 43-kilodalton pneumococcal surface protein, PspA: isolation, protective abilities, and structural analysis of the amino-terminal sequence. *Infec. Imunun.* 1991, 59:, 1285–1289
33. McDaniel, L. S., McEdaniel, D. O. *Genetic analysis of the gene encoding type 12 PspA of Streptococcus pneumoniae strain EF5668* In: Feretti, J. J., Gilmore, M. S., Khenhammer, T. R., Brown, F. ed. Genetics of the streptococci, enterocococci, and lactococci. Basel: Dev. Biol. Stand. Basel Krager, 1995, 283–286
34. Fischetti, V. A., Pancholi, V., Schneewind, O. Conservation of a hexapeptide sequence in the anchor region of surface proteins from gram-positive cocci. *Molec. Microbiol* 1990, 4, 1603–1605
35. Schneewind, O., Fowler, A., Faull, K. F. Structrure of cell wall anchor of cell surface proteins in *Staphylococcus aureus*. *Science* 1995, 268, 103–106
36. Yother, J., White, J. M. Novel surface attachment mechanism for the streptococcus pneumoniae protein PspA. *J. Bact.* 1994, 176, 2976–2985
37. Yother, J., Handsome, G. L., Briles, D. E. Truncated forms of PspA that are secreted from *Streptococcus pneumoniae* and their use in functional studies and cloning of the pspA gene. *J. Bact.* 1992, 174, 610–618
38. Talkington, D. F., Voellinger, D. C., McDaniel, L. S., Briles, D. E. Analysis of pneumococcal PspA microheterogeneity in SDS polyacrylamide gels and the association of PspA with the cell membrane. *Microbial Pathogenesis* 1992, 13, 343–355
39. Smith, M. D., Guild, W. R. A plasmid in *Streptococcus pneumoniae*. *J. Bacteriol.* 1979, 137, 735–739
40. Shoemaker, N. B., Guild, W. R. Destruction of low efficiency markers is a slow process occurring at a heteroduplex stage of transformation. *Mol. Gen. Genet.* 1974, 128, 283–290
41. Raven, A. W. Reciprocal capsular transformations of pneumococci. *J. Bact.* 1959,77, 296–309
42. McDaniel, L. S., Sheffield, J. S., Swiatlo, E., Yother, J., Crain, M. J., Briles, D. E. Molecular localization of variable and conserved regions of pspA, and idnetification of additional pspA homologous sequences in *Streptococcus pneumoniae. Microbial Pathogenesis* 1992, 13, 261–269

43. Rijn, V. D., Kessler, R. E. Growth characteristics of Group A Streptococci in a new chemically defined medium. *Infec. Immun.* 1980, 27, 444–448

44. Avery, O. T., MacLeod, C. M., McCarty, M. Studies on the chemical nature of the substance inducing transformation of pneumococcal types. Induction of transformation by a desoxyribonucleic acid fraction isolated from pneumococcus type III. *J. Exp. Med* 1944, 79, 137–158

45. McCarty, M. *The transforming principle.* New York, Norton, 1985, 252.

46. Briles, D. E., Nahm, M., Schroer, K., Davie, J., Baker, P., Kearney, J., Barletta, R. Antiphosphochollne antibodies found in normal mouse serum are protective against intravenous infection with type 3 *Streptococcus pneumoniae. J. Exp. Med.* 1981, 153, 694–705

47. Briles, D. E., Crain, M. J., Gray, B. M., Forman, C., Yother, J. A strong association between capsular type and mouse virulence among human isolates of *Streptococcus pneumoniae. Infect. Immun.* 1992, 60, 111–116

48. Waltman, W. D., II, McDaniel, L. S., Andersson, B., Bland, L., Gray, B. M., Svanborg-Eden, C., Briles, D. E. Protein serotyping of *Streptococcus pneumoniae* based on reactivity to six monoclonal antibodies. *Microb. Pathog.* 1988, 5, 159–167

49. Tomasz, A. Surface components of *Streptococcus pneumoniae. Rev. Infect. Dis* 1981, 3, 190–211

50. Garcia, J. L., Garcia, E., Lopez, R. Overproduction and rapid purifcation of the amidase of *Streptococcus pneumoniae. Arch. Microbiol.* 1987, 149, 52–56

51. Osborn, M. J., Munson, J. Separation of the inner (cytoplasmic) and outer membranes of gram negative bacteria. *Methods Enzymol.* 1974, 31A, 642–653

52. Briles, D. E., Horowitz, J., McDaniel, L. S., Benjamin, W. H., Jr., Claflin, J. L., Booker, C. L., Scott, G., Forman, C. Genetic control of susceptibility to pneumococcal infection. *Curr. Top. Microbiol. Immunol.* 1986, 124, 103–120

53. Briles, D. E., Forman, C., Crain, M. Mouse antibody to phosphocholine can protect mice from infection with mouse-virulent human isolates of *Streptococcus pneumoniae. Infect. Immun.* 1992, 60, 1957–1962

54. Weigle, W. O. *Immunological unresponsiveness.* Academic Press, New York, N.Y., 1973, 55. Dillard, J. P., Yother, J. Genetic and molecular characterization of capsular polysaccharide biosynthesis in *Streptococcus pneumoniae* type 3. *Molec. Microbiol.* 1994, 12, 959–972

56. Amsbaugh, D. F., Hansen, C. T., Prescott, B., Stashak, P. W., Barthold, D. R., Baker, P. J. Genetic control of the antibody response to type m pneumococcal polysaccharide in mice. I. Evidence that an X-linked gene plays a decisive role in determining responsiveness. *J. Exp. Med* 1972, 136, 931–949

57. Tomasz, A. Biolobical consequences of the replacement of choline by ethanolamine in the cell wall of pneumococcus: chain formation, loss of transformability, and loss of autolysis. *Proc. Natl. Acad. Sci. USA* 1968, 59, 86–93

58. Paton, J. C., Lock, R. A., Hansman, D. C. Effect of immunization with pneumolysin on survival time of mice challanged with *Streptococcus pneumoniae. Infect. Immun.* 1983, 40, 548–552

59. Berry, A. M., Lock, R. A., Hansman, D., Paton, J. C. Contribution of autolysin to virulence of *Streptococcus pneumoniae. Infect. Immun.* 1989, 57, 2324–2330

60. Lock, R. A., Paton, J. C., Hansman, D. Purification and immunologic characterization of neuraminidase produced by *Streptococcus pneumoniae. Microbial Pathogenesis* 1988, 4, 33–43

61. Tuomanen, E., Liu, H., Hengstler, B., Zak, O., Tomasz, A. The Induction of meningeal inflammation by components of the pneumococcal cell wall. 1985, 151, 859–868

62. Tuomanen, E., Tomasz, A., Hengstler, B., Zak, O. The relative role of bacterial cell wall and capsule in the induction of inflammation in pneumococcal meningitis. *J. Infect. Dis.* 1985, 151, 535–540

63. Paton, J. C. Pathogenesis of pneumococcal disease. 1993, 363–368

64. Briese, T., Hakenbeck, R. Interaction of the pneumococcal amidase with lipoteichoic acid and choline. 1985, 146, 417–427

65. Briles D. E., J. Yother and L. S. McDaniel. Role of pneumococcal surface protein A in the virulence of *Streptococcus pneumoniae.* Rev Infect Dis 1988; 10:S372–374.

66. Crain M. J. Unpublished data.

67. Munoz R., J. M Musser, M. Crain, D. E. Briles, A. Marton, A. J. Parkinson, U. Sorensen and A. Tomasz. Geographical distribution of penicillin-resistant clones of *Streptococcus pneumoniae:* characterization by penicillin-binding protein profile, surface protein A typing, and multilocus enzyme analysis. Clinic Infect Dis 1992; 15:112–118.

68. Brooks-Walter A. and L. S. McDaniel. 1994. Unpublished data.

69. Sheffield J. S., W. H. Benjamin and L. S. McDaniel. Detection of DNA in Southern Blots by Chemiluminescence is a sensitive and rapid technique. Biotechniques 1992; 12:836–839.

Example 4

Evidence For Simultaneous Expression of Two PspAs

From Southern blot analysis there has been an issue as to whether most isolates of *S. pneumoniae* has two DNA sequences that hybridize with both 5' and 3' halves of Rx1 pspA, or whether this is an artifact of Southern blot. When bacterial lysates have been examined by Western blot, the results have always been consistent with the production of a single PspA by each isolate. This Example provides evidence for the first time that two PspAs of different apparent molecular weights and different serotypes can be simultaneously expressed by the same isolate.

Different PspAs frequently share cross-reactive epitopes, and an immune serum to one PspA was able to recognize PspAs on all pneumococci. In spite of these similarities, PspAs of different strains can generally be distinguished by their molecular weights and by their reactivity with a panel of PspA-specific monoclonal antibodies (MAbs).

A serotyping system for PspA has been developed which uses a panel of seven MAbs. PspA serotypes are designated based on the pattern of positive or negative reactivity in immunoblots with this panel of MAbs. Among a panel of 57 independent isolates of 9 capsular groups/types, 31 PspA serotypes were observed. The large diversity of PspA was substantiated in a subsequent study of 51 capsular serotype 6B isolates from Alaska, provided by Alan Parkinson at the Arctic Investigations Laboratory of the Centers for Disease Control and Prevention. Among these 51 capsular type 6B isolates were observed 22 different PspAs based on PspA serotype and molecular weight variations of PspA.

While most pneumococcal strains appear to have two DNA sequences homologous with both the 5' and 3' halves of pspA, site-specific truncation mutations of Rx1 have revealed that one these, pspA, encodes PspA. The other sequence has been provisionally designated as the pspA-like sequence. At present whether the pspA-like sequence makes a gene product is unknown. Evidence that the pspA and pspA-like genes are homologous but distinct groups of alleles comes from Southern blot analysis at high stringencies. Additional evidence that pspA and the pspA- like loci are distinct comes from studies using PCR primers that permit amplification of a single product approximately 2 Kb in size from 70% of pneumococci. For the remaining 30% of pneumococci no amplification was observed with the primers used.

Figure 4:
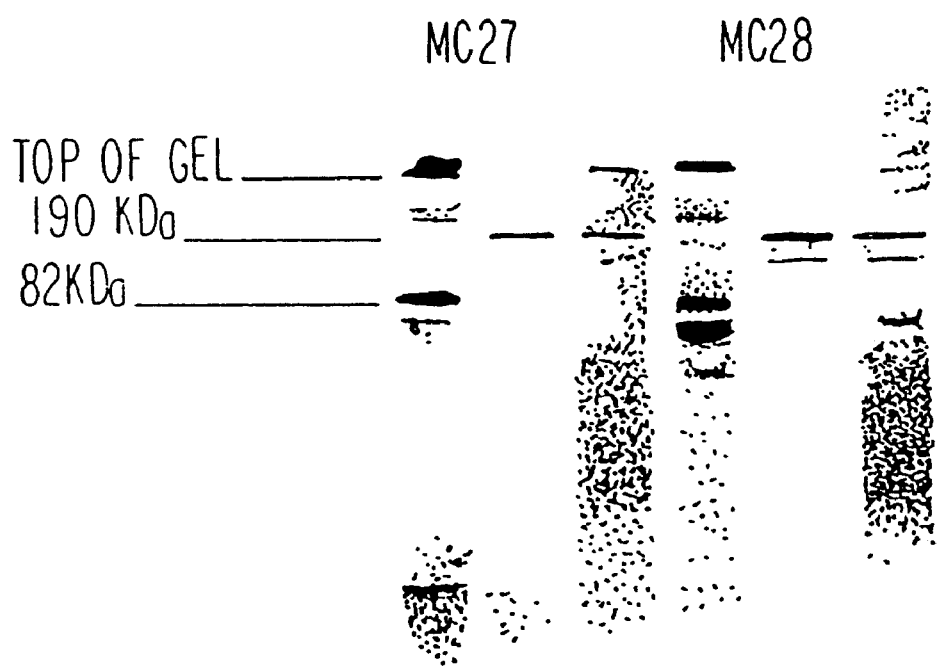
FIG. 4 shows: Cell lysates of pneumococcal isolates MC27 and MC28 were subjected to SDS-PAGE and transferred to nitrocellulose for Western blotting with seven MAb to PspA. 7D2 detected a protein of 82 kDa in each isolate and XiR278 and 2A4 detected a protein of 190 kDa in each isolate. MAb Xi64, Xi126, 1A4 and SR4W4 were not reactive. Strains MC25 and MC26 yielded identical results.

Evidence for two PspAs:

When the strains of MC25-28 were examined with the panel of seven MAbs specific for different PspA epitopes, all four demonstrated the same patterns of reactivity (FIG. 4). The MAbs XiR278 and 2A4 detected a PspA molecule with an apparent molecular weight of 190 KDa in each isolate. In accordance with the previous PspA serotyping system, the 190 KDa molecule was designated as PspA type 6 because of its reactivity with XiR278 and 2A4, but none of the five other MAbs in the typing system. Each isolate also produced a second PspA molecule with an apparent molecular weight 82 KDa. The 82 KDs PspA in each isolate was detected only with the MAb 7D2 and was designated as type 34. No reactivity was detected with MAbs Xi126, Xi64, 1A4, or SR4W4. The fact that all four capsular 6B strains exhibit two PspAs, based on both molecular weights and PspA serotypes, suggested that they might be members of the same clone.

Simultaneous production of both PspAs:

Results from the colony immunobloting showed that both PspAs were present simultaneously in each colony of these isolates when grown in vitro. All colonies on each plate of the original culture, as well as all of the progeny colonies from a single colony, reacted with MAbs XiR278, 2A4, and 7D2.

Number of pspA genes:

One explanation for the second PspA molecule was that these strains contained an extra pspA gene. Since most strains contain a pspA gene and a pspA-like gene it was expected that if an extra gene were present one might observe at least three pspA homologous loci in isolates MC25–28. In Hind III digests of MC25–28 each strain revealed a 7.7 and 3.6 Kb band when probed with plSMpspA13/2 (FIG. 5A). In comparison, when Rx1 DNA was digested with Hind III and hybridized with plSMpspA13.2, homologous sequences were detected on 9.1 and 4.2 Kb fragments as expected from previous studies (9) (FIG. 5A). Results consistent with only two pspA- homologous genes in MC25–28 were also obtained with digestion using four additional enzymes (Table 15).

In previous studies it has been reported that probes for the 5' half of pspA (encoding the alpha-helical half of the protein) bind the pspA-like sequence of most strains only at a stringency of around 90%. With chromosomal digests of MC25–28 we observed that the 5' Rx1 probe of pLSMpspA12/6 bound both pspA homologous bands at a stringency of greater than 95 percent. The same probe bound only the pspA containing fragment Rx1 at a stringency above 95 percent (FIG. 5B).

Figure 6:
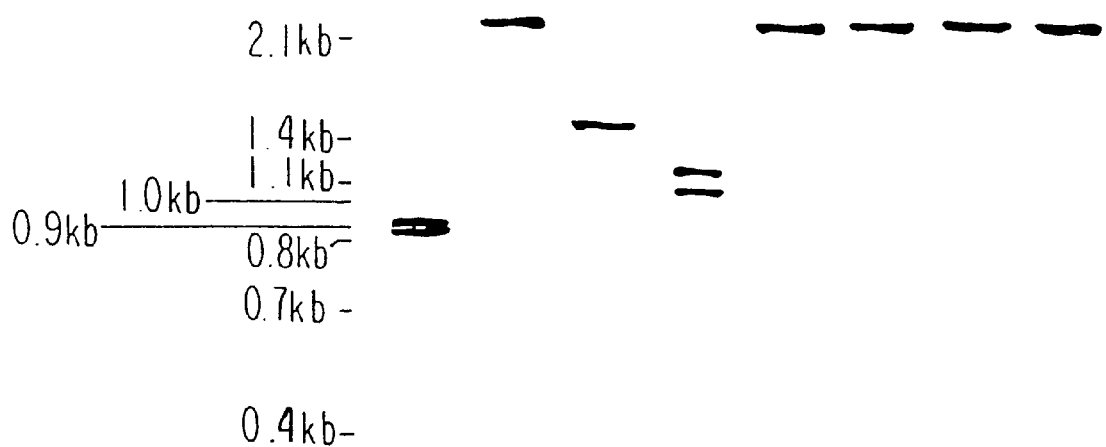
FIG. 6 shows: RFLP of amplified pspA. PspA from MC25 was amplified by PCR using 5' and 3' primers for pspA (LSM13 and LSM, respectively). The amplified DNA was digested with individual restriction endonucleases prior to electrophoresis and staining with ethidium bromide. Lane 1 BclI, Lane 2 BAMHI, Lane 3 BstNI, Lane 4 PstI, Lane 5 SacI, Lane 6 EcoRI, Lane 7 SmaI, Lane 8 KpnI.

Further characterization of the pspA gene was done by RFLP analysis of PCR amplified pspA from each strain. Since previous studies indicated that individual strains yielded only one product, and since the amplification is carried out with primers based on a known pspA sequence, it seems likely that in each case the amplified products represent the pspA rather than the pspA-like gene. When MC25–28 were subjected to this procedure, an amplified pspA product of 2.1 Kb was produced in each case. When digested with Hha 1 digest the sum of the fragments obtained with each enzyme was approximately equal to the size of the 2.1 Kb amplified product (FIG. 6). These results suggest that the 2.1 Kb amplified DNA represents the amplified product of only a single DNA sequence. Rx1, by comparison, produced an amplified product of 2.0 Kb and five fragments of 0.76, 0.468, 0390, 0.349 and 0.120, when digested with Hha 1 as expected from its known pspA sequence.

The four isolates examined in this Example are the first in which two PspAs have unambiguously been observed. The interpretation that two PspAs are simultaneously expressed by a single pneumococcal isolate is based on the observation that bands of different molecular weights were detected by different MAbs to PspA. Isolates used in this study were from a group originally selected for study by Brian Spratt because of their resistance to penicillin. It is very likely that all four of the isolates making two PspAs are related since they share PspA serotypes, amplified pspA RFLPs, chromosomal pspA RFLPs, capsule type, and resistance to penicillin.

The interpretation of studies presented here, showing the existence of two PspAs in the four strains MC25–28, must be suit in the context of what is know about the serology PspA as detected by Western blots. PspAs of different strains have been shown previously to exhibit apparent molecular weight sizes ranging from 60 to 200 KDa as detected by Western blots. At least part of this difference in size is attributable to secondary structure. Even for the PspA of a single isolate, band of several sizes are generally observed. Mutation and immunochemistry studies have demonstrated, however, that all of the different sized PspA band from Rx1 are made by a single gene capable of encoding a 69 KDa protein. The heterogeneity of band size on Western blots of PspA made by a single strain appears to be due to both degradation and polymerization.

PspA was originally defined by reciprocal absorption studies demonstrating that a panel of MAbs to Rx1 surface proteins each reacted with some protein and later by studies using Rx1 and WU2 derivatives expressing various truncated forms of PspA. In both cases it was clear that each MAbs to the PspA of a given strain reacted with the same protein. Such detailed studies have not been done with each of the several hundred human isolates. It is possible that with some isolates, reactivity of the MAbs with two PspAs may have gone unnoticed. This could have happened if all reactive antibodies detected both PspAs of the same isolate, or if the most prominent migration bands from each of the two PspAs co-migrated. With isolates MC25–28 the observation of two PspAs was possible because clearly distinguishable bands of different molecular weights reacted preferentially with different MAbs.

Applicants favor the interpretation that isolates MC25–28 each make two PspAs, because an alternative possibility, namely, that the 190 KDa PspA detected by MAbs XiR278 and 2A4 might be a dimer of the 84 KDa monomer detected by MAb 7D2, if the epitopes recognized by the different MAbs were dependent on either the dimeric or monomeric status of the protein, seems unlikely since whenever MAbs react with the PspA of a strain, they usually detect both the monomeric and the dimeric forms. No other isolates have been observed where some MAbs detected only the apparent dimeric form of PspA while others detected only the monomeric form.

There could be several possible explanations for the failure to observe two PspAs produced by most strains. 1) All pneumococci might make two pspAs in culture, but MAbs generally recognize only one of them (perhaps in this isolate there has been a recombination between pspa DNA and the pspA-like locus, thus allowing that locus to make a product detected by MAb to PspA). 2) All pneumococci can have two pspAs but the expression one of them generally does not occur under in vitro growth conditions. 3) The pspA-like locus is normally a nonfunctional pseudogene sequence that for an unexplained reason has become functional in these isolates.

It seems unlikely that the expression of only a single PspA by most strains is the result of a phase shift that permits the expression of only the pspA or pspA-like gene at any one time, since many of the strains examined repeatedly and consistently produce the same PspA. In the case of strains MC25–28, the appearance of two PspAs is apparently not the result of a phase switch, since individual colonies produced both the type 6 and the type 34 PspAs.

Presumably in these four strains, the second PspA protein is produced by the pspA-like DNA sequence. At high stringency, the probe comprising the coding region of the alpha-helical half of PspA recognized both pspA homologous sequences of MC25–28 but not the pspA-like sequence of Rx1. This finding indicates that the pspA-like sequence of MC25–28 is more similar to the Rx1 pspA sequence than is the Rx1 pspA-like sequence. If the pspA-like sequence of these strains is more similar to pspA than most pspA-like sequences, it could explain why we were able to see the products of pspA-like genes of these strains with our MAbs. The finding of two families of PspAs made in vivo by pneumococci, allows for use of the second PspA in compositions, as well as the use of DNA primers or probes for the second gene for more conclusive detecting, determining or isolating of pneumococci.

Isolates and Bacterial Cell Culture:

Pneumococcal isolates described in these studies were cultured from patients in Barcelona, Spain (one adult at Bellvitge Hospital, and three children at San Juan de Dios) between 1986 and 1988 (Table 2). These penicillin resistant pneumococci originally in the collection of Dr. Brian Spratt were shared with applicants by Dr. Alexander Tomasz at the Rockefeller Institute. Rx1 is a rough pneumococcus used in previous studies, and it is the first isolate in which pspA was sequenced. Bacteria were grown in Todd-Hewitt broth with 0.5% yeast extract or on blood agar plates overnight in a candle jar. Capsular serotype was confirmed by cell agglutination using Danish antisera (Statens Seruminstitut, Copenhagen, Denmark) as previously described. The isolates were subsequently typed as 6B by Quellung reaction, utilizing rabbit antisera against 6A or 6B capsule antigen prepared by Dr. Barry Gray.

Bacterial lysates:

Cell lysates were prepared by incubating the bacterial cell pellet with 0.1% sodium deoxycholate, 0.01% sodium dedecylsulfate (SDS), and 0.15 M sodium citrate, and then diluting the lysate in 0.5M Tris hydrochloride (pH 6.8) as previously described. Total pneumococcal protein in the lysates was quantitated by the bicinchonic acid method (BCA Protein Assay Reagent; Pierce Chemical Company, Rockford, Ill.).

PspA serotyping:

Serotyping of PspA was performed according to previously published methods. Briefly, pneumococcal cell lysates were subjected to SDS-PAGE, transferred to nitrocellulose membranes, and developed as Western blots using a panel of seven MAbs to PspA. PspA serotypes were assigned based on the particular combination of MAbs with which each PspA was reactive.

Colony Immunoblotting:

A ten ml tube of Todd-Hewitt broth with 0.5% yeast extract was inoculated with overnight growth of MC23 from a blood agar plate. The isolate was allowed to grow to a concentration of $10^7$ cells/ml as determined by an O.D. of 0.07 at 590 nm. MC23 was serially diluted and spread-plated on blood agar plates to give approximately 100 cells per plate. The plates were allowed to grow overnight in a candle jar, and a single block agar plate with well-defined colonies was selected. Four nitrocellulose membranes were consecutively placed on the plate. Each membrane was lightly weighted and left in place for 5 minutes. In order to investigate the possibility of phase-variation between the two proteins detected on Western blots a single colony was picked from the plate, resuspended in ringers, and spread-plated onto a blood agar plate. The membranes were developed as Western blots according to PspA serotyping methods.

Chromosomal DNA Preparation:

Pneumococcal chromosomal DNA was prepared as in Example 9. The cells were harvested, washed, lysed, and digested with 0.5% (wt/vol) SDS and 100 $\mu$g/ml proteinase K at 37° C. for 1 hour. The cell wall debris, proteins, and polysccharides were complexed with 1% hexadecyl trimethyl ammonium bromide (CTAB) and 0.7M sodium chloride at 65° C. for 20 minutes, then extracted with chloroform/isoamyl alcohol. DNA was precipitated with 0.6 volumes isopropanol, washed, and resuspended in 10 mM Tris-HCl, 1 mM EDTA, pH 8.0. DNA concentration was determined by spectrophotometric analysis at 260 nm.

Probe preparation:

5' and 3' oligonucleotide primers homologous with nucleotides 1 to 26 and 1967 to 1990 of Rx1 pspA (LSM 13 and LSM2, respectively) were used to amplify the full length pspA and construct probe LSMpspA13/2 from Rx1 genomic DNA. 5' and 3' oligonucleotide primers homologous to nucleotides 161 to 187 and nucleotides 1093 to 1117 (LSM 12 and LSM 6, respectively) were used to amplify the variable alpha-helical region to construct probe LSMpspA12/6. PCR generated DNA was purified by Gene Clean (Bio101 Inc., Vista, Calif.) and random prime-labeled with digoxigenin-11-dUTP using the Genius 1 Nonradioactive DNA Labeling and Detection Kit as described by the manufacturer (Boehringer Mannheim, Indianapolis, Ind.).

DNA electrophoresis:

For Southern blot analysis, approximately long of chromosomal DNA was digested to completion with a single restriction endonuclease, (Hind III, Kpn 1, EcoR 1, Dra 1, or Pst 1) then electrophoresed on a 0.7% agarose gel for 16–18 hours at 35 volts. For PCR analysis, 5 $\mu$l of product were incubated with a single restriction endonuclease, (Bcl 1, BamH 1, Pst 1, Sac 1, EcoR 1 Sma 1, and Kpn 1) then electrophoresed on a 1.3% agrose gel for 2–3 hours at 90 volts. In both case, 1 Kb DNA ladder was used for molecular weight makers (BRL, Gaithersburg, Md.) and gels were stained with ethidium bromide for 10 minutes and photographed with a ruler.

Southern blot hybridization

The DNA in the gel was depurinated in 0.25N HCl for 10 minutes, denatured in 0.5M NaOH and 1.5M NsCl for 30 minutes, and neutralized in 0.5M Tric-HCl (pH 7.2), 1.5M NaCl and 1 mM disodium EDTA for 30 minutes. DNA was transferred to a nylon membrane (Micron Separations INC, Mass.) using a POSIBLOT pressure blotter (Strategene, La Jolla, Calif.) for 45 minutes and fixed by UV irradiation. The membranes were prehybridized for 3 hours at 42° C. in 50% formamide, 5× SSC, 5× Denhardt solution, 25 mM sodium phosphate (pH 6.5), 0.5% SDS 3% (wt/vol) dextran sulfate and 500 μg/ml of denatured salmon containing 45% formamide, 5× SSC, 1× Denhardt solution, 20 mM sodium phosphate (pH 6.5), 0.5% SDS, 3% dextran sulfate, 250 g/ml denatured sheared salmon sperm DNA and about 20 ng of heat-denatured diogoxigenin-labeled probe DNA. After hybridization, the membranes were washed twice in 0.1% SDS and 2× SSC for 3 minutes at room temperature. The membranes were washed twice to a final stringency of 0.1% SDS in 0.3× SSC at 65° C. for 15 minutes. This procedure yields a stringency greater than 95 percent. The membranes were developed using the Genius 1 Nonradioactive DNA Labeling and Detection Kit as described by the manufacturer (Boehringer Mannheim, Indianapolis, Ind.). To perform additional hybridization with other probes, the membranes were stripped in 0.2N NaOH/0.1%SDS at 40° C. for 30 minutes and then washed twice in 2× SSC.

Polymerase Chain Reaction (PCR):

5' and 3' primers homologous with the DNA encoding the N- and C-terminal ends of PspA (LSM13 and LSM2, respectively) were used in these experiments. Amplifications were made using Taq DNA polymerase, $MgCl^2$ and 10× reaction buffer obtained from Promega (Madison, Wis.). DNA used for PCR was prepared using the method previously described in this paper. Reactions were conducted in 50 ml volumes containing 0.2 mM of each dNTP, and 1 ml of each primer at a working concentration of 50 mM. $MgCl_2$ was used at an optimal concentration of 1.75 mM with 0.25 units of Taq DNA polymerase. Ten to thirty ng of genomic DNA was added to each reaction tube. The amplification reactions were performed in a thermal cycler (M.J. Research, Inc.) using the following three step program. Step 1 consisted of a denaturing temperature of 94° C. for 2 minutes. Step 2 consisted of 9 complete cycles of a denaturing temperature of 94° C. for 1 minute, an annealing temperature of 50° C. for 2 minutes, and an extension temperature of 72° C. for 3 minutes. Step 3 cycled for 19 times with a denaturing temperature of 94° C. for 1 minute, an annealing temperature of 60° C. for 2 minutes, and an extension temperature of 72° C. for 3 minutes. At the end of the last cycle, the samples were held at 72° C. for 5 minutes to ensure complete extension.

Band size estimation:

Fragment sizes in the molecular weight standard and in the Southern blot hybridization patterns were calculated from migration distances. The standard molecular sizes were fitted to a logarithmic regression model using Cricket Graph (Cricket Software, Malvern, Pa.). The molecular weights of the detected bands were estimated by entering the logarithmic line equation obtained by Cricket Graph into Microsoft Excel (Microsoft Corporation, Redmond, Wash.) in order to calculate molecular weights based in migration distances observed in the Southern blot.

TABLE 15

| Restriction Enzyme | Strains Examined | | | | | Restriction Fragments (sizes in kilobases) | |
|---|---|---|---|---|---|---|---|
| | MC 25 | MC 26 | MC 27 | MC 28 | RX1 | MC25–MC28 | RX1 |
| Hind III | + | + | + | + | + | 7.7, 3.6 | 9.1, 4.2 |
| Kpn I | + | + | + | + | + | 11.6, 10.6 | 10.6, 9.8 |
| EcoR I | + | | | | + | 8.4, 7.6 | 7.8, 6.6 |

TABLE 15-continued

| Restriction Enzyme | Strains Examined | | | | | Restriction Fragments (sizes in kilobases) | |
|---|---|---|---|---|---|---|---|
| | MC 25 | MC 26 | MC 27 | MC 28 | RX1 | MC25–MC28 | RX1 |
| Dra I | + | | | | + | 2.1, 1.1 | 1.9, 0.9 |
| Pst I | + | | | | + | >14, 6.1 | 10.0, 4.0 |

TABLE 16

Penicillin Resistant Capsular Serogroup 6 Strains from Spain

| Isolate | Penicillin MIC (μg/ml) | Year | Site | Hospital |
|---|---|---|---|---|
| MC25 | 1 | 1986 | sputum | Bellvitge |
| MC26 | 4 | 1988 | ear | San Juan de Dios |
| MC27 | 1 | 1988 | ear | San Juan de Dios |
| MC28 | 2 | 1988 | ? | San Juan de Dios |

Example 5

Southern blot analysis of pspAs and Fragments of pspA

In this example, Applicants used oligonucleotides derived from the DNA sequence of pspA of S. pneumoniae Rx1 both as hybridization probes and as primers in the polymerase chain reaction to investigate the genetic variation and conservation of the different regions of pspA and pspA-like sequences. The probes used ranged in size from 17 to 33 bases and included sequences representing the minus 35, the leader, the α-helical region, the proline-rich regions, the repeat regions, and the C-terminus. Applicants examined 18 different isolates representing capsular and 9 PspA serotypes. The proline-rich, repeat, and leader, regions were highly conserved among pspA and pspA-like sequence.

In the previous Example, it was shown that strain Rx1 and most other strains of S. pneumoniae had two homologous sequences that could hybridize with probes encoding the N terminal and C terminal halves of PspA. This conclusion that these were separate sequences was supported by the fact that no matter which restriction enzymes was used there were always at least two (generally two sometimes three or four) restriction fragments of Rx1 and most other strains hybridized with the pspA probes. When the genome of Rx1 was digested with HindIII and hybridized with these, two pspA-homologous sequences were found to be in 4.0 and 9.1 kb fragments. Using derivative of Rx1 which had insertion mutations in pspA, it was possible to determine that the 4.0 kb fragment contained the functional pspA sequence. The pspA-homologous sequence included within the 9.1 kb band was referred to as the pspA-like sequence. Whether or not the pspA-like sequences makes a product is not know, and none has been identified in vitro. Since pspA-specific mutants can be difficult to produce in most strains, and exist for only a limited number of pneumococcal isolates, this Example identifies oligonucleotide probes that could distinguish between the pspA and pspA-like sequences.

The purpose of this Example was to further define both the conserved and variable regions of pspA, and to determine whether the central proline-rich region is variable or conserved, and identify those domains of pspA that are most highly conserved in the pspA-like sequence (and ergo, provide oligonucleotides that can distinguish between the two). Oligonucleotides were used and are therefore useful as both hybridization probes and as primers for polymerase chain reaction (PCR) analysis.

Hybridization with oligonucleotide probes.

Figure 7:
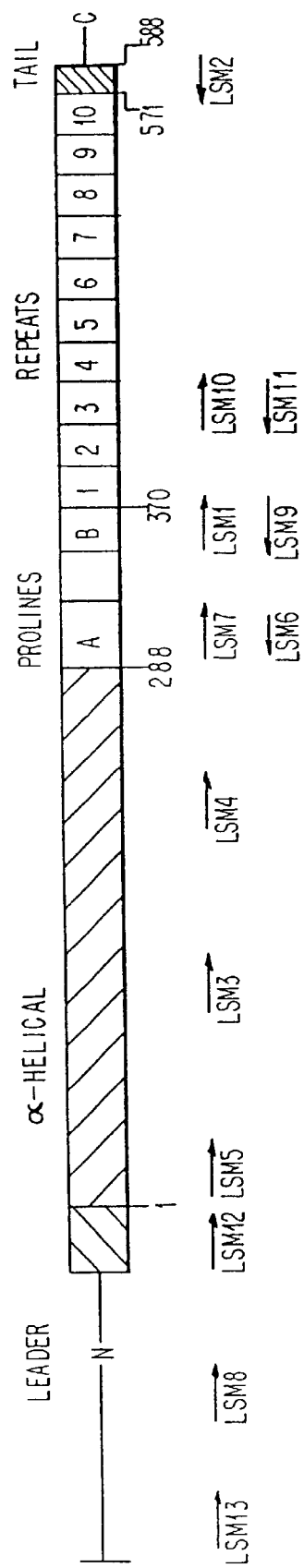
FIG. 7 shows: A depiction of PspA showing the relative location and orientation of the oligonucleotides.

The oligonucleotides used in this study were based on the previously determined sequence of Rx1 PspA. Their position and orientation relative to the structural domains of Rx1 PspA are shown in FIG. 7. The reactivity of these oligonucleotide probes with the pspA and pspA-like sequences was examined by hybridization with a HindIII digest of Rx1 genomic DNA (Table 17). As expected, each of the eight probes recognized the pspA-containing 4.0 kb fragment of the HindIII digested Rx1 DNA. Five of the 8 probes (LSM1, 2, 3, 7, and 12) could also recognize the pspA-like sequence of the 9.1 kb band at least at low stringency. At high stringency four of the probes (LSM2, 3, 4 and 5) were specific for the 4.0 kb.

These 8 probes were used to screen HindIII digest of the DAN from 18 strains of S. pneumoniae at low and high stringency. For comparison to earlier studies each of the strains was also screened using a full-length pspA probe. Table 23 illustrates the results obtained with each strain at high stringency. Table 18 summarizes the reactivities of the probes with the strains at high and low stringency. Strain Rx1 is a laboratory derivative of the clinical isolate, D39. The results obtained with both strains were identical. They are listed under a single heading in Table 23 and are counted as a single strain in Table 28. Although AC17 and AC94 are related clinical isolates, they have distinguishable pspAs and are listed separately. All of the other strains represent independent isolates.

The only strain not giving at least two pspA-homologous HindIII fragments was WU2. This observation was expected since WU2 was previously shown to have only one pspA-homologous sequence and to give only a single HindIII fragment that hybridizes with Rx1 pspA. Even at high stringency 6 of the 8 probes detected more than one fragment in at least one of the 18 strains Tables 18 and 23. Probes LSM7, 10 and 12 reacted with DNA from a majority of the strains and detected two fragments in over 59% of the strains they reacted with. In almost every case the fragments detected by the oligonucleotide probes were identical in size to those detected by the full-length pspA probe. Moreover, the same pairs of fragments were frequently detected by probes from the 3' as well as the 5' half Rx1 pspA. These results are consistent with earlier findings that the pairs of HindIII fragments from individual isolated generally include two separate but homologous sequences, rather than fragments of a single pspA gene.

The differences in the frequency with which the oligonucleotides reacted with (at least one fragment) of the strains in the panel was significant at P<0.0001 by 2×8 chi square). When the oligonucleotides were compared in terms of their ability to react with both fragments of each strain the P value was also <0.0001. Table 18 gives the percentage of strains reactive with each probe, the percentage in which only one fragment was reactive, and the percentage in which two (or more) fragments were reactive.

The last column in Table 18 give the ratio of strains that showed one reactive HindIII fragment at high stringency divided by the total number of reactive strains. In this column values of 1 were obtained with probes that only reacted with one band in each reactive strain. Such probes are assumed to be those that are most specific for pspA. The lowest values were obtained with probes that generally see two bands in each strain. Such probes are assumed to be those that represent regions relatively conserved between the pspA and pspA-like sequences. At high stringency, probes LSM3 and LSM4 detected only a single HindIII fragment in the DAN of strains they reacted with. These findings suggested probes LSM3 and LSM4 were generally detecting alleles of pspA rather than the pspA-like sequence. The observation that the fragments detected by LSM3 or LSM4 were also detected by all of the other reactive probes, strengthened the inclusion that these probes generally detected the pspA rather than the pspA-like sequence. WU2 has only one pspA-homologous DNA sequence and secretes a serologically detectable PspA. The fact that LSM3 reacts with the single HindIII fragment of WU2 is consistent with the interpretation that LSM3 detects the pspA sequences. Sequences representing the second proline region (LSM1) and the C-terminus (LSM2) appeared to also be relatively specific for the pspA sequences since they were generally detected in only one of the HindIII fragments of each strain.

Oligonucleotides, LSM12, and LSM10 detected the most conserved epitopes of pspA and generally reacted with both pspA-homologous fragments of each strain (Table 18). LSM7 was not quite as broadly cross-reactive but detected two PspAs in 41% of strains including almost 60% of the strains it reacted with. Thus, sequences representing the leader, first proline region, and the repeat region appear to be relatively conserved not only within pspA but between the pspA and pspA-like sequences. LSM3, 4, and 5 reacted with the DNA from the smallest fraction of strains of any oligonucleotide (29–35 percent), suggesting that the portion of pspA encoding the α-helical region is the least conserved region of pspA.

With two strains BG85C and L81905, the oligonucleotides detected more than two HindIII fragments containing pspA- homologous sequences. Because of the small size of the oligonucleotide probes and the absence of HindIII restriction sites within any of them, it is very unlikely that these multiple fragments were the results of fragmentation of the target DNA within the probed regions. In almost every case the extra oligonucleotides were detected at high stringency by more than one oligonucleotide. These data strongly suggest that at least in these two strains there are 3 or 4 sequences homologous to at least portions of the pspA. The probes most reactive with these additional sequences are those for the leader, the α-helical region and the proline rich region. The evidence for the existence of these additional pspA-related sequences was strengthened by results with BG58C and L81905 at low stringency where the LSM3 (α-helical) primer picked up the extra 1.2 kb band of L81905 (in addition to the 3.6 kb band) and the LSM7 (proline-rich) primer picked up the extra 3.2 and 1.4 kb bands (in addition to the 3.6 kb band) of BG58C.

Amplification of pspA

The utility of these oligonucleotides as PCR primers was examined by determining if they could amplify fragments of pspA from the genomic DNA of different pneumococcal isolates. Applicants attempted to amplify pspAs from 14 diverse strains of S. pneumoniae comprising 12 different capsular types using primers based on the Rx1 pspA sequence. Applicants observed that the 3' primer LSM2, which is located at the 3' end of pspA, would amplify an apparent pspA sequence from each of the 14 pneumococcal strains when used in combination with LSM1 located in the region of pspA encoding the proline-rich region (Table 19). LSM2 was also used in combination with four other 5' primers LSM1, 3, 7, 8 and 12. LSM8 is located 5' of the pspA start site (near the −35 region).

If a predominant sequence of the expected length was amplified that could be detected on a Southern blot with a full-length pspA probe, we assumed that pspA gene of the amplified DNA had homologous sequences similar to those of the pspA primers used. Based on these criteria the primer representing the α-helical sequence was found to be less conserved than the primers representing the leader, proline, and C-terminal sequences. These results were consistent with those observed for hybridization. The lowest frequency of amplification was observed with LSM8 which is from the Rx1 sequence 5' of the pspA start site. This oligonucleotide was not used in the hybridization studies.

Further evidence for variability comes from differences in the sizes of the amplified pspA gene. The Example showed that when PCR primers LSM12 and LSM2 were used to amplify the entire coding region of PspA, PCR products from different pneumococcal isolates ranged in size from 1.9 and 2.3 kb (Table 20). The regions within pspA encoding the α-helical, proline-rich, and repeats were also amplified from the same isolates. As seen in Table 20, the variation in size of pspA appeared to come largely from variation in the size of pspA encoding encodes the α-helical region.

Using probes that consisted of approximately the 5' and 3' halves of pspA it has been determined that the portion of pspA that encodes the α-helical regions is less conserved than the portion of pspA that encodes the C-terminal half of the molecule. This Example show using 4 oligonucleotide probes from within each half of the DNA encoding PspA. Since a larger number of smaller probes were used, Applicants have been able to obtain a higher resolution picture of conserved and variable sequences within pspA and have also been able to identify regions of likely differences and similarities between pspA and the pspA-like sequences.

The only strains in which the pspA gene has been identified by molecular mutations are Rx1, D39 and WU2. Rx1 and D39 apparently have identical pspA molecules that are the result of the common laboratory origin of these two strains. WU2 lacks the pspA-like gene. Thus, when most pneumococci are examined by Southern blotting using full length-pspA as a probe, it is not possible to distinguish between the pspA and pspA-like loco, since both are readily detected. A major aim of these studies was to attempt to identify conserved and variable regions within the pspA and pspA-like loci. A related aim was to determine whether probes based on the Rx1 pspA could be identified that would permit one to differentiate pspA from the pspA-like sequence. Ideally such probes would be based on relatively conserved portion of the pspA sequence that was quite different in the pspA-like sequence. A useful pspA specific probe would be expected to identify the known Rx1 and WU2 pspA genes and identify only a single HindIII fragment in most other strains. Two probes (LSM3 and LSM4) never reacted with more than one pspA-homologous sequence in any particular strain. Both of reacted with Rx1 pspA and LSM3 reacted with WU2 pspA. Each of these probes reacted with 4 of the other 15 strains. When these probes identified a band, however, the band was generally also detected by all other Rx1 probes reactive with that strain's DNA. Additional evidence that the LSM3 and LSM4 were restricted to reactivity with pspA was that they reacted with the same bands in all three non-Rx1 strains. Each probe identifies pspA in certain strains and even when used in combination they recognized pspA in over 40 percent of strains. Probes for the second proline-rich region (LSM1) and the C-terminus of pspA (LSM2) generally, but not always, identified only one pspA-homologous sequence at high stringency. Collectively LSM1, 2, 3, and 4 reacted with 16 of the 17 isolates and in each case revealed a consensus band recognized by most to all of the reactive probes.

By making the assumption that in different strains the Rx1 pspA probes are more likely to recognize pspA than the pspA-like sequences, it is possible to make some predictions about areas of conservation and variability within the pspA and pspA-like sequences. When a probe detected only a single pspA-homologous sequence in an isolate, it was assumed that it was pspA. If the probe detected two pspA-homologous sequences, it was assumed that it was reacting with both the pspA and pspA-like sequence. Thus, the approximate frequency with which a probe detects pspA can be read from Table 18 as the percent of strains where it detects at least one pspA-homologous band. The approximate frequency with which the probes detect the pspA-like sequence is the percent of strains in which two or more pspA-homologous band are detected.

Using these assumptions the most variable portion of portion of the pspA gene was observed to be the −35 region and the portion encoding α-helical region. The most conserved portion of pspA was found to be the repeat region, the leader and the proline rich region. Although only one probe from the region was used, the high degree of conservation among the 10 repeats in the Rx1 sequence makes it likely that other probes for the repeat regions give similar results.

The portion of the pspA-like sequence most similar to Rx1 pspA was that encoding the leader sequence, the 5' portion of the proline rich region, and the repeat region, and those portions encoding the N-terminal end of the proline-rich and repeat regions. The repeat region of PspA has been shown to be involved in the attachment to PspA to the pneumococcal surface. The conservation of the repeat region among both pspA and pspA-like genes suggests that if is PspA-like protein is produced, that it may have a surface attachment mechanism similar to that of PspA. The need for a functional attachment site may explain the conservation of the repeat region. Moreover, the conservation in DNA encoding the repeat regions of the pspA and pspA-like genes suggests that the repeat regions may serve as a potential anti-pneumococcal drug target. The conservation in the leader sequence between pspA and the pspA-like sequence was also not surprising since similar conservation has been reported for the leader sequence of other gram positive proteins, such as M protein of group A streptococci. It is noteworthy, however, that there is little evidence at the DNA level that the PspA lead is shared by many genes other than PspA and the possible gene product of the pspA-like locus.

Although the region encoding the C-terminus of pspA (LSM12) or the 3' portion of the proline-rich sequence (LSM1) appear to be highly conserved within pspA genes, corresponding regions in the pspA-like sequences are either lacking, or very distinct from those in pspA. The reason for conservation at these sites is not apparent. In the case of the PspA, its C-terminus does not appear to be necessary for attachment, since mutants lacking the C-terminal 49 amino acids are apparently as tightly attached to the cell surface as those with the complete sequence. Whether these difference from pspA portends a subtle difference in the mechanism of attachment of proteins produced by these two sequences in unknown. If the C-terminal end of the pspA-like sequence, or the 3' portion of the proline-rich sequence in the pspA-like sequence are as conserved within the pspA-like family of genes as it is within pspA, then this region of pspA and the pspA-like sequence serve as targets for the development of probes to distinguish between all pspA and pspA-like genes.

With two strains, some of the oligonucleotide probes identified more than two pspA-homologous sequences. In the case of each of these strains, there was a predominant sequence recognized by almost all of the probes, and two or three additional sequences that were each recognized by at least two of the probes. One interpretation of the data is that there may be more than two pspA-homologous genes in some strains. The significance of such sequences is far from established. It is of interest however, that although the additional sequences share areas of homology with the leader, α-helical, and proline region, they exhibited no homology with the repeat region of the C-terminus of pspA. These sequences, thus, might serve as elements that can recombine with pspA and/or the pspA-like sequences to generate sequence diversity. Alternatively the sequences might produce molecules with very different C-terminal regions, and might not be surface attached. it these pspA-like sequences make products, however, they, like PspA, may be valuable as a component of a pneumococcal antigenic, immunological vaccine compositions.

Bacterial strains, growth conditions and isolation of chromosomal DNA.

S. pneumoniae strains used in this study are listed in Table 5. Strains were grown in 100 ml of Todd-Hewitt broth with 0.5% yeast extract at 37° C. to an approximate density of $5 \times 10^8$ cells/ml. Following harvesting of the cells by centrifugation (2900× g, 10 minutes), the DNA was isolated as previously described and stored at 4° C. in TE (10 mM Tris, 1 mM EDTA, pH 8.0).

Amplification of pspA sequences.

Polymerase chain reaction (PCR) primers, which were also used as oligonucleotide probes in Southern hybridizations, were designed based on the sequence of pspA from pneumococcal strain Rx1. These oligonucleotides were obtained from Oligos Etc. (Wilsonville, Oreg.) and are listed in Table 22.

PCRs were done with a MJ Research, Inc., Programmable Thermal Cycler (Watertown, Mass.) as previously described using approximately 10 ng of genomic pneumococcal DAN with appropriate 5' and 3' primer pair. The sample was brought to a total volume of 50 µl containing a final concentration of 50 mM KCl, 10 mM Tris-HCl (PH 8.3), 1.5 mM $MgCl_2$, 0.001% gelatin, 0.5 mM each primer, 200 mM of each deoxynucleotide triphosphate, and 2.5 U of Taq DNA polymerase. Following overlaying of the samples with 50 Al of mineral oil, the samples were denatured at 94° C. for 2 minutes. Then the samples were subjected to 10 cycles consisting of 1 minute at 94° C., 2 minutes at 50° C., and 3 minutes at 72° C. followed by another 20 cycles of 1 minute at 94° C., 2 minutes at 50° C., and 3 minutes at 72° C. followed by another 20 cycles of 1 minute at 94° C., 2 minutes at 60° C., and 3 minutes at 72° C. After all 30 cycles, the samples were held at 72° C. for an additional 5 minutes prior to cooling to 4° C. The PCR products were analyzed by agarose gel electrophoresis.

DNA hybridization analysis.

Approximately 5 µg of chromosomal DNA was digested with HindIII according to the manufacturer's instructions (Promega, Inc., Madison, Wis.). The digested DNA was electrophoresed at 35 mV overnight in a 0.8% agarose gels and then vacuum-blotted onto Nytran membranes (Schleicher & Schuell, Keene, N.H.).

Labeling of oligonucleotide with and detection of probe-target hybrids were both performed with the Genius System according to the manufacturer's instructions (Mannheim, Indianapolis, Ind.). All hybridizations were done for 18 hours at 42° C. without formamide. By assuming that 1% base-pair mismatching results in a 1° C. decrease in $T_m$ designations of "high" and "low" stringency were defined by salt concentration and temperature of post-hybridization washes. Homology between probe and target sequences was derived using calculated $T_m$ the established method. High stringency is defined as 90% or greater homology, and low stringency is 80–85% sequence homology.

TABLE 17

Hybridization of oligonucleotides with HindIII restriction fragments of Rx1 DNA.

| | | Stringency | |
|---|---|---|---|
| Oligonucleotide | Region | Low | High |
| LSM12 | Leader | N.D. | 4.0, 9.1 |
| LSM5 | α-helix | N.D. | 4.0 |
| LSM3 | α-helix | 4.0, 9.1 | 4.0 |
| LSM4 | α-helix | 4.0 | 4.0 |
| LSM7 | Proline | 4.0, 9.1 | 4.0, 9.1 |
| LSM1 | Proline | 4.0, 9.1 | 4.0, 9.1 |
| LSM10 | Repeats | N.D. | 4.0, 9.1 |
| LSM2 | C-terminus | 4.0, 9.1 | 4.0 |

Note.
Values indicated are the sizes of restriction fragments expressed as kb.

TABLE 18

Summary of Hybridization at High and Low Stringency of 8 Oligonucleotides with HindIII Restriction Fragments of the 17 Pneumococcal Isolates Listed in FIG. 2

| | Percent with ≧ band | | Percent with ≧2 bands | | Percent with 1 band | | 1 band/ ≧1 band | |
|---|---|---|---|---|---|---|---|---|
| Oligo-nucleotide | Low | High | Low | High | Low | High | Low | High |
| LSM12 | | 82 | | 59 | | 24 | | 0.29 |
| LSM5 | | 29 | | 18 | | 12 | | 0.40 |
| LSM3 | 65 | 35 | 41 | 0 | 24 | 35 | 0.36 | 1.00 |
| LSM4 | 35 | 29 | 0 | 0 | 35 | 29 | 1.00 | 1.00 |
| LSM7 | 94 | 71 | 71 | 41 | 24 | 29 | 0.25 | 0.42 |
| LSM1 | 100 | 65 | 53 | 12 | 47 | 53 | 0.47 | 0.82 |
| LSM10 | | 94 | | 59 | | 35 | | 0.37 |
| LSM2 | 88 | 53 | 41 | 12 | 47 | 41 | 0.53 | 0.78 |

Note, for all values listed all 17 strains were examined. If no value is listed, then no strains were examined.

TABLE 19

Amplification of Pneumococcal Isolates using the Indicated 5' Prime Combination with the 3' Primer LSM2 at the 3' end of pspA

| 5' Primer | Region | Nucleotide Position | Amplified/ Tested | Percent Amplified |
|---|---|---|---|---|
| LSM8 | −35 | 47 to 70 | 2/14 | 14 |
| LSM12 | leader | 162 to 188 | 8/14 | 57 |
| LSM3 | a-helical | 576 to 598 | 3/14 | 21 |
| LSM7 | proline | 1093 to 1117 | 12/14 | 86 |
| LSM1 | proline | 1312 to 1331 | 14/14 | 100 |

Note, by 2 × 5 chi square analysis the different primers amplified different frequencies of pspAs (P < 0.0001). The tendency for there to be more amplification with the 3' most primers was significant at P < 0.0001.

TABLE 20

Size of amplified pspA fragments in kilobases

| pspA Region | Primer Pairs | number pspAs examined | Size | Range | S.D. |
|---|---|---|---|---|---|
| Full length | LSM12 + LSM2 | 9 | 1.9–2.3 | 0.4 | 0.17 |
| α-helical | LSM12 + LSM6 | 6 | 1.1–1.5 | 0.4 | 0.17 |

TABLE 20-continued

Size of amplified pspA fragments in kilobases

| pspA Region | Primer Pairs | number pspAs examined | Size | Range | S.D. |
|---|---|---|---|---|---|
| Proline Repeats | LSM7 + LSM9 | 3 | 0.23 | 0 | 0 |
|  | LSM1 + LSM2 | 19 | 0.6–0.65 | 0.05 | 0.01 |

Note:
amplification was attempted with each set of primers on a panel of 19 different pspAs. Data is shown only for pspAs that could be amplified with the indicated primer pairs.

TABLE 21

Pneumococcal strains

| Strain | Relevant characteristics |
|---|---|
| WU2 | Capsular type 3, PspA type 1 |
| D39 | Capsular type 2, PspA type 25 |
| R36A | Nonencapsulated mutant of D39, PspA type 25 |
| Rx1 | Nonencapsulated variant of R36A, PspA type 25 |
| DBL5 | Capsular type 5, PspA type 33 |
| DBL6A | Capsular type 6A, PspA type 19 |
| A66 | Capsular type 3; PspA type 13 |
| AC94 | Capsular type 9L, PspA type 0 |
| AC17 | Capsular type 9L, PspA type 0 |
| AC40 | Capsular type 9L, PspA type 0 |
| AC107 | Capsular type 9V, PspA type 0 |
| AC100 | Capsular type 9V, PspA type 0 |
| AC140 | Capsular type 9N, PspA type 18 |

TABLE 21-continued

Pneumococcal strains

| Strain | Relevant characteristics |
|---|---|
| D109-1B | Capsular type 23, PspA type 12 |
| BG9709 | Capsular type 9, PspA type 0 |
| BG58C | Capsular type 6A, PspA type ND |
| L81905 | Capsular type 4, PspA type 25 |
| L82233 | Capsular type 14, PspA type 0 |
| L82006 | Capsular type 1, PspA type 0 |

TABLE 22

PCR primes.

| Primer | Sequence (5' to 3') |
|---|---|
| LSM1 | CCGGATCCAGCTCCTGCACCAAAAAC |
| LSM2 | GCGCGTCGACGGCTAAACCCATTCACCATTGG |
| LSM3 | CCGGATCCTGAGCCAGAGCAGTTGGCTG |
| LSM4 | CCGGATCCGCTCAAAGAGATTGATGAGTCTG |
| LSM5 | GCGGATCCCGTAGCCAGTCAGTCTAAAGCTG |
| LSM6 | CTGAGTCGACTGGAGTTTCTGGAGCTGGAGC |
| LSM7 | CCGGATCCAGCTCCAGCTCCAGAAACTCCAG |
| LSM8 | GCGGATCCTTGACCAATATTTACGGAGGAGGC |
| LSM9 | GTTTTTGGTGCAGGAGCTGG |
| LSM10 | GCTATGGCTACAGGTTG |
| LSM11 | CCACCTGTAGCCATAGC |
| LSM12 | CCGGATCCAGCGTGCCTATCTTAGGGGCTGGTT |
| LSM13 | GCAAGCTTATGATATAGAAATTTGTAAC |

TABLE 23

Hybridization at high stringencyh of eight different PspA probes with HindIII digests of 18 strains of *Streptococcus pneumoniae*

| Probe | Rx1/D39 | WU2 | DBL5 | DBL6A | A66 | AC94 | AC17 | AC40 | AC107 | AC100 | AC140 | DC109 | BG9709 | BG58C | L81905 | L82233 | L82006 |
|---|---|---|---|---|---|---|---|---|---|---|---|---|---|---|---|---|---|
| FL-Rx1 | 4.0, 9.1 | 3.8 | 3.7, 5.8 | 3.0, 3.4 | 3.6, 4.3 | 3.6, 6.3 | 3.6, 6.3 | 3.2, 3.6 | 3.6, 6.3 | 4.0, 8.0 | 3.0, 4.0 | 3.3, 4.7 | 2.2, 9.6 | 1.4, 3.2 | 3.6, 5.2 | 3.7 8.2 | 4.3, 6.4 |
| LSM12 | 4.0, 9.1 | 3.8 | 3.7, 5.8 | 3.0, 3.4 | 4.3 | | 3.6, 6.3 | 3.2, 3.6 | | 4.0, 8.0 | 4.0 | 3.3, 4.7 | 2.2, 9.6 | 1.4, 3.2 3.6 | 3.6 1.2, 2.3 3.6 | 1.3, 3.7 | |
| LSM5 | 4.0 | | | | | 3.6, 6.3 | | | | | | | 2.2, 9.6 | 3.6 | | | |
| LSM3 | 4.0 | 3.8 | | | | 6.3 | | | | | | | 2.2 | 3.6 | 3.6 | | |
| LSM4 | 4.0 | | | | | | | | | | | | 2.2 | 3.6 | | 3.7 | |
| LSM7 | 4.0, 9.1 | 3.8 | 3.7 | 3.0, 3.4 | 3.6 | | | 3.2, 3.6 | | | 3.0, 4.0 | 3.3, 4.7 | 2.2, 9.6 | 3.6 | 3.6 2.3 3.6 | 3.7 | |
| LSM1 | 4.0, 9.1 | 3.8 | 3.7, 5.8 | 3.4 | | 6.3 | | 3.2 | 3.6 | 4.0 | 4.0 | | 2.2 | | 5.2 | | |
| LSM10 | 4.0, 9.1 | 3.8 | 3.7 | 3.4 | 3.6, 4.3 | | 3.6, 6.3 | 3.2 | 3.6, 6.3 | 4.0 | 4.0 | 3.3, 4.7 | 2.2, 9.6 | 3.2 3.6 | 3.6, 5.2 | 1.3, 3.7 | 4.3, 6.4 |
| LSM2 | 4.0 | | 3.7 | | | | 3.6 | | 3.6, 6.3 | 4.0 | 3.0, 4.0 | 4.7 | | | | | 4.3 |

Note:
All probes were tested versus HindIII digests of all strains. If no bands are listed none were detected. Strains Rx1 and D39 gave identical results and are shown in a single column. The full name os strain AC109 is AC109-1B

Example 6
Restriction Fragment Length Polymorphisms of pspA Reveals Grouping Pneumococcal surface A (PspA) is a protection eliciting protein of *Streptococcus pneumoniae*. The deduced amino acid sequence of PspA predicts three distinct domains; an a helical coiled-coil region, followed by two adjacent proline-rich regions, and ten 20 amino acid repeats. Almost all PspA molecules are cross-reactive with each other in variable degrees. However, using a panel of monoclonal antibodies specific for individual epitopes, this protein has been shown to exhibit considerable variability even within strains of the same capsular type. Oligonucleotide primers based on the sequence of pspA from *S. pneumoniae* Rx1 were used to amplify the full-length pspA gene and the 5' portion of the gene including the α-helical and the proline-rich region. PCR-amplified product were digested with Hha I or Sau3A I to visualize restriction fragment length polymorphism of pspA. Although strains were collected from around the world and represented 21 different capsular types, isolates could be grouped into 17 families or subfamilies based on their RFLP pattern. The validity of this approach was confirmed by demonstrating that pspA of individual strains which are known to be clonally related were always found within a single pspA family.

Numerous techniques have been employed in epidemiological surveillance of pneumococci which include serotyping, ribotyping, pulsed field electrophoresis, multilocus enzyme electrophoresis, penicillin-binding protein patterns, and DNA fingerprinting. Previous studies have also utilized the variability of pneumococcal surface protein A (PspA) to differentiate pneumococci. This protein, which can elicit protective antipneumococcal antibodies, is a virulence factor found on all pneumococcal isolates. Although PspA molecules are commonly cross-reactive, they are seldom antigenically identical. This surface protein is the most serologically diverse protein know on pneumococci; therefore, it is an excellent market to be fed to follow individual strains. Variations in PspA and the DNA surrounding its structural gene have proven useful for differentiation of *S. pneumoniae*.

When polyclonal sera are used to identify PspA, cross-reaction is observed between virtually all isolates. Conversely, when panels of monoclonal antibodies are used to compare PspA of independent isolation they are almost always observed to express different combinations of PspA epitopes. A typing system based on this approach has limitations because it does not easily account for differences in monoclonal binding strength to different PspA molecules. Moreover, some strains are weakly reactive with individual monoclonal antibodies and may not always give consistent results.

A less ambiguous typing system that takes advantage of the diversity of PspA was therefore necessary to develop and was used to examine the clonality of strains. This method involves examination of the DNA within and adjacent to the pspA locus. Southern hybridizations of pneumococcal chromosomal DNA digested with various endonucleases, such as Hind III, Dra I, or Kpn I, and probed with labeled pspA provided a means to study the variability of the chromosome surrounding pspA. When genomic DNA is probed, the pspA and the pspA-like loci are revealed. In most digests the pspA probe hybridizes to 2–3 fragments and, digests of independent isolates were generally dissimilar.

Like the monoclonal typing system, the Southern hybridization procedure permitted the detection of clones of pneumococci. However, it did not provide a molecular approach for following pspA diversity. Many of the restriction sites defining the restriction fragment length polymorphism (RFLP) were outside of the pspA gene, and it was difficult to differentiate the pspA gene from the pspA-like locus. In an effort to develop a system to follow pspA diversity Applicants examined the RFLP of PCR-amplified pspA. Amplified pspA was digested with Sau3A I and Hha I, restriction enzymes with four base recognition sites. To evaluate the utility of this approach pspA from clinical and laboratory strains known to be clonally related as well as random isolates were examined.

Bacterial strains

Figure 8:
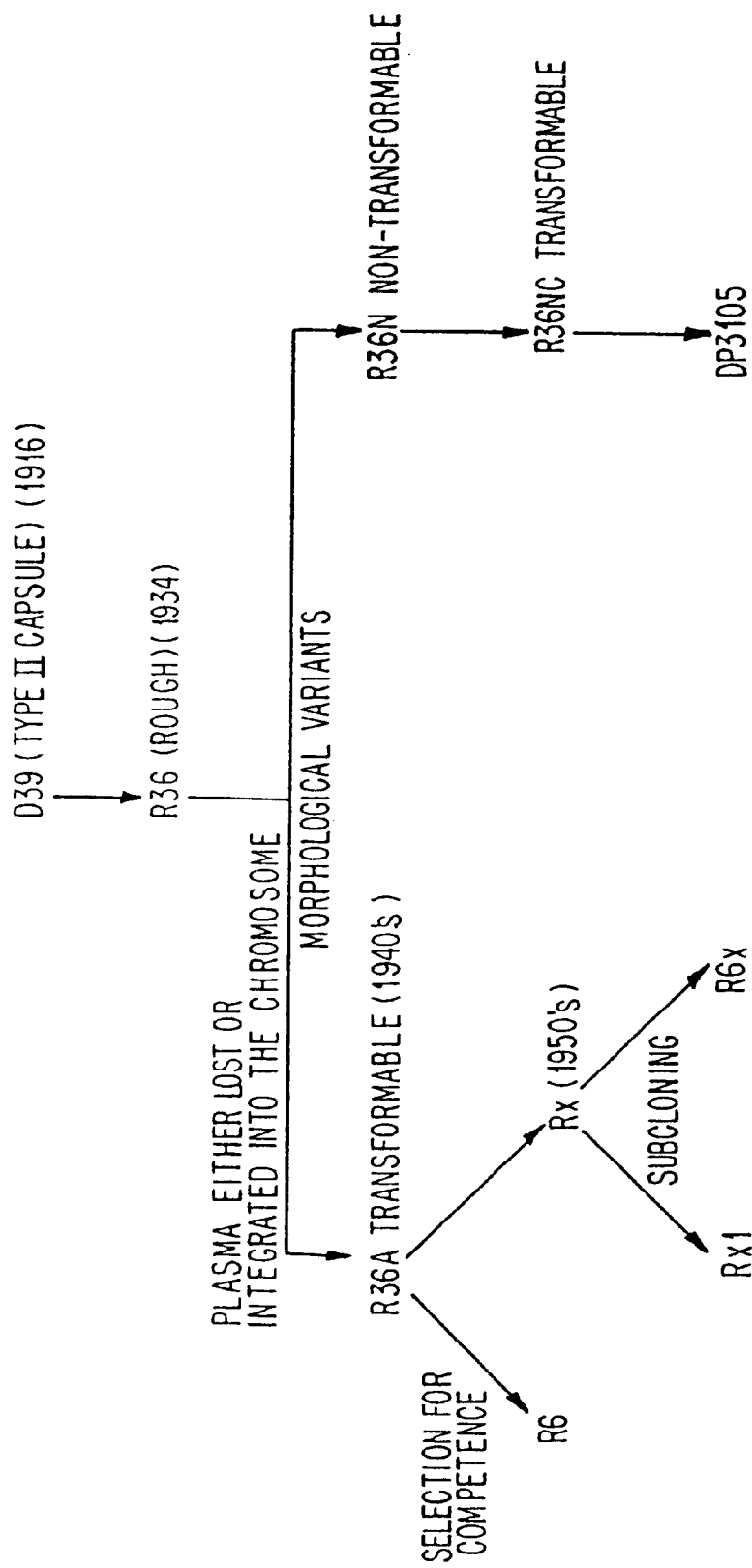
FIG. 8 shows: Derivatives of the *S. pneumoniae* D39-Rx1 family.

Derivatives of the *S pneumoniae* D39-Rx1 family were kindly provided by Rob Massure and Sanford Lacks (FIG. 8). Eight clinical isolates from Spain and four isolates from Hungary, a gift from Alexander Tomasz. Seventy-five random clinical isolates from Alabams, Sweden, Alaska, and Canada were also studied.

PCR amplifications

The oligonucleotide primers used in this study are listed in Table 24. Chromosomal DNA, which was isolated according to procedures described by Dillard et al., was used as template for the PCR reactions. Amplification was accomplished in a 50 µl reaction containing approximately 50 ng template DNA, 0.25U Taq, 50 µM of each primer, 175 µM MgCl$_2$, and 200 µM dNTP in a reaction buffer containing 10 µM Tris-HCl, pH 9.0, 50 µM KCl, 0.1% Triton X-100, 0.01% wt/vol. gelatin. The mixture was overlaid with mineral oil, and placed in a DNA thermal cycler. The amplification program consisted on an initial denaturation step at 94° C., followed by 29 cycles opf 94° C. for 1 min, 55° C. for 2 min, and 72° C. for 3 min. The final cycle included an incubation at 72° C. for 5 min.

Restriction fragment analysis of PCR-amplified product

Aliquots of the PCR mixtures were digested with Hha I or Sau3A I in a final volume of 20 µl according to manufacturer's protocols. After digestion the DNA fragments were electrophoresed on a 1.3% TBE agarose gel and stained with ethidium bromide. Fragment sizes were estimated by comparison to a 1 kb DNA ladder (Gibco BRL).

Because of the variability of pspA, and the fact that the entire pspA sequence is known for only one gene, it has not been possible to design primers which amplify pspA from 100% of pneumococcal strains. However, oligonucleotide primers, LSM2 and LSM1, can amplify an 800 bp region of the C-terminal end in 72 of the 72 stains tested. Based on hybridizations at different stringencies, this region was found to be relatively conserved in pneumococcal strains, and thus would not be expected to be optimal for following restriction polymorphisms within the pspA molecule. LSM13 and LSM2, primers which amplify the full length pspA gene, can amplify pspA from approximately 79% 55/75 of the strains tested (Table 25).

Stability of amplified RFLP pattern within clonally related pneumococci

Figure 9:
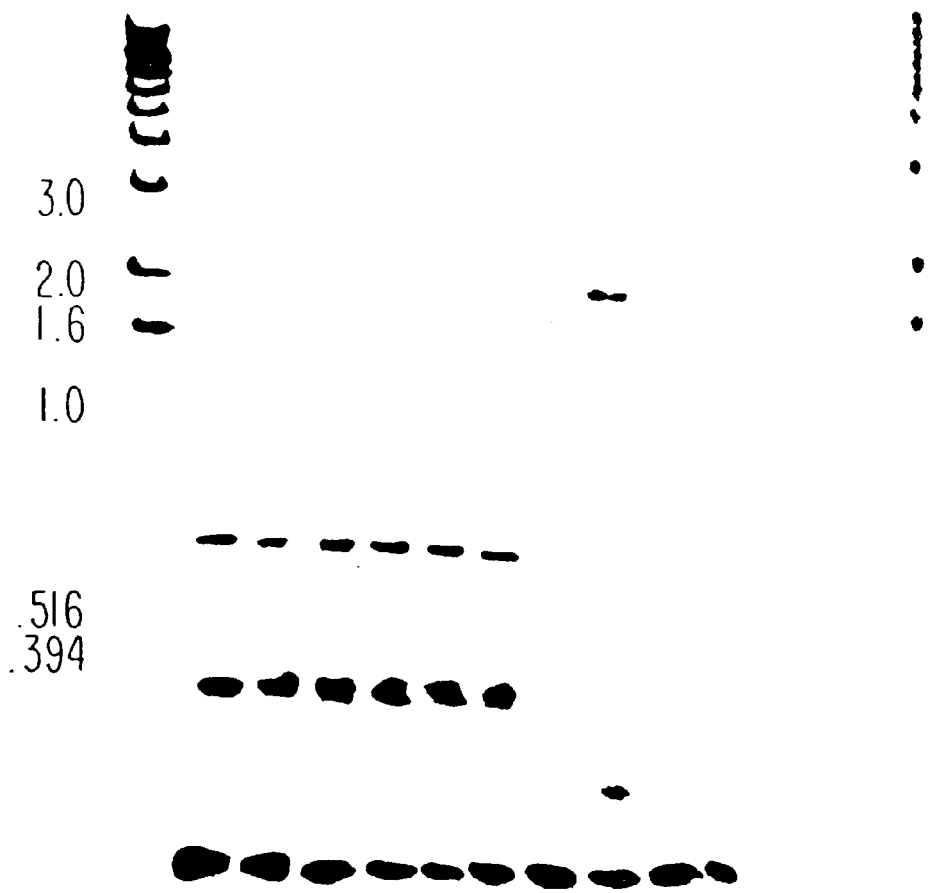
FIGS. 9 to 10 show: Electrophoresis of pspA or amplified pspA product with HhaI (FIG. 9), Sau3AI (FIG. 10).

To determine the stability of pspA during long passages in vitro, we examined the RFLP pattern of the pspA gene of the derivatives of the *S. pneumoniae* D39-Rx1 family. Rx1 is an acapsular derivative of *S. pneumoniae* D39, the prototypical pneumococcal laboratory strain isolated by Avery in 1914. Throughout the 1900's spontaneous and chemical mutations have been introduced into D39 by different laboratories (FIG. 8). During this period unencapsulated strains were maintained in vitro, and D39 was passed both in vivo and in vitro passage. All the derivatives of D39, including Rx1, R6, RNC, and R36A, produced a 1.9 kb fragment upon PCR amplification of full length pspA. All members of the family exhibited the RFLP pattern. Digestion with Sau3A I of PCR amplified full length pspA revealed a 0.83, 0.58, 0.36 and a 0.27 kb fragment in all of the D39-rX1 derivatives of the family. Digesting the full length pspA with Hha I resulted in bands which were 0.76. 0.47, 0.39, 0.35, and 0.12 kb (FIG. 9 or Table 26).

Figure 10:
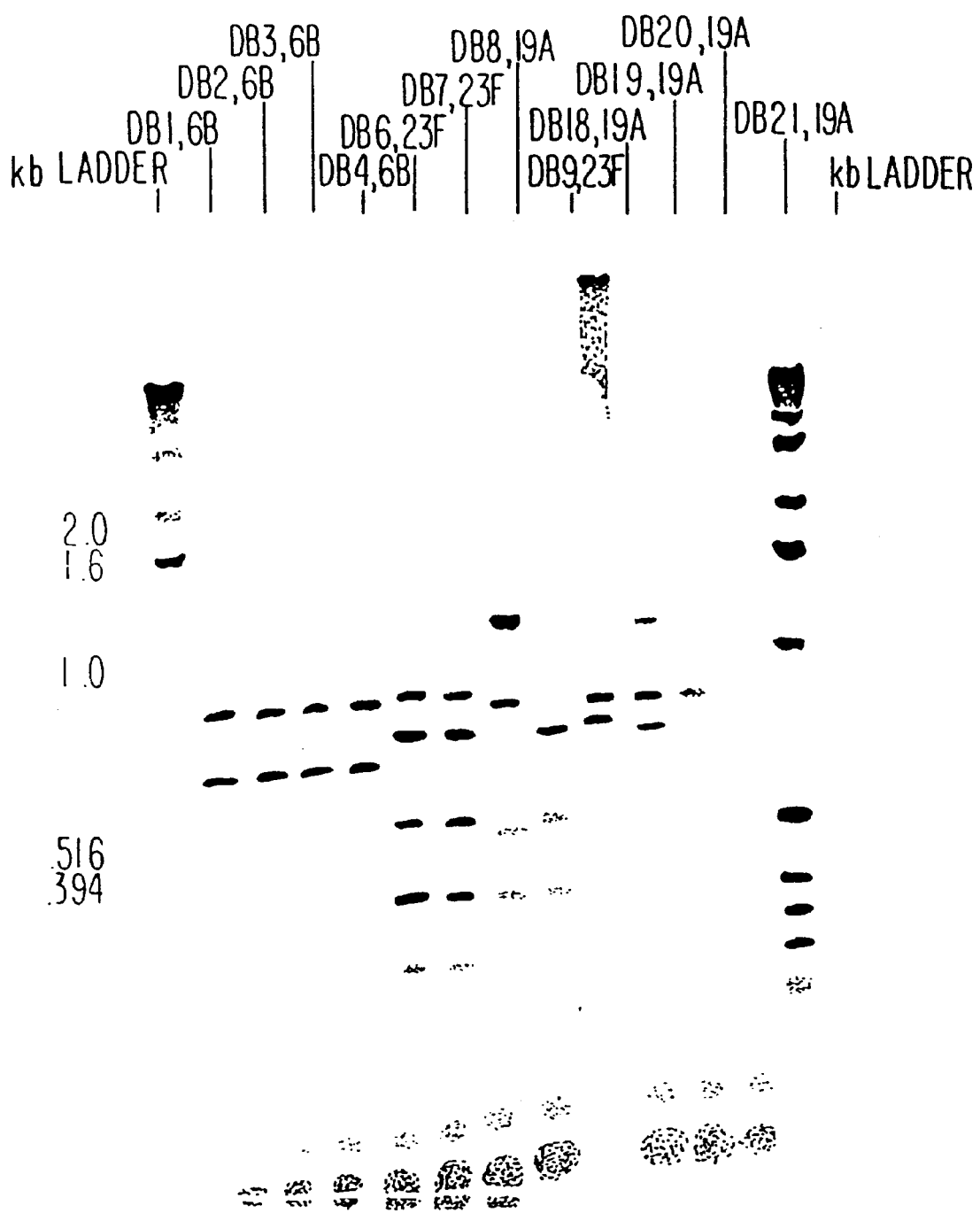

The stability of pspA polymorphism was also investigated using pneumococcal isolates which had previously been shown to be clonally related by other criteria, including capsule type, antibiotic resistance, enzyme electromorph, and PspA serotype. Three sets of isolates, all of which were highly penicillin resistant, were collected from patients during an outbreak in Hungary and two separate outbreaks in Spain. PCR amplified full length pspA from the capsular type 19A pneumococcal strains from the outbreak in Hungary, DB18, DB19, DB20, and DB21, resulted in a band approximately 2.0 kb. After digesting full length pspA with Hha I, four fragments were visualized., 89, 0.48, and 0.28 kb. Digestion with Sau3A I yielded five fragments 0.880, 0.75, 0.35, 0.34, and 0.10 kb. Capsule type 6B pneumococcal strains, DB1, DB2, DB3, and DB4, were obtained from an outbreak in Spain. Full length pspA from these strains were approximately 1.9 kb. Digestion of the PCR-amplified fragment with Hhs I resulted in four fragments which were 0.83, 0.43, 0.33, and .28 kb. Sau3A I digestion yield a 0.88, 0.75, 0.34, and 0.10 kg fragments. DB6, DB8, and DB9, which are capsular serotype 23F strains, were isolated from a second outbreak in Spain. DB6, DB8, and DB9 had an amplified pspA product which was 2.0 kb. Hha I digested fragments were 0.90, 0.52, 0.34, and 0.30 kb and Sau3A I fragments were 0.75, 0.52, 0.39, 0.22, 0.20, and 0.10 kb in size (FIG. 10). DB7 had a 19A capsular serotype and was not identical to DB6, DB8, and DB9. In the D39/Rx1 family and in each of the three outbreak families the size of the fragments obtained from the Hha I and the Sau3A I digests totaled approximately 2.0 kb which is expected if the amplified product represents a single pspA sequence.

Diversity of RFLP pattern of amplified pspA from random pneumococcal isolates

PCR amplification of the pspA gene from 70 random clinical pneumococcal isolates yielded full-length pspA ranging in size from 1.8 kb to 2.3 kb. RFLP analysis of PCR-derived pspA revealed two to six DNA fragments ranging in size from 100 bp to 1.9 kb depending on the strain. The calculated sum of the fragments never exceeded the size of the original amplified fragment. Not all pneumococcal strains had a unique pspA, and some seemingly unrelated isolates from different geographical regions and different capsular types exhibited similar RFLP patterns. Isolates were grouped into families based on the number of fragments produced by Hha I and Sau3A I digests and the relative size of these fragments.

Based on the RFLP patterns it was possible to identify 17 families with four of the families containing pairs of subfamilies. Within families all of the restriction fragments were essentially the same regardless which restriction enzyme was used. The subfamilies represent situations where two families share most but not all the restriction fragments. With certain strains an FRLP pattern was observed where detectable fragment size differed from the pattern of the established family by less than 100 bp. Since the differences were considered small compared to the differences in the fragment size and the number it fragments between families, they were not considered in family designation. The RFLP pattern of two isolates from six of the families is pictured in FIG. 11, Table 27. These families were completely independent of the capsular type or the protein type as identified by monoclonal antibodies (Table 28 and 29).

Previous DNA hybridization studies have demonstrated that the pspA gene of different isolates are the most conserved in their 3' region of the gene and more variable in the 5' region of the gene. Thus, if seemed likely that the differences in the pspA families reflected primarily differences in the 5' end of the gene. To confirm this theory, the a helical and proline region of pspA was examined without the amino acid repeats. Nucleotide primers LSM13 and KSH2 were used to amplify this fragment which is approximately 1.6 kb. Examination of this region of pspA afforded two things.

This primer pair permitted amplification of 90% of the strains which is greater than the 75% of the strains which can be amplified with oligonucleotides which amplify the full length gene. Second, it allowed Applicants to examine if the original groupings which were based on the full length gene coincide with the fingerprint patterns obtained by looking at the 5' half of the gene.

Figure 11:
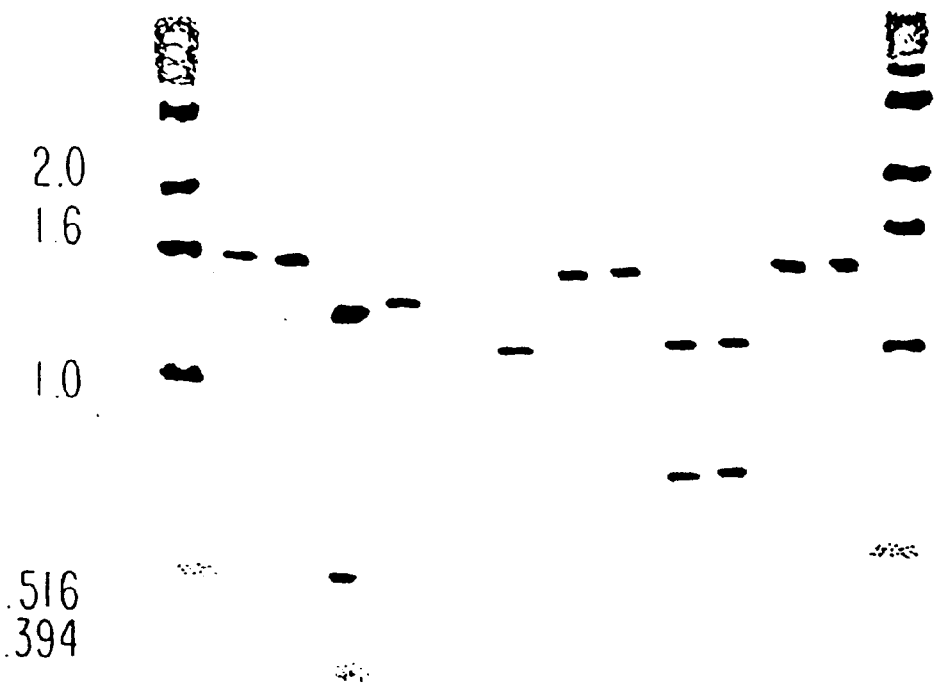
FIG. 11 shows: RFLP pattern of two isolates from six families.
Figure 12:
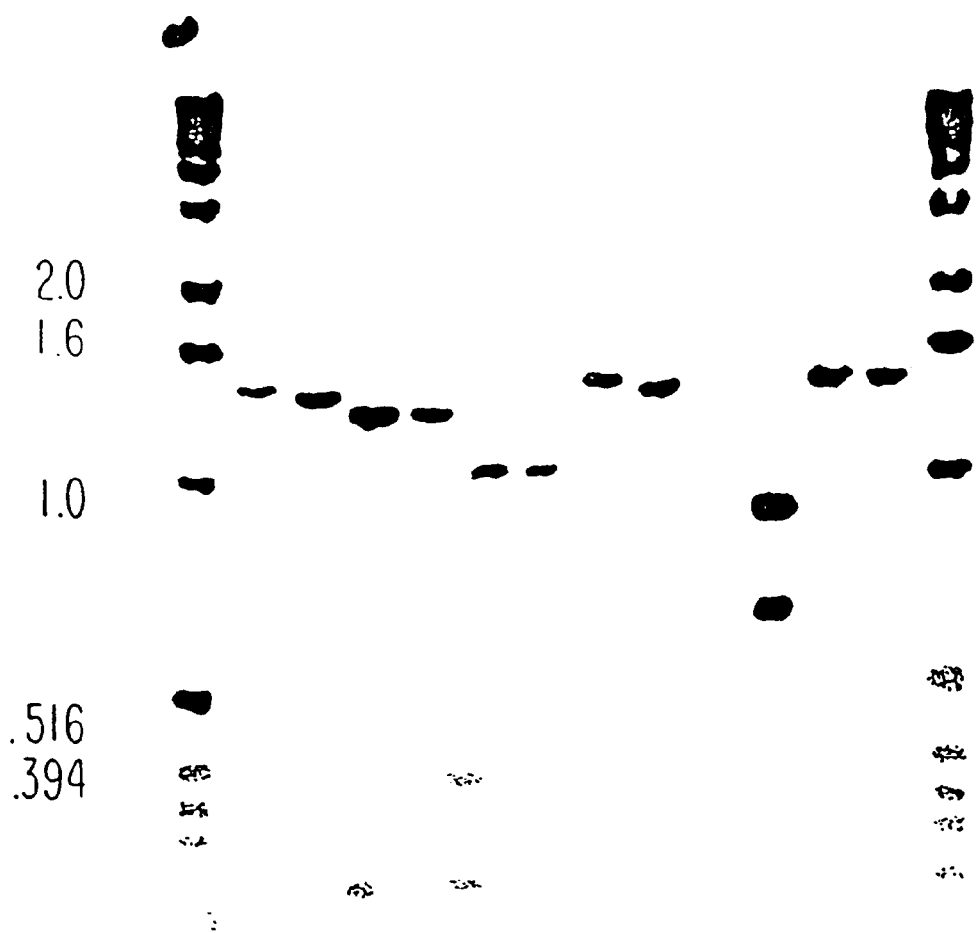
FIG. 12 shows: RFLP pattern of two isolates from six families (using products from amplification with SKH2 and LSM13).

FIG. 12 contains the same strains which were examined in FIG. 11 but the PCR products were amplified with SKH2 and LSM13. The RFLP patterns obtained from digestion of the Amplified α helical and proline rich region confirms the original designated families. However, these primers amplify a smaller portion of the psaA and therefore the difference is the families is not as dramatic as the RFLP patterns obtained from the RFLP pattern of the full length gene.

The polymerase chain reaction has simplified the process of analyzing pspA gene and have provided a means of using pspA diversity to examine the epidemiology of *S. pneumoniae*. Because not all strains contained a unique fingerprint of pspA, RFLP patterns of pspA cannot be used alone to identify the clonality of a strain. These results indicate the RFLP of PCR-amplified pspA from pneumococcal strains in conjunction with other techniques may be useful for identifying the clonal relatedness among pneumococcal isolates, and that this pattern is stable over long passages in vitro.

These findings suggests that the population of pspA is not as diverse as originally believed. PCR-RFLP of pspA may perhaps represent a relatively simplistic technique to quickly access the variability of the gene within a population. Further, these findings enable techniques to diagnose. S. pneumoniae via PCR or hybridization by primers on probes to regions of pspA common within groupings.

The sequence studies divide the known strains into several families based on sequence homologies. Sequence data demonstrates that there have been extensive recombinations occurring in nature within pspA genes. The net effect of the recombination is that the "families" identified by specific sequences differ depending upon which part of the pspA molecule is used for analysis. "Families" or "grouping identified by the 5' half of the alpha-helical region, the 3' half of the α-helical region and the proline rich region are each distinct and differ slightly from each other. In addition there is considerable evidence of other diversity (including base substitutions and deletions and insertions in the sequences) among otherwise closely related molecules.

This result indicates that it is expected that there will be a continuum of overlapping sequences of PspAs, rather than a discrete set of sequences.

The findings indicate that there is the greatest conservation of sequence in the 3' half of the α-helical region and in the immediate 5' tip. Because the diversity in the mid half of the α-helical region is greater, this region is of little use in predicting cross-reactivity among vaccine components and challenge strains. Thus, the sequence of 3' half of the alpha-helical region and the 5' tip of the coding sequence are likely to the critical sequences for predicting PspA cross-reactions and vaccine composition.

The sequence of the proline-rich region may not be particularly important to composition of a vaccine because this region has not been shown to be able to elicit cross-protection even though it is highly conserved. The reason for this is presumably because antibodies to epitopes in this region are not surface exposed.

Based on our present sequences of 27 diverse pspAs we have found that there are 4 families of the 3' half of the α-helical region and 2–3 families of the very 5' tip the α-helical region. Together these form 6 combinations of the 3' and 5' families. This approach therefore should permit us to identify a panel of pspAs with 3' and 5 helical sequences representative of the greatest number of different pspAs. See FIG. 13.

TABLE 25

Amplification of pspA from a panel of 72 independent isolates* of S. pneumaniae.

| CAPSULE TYPE | NUMBER OF STRAINS EXAMINED | LSM13 AND LSM2 % OF STRAINS AMPLIFIED | LSM13 AND SKH2 % OF STRAINS AMPLIFIED |
| --- | --- | --- | --- |
| 1 | 3 | 100 | 100 |
| 2 | 1 | 100 | 100 |
| 3 | 6 | 50 | 87 |
| 4 | 6 | 67 | 100 |
| 5 | 1 | 100 | 100 |
| 6 | 7 | 29 | 86 |
| 6A | 2 | 100 | 100 |

TABLE 29

RELATIONSHIP BETWEEN CAPSULAR TYPE AND RFLP FAMILY

| pspA Family | 1 | 2 | 3 | 4 | 5 | 6 | 6A | 6B | 7 | 8 | 9A | 9L | 9N | 9V | 10 | 11 | 12 | 13 | 14 | 15 | 19 | 22 | 23 | 31 | 33 | 35 | ND |
| --- | --- | --- | --- | --- | --- | --- | --- | --- | --- | --- | --- | --- | --- | --- | --- | --- | --- | --- | --- | --- | --- | --- | --- | --- | --- | --- | --- |
| A |   |   | 3 |   |   |   |   |   |   |   |   |   |   |   |   |   |   |   |   |   |   |   |   |   |   |   |   |
| B |   | 1 | 1 |   |   |   |   |   |   |   |   |   |   |   |   |   |   |   |   |   |   |   |   |   |   |   |   |
| C |   |   |   |   | 2 | 1 | 2 |   |   |   |   |   |   |   |   |   |   |   |   |   |   | 2 |   |   |   |   | 1 |
| D |   | 1 |   |   |   | 1 |   |   |   |   |   |   |   |   |   |   |   |   |   |   |   |   |   |   |   |   |   |
| DD |   |   |   | 2 |   |   |   |   |   |   |   |   |   |   |   |   |   |   |   |   |   |   |   |   |   |   |   |
| E |   | 1 | 2 |   | 1 |   |   |   |   |   |   |   |   |   |   |   |   |   |   |   |   |   |   |   |   |   |   |
| F |   |   |   |   | 1 |   |   |   |   |   |   |   |   |   |   |   |   | 1 |   |   |   |   | 3 |   |   |   | 1 |
| FF |   | 1 |   |   | 1 |   |   |   |   |   | 1 | 1 |   |   |   |   |   |   |   |   |   |   |   |   |   |   |   |
| G |   |   |   |   |   |   |   |   |   |   |   |   |   |   |   |   |   | 1 |   |   |   | 1 |   |   |   |   |   |
| H |   | 1 |   |   | 1 |   |   |   | 2 | 1 |   |   |   |   |   |   |   | 1 |   | 1 | 1 | 1 |   |   |   |   |   |
| I |   |   |   |   |   |   |   |   |   |   | 2 |   | 2 | 4 |   |   |   |   |   |   |   |   |   |   |   |   |   |
| II |   |   |   | 1 |   |   |   |   |   |   |   |   |   |   |   |   |   |   |   |   |   |   |   |   |   |   |   |
| J | 2 |   |   |   | 2 |   |   |   |   |   | 1 | 1 |   |   |   |   | 1 | 2 |   | 2 |   |   |   |   |   |   | 1 |
| K |   | 1 |   |   |   |   |   |   |   |   |   |   |   |   |   |   |   |   |   |   |   | 1 |   | 1 |   |   |   |
| KK | 1 |   |   |   | 1 | 1 |   |   |   |   |   |   |   |   |   |   |   | 1 |   | 1 |   |   |   |   |   |   |   |
| L |   |   |   |   |   |   |   |   |   |   |   |   |   |   |   |   |   |   |   |   |   |   | 1 |   |   |   | 1 |
| M |   |   |   |   |   | 1 |   |   |   |   |   |   |   |   |   |   |   |   |   |   |   |   |   | 1 |   |   |   |
| MM |   |   |   |   |   |   |   |   |   |   |   |   |   |   |   |   |   | 1 |   |   |   |   |   |   |   |   |   |

TABLE 24

Oligonucleotides used in this study

| Designation | Sequence 5'-3' | Nucleotide position |
| --- | --- | --- |
| LSM2 (SEQ ID NO: 18) | GCG CGT CGA CGG CTT AAA CCC ATT CAC CAT TGG | 1990 to 1967 |
| LSMI (SEQ ID NO: 19) | CCG GAT CCA GCT CCT GCA CCA AAA AC | 1312 to 1331 |
| LSM13 (SEQ ID NO: 20) | GCA AGC TTA TGA TAT AgA AAT TTG TAA C | 1 to 26 |
| SKH2 (SEQ ID NO: 21) | CCA CAT ACC GTT TTC TTG TTT CCA GCC | 1333 to 1355 |

TABLE 25-continued

Amplification of pspA from a panel of 72 independent isolates* of S. pneumaniae.

| CAPSULE TYPE | NUMBER OF STRAINS EXAMINED | LSM13 AND LSM2 % OF STRAINS AMPLIFIED | LSM13 AND SKH2 % OF STRAINS AMPLIFIED |
| --- | --- | --- | --- |
| 6B | 6 | 100 | 100 |
| 7 | 2 | 50 | 100 |
| 8 | 1 | 100 | 100 |
| 9V | 3 | 100 | 100 |
| 9A | 2 | 100 | 100 |
| 9L | 1 | 100 | 100 |
| 9N | 3 | 100 | 100 |
| 10 | 1 | 100 | 100 |
| 11 | 2 | 50 | 100 |
| 12 | 2 | 0 | 100 |
| 13 | 1 | 100 | 100 |
| 14 | 4 | 0 | 75 |

TABLE 25-continued

Amplification of pspA from a panel of 72 independent isolates* of S. pneumaniae.

| CAPSULE TYPE | NUMBER OF STRAINS EXAMINED | LSM13 AND LSM2 % OF STRAINS AMPLIFIED | LSM13 AND SKH2 % OF STRAINS AMPLIFIED |
|---|---|---|---|
| 15 | 2 | 50 | 50 |
| 19 | 5 | 100 | 100 |
| 22 | 3 | 33 | 100 |
| 23 | 1 | 100 | 100 |
| 33 | 1 | 0 | 100 |
| 35 | 1 | 0 | 100 |
| nd | 3 | 100 | 100 |

*Our strain collection contains several groups of isolates known to be previously to be clonal and collected for that purpose. The data reported in the table includes only one representative isolate from such clonal groups.

TABLE 36

Rx1–D39 derivatives

| ISOLATE | SIZE OF Hha I DIGESTS (Kb) | SIZE OF Sau3A I DIGESTS (Kb) |
|---|---|---|
| D39 | .76, .47, .39, .35, .12 | .83, .58, .36, .27 |
| Rx1 | .76, .47, .39, .35, .12 | .83, .58, .36, .27 |
| R800 | .76, .47, .39, .35, .12 | .83, .58, .36, .27 |
| R6 | .76, .47, .39, .35, .12 | .83, .58, .36, .27 |
| R61 | .76, .47, .39, .35, .12 | .83, .58, .36, .27 |
| R6X | .76, .47, .39, .35, .12 | .83, .58, .36, .27 |
| R36NC | .76, .47, .39, .35, .12 | .83, .58, .36, .27 |
| R36A | .76, .47, .39, .35, .12 | .83, .58, .36, .27 |

TABLE 27

Strain information and family designation of independent isolates.

| STRAIN | CAPSULE TYPE | PspA TYPE | FAMILY | SIZE OF Hha I FRAGMENTS | SIZE OF Sau3A I FRAGMENTS |
|---|---|---|---|---|---|
| BG9163 | 6B | 21 | C | 1.55, .35 | 1.05, .35, .22 |
| EF6796 | 6A | 1 | C | 1.5, .35 | 1.05, .35, .22 |
| EF5668 | 4 | 12 | DD | 1.25, .49, .32 | 1.0, .80, .35 |
| EF8616A | 4 | ND | DD | 1.25, .49, .32 | 1.0, .80, .35 |
| EF3296 | 4 | 20 | E | 1.0, .40, .33 | 1.15, .50, .34 |
| EF4135 | 4 | ND | E | 1.0, .40, .33 | 1.15, .50, .34 |
| BG7619 | 10 | ND | F | 1.3, .40, 29, .10 | .82, .76, .35 |
| BG7941 | 11 | ND | F | 1.3, .40, .29, .10 | .82, .76, .35 |
| BG7813 | 14 | 8 | H | 1.05, .70, .36 | .90, .77, .35 |
| BG7736 | 8 | ND | H | 1.05, .70, .36 | .99, .77, .35 |
| AC113 | 9A | ND | I | 1.4, .34, .28 | 1.2, .80 |
| AC99 | 9V | 5 | I | 1.4, .34, .28 | 1.2, .80 |

TABLE 28

Relationship of RFLP family and PspA type.

RELATIONSHIP BETWEEN PSPA TYPE AND RFLP FAMILY

| PspA FAMILY | \ PspA Type | | | | | | | | | | | | | | | | | | |
|---|---|---|---|---|---|---|---|---|---|---|---|---|---|---|---|---|---|---|---|
|  | 0 | 1 | 3 | 5 | 8 | 12 | 13 | 16 | 18 | 19 | 20 | 21 | 24 | 25 | 26 | 30 | 33 | 34 | 36 | 37 | ND |
| A |  | 1 |  |  |  |  |  | 1 |  |  |  |  |  |  |  |  |  |  |  |  |  |
| B |  |  |  |  |  |  |  |  |  |  |  |  |  | 1 | 1 |  |  |  |  |  | 1 |
| C |  | 2 |  |  |  |  |  |  |  |  |  | 1 | 1 |  |  |  |  |  |  |  | 4 |
| D |  |  |  |  |  |  | 1 |  | 1 |  |  |  |  |  |  |  |  |  |  |  |  |
| DD |  |  |  |  |  | 2 |  |  |  |  |  |  |  |  |  |  |  |  |  |  |  |
| E |  |  |  | 1 |  |  |  |  |  |  | 1 |  |  |  |  | 1 |  |  |  |  |  |
| F |  |  |  |  |  | 1 |  |  |  |  |  |  |  |  |  |  | 1 |  |  |  | 4 |
| FF |  |  |  |  |  |  |  |  |  |  |  |  |  |  | 1 |  |  |  |  |  | 3 |
| G |  |  |  |  |  |  | 1 |  |  |  |  |  |  |  |  |  |  | 1 |  |  |  |
| H | 1 |  |  |  | 1 |  | 1 | 1 |  |  |  |  |  |  |  |  |  |  |  |  | 5 |
| I | 3 |  |  | 1 |  |  | 2 | 2 |  |  |  |  |  |  |  |  |  |  |  |  | 1 |
| II |  |  |  |  |  |  |  |  |  |  |  |  |  |  |  | 1 |  |  |  |  |  |
| J | 4 |  |  |  |  |  |  |  |  | 1 | 1 |  |  |  |  |  |  |  |  | 1 | 3 |
| K | 1 |  |  |  |  |  |  | 1 |  |  |  |  | 1 |  |  |  |  |  |  |  |  |
| KK | 1 |  |  |  |  |  |  |  |  |  |  |  |  |  |  |  |  |  |  | 1 | 3 |
| L |  |  |  |  |  |  | 1 |  |  |  |  |  |  |  |  |  |  |  |  |  | 1 |
| M |  |  |  |  |  |  | 1 | 1 |  |  |  |  |  |  |  |  |  |  | 1 |  | 1 |
| MM |  |  |  |  |  | 1 |  |  |  |  |  |  |  |  |  |  |  |  |  |  |  |

Example 7
Ability of PspA immunogens to protect against individual challenge strains CBA/N or BALB cJ mice were given 1 injection of 0.5 -μg PspA in CFA, followed 2 weeks later by a boost in saline, and challenged between 7 and 14 (average 10) days post boost. Control mice were administered a similar immunization regimen, except that the immunization came from an isogeneic strain unable to make PspA. The PspA was either full length, isolated from pneumococci or cloned full length or BC100 PspA, as little statistical significance has been seen in immunogenicity between full length PspA and BC100. The challenge doses ranged from about $10^3$ to $10^4$ pneunocci in inoculum, but in all cases the challenge was at least 100 times $LD_{50}$.

The results are shown in the following Tables 30 to 60, and the conclusions set forth therein.

From the data, it appears that an antigenic, immunological or vaccine composition can contain any two to even, preferably three to five PspA, e.g., PspAs from R36A and BG9739, alone, or combined with any or all of PspAs from Wu2, Ef5668, and DB15. Note that surprisingly WU2 PspA provided better protection against D39 that did R36a/Rx1/D39, and that also surprisingly PspA from Wu2 protected better against BG9739 than did PspA from BG9739. Combinations containing R36A, BG9739 and WU2 PspAs were most widely protective; and therefore, a preferred composition can contain any three PspA, preferably R36A, BG9739 and WU2. The data in this Example shows that PspA from varying strains is protective, and that it is possible to formulate protective compositions using any PspA or any combination of the PspAs from the eight different PspAs employed in the tests. Similarly, one can select PspaS on the basis of the groupings in the previous Example. Note additionally that each of PspA from R36A, BG9739, EF5668 and DBL5 are, from the data, good for use in compositions.

A note about use of medians rather than averages. Applicants have chosen to express data as median (a non-parametric parameter) rather than averages because the times to death do not follow a normal distribution. In fact there are generally two peaks. One is around day 3 or 6 when most of the mice die and the other is at >21 for mice that live. Thus, it becomes nonsensical to average values like 21 or 22 with values like 3 or 6. One mouse that lives out of 5 has a tremendous effect on such an average but very little effect on the median. Thus, the median becomes the most robust estimator of time to death of most of the mice.

TABLE 30

Relative ability of different PspAs to Protect against each challenge strains of *S. pneumoniae*
(Summary of statistically significant protection)

| Challenge Strain | Caps type | PspA type | pspA family | R36A, Rx1, D39 K | JD908/ WU2 a | JS1020/ BG9739 b | EF3296 E | EF5668 DD | L81905 b | JS5010.3 DBL5 II | JS3020 DBL6A D | All immune — | best protect — |
|---|---|---|---|---|---|---|---|---|---|---|---|---|---|
| D39 | 2 | 25 | K | ++ | +++ | | + | | | | | ++ | +++ |
| WU2 | 3 | 1 | a | +++ | +++ | +++ | | +++ | +++ | +++ | +++ | +++ | +++ |
| A66 | 3 | 13 | a | +++ | +++ | +++ | | +++ | +++ | +++ | +± | +++ | +++ |
| EF10197 | 3 | 18 | M | +++ | | +++ | | | | | | +++ | +++ |
| ATCC6303 | 3 | 7 | a | +++ | | | | | | | | +++ | +++ |
| BG9739 | 4 | 26 | b | + | +++ | + | 0+ | 0 | +± | 0 | 0 | ++ | +++ |
| EF3296 | 4 | 20 | E | +± | +± | 0+ | | | | 0 | 0 | 0 | +± |
| EF5668 | 4 | 12 | DD | + | 0 | +++ | 0+ | +++ | 0+ | + | 0+ | ++ | +++ |
| L81905 | 4 | 23 | b | + | + | ++ | ++ | 0 | + | +± | +± | ++ | ++ |
| DBL5 | 5 | 33 | II | + | | + | | + | + | ++ | 0 | ++ | ++ |
| EF6796 | 6A | 1 | C | +++ | | | | | | | | +++ | +++ |
| DBL6A | 6A | 19 | D | +++ | +± | ++ | +± | +++ | +± | +± | +++ | ++ | +++ |
| BG9163 | 6B | 21 | C | +++ | | +++ | | | | | | +++ | +++ |
| BG7322 | 6B | 24 | C | +++ | +++ | +± | 0 | +++ | +± | +++ | +± | +++ | +++ |

Note:
Empty cells indicate that no experiment has been done. Bold means significant at P < 0.05, Small font bold (+) means $0.02 \leq P < 0.05$. Large font bold means P = 0.02. For this table statistical significance refers to delay in time to death except as indicate in the (+) footnote below. When "all immune" showed significant protection against death but individual data cells did not, the result for "all immune" is presented under best protection on the assumption that if more mice were done in each data cell one or more of them would have exhibited significant protection against death.

+++ = statistically significant protection against death; ≥50% protection from death ++ = statistically significant protection against death; <50% protection from death +± = statistically significant delay in death; ≥20 protection from death + = statistically significant delay in death; <20 protection from death, (or significant protection against death but not a significant delay in death)

0++ = Not statistically delay in time to death; but ≥ 50% protection from death

0+ = Not statistically delay in time to death; but >1.5 day extension in median time to death or ≥20% protection from death.

0 = No apparent extension in time to death or protection from death.

TABLE 31

Relative ability of different PspAs to Protect against each challenge strains of *S. pneumoniae*
(Expressed as Median days Alive post challenge)

| Challenge Strain | Caps type | PspA type | pspA family | R36A Rx1, D39 K | JD908 WU2 a | JS1020/ BG9739 b | EF3296 E | EF568 DD | L81905 b | JS5010.3 DBL5 II | JS3020 DBL6A D | All immune | All control |
|---|---|---|---|---|---|---|---|---|---|---|---|---|---|
| D39 | 2 | 25 | K | 4.5 | >21 | | | 4 | | | | 5 | 2 |
| WU2 | 3 | 1 | a | >21 | >21 | >21 | | >21 | >21 | >21 | >21 | >21 | 2 |
| A66 | 3 | 13 | a | >21 | >21 | >21 | | >21 | >21 | >21 | 4 | >21 | 2 |
| Ef10197 | 3 | 18 | M | >21 | | >21 | | | | | | >21 | 2 |
| ATCC6303 | 3 | 7 | a | >21 | | | | | | | | >21 | 5 |
| BG9739 | 4 | 26 | b | 3 | >21 | 6 | 3 | 3 | 5, 13 | 2 | 2 | 3 | 2 |
| EF3296 | 4 | 20 | E | 5 | 5 | 4.5 | | | | 2 | 2 | 3 | 2 |
| EF5668 | 4 | 12 | DD | 6 | 2 | >21 | 13 | >21 | 4 | >21 | 5 | 8 | 3 |
| L81905 | 4 | 23 | b | 5 | 5 | 8 | 6 | 3 | 5 | 3 | 3.5 | 5 | 2 |
| DBL5 | 5 | 33 | II | 4 | | 3 | | 3 | 3.5 | 6 | 2 | 3.5 | 2 |
| EF6796 | 6A | 1 | C | >21 | | | | | 8 | | | >21 | 1 |
| DBL6A | 6A | 19 | D | >21 | 8.5 | 13 | 9 | >21 | | 12 | >21 | 12.5 | 5.5 |
| BG9163 | 6B | 21 | C | >21 | | >21 | | | | | 11 | >21 | 8.5 |
| BC7322 | 6B | 24 | C | >21 | >21 | 14.5 | 6 | >21 | 12.5 | >21 | | >21 | 7 |

Note:
Bold denotes statistically significant extension of life at $P < 0.05$. Small font denotes $0.02 \leq P < 0.05$; large font denotes $P < 0.02$. Median times to death indicated as 8, >21, are situations where the medium as not within a continuum of values. In those cases the numbers shown are those closest to the median. In these cases the values give are those closest to the calculated median. Fractional values such as 3.5, indicate that the median is halfway between two numbers, in this case 3 and 4. As indicated in the original data (S103B), some experiments were terminated prior to 21 days post infection. There is little reason to assume, however, that results would have been significantly effected by the early termination's since very few mice infected with the strains used in those studies, have ever been observed to die later than 10 or 15 days post challenge. For statistical purposes all mice alive at the end of experiments were assumed to have been completely protected, and for the sake of calculations all surviving mice were assigned values of >21.

TABLE 32

Ability of different PspAs to Protect Against each Challenge strain of
*S. pneumoniae*
(Expressed as increase in survival time in days)
(A denotes $\geq 50\%$ immune mice alive)

| Challenge Strain | Caps type | PspA type | pspA family | R36A, Rx1, D39 K | JD908 WU2 a | JS1020/ BG9739 b | EF3296 E | EF5668 DD | L81905 b | JS5010.3 DBL5 II | JS3020 DBL6A D | All immune | Best Result |
|---|---|---|---|---|---|---|---|---|---|---|---|---|---|
| D39 | 2 | 25 | K | 2.5 | A | | | 2 | | | | 3 | A |
| WU2 | 3 | 1 | a | A | A | A | | A | A | A | A | A | A |
| A66 | 3 | 13 | a | A | A | A | | A | A | A | 2 | A | A |
| EF10197 | 3 | 18 | M | A | | A | | | | | | A | A |
| ATCC6303 | 3 | 7 | a | A | | | | | | | | A | A |
| BG9739 | 4 | 26 | b | 1 | A | 4 | 1 | 1 | 3, 11 | 0 | 0 | 1 | A |
| EF3296 | 4 | 20 | E | 3 | 3 | 2.5 | | | | 0 | 0 | 1 | 3 |
| EF5668 | 4 | 12 | DD | 3 | −1 | A | 10 | A | 1 | A | 2 | 5 | A |
| L81905 | 4 | 23 | b | 3 | 3 | 6 | 4 | 1 | 3 | 1 | 1.5 | 3 | 6 |
| DBL5 | 5 | 33 | II | 2 | | 1 | | 1 | 1.5 | 4 | 0 | 1.5 | 4 |
| EF6796 | 6A | 1 | C | A | | | | | | | | A | A |
| DBL6A | 6A | 19 | D | A | 3 | 7.5 | 3.5 | A | 2.5 | 6.5 | A | 7 | A |
| BG9163 | 6B | 21 | C | A | | A | | | | | | A | A |
| BG7322 | 6B | 24 | C | A | A | 7.5 | −1 | A | 5.5 | A | 4 | A | A |
| | | | | R36A | WU2 | BG9739 | EF3296 | EF5668 | L81905 | DBL5 | DBL6A | All | Best |

Note:
Bold denotes statistically significant extension of life at $P < 0.05$. Small font denotes $0.02 \leq P < 0.05$; large font denotes $P < 0.02$. Median increases in survival listed as 3, 9 or 1, A denote groups where the median does not fall within a continuum of values. In these cases the values give are those closest to calculated median. Fractional values such as 3.5, indicate that the median is halfway between two numbers, in this case 3 and 4.

TABLE 33

Relative ability of different PspAs to Protect against each challenge strains of *S. pneumoniae*
(express % alive at 21 days post challenge)

| Challenge Strain | Caps type | PspA type | pspA family | R36A, Rx1, D39 K | JD908 WU2 a | JS1020/ BG9739 b | EF3296 E | EF5668 DD | L81905 b | JS5010.3 DBL5 II | JS3020 DBL6A D | All immune — | All control |
|---|---|---|---|---|---|---|---|---|---|---|---|---|---|
| D39 | 2 | 25 | K | 38 | 60 | | | 30 | | | | 38 | 3 |
| WU2 | 3 | 1 | a | 100 | 100 | 100 | | 100 | 100 | 100 | 100 | 100 | 1.5 |
| A66 | 3 | 13 | a | 75 | 100 | 80 | | 75 | 100 | 60 | 20 | 76 | 5 |
| EF10197 | 3 | 18 | M | 100 | | | | | | | | 90 | 0 |
| ATCC6303 | 3 | 7 | a | 100 | | | | | | | | 100 | 0 |
| BG9739 | 4 | 26 | b | 11 | 60 | 13 | 25 | 0 | 25 | 0 | 0 | 12 | 0 |
| EF3296 | 4 | 20 | E | 25 | 20 | 10 | | | | 0 | 0 | 8 | 0 |
| EF5668 | 4 | 12 | DD | 22 | 25 | 60 | 40 | 100 | 40 | 60 | 0 | 41 | 9 |
| L81905 | 4 | 23 | b | 10 | 0 | 31 | 40 | 0 | 0 | 14 | 0 | 14 | 0 |
| DBL5 | 5 | 33 | II | 10 | | 14 | | | | 29 | 0 | 4 | 0 |
| EF6796 | 6A | 1 | C | 100 | | | | | | | | 100 | 0 |
| DBL6A | 6A | 19 | D | 67 | 25 | 33 | 0 | 60 | 25 | 0 | 80 | 35 | 4 |
| BG9163 | 6B | 21 | C | 89 | | 80 | | | | | | 86 | 20 |
| BG7322 | 6B | 24 | C | 100 | 60 | 25 | 0 | 89 | 25 | 80 | 25 | 55 | 6 |

Bold, denotes statistically significant protection against death at $P < 0.05$. Bold small font, indicates significant protection against death at $0.02 \leq P < 0.05$. Bold large font, indicates significant protection against death at $P < 0.02$.

TABLE 34

Relative ability of different PspAs to Protect against each challenge strain of *S. pneumoniae*
(% protected from death at 21 days post challenge)

| Challenge Strain | Caps type | PspA type | pspA family | R36A, Rx1, D39 K | WU2 JD908 a | BG9739 JS1020 b | EF3296 E | EF5668 DD | L81905 b | DBL5 JS5010.3 II | DBL6A JS3020 D | All immune — | Best result |
|---|---|---|---|---|---|---|---|---|---|---|---|---|---|
| D39 | 2 | 25 | K | 36 | 59 | | | 28 | | | | 36 | 59 |
| WU2 | 3 | 1 | a | 100 | 100 | 100 | | 100 | 100 | 100 | 100 | 100 | 100 |
| A66 | 3 | 13 | a | 71 | 100 | 79 | | 74 | 100 | 58 | 16 | 75 | 100 |
| EP10197 | 3 | 18 | M | 100 | | 80 | | | | | | 90 | 100 |
| ATCC6303 | 3 | 7 | a | 100 | | | | | | | | 100 | 100 |
| BG9739 | 4 | 26 | b | 11 | 60 | 13 | 25 | 0 | 25 | 0 | 0 | 12 | 60 |
| EF3296 | 4 | 20 | E | 25 | 20 | 10 | | | | 0 | 0 | 8 | 25 |
| EF5668 | 4 | 12 | DD | 14 | 18 | 56 | 34 | 100 | 34 | 56 | −10 | 35 | 100 |
| L81905 | 4 | 23 | b | 10 | 0 | 31 | 40 | 0 | 0 | 14 | 0 | 14 | 40 |
| DBL5 | 5 | 33 | II | 10 | | 14 | | | | 29 | 0 | 4 | 29 |
| EF6796 | 6A | 1 | C | 100 | | | | | | | | 100 | 100 |
| DBL6A | 6A | 19 | D | 66 | 22 | 30 | −4 | 58 | 22 | −4 | 79 | 33 | 79 |
| BG9163 | 6B | 21 | C | 86 | | 75 | | | | | | 83 | 86 |
| BG7322 | 6B | 24 | C | 100 | 57 | 22 | 0 | 88 | 22 | 79 | 22 | 52 | 100 |

Bold, denotes statistically significant protection against death at $P < 0.05$. Bold small fonet, indicates significant protection against death at $0.02 \leq P < 0.05$. Bold large font, indicates significant protection against death at $P < 0.02$.

% protected has been corrected for any survivors in the control mice.

% protected = 100 × (% alive in immune − % alive in control)/(100 −% alive in control). Thus, if there were any mice alive in the control animals, the calculated "% protected" is less than the observed "% alive" listed in the previous table. The only exceptions to this are if 100% of immunized mice lived. Negative numbers mean that less immunized mice lived than did control mice. Please note that none of these negative numbers are significant even thoughwe are using a one tailed test.

TABLE 35

Recommended Immunogens Protection against the indicated challenge
strains of S. pneumoniae Based on Protection Score
Based on median days alive and percent protected
(numbers refer to preference as a vaccine strain with respect to the indicated
challenge strain,
1 = best)

| Challenge Strain | Caps type | PspA type | pspA family | Vaccine PspA R36A, Rx1, D39 K | WU JD908 a | BG9739 JS1020 b | EF3296 E | EF5668 DD | L81905 b | DBLS JS5010.3 II | DBL6A JS3020 D |
|---|---|---|---|---|---|---|---|---|---|---|---|
| D39 | 2 | 25 | K | 2 | 1 |  |  | 3 |  |  |  |
| WU2 | 3 | 1 | a | 1 | 1 | 1 |  | 1 | 1 | 1 | 1 |
| A66 | 3 | 13 | a | 2 | 1 | 2 |  | 2 | 1 | 3 | 0 |
| EF10197 | 3 | 18 | M | 1 |  | 2 |  |  |  |  |  |
| ATCC6303 | 3 | 7 | a | 1 |  |  |  |  |  |  |  |
| BG9739 | 4 | 26 | b | 3 | 1 | 2 | 3 | 3 | 2 | 0 | 0 |
| EF3296 | 4 | 20 | E | 1 | 1 | 2 |  |  |  | 0 | 0 |
| EF5668 | 4 | 12 | DD | 0 | 0 | 2 | 3 | 1 | 0 | 2 | 0 |
| L81905 | 4 | 23 | b | 2 | 0 | 1 | 1 | 0 | 0 | 0 | 0 |
| DBL5 | 5 | 33 | II | 2 |  | 3 |  | 0 | 3 | 1 | 0 |
| EF6796 | 6A | 1 | C | 1 |  |  |  |  |  |  |  |
| DBL6A | 6A | 19 | D | 2 | 0 | 3 | 0 | 2 | 0 | 0 | 1 |
| BG9163 | 6B | 21 | C | 1 |  | 1 |  |  |  |  |  |
| BG7322 | 6B | 24 | C | 1 | 2 | 3 |  | 1 | 3 | 1 | 3 |
| Number of #1's |  |  |  | 7 | 5 | 3 | 1 | 3 | 2 | 3 | 2 |

Bold, denotes statistically significant protection against death at P < 0.05. Where more than one PspA were equally protective, the same values were given to each. Recommendations are based on days to death with % protection dividing ties, especially among those where greater than 50% of mice lived to 21 days. "0" indicates test were conducted but compared to the other PspAs this one is not recommended.

TABLE 36

Best Choice for Vaccine Components as of 95/8/27

| Criterion | Vaccine Component (cumulative strains protected) % maximally protected | | | | | |
|---|---|---|---|---|---|---|
|  | 1 | 2 | 3 | 4 | 5 | 6 |
| ≧ #1 PspA for each challenge strain | R36A (7) 50% | WU2 (10) 71% | BG9739* (11) 79% | EF5668 (12) 86% | DBL5 (13) 93% | DBL6A (14) 100% |
| ≧ #2 PspA for each challenge strain | R36A (12) 86% | BG9739 (12) 100% |  |  |  |  |
| Max score (+) type score | R36A (9) 64% | WU2 (11) 79% | BG9739 (13) 92% | DBL5 (14) 100% |  |  |
| Max Increase in Days alive | R36A (9) 64% | WU2 (11) 79% | BG9739 (13) 92% | DBL5 (14) 100% |  |  |
| % protected | R36A (7) 50% | WU2 (10) 64% | DBL5 (11) 79% | EF5668 (12) 86% | DBL6A (13) 92% | EF3296 (14) 100% |
| Theoretical mixture based on a few testable assumptions (see below) | R36A (10) 64% | BG9739 (12) 86% | DBLS (13) 92% | EF3296 (14) 100% |  |  |

*This is not a unique combination. See table below.

TABLE 37

Combinations where all Challenge Strains have a Vaccine strain with a score of ≧#2

| Number of PspAs in Combination | Combination | Number of #1 strains | Total #1s | Total #1s and #2s |
|---|---|---|---|---|
| 2 | R36A + BG9739 | 8 | 10 | 20 |
| 3 | R36A + BG9739 + WU2 | 11 | 15 | 25 |
| 3 | R36A + WU2 + DBL5 | 11 | 15 | 21 |
| 3 | R36A + WU2 + EF5668 | 11 | 15 | 23 |
| 3 | R36A + WU2 + DBL5 | 11 | 15 | 22 |

TABLE 38

Pooled Data for Protection against D39 by various PspAs;
Days alive for each mouse

| Exp. | Log CFU D39 | Mice | Rx1/R36A D39 | JD908 (WU2) | EF5668 | All Immune | control |
|---|---|---|---|---|---|---|---|
| 143 | 4.5 | CBA/N | | | 1, 1, 2, 2, 2 | | 1, 1, 2, 2, 3 |
| E145 | 4.0 | CBA/N | 2, 3, 3, 3, 4 | | | | 1, 1, 2, 3, 4 |
| E028 BCG | 5.93 | BALB/c | 3, 3x > 21 | | | | 2, 2, 2, 4 |
| E143 | 3.0 | CBA/N | | | 2, 6, 3x > 10 | | 3, 3, 3, 5, 5 |
| E140 BC100 | 2.81 | CBA/N | 4, 4, 5, 7, 15 | | | | 2, 2, 2, |
| E169 | 2.7 | CBA/N | 2.4x > 21 | 2, 5, 3x > 21 | | | 1, 2, 2, 3 |
| E154 | 2.6 | CBA/N | 2, 2, 3, 2x >21 | | | | 4x 2, 5, > 21 |
| All ≤3.0 | | | 2, 3, 3, 3, 4, 4, 4, 5, 7, 15 | | 1, 1, 2, 2, 2 | | 4x 1, 6x 2, 3, 3, 4 |
| All | | | 4x 2, 5x 3, 3x 4, 5, 7, 15, 9x > 21 | 2, 5, 3x > 21 | 1, 1, 2, 2, 2, 2, 6 3x > 21 | 1, 1, 9x 2, 5x 3, 3x 4, 5, 5, 6, 7, 15, 15x > 21 | 5x 1, 16x 2, 6x 3, 4, 4, 5, 5, 5, > 21 |

TABLE 39

Pooled Data for Protection against D39 by various PspAs
Median Days Alive & alive:dead
with corresponding P values.

| | Log CFU | | Rx1/R36A D39 | | JD908 (WU2) | | EF5668 | | All Immune | | Control | |
|---|---|---|---|---|---|---|---|---|---|---|---|---|
| Exp. | D39 | Mice | med | a:d | med | a:d | med | a:d | med | a:d | med | a:d |
| 143 | 4.5 | CBA/N | | | | | 2 n.s. | 0:5 | | | 2 | 0:5 |
| E145 | 4.0 | CBA/N | 3 n.s. | 0:5 | | | | | | | 2 | 0:5 |
| E028 BCG | 5.93 | BALB/c | >21 0.29 | 3:1 n.s. | | | | | | | 2 | 0:4 |
| E143 | 3.0 | CBA/N | | | | | >21 n.s. | 3:2 n.s. | | | 3 | 0:5 |
| E140 BC100 | 2.81 | CBA/N | 5 0.018 | 0:5 | | | | | | | 2 | 0:3 |
| E169 | 2.7 | CBA/N | >21 .016 | 4:1 .024 | >21 .016 | 3:2 n.s. | | | | | 2 | 0:5 |
| E154 | 2.6 | CBA/N | 3 n.s. | 2:3 n.s. | | | | | | | 2 | 1:5 |
| All ≤3.0 | | | 4 .008 | 0:10 | | | 2 n.s. | 0:5 | | | 2 | 0:13 |
| All | | | 4.5 .0057 | 9:15 .001 ++ | >21 .006 | 3:2 .0045 +++ | 4(2.6) n.s. | 3:7 .034 + | 5 .0001 | 15:24 .0002 ++ | 2 | 1:32 |
| % alive | | | | 38 36 Rx1/D39 | | 60 59 WU2 | | 30 28 EF5668 | | 38 36 All immune | | 3 controls |

TABLE 40

Pooled Data for Protection against WU2. by various PspAs

Days to Death/immunogen

| Exp. | CFU WU2 | Mice | FL-R36A | Rx1 BC100 | JD108 (WU2) | JS1020 (BG9739) | BG9739 bc100 | EF5668 | L81905 bc100 | CGL5 bc100 | JS3020 (DBL6A) | control |
|---|---|---|---|---|---|---|---|---|---|---|---|---|
| Dr. Ed, expt. lots of prior expts. | | | +++ | | | | | | | +++ | | |
| E012 | 3.0 | CBA/N | >21 | | | | | | | | | 1, 1, 11x, 2 7x 3, 4 |
| E028 | 6.01 | BALB/c | 4x > 21 0.05/n.s. | | | | | | | | | 4, 6, 6, > 21 |

TABLE 40-continued

Pooled Data for Protection against WU2. by various PspAs

Days to Death/immunogen

| Exp. | CFU WU2 | Mice | FL-R36A | Rx1 BC100 | JD108 (WU2) | JS1020 (BG9739) | BG9739 bc100 | EF5668 | L81905 bc100 | CGL5 bc100 | JS3020 (DBL6A) | control |
|---|---|---|---|---|---|---|---|---|---|---|---|---|
| E084 | 3.75[1] | CBA/N | | | | 3x × 15 | | | | | | 1, 2, 2, 2, 3, 3, >15 |
| E125 bc100 | 3.57 | CBA/N | | | | | 4x > 21 | | 4x > 21 | 4x > 21 | | 2, 2, 3, 3, 3, >21 |
| E129 | 3.18 | CBA/N | | | | 5x × 23 | | | | | | 2, 2, 2, 2, 3 |
| E140 BC100 | 3.43 | CBA/N | | 4x > 21 | | | | | | | | 1, 5x 2, 3, 4 |
| E143 | 3.0 | CBA/N | | | | | | 8x > 10 | | | | 1, 1, 2, 2, 2, 3 |
| E144 | 3.9 | CBA/N | | | | | | | | | 5x × 21 | 5x 2 |
| E172 | 3.98 | CBA/N | | | 5x > 21 | | | | | | | 5x 3 |
| All | | | 19x > 21 | 4x > 21 | 5x > 21 | 8x > 21 | 4x > 21 | 8x > 21 | 4x > 21 | 4x > 21 | 5x > 21 | 6x 1, 33x 2, 20x 3, 4, 4, 4, 6, 6, >21 |
| All Immune | | | 61x > 21 | | | | | | | | | |

TABLE 41

Pooled Data for Protection against WU2 by various PspAs

Median days Alive
Alive:Dead
P value based on Alive:Dead
P value calculated compared to pooled controls (in this case 65 control mice)
Score

| Exp. | CFU WU2 | Mice | FL-R36A | Rx1 BC100 | JD108 (WU2) | JS1020 (BG9739) | BG9739 bc100 | EF5668 | L81905 bc100 | DBL5 bc100 | JS3020 (DBL6A) | control |
|---|---|---|---|---|---|---|---|---|---|---|---|---|
| Dr. Ed, expt. lots of prior expts. | | | +++ | | | | | | +++ | | | |
| E012 | 3.0 | CBA/N | >21 15:0 | | | | | | | | | 1,1, 11x 2, 7x 3, 4 |
| E028 | 6.01 | BALB/c | 4x > 21 | | | | | | | | | 4, 6, 6, > 21 |
| E084 | 3.75[1] | CBA/N | | | | 3x > 15 | | | | | | 1, 2, 2, 2, 3, 3, >15 |
| E125 bc100 | 3.57 | CBA/N | | | | | 4x > 21 | | 4x > 21 | 4x > 21 | | 2, 2, 3, 3, 3, >21 |
| E129 | 3.18 | CBA/N | | | | 5x > 23 | | | | | | 2, 2, 2, 2, 3 |
| E140 BC100 | 3.43 | CBA/N | | 4x > 21 | | | | | | | | 1, 5x 2, 3, 4 |
| E143 | 3.0 | CBA/N | | | | | | 8x > 10 | | | | 1, 1, 2, 2, 2, 3 |
| E144 | 3.9 | CBA/N | | | | | | | | | 5x > 21 | 5x 2 |
| E172 | 3.98 | CBA/N | | | 5x > 21 | | | | | | | 5x 3 |
| All | | | >21 19:0 <.0001 +++ | >21 4:0 <.0001 +++ | >21 5:0 <.0001 +++ | >21 8:0 <.0001 +++ | >21 4:0 <.0001 +++ | >21 8:0 <.0001 +++ | >21 4:0 <.0001 +++ | >21 4:0 <.0001 +++ | >21 4:0 <.0001 +++ | 2 1:64 |
| % alive | | | 100 FL-R36A | 100 Rx1 BC100 | 100 JD108 (WU2) | 100 JS1020 (BG9739) | 100 BG9739 | 100 EF5668 | 100 L81905 bc100 | 100 DBL5 bc100 | 100 JS3020 (DBL6A) | 2 control |

| V/U2 Challenge | days of death | median days of death | amount dead | P value based on days to death | P value based on alive:dead | Score | % alive | % prot. |
|---|---|---|---|---|---|---|---|---|
| All immune | 61x > 21 | >21 | 61:0 | <.0001 | <.0001 | +++ | 100 | 100 |
| All controls | 6x 1, 33x, 2, 20x 3, 4, 4, 4, 6, 6, >21 | 2 | 1:64 | | | 2 | 2 | |

TABLE 42

Pooled Data for Protection against A66, by various PspAs

Days to Death/immunogen

| Exp. | CFU A66 | Mice | FL-R36A/ D39 | Rx1 BC100 | JD908 (WU2) | JS102.0 (BG9739) | BG9739 bc100 | EF5668 | L81905 FL | L81905 bc100 | JSS010.3 FL (DBL5) | DBL5 bc100 | JS3020 (DBL6A) | control |
|---|---|---|---|---|---|---|---|---|---|---|---|---|---|---|
| E169 | 2.60 | CBA/N | 5x > 21 | | | | | | | | | | | 1, 1, 2, 2, 6 |
| E152 bc100 | 2.78 | CBA/N | | | | | 4x > 21 | | | 4x > 21 | | 4x > 21 | | 3x 2, 3, 6, 6, >21 |
| E104 | 3.0 | CBA/N | | | 2, 8, 3x > 22 | | | 4.4x >10 | | | | | 2, 4, 4, 5, > 22 | 2, 2, 2, 2, 3 |
| E143 | 3.0 | CBA/N | | | | | | | | | 3, 4, 4, 2x > 22 | | | 2, 2, 3, 3 |
| E140 | 3.43 | CBA/N | | 4x > 21 | | | | | | | | | | 1, 1, 1 |
| E172 | 3.94 | CBA/N | | | | | | | 5x > 21 | | | | | |
| E145 | 3.97 | CBA/N | 13, 4x > 21 | | | | | | | | | | | 1, 2, 2, 2, 4 |
| E121 | 4.16 | CBA/N | 3x 3, 2x 4, 5x > 21 | | | | | | | | | | | 1, 8x 2, > 21 |
| All | | | 3x 3, 2x 4, 13, 14x > 21 | 4x > 21 | 5x > 21 | 2, 8, 3x > 21 | 4x > 21 | 4, 4x >21 | 5x x 21 | 4 > 21 | 3, 4, 4, 2x > 21 | 4x > 21 | 2, 4, 4, 5, > 21 | 7x 1, 22x 2, 3x 3, 4, 3x 6, 2x > 21 |
| median; A:D | | | >21 14:6 | >21 4:0 | >21 5:0 | >21 3:2 | >21 5:0 | >21 4:1 | >21 5:0 | >21 4:0 | 4 2:3 | >21 4:0 | 4 1:4 | 2 2:36 |
| P values | | | <0.0001 <0.0001 | 0.0002 0.0001 | <0.0001 <0.0001 | 0.004 0.0075 | 0.0002 <0.0001 | 0.0006 0.006 | <0.0001 0.0001 | 0.0002 0.0001 | 0.0025 n.s. | 0.0002 0.001 | 0.015 n.s. | |
| Mini Pools | | | R36A/Rx1/WG44.1 | | JD908 | BG9739 | | EF5668 | | L81905 | DBL5 3, 4, 4, 4, 6x > 21 | | DBL6A | Control |
| | | | >21 18:6 | | >21 5:0 8:2 | >21 8:2 | | >21 4:1 | | >21 9:0 | >21 6:4 | | 4 1:4 | 2 2:36 |
| P values rank/a:d | | | <0.0001 | | <0.0001 <0.0001 | <0.0001 | | 0.0006 0.006 | | <0.0001 <0.0001 | 0.0004 | | 0.015 n.s. | |
| Score | | | +++ | | +++ | +++ | | +++ | | +++ | +++ | | +± | |
| % alive | | | 72 | | 100 | 80 | | 75 | | 100 | 60 | | 20 | 5 |
| | | | 71 | | 100 | 79 | | 74 | | 100 | 58 | | 16 | 0 |
| A66 challenge | | | R36A/Rx1/WG44.1 | | JD908 | BG9739 | | EF5668 | | L81905 | DBL5 | | DBL6A | Control |

| A66 challenge | days of death | median days alive | alive: dead | P-days to death | P-alive: dead | Score | % alive | % protected |
|---|---|---|---|---|---|---|---|---|
| All immune | 2, 2, 4x 3, 7x 4, 5, 8, 13, 50x > 21 7x 1, 22x 2, 3x 3, 4, 3x 6, 2x > 21 | >21 | 50:16 | <0.0001 | <0.0001 | +++ | 76 | 75 |
| All controls | | 2 | 2:36 | | | | 5 | 0 |

TABLE 43

Pooled Data for Protection against EF10197. byvarious PspAs

| Exp. | CFU EF 10197 | Mice | Rx1 BC100 | JS1020 (BG9739) | L81905 | JS3020 (DBL6A) | EF5668 | JS5010.3 FL (DBL5)0 | control |
|---|---|---|---|---|---|---|---|---|---|
| E140 | 3.00 | CBA/N | 5x > 21 | | | | | | 2, 2, 2 |
| MI BCG | 2.70 | CBA/N | . | | | | | | 2, 2, 2, 2, 2 |
| E129 | 3.34 | CBA/N | | 8, 4x > 23 | | | | | 2, 2, 2, 2, 9 |

*This was a passive protection study. Its controls have been included to increase the numbers of control mice.

TABLE 44

Pool of Pools for protection against EF10197

| | Group | Delay in death and/or survival | | Survival | |
|---|---|---|---|---|---|
| line | Description | days to death (medain) | P values, etc. | alive:dead | P values etc. |
| 1a | Rx1 (E140) | 5x > 21 | 0.017 vs 1b | 5:0 | 0.018 vs 1b |
| | | | 0.0013 vs 4b | | 0.008 vs 4b |
| 3a | JS1020 (E129) | 8, 4x > 23 | 0.0007 vs 3b | 4:1 | 0.0024 vs 3b |
| 4a | all immune | 8, 9x >21 | <0.0001 vs 4b | 9:1 | 0.0002 vs 4b |
| 1b | Rx1 controls (E140) | 2, 2, 2 | | 0:3 | |
| 2b | MI BCG | 2, 2, 2, 2, 2 | | 0:5 | |
| 3b | JS1020 cont. (E129) | 2, 2, 2, 2, 9 | | 0:5 | |
| 4b | all controls (without MI BCG) | 2, 2, 2, 2, 2, 2, 2, 9 | | 0:8 | |

TABLE 45

Summary of protection against EF10197

| Immunogen | alive:dead | % alive | % protected | median DOD | P time alive | P alive: dead | Score* |
|---|---|---|---|---|---|---|---|
| Rx1 | 5:0 | 100 | 100 | >21 | 0.017 | 0.018 | +++ |
| JS1020 | 4:1 | 80 | 80 | >21 | 0.0007 | 0.024 | +++ |
| all immune | 9:1 | 90 | 90 | >21 | <0.0001 | 0.0002 | +++ |
| all controls | 0:8 | 0 | 0 | 2 | — | — | — |

*+++ = statistically significant protection against death with ≥50% protected.

TABLE 46

Pooled Data for Protection against ATCC6303, by various PspAs

| Exp. | CFU ATCC 6303 | Mice | Rx1 BC100 | JS1020 (BG9739) | L81905 | JS3020 (DBL6A) | EF5668 | JS5010.3 FL (DBL5)0 | control |
|---|---|---|---|---|---|---|---|---|---|
| E140 | 2.30 | CBA/N | 5x > 21 | | | | | | 4, 4x 5 |
| E129 | 3.80 | CBA/N | | n.v. | | | | | |

TABLE 47

Pool of Pools for protection against ATCC6303

| | Group | Delay in death and/or survival | | | Survival | |
|---|---|---|---|---|---|---|
| line | Description | days to death | (medain) | P values etc. | alive:dead | P values etc. |
| 1a | Rx1 (E140) | 5x > 21 | (>21) | 0.0040 | 5:0 | 0.004 |
| 1b | RX1 controls (E140) | 4, 4x 5 | 5 | — | 0:5 | — |

TABLE 48

Summary of protection against ATCC6303

| Immunogen | alive:dead | % alive | % protected | median DOD | P time alive | P alive:dead | Score* |
|---|---|---|---|---|---|---|---|
| Rx1 | 5:0 | 100 | 100 | >21 | 0.004 | 0.004 | +++ |
| Rx1 controls | 0:5 | 0 | 0 | 5 | — | — | — |

*+++ = statistically significant protection against death with ≧50% protected.

TABLE 49

Pooled Data for Protection against BG9739, by various FL PspAs

| | | | Days to Death/Immunogen | | | | | |
|---|---|---|---|---|---|---|---|---|
| Exp. | CFU BG9739 | Mice | R36A FL | BC100 (Rx1) | JD908 (WU2) | JS1020 (BG9739) | bc100 (BG9739) | EF3296 FL |
| E140 | 2.76 | CBA/N | | 3, 3, 10, 11 | | | | |
| E104 | 2.89 | Xid | | | | 6, 6, 7, 8, 8 | | |
| E125 | 3.56 | CBA/N | | | | | 5, 5, 5, 7 | |
| E172 | 3.71 | CBA/N | | | 6, 7, 3x >21 | | | |
| E124 | 3.76 | Xid | | | | | | |
| E084 | 4.05 | BALB/c | | | | 4x2, 2x >14 | | |
| E144 | 4.09 | Xid | 2, 3, 3, 6, > 21 | | | | | 2, 3, 3, 7, >10 |
| All | | | 2, 3, 3, 6, > 21 | 3, 3, 10, 11 | 6, 7, 3x > 21 | 4x 2, 6, 6, 7, 8, 8, 2x > 21 | 5, 5, 5, 7 | 2, 3, 3, 7 >21 |
| median | | | 3 | 3.10 | >21 | 6 | 5 | 3 |
| a:d | | | 1:4 | 0:4 | 3:2 | 2:9 | 0:4 | 1:4 |
| P rank | | | | | | | | |
| P a:d | | | | | | | | |

| | | | Days to Death/immunogen | | | | |
|---|---|---|---|---|---|---|---|
| Exp. | CFU BG9739 | Mice | EF5668 FL | bc100 (L81905) | JS50103 FL (DBL5) | bc100 (DBL5) | JS3020 (DBL6A) | control |
| E140 | 2.76 | CBA/N | | | | | | 2, 2, 3 |
| E104 | 2.89 | Xid | | | 2, 2, 2, 3, 4 | | 2, 2, 2, 2, 3 | 2, 2, 3, 5, 5 |
| E125 | 3.56 | CBA/N | | 4, 5, 13, >21 | | 2, 2, 2, 2, 4 | | 3, 3, 4, 4, 5, 6 |
| E172 | 3.71 | CBA/N | | | | | | 3, 4, 6, 6, 7 |
| E124 | 3.76 | Xid | | | 2, 2, 2, 2, 3 | | 2, 2, 2, 2, 9 | 2, 2, 2, 2, 2 |
| E084 | 4.05 | BALB/c | | | | | | 9x 2 |
| E144 | 4.09 | Xid | 2, 3, 3, 3, 4 | | | | | 2, 2, 2, 3, 3 |
| All | | | 2, 3, 3, 3, 4 | | 7x 2, 3, 3, 4 | | 8x 2, 3, 9 | 21x 2, 7x 2, 3x 4, 3x 5, 3x 6, 7 |
| median | | | 3 | 5, 13 | 2 | 2 | 2 | 2 |
| a:d | | | 0:5 | 1:3 | 0:10 | 0:4 | 0:10 | 0:38 |
| P rank | | | | | | | | |
| P a:d | | | | | | | | |

TABLE 50

Pooled Data for Protection against BG9739, by bc100s and FL PspAs

| | | | | | | | Days to Death/immunogen | | | | | | | |
|---|---|---|---|---|---|---|---|---|---|---|---|---|---|---|
| Exp. | CFU BG9739 | Mice | R36A FL | BC100 (Rx1) | JD908 (WU2) | JS1020 (BG9739) | bc100 (BG9739) | EF3296 FL | EF5668 FL | bc100 (L81905) | JS5010.3 FL (DBL5) | bc100 (DBL5) | JS3020 (DBL6A) | control |
| E140 | 2.76 | CBA/N | | 3, 3, 10, 11 | | | | | | | | | | 2, 2, 3 |
| E104 | 2.89 | Xid | | | | | | | | | | | | 2, 2, 3, 5, 5 |
| E125 | 3.56 | CBA/N | | | 6, 7, 3x >21 | | | | | | | | | 3, 4, 6, 6, 7 |
| E124 | 3.76 | Xid | | | | | | | | | 2, 2, 2, 3, 4 | | 2, 2, 2, 2, 3 | 2, 2, 2, 2, 2 |
| E084 | 4.05 | BALB/c | | | | 4x2, 2x >14 | | | | | | | | 9x 2 |
| E144 | 4.09 | Xid | 2, 3, 3, 6, >21 | | | | | 2, 3, 3, 7, >10 | 2, 3, 3, 3, 4 | | 2, 2, 2, 2, 3 | | 2, 2, 2, 2, 9 | 2, 2, 2, 3, 3 |

| FL + bc10C BG9739 | R36A/Rx1/D39 | WU2 | BG9739 | EF3296 | EF5668 | L81905 | DBL5 | DBL6A, | Cont. |
|---|---|---|---|---|---|---|---|---|---|
| All | 2, 4x 3, 6, 10, 11, >21 | 6, 7, 3x >21 | 4x 2, 3x 5, 2x 6, 2x 7, 2x 8, 2x > 21 | 2, 3, 3, 7, >21 | 2, 3x 3, 4 | 4, 5, 13, >21 | 10x 2, 3, 3, 4, 4 | 8x 2, 3, 9 | 21x 2, 7x 3, 3x 4, 3x 5, 3x 6, 7 |
| median days alive | 3 | >21 | 6 | 3 | 3 | 5, 13 | 2 | 2 | 2 |
| alive:dead | 1:8 | 3:2 | 2:13 | 1:4 | 0:5 | 1:3 | 0:14 | 0:10 | 0:38 |
| P - days alive | 0.0096 | <0.0001 | 0.0013 | n.s. | n.s. | 0.0022 | n.s. | n.s. | |
| P - alive:dead | n.s. | 0.0008 | n.s. | n.s. | n.s. | ++ | n.s. | n.s. | |
| Score | + | +++ | + | 0+ | 0 | 25 | 0 | 0 | |
| % alive | 11 | 60 | 13 | 25 | 25 | 25 | 0 | 0 | 0 |
| % protected BG9739 challenge | 11 | 60 | 13 | 25 | 25 | L81905 | DBL5 | DBL6A | Cont. |
| | R36A/Rx1/D39 | WU2 | BG9739 | EF3296 | EF5668 | | | | |

| | median days of death | alive: dead | P value based on days to death | P value based on alive: dead | | |
|---|---|---|---|---|---|---|
| BG9739 | 3 | 8:59 | 0.009 | 0.023 | Score | % Alive |
| All immune | 2 | 0:38 | | | ++ | 12 |
| All controls | | | | | | 12 |

TABLE 51

Pooled Data for Protection against EF3296, by various PspAs

| | | | | | Days to Death/immunogen | | | |
|---|---|---|---|---|---|---|---|---|
| Exp. | CFU EF3296 | Mice | Rx1 BC100 | JD908 WU2 | JS1020 (BG9739) | JS5010.3 FL (DBL5) | JS3020 (DBL6A) | control |
| E84[1] | 3.99 | BALB/c | | | 4x 2, > 14 | | | 9x 2 |
| E140 | 2.92 | CBA/N | 3, 4, 6, >21 | | | | | 3, 3, 3 |
| E104 | 3.11 | CBA/N | | | 4, 5, 5, 5, 6 | 2, 2, 2, 3, 3 | 2, 2, 3, 4, 5 | 2, 2, 2, 3, 4 |
| E124 | 3.94 | CBA/N | | | | 1, 2, 3, 3, 3 | 1, 1, 2, 2, 2 | 1, 1, 2, 2, 2 |
| E172 | 4.05 | CBA/N | | | | | | 3.4x 6 |
| All | | | 3, 4, 6, >21 | 3, 3, 5, 5, >21 | 4x 2, 4, 3x 5, 6, > 21 | 1, 1, 5x 2, 3, 3 | 1, 1, 5x 2, 3, 4, 5 | 1, 1, 15x 2, 5x 3, 4, 4x 6 |
| median days to death | | | 5 | 5 | 4.5 | 2 | 2 | 2 |
| alive:dead | | | 1:3 | 1:4 | 1:9 | 0:9 | 0:10 | 0:27 |
| P - days to death | | | 0.0077 | 0.0094 | n.s. | n.s. | n.s. | |
| P - alive:dead | | | n.s. | n.s. | n.s. | n.s. | n.s. | n.s. |
| Score | | | +± | +± | 0+ | 0 | 0 | |
| % alive | | | 25 | 20 | 10 | 0 | 0 | 0 |
| % prot. | | | 25 | 20 | 10 | 0 | 0 | 0 |
| Best EF3296 challenge | | | Rx1 BC100 | JD908 WU2 | JS1020 (BG9739) | JS5010.3 FL (DBL5) | JS3020 (DBL6A) | control |

| EF3296 challenge | median days alive | alive: dead | P - days to death | P - alive: dead | Score | % alive | % prot |
|---|---|---|---|---|---|---|---|
| All immune | 3 | 3:35 | n.s. | n.s. | 0 | 8 | 8 |
| All control | 2 | 0:27 | | | | | |

TABLE 52

Pooled Data for Protection against EF5668, by various FL-PspAs and bc100shz,1/64

| | | | | | | Days to Death/immunogen | | | | | |
|---|---|---|---|---|---|---|---|---|---|---|---|
| Exp. | CFU EF 5668 | Mice R36A | Rx1 BC100 | JD908 (WU2) | JS1020 (BG9739) | EF3296 | EF5668 | L81905 | JS5010.3 FL DBL5 | JS3020 DBL6A | control |
| E143 | 3.0 | CBA/N | | | | | 5x > 10 | | | | 1, 1, 2, 2, >10 |
| E140 | 3.59 | CBA/N | 4, 6, 12, >21 | | | | | | | | 2, 4, 6 |
| E171 | 3.69 | CBA/N | | 2, 2, 2, 3, >21 | | | | 3, 3, 4, 2x > 21 | | | 1, 3, 6, 6, 7 |
| E124 | 3.90 | CBA/N | | | | | | | 3, 3, 3x >15 | 3, 4, 5, 6, 6 | 3, 3, 3, 4, 9 |
| E145 | 3.94 | CBA/N | 3, 4, 4, 16, >10 | | 2, 10, 3x > 19 | 2, 4, 13, 2x > 10 | | | | | 2, 3, 3, 4, >21 |
| Pool | | | 3, 3x 4, 6, 12, 16, 2x >21 | 2, 2, 2, 3, >21 | 2, 10, 3x > 21 | 2, 4, 13, 2x > 21 | 5x > 21 | 3, 3, 4, 2x > 21 | 3, 3, 3x >21 | 3, 4, 5, 6, 6 | 3x 1, 4x 2, 6x 3, 3x 4, 3x 6, 7, 9, 2x > 21 |
| median days alive | | | 6 | 2 | >21 | 13 | >21 | 4 | >21 | 5 | 3 |
| alive:dead | | | 2:7 | 1:4 | 3:2 | 2:3 | 5:0 | 2:3 | 3:2 | 0:5 | 2:21 |
| P - days alive | | | 0.013 | n.s. | 0.0187 | n.s. | 0.001 | n.s. | n.s. | n.s. | |
| P - alive:dead | | | n.s. | n.s. | 0.027 | n.s. | 0.0002 | n.s. | 0.027 | n.s. | |
| Score | | | + | 0 | 0+ | +++ | 0+ | +++ | 0+ | + | 0+ |
| % alive | | | 22 | 25 | 60 | 40 | 100 | 40 | 60 | 0 | 9 |
| % prot | | | 14 | 18 | 56 | 34 | 100 | 34 | 56 | -10 | 9 |
| EF5668 | | | R36A/Rx1/D39 | WU2 | BG9739 | EF3296 | EF5668 | L81905 | DBL5 | DBL6A | control |

| | Summary of protection against EF6796 | | | | | |
|---|---|---|---|---|---|---|
| Immunogen | alive:dead | % alive | % protected | median DOD | P - time alive | P alive vs dead |
| Rx1 | 4:0 | 100 | 100 | >21 | 0.029 | 0.029 |
| controls | 0:3 | 0 | 0 | 1 | — | — |

*+++ = statistically significant protection from death with ≥ 50% protected;

TABLE 53

Pooled Data for Protection against DBL6A, by various FL PspAs and bc100 PspAs

| CFU | | | | Days to Death/immunogen | | | | | | | | |
|---|---|---|---|---|---|---|---|---|---|---|---|---|
| Exp. | DBL6 A | Mice | BC100 Rx1 | R36A | JD908 WU2 | JS1020 BG9739 | bc100 BG9739 | EF3296 | EF5668 | L81905 FL | bc100 L81905 | JS5010.3 DBL5 | bc100 DBL5 | JS3020 DBL6A | control |
| E171 | 2.69 | CBA/N | | | 6, 7, 8, 9, >21 | | | | | 3, 3, 7, 9, >21 | | | | | 2, 3, 4, 6, 6 |
| E152 | 3.24 | CBA/N | | | | | 15, 3x >21 | | | | 7, 16, 2x >21 | | 8, 10, 13, 21 | | 3x 3, 4, 3x 6 |
| E140 | 3.25 | CBA/N | 4x > 21 | | | | | | | | | | | | 4, 7, 7 |
| E146 | 3.57 | CBA/N | | 7, 8, 10, 2x > 21 | | | | 6, 8, 9, 10, 10 | 19, 13, 3x > 21 | | | 7, 8, 12, 13, 13 | | | 4, 4, 5, 5, 18 |
| E129 | 4.14 | CBA/N | | | | 3, 6, 8, 10, 13 | | | | | | | | 9, 4x > 21 | 4, 5, 6, 8, > 23 |
| Total | | | | | | | | | | | | | | | |

| Name of Pools | R36A/Rx1/D39 | WU2 | BG9739 | EF3296 | EF5668 | L81905 | DBL5 | DBL6A | controls |
|---|---|---|---|---|---|---|---|---|---|
| Pooled data | 7, 8, 10, 6x > 21 | 6, 8, 9, >21 | 3, 6, 8, 10, 13, 15, 3x > 21 | 6, 8, 9, 10, 10 | 10, 13, 3x > 21 | 3, 3, 7, 7, 9, 16, 2x > 21 | 7, 8, 8, 10, 12, 3x 13, 21 | 9, 4x > 21 | 2, 4x 3, 6x 4, 3x 5, 6x 6, 7, 7, 8, 18, > 21 |
| median days alive alive:dead | >21 6:3 | 8.5 1:3 | 13 3:6 | 9 0:5 | >21 3:2 | 8 2:6 | 12 0:9 | >21 4:1 | 5 1:24 |
| P - days alive | <0.0001 | 0.0082 | 0.0025 | 0.0036 | 0.0001 | 0.037 | 0.002 | <0.0001 | |
| P - alive:dead | 0.0019 | n.s. | 0.048 | n.s. | 0.0093 | n.s. | n.s. | 0.0009 | |
| Score | +++ | +± | ++ | +± | +++ | +± | +± | +++ | |
| | 67 | 25 | 33 | 0 | 60 | 25 | 0 | 80 | 4 |
| | 66 | 22 | 30 | -4 | 58 | 22 | -4 | 79 | 0 |
| DBL6A challenge | R36A/Rx1/D39 | WU2 | BG9739 | EF3296 | EF5668 | L81905 | DBL5 | DBL6A | controls |

| DBL6A challenge | days of death | median days of death | alive: dead | P value based on days to death | P value based on alive:dead | | % alive | % prot. |
|---|---|---|---|---|---|---|---|---|
| All immune | | 12.5 | 19:35 | <0.0001 | 0.0019 | Score | 35 | 33 |
| All control | | 5 | 1:24 | | | ++ | | |

TABLE 54

Pooled Data for Protection against BG9163 by various PspAs

| Exp. | CFU BG9163 | Mice | Rx1 | Rx1.BCG | JS1020 (BG9739) | all immune | control |
|---|---|---|---|---|---|---|---|
| E169 | 2.67 | CBA/N | 5x > 24 | | | | 4, 5, 8, 8, > 24 |
| E140 | 3.14 | CBA/N | n.v. | | | | |
| E129 | 4.0 | CBA/N | | | 12, 4x > 23 | | 7, 9, 9, 13, >23 |
| E028 | 6.217 | CBA/N | 6, 3x > 21 | | | | 5, 6, 8, 10 |
| Immunogens | | | Rx1/R36A/D39 | | BG9739 | all immune | control |
| Pooled Data | | | 6, 8x > 21 | | 12, 4x > 21 | 6, 12, 12x >21 | 4, 5, 7, 8, 8, 9, 9, 12, 2x > 21 |
| median days alive | | | >21 | | >21 | >21 | 8.5 |
| alive:dead | | | 8:1 | | 4:1 | 12:2 | 2:8 |
| P - days alive | | | 0.0086 | | 0.0097 | 0.0027 | |
| P - alive:dead | | | 0.0045 | | 0.047 | 0.0022 | |
| % alive | | | 89 | | 80 | 86 | 20 |
| % prot. | | | 86 | | 75 | 83 | 0 |
| score | | | +++ | | +++ | +++ | |

EG9163 Challenge Rx1/R36A/D39 BG9739 all immune control

| EF5668 | median days of death | days of death | alive: dead | P value based on days to death | P value based on alive:dead | Score | % alive | % prot. |
|---|---|---|---|---|---|---|---|---|
| All immune | | 8 | 18:26 | 0.0015 | 0.005 | ++ | 41 | 35 |
| All control | | 3 | 2:21 | | | | | |

TABLE 55

Pooled Data for Protection against L81905. by various FL-PspAs

| Exp. | CFU L81905 | Mice | R36A | BC100 (Rx1) | JD908 (WU2) | JS1020 (BG9739) | bc100 BG9739 | EF3296 | EF5668 |
|---|---|---|---|---|---|---|---|---|---|
| E172 | 2.45 | CBA/N | | | 3, 4, 5, 6, 6 | | | | |
| E140 | 3.11 | CBA/N | | 2, 5, 5, 6, 8 | | | | | |
| E084 | 3.86 | BALB | | | | 2, 2, 5x >14 | | | |
| E104 | −3.5 | CBA/N | | | | 3, 7, 8, 8, 11 | | | |
| E124 | −3.5 | CBA/N | | | | | | | |
| E125 | 3.6 | CBA/N | | | | | 5, 6, 8, 8 | | |
| E144 | 4.11 | CBA/N | 3, 3, 5, 6, >10 | | | | | 6, 6, 6, 2x >10 | 2, 2, 3, 3, 3 |
| All | | | 3, 3, 5, 6, >21 | 3, 3, 5, 6, | 3, 4, 5, 6, 6 | 2, 3, 4, 7, 8, 8 11, 5x > 21 | 5, 6, 8, 8 | 6, 6, 6, 2x >10 | 2, 2, 3, 3, 3 |
| median | | | 5 | 5 | 5 | >21 | 7 | 6 | 3 |
| alive:dead | | | 1:4 | 0:5 | 0:5 | 5:7 | 0:4 | 2:3 | 0:5 |
| P rank | | | | | | | | | |
| P a:d | | | | | | | | | |
| score | | | | | | | | | |

TABLE 55-continued

Pooled Data for Protection against L81905. by various FL-PspAs

| Exp. | CFU L81905 | Mice | Days to Death/immunogen | | | | |
|---|---|---|---|---|---|---|---|
| | | | bc100 K81905 | JS50103 (DBL5) | bc100 (DBL5) | JS3020 (DBL6A) | control |
| E172 | 2.45 | CBA/N | | | | | 3, 3, 4, 4, 4 |
| E140 | 3.11 | CBA/N | | | | | 2, 2, 2, 3, 3 |
| E084 | 3.86 | BALB | | | | | 1, 8x 2 |
| E104 | −3.5 | CBA/N | | 3, 3, 3, 2x >22 | | 3, 4, 5, 5, 6 | 2, 4, 4, 4, 5 |
| E124 | −3.5 | CBA/N | | 2, 2, 2, 2, 3 | | 2, 2, 2, 3, 5 | 1, 2, 2, 2, 2 |
| E125 | 3.6 | CBA/N | 3, 4, 6, 8 | | 4, 5, 5, 5 | | 2, 2, 3, 5, 5, 5 |
| E144 | 4.11 | CBA/N | | | | | 2, 2, 3x 3 |
| All | | | 3, 4, 6, 8 | 4x 2, 4x 3, 2x > 21 | 4, 5, 5, 5 | 3x 2, 3, 3, 4, 3x 5, 6 | 1, 1, 20x 2 8x 3, 6x 4, 4x 5 |
| median | | | 5 | 3 | 5 | 3.5 | 2 |
| alive: dead | | | 0:4 | 2:8 | 0:4 | 0:10 | 0:40 |
| P rank | | | | | | | |
| P a:d | | | | | | | |
| score | | | | | | | |

Protection against L81905. by various bc100s & FL-PspAs pooled together

| | | | | | | | Days to Death/immunogen | | | | | | | |
|---|---|---|---|---|---|---|---|---|---|---|---|---|---|---|
| Exp. | CFU L81905 | Mice | R36A | BC100 (Rx1) | JD908 (WU2) | JS1020 (BG9739) | bc100 BG9739 | EF3296 | EF5668 | bc100 L81905 | JS5010.3 (DBL5) | bc100 (DBL5) | JS3020 (DBL6A) | control |
| E172 | 2.45 | CBA/N | | | 3, 4, 5, 6, 6 | | | | | | | | | 3, 3, 4, 4, 4 |
| E140 | 3.11 | CBA/N | | 2, 5, 5, 6, 8 | | | | | | | | | | 2, 2, 2, 3, 3 |
| E084 | 3.86 | BALB | | | | 2, 2, 5x >14 | | | | | | | | 1, 8x 2 |
| E104 | 3.5 | CBA/N | | | | 3, 7, 8, 8, 11 | | | | | 3, 3, 3, 2x >22 | | 3, 4, 5, 5, 6 | 2, 4, 4, 4, 5 |
| E124 | -3.5 | CBA/N | 3, 3, 5, 6, >10 | | | | 5, 6, 8, 8 | | | | 2, 2, 2, 2, 3 | 4, 5, 5, 5 | 2, 2, 2, 3, 5 | 1, 2, 2, 2, 2 |
| E125 | 3.6 | CBA/N | | | | | | | | 3, 4, 6, 8 | | | | 2, 2, 3, 5, 5, 5 |
| E144 | 4.11 | CBA/N | | | | | | 6, 6, 6, 2x >10 | 2, 2, 3, 3, 3 | | | | | 2, 2, 3x 3 |
| | Pooled | | 2, 3, 3x 5, 6, 6, 8, >21 | | 3, 4, 5, 6, 6 | 2, 2, 3, 5, 6, 7, 4x 8, 11, 5x >21 | | 6, 6, 6, 2x >10 | 2, 2, 3, 3, 3 | 3, 4, 6, 8 | 4x 2, 4x 3, 4, 5, 5, 5, 2x >21 | | 3x 2, 3, 3, 3, 4, 3x 5, 6 | 1, 1, 20x 2, 8x 3, 6x 4, 4x 5 |
| median days alive | | | 5 | 5 | 5 | 8 | | 6 | 3 | 5 | 3 | 3.5 | | 2 |
| alive:dead | | | | 1:9 | 0:5 | 5:11 | | 2:3 | 0:5 | 0:4 | | 2:12 | 0:10 | 0:40 |
| P - days alive | | | | 0.0005 | 0.0035 | <0.0001 | | 0.0002 | n.s. | 0.01 | | 0.035 | 0.044 | |
| P - alive:dead | | | | n.s. | n.s. | 0.0001 | | 0.01 | n.s. | n.s. | | n.s. | n.s. | |
| score | | | | + | + | ++ | | ++ | 0 | + | | + | + | |
| % alive | | | | 10 | 0 | 31 | | 40 | 0 | 0 | | 14 | 0 | 0 |
| % protected challenge with L81905 | | | R36A/Rx1/D39 | | WU2 | BG9739 | | EF3296 | EF5668 | L81905 | | DBL5 | DBL6A | controle |

| | | |
|---|---|---|
| L81905 challenge | days of death | alive:dead |
| | median days of death | alive: dead |
| All immune | 5 | 10:59 |
| All control | 2 | 0:40 |

| | P value based on alive:dead | |
|---|---|---|
| | 0.008 | |
| | to death | |
| | <0.0001 | |

| % Score | % alive | prot. |
|---|---|---|
| ++ | 14 | 14 |

TABLE 57

Pooled Data for Protection against DBL5 by various FL-PspAs & bc100s

| | | | | | | Days to Death/immunogen | | | | | |
|---|---|---|---|---|---|---|---|---|---|---|---|
| Exp | CFU DBL5 | Mice | BC100 R36A Rx1 | JS1020 BG9739 | bc100 JS1020 | EF5668 | bc100 L81905 | JS5010.3 DBL5 | bc100 DBL5 | JS3020 DBL6A | control |
| E84[1] | 3.90 | BALB/c | | 6x 2 | | | | | | | 9x 2 |
| E140 | 3.27 | CBA/N | 4, 4, 5, 5, 5 | | | | | | | | 2, 2, 2 |
| E104 | 3.39 | Xid | | 3, 3, 6, >22, >22 | | | | 7, 7, 15, >22, >22 | | 2, 2, 4, 5, 5 | 2,4x 3 |
| E124 | 3.76 | Xid | | | | | | 2, 2, 2, 5, >15 | | 5x 2 | 1, 1, 2, 2, 2 |
| E125 | 3.81 | CBA/N | | | 3, 3, 4, 5 | | 3, 3, 4, 4 | | 2, 2, 2, > 21 | | 5x 2, 5 |
| E144 total | 4.13 | XID | 3, 3, 3, 3, >10 | | | 2, 2, 3, 4, 4 | | | | | 5x 2 |
| | name of pool | | R36A/Rx1/D39 | BG9739 | | EF5668 | L81905 | DBL5 | DBL6A | | controls |
| | pooled data | | 4x 3, 2x 4, 3x 5, >21 | 6x 2, 4x 3, 4, 5, >21, >21 | | 2, 2, 3, 4, 4 | 3, 3, 4, 4 | 6x 2, 5, 7, 7, 15, 4x > 21 | 7x 2, 4, 5, 5 | | 1, 1, 26x 2, 4x 3, 5 |
| | median days alive | | 4 | 3 | | 3 | 3.5 | 6 | 2 | | 2 |
| | alive:dead | | 1:9 | 2:12 | | 0:4 | 0:4 | 4:10 | 0:10 | | 0:32 |
| | P - days alive | | <0.0001 | 0.0063 | | .041 | 0.001 | 0.0025 | n.s. | | |
| | P - alive:dead | | n.s. | n.s. | | n.s. | n.s. | 0.0056 | n.s. | | |
| | Score | | + | + | | +* | + | ++ | 0 | | |
| | % Alive | | 10 | 14 | | 0 | 0 | 29 | 0 | | 0 |
| | % protected | | 10 | 14 | | 0 | 0 | 29 | 0 | | 0 |
| | DBL5 challenge | | R36A/Rx1/D39 | BG9739 | | EF5668 | L81905 | DBL5 | DBL6A | | controls |

| DBL5 challenge | median days of death | median days of death | alive: dead | P value based on days to death | P value based on alive:dead | Score | % alive | % prot. |
|---|---|---|---|---|---|---|---|---|
| All immune | | 3.5 | 7:49 | <0.0001 | 0.034 | ++ | 3.6 | 3.6 |
| All control | | 2 | 0:33 | | | | | |

[1]This immunization was with cell eluted PspA. Note Balb/cJ mice were used. Also note 10[4] Challenge CFU.

TABLE 58

Pooled Data for Protection against EF6796 by various PspAs

| | | | | | | Days to Death/immunogen | | | |
|---|---|---|---|---|---|---|---|---|---|
| Exp. | CFU WU2 | Mice | Rx1 BC100 | JS1020 (BG9739) | L81905 | JS3020 (DBL6A) | JS5010.3 FL (DBL5) | DBL5 bc100 | control |
| E140 | 3.75 | CBA/N | 4x > 21 | | | | | | 1, 1, 1, |
| E28 | ? | BALB | n.v. | | | | | | |

TABLE 59

Pool of Pools for protection against EF6796

| Group | | Delay in time to death and/or survival | | | Protection against death | |
|---|---|---|---|---|---|---|
| line | Description | days to death | (medain DOD) | P values etc. | alive:dead | P values etc. |
| 1a | Rx1 | 4x > 21 | (>21) | 0.029 | 4:0 | 0.029 |
| 1b | Rx1 controls | 1, 1, 1 | (1) | — | 0:3 | — |

TABLE 60

Pooled Data for Protection against BG7322, by various FL-Ps and bc100s

| Exp. | CFU BG 7322 | Mice | D39/ R36A | Rx1 BC100 | JD908 (WU2) | bc100 BG9739 | EF3296 | EF5668 | bv100 L81905 | JS50103 DBLS | bc100 DBLS | JS3020 DBL6A | control |
|---|---|---|---|---|---|---|---|---|---|---|---|---|---|
| E171 | 2.78 | CBA/N | | | 10, 15, 3x > 21 | | | | | | | | 1, 3, 6, 6, 7 |
| S143 | 3.0 | CBA/N | | | | | | 7, 8x > 10 | | | | | 2, 2, 4, 5, 7, 7, 8, 8 |
| E140 BC100 | 3.14 | CBA/N | 4x > 21 | | | | | | | | | | 3, 6, 6, >21 |
| E152 | 3.11 | CBA/N | | | | 12, 13, 16, >21 | | | 10, 12, 13, >21 | | >21, >21, >21, >21 | | 6, 7, 7, 8, 8, 9, 14 |
| E146 | 3.57 | CBA/N | 18, 20, 3x > 21 | | | | 5, 3x 6, 10 | | | 6, 10, 11, 11, 19 | | 4, 8, 11, 18, >21 | 4, 5, 5, 6, >21 |
| E169 | 3.94 | CBA/N | 5x > 21 | | | | | | | | | | 2, 5, 5, 6, 7 |
| Immunogens Pools | | | R36A/Rx1/D39 18, 20, 12x > 21 | | JD908 10, 15, 3x > 21 | BG9739 12, 13, 16, >21 | EF3296 5, 3x 6, 10 | EF5668 7, 8x > 21 | L81905 10, 12, 13, >21 | | DBL5 6, 10, 11, 11, 19 >21, >21, >21, >21 | DBL6A 4, 8, 11, 18, >21 | Cont. 1, 3x 2, 3, 3, 4, 4, 5x 5, 7x 6, 6x 7, 4x 8, 9, 14, 2x > 21 |
| median day alive | | | >21 | >21 | 14.5 | 6 | >21 | 12.5 | >21 | | 11 | 6 | |
| alive:dead | | | 9:0 | 3:2 | 1:3 | 0:5 | 8:1 | 1:3 | | 4:5 | 1:3 | 2:32 | |
| P - days alive | | | <0.0001 | 0.0007 | 0.001 | n.s. | <0.0001 | 0.013 | | 0.0002 | 0.028 | | |
| P - alive:dead | | | <0.0001 | 0.004 | n.s. | n.s. | <0.0001 | n.s. | | 0.0076 | n.s. | | |
| % alive | | | 100 | 60 | 25 | 0 | 89 | 25 | | 80 | 25 | 6 | |
| % protected | | | 100 | 57 | 22 | 0 | 88 | 22 | | 79 | 22 | 6 | |
| Score | | | +++ | +++ | +± | 0 | +++ | +± | | +++ | +± | | |
| BG7322 Challenge | | | R36A/Rx1/D39 | JD908 | BG9739 | EF3296 | EF5668 | L81905 | | DBLS | DBL6A | Cont. | |

| BG7322 Challenge | median days of death | alive: dead | P value based on days to death | P value based on alive:dead | Score | % alive | % prot. |
|---|---|---|---|---|---|---|---|
| All immune | >21 | 30:25 | <0.0001 | <0.0001 | +++ | 55 | 52 |
| All controls | 6 | 2:32 | | | | | |

TABLE 60A

Days of death of BALB/cByJ mice after immunization with monovalent and polyvalent vaccine.

| Challenge Strains | | | | | Immunogen | | | |
|---|---|---|---|---|---|---|---|---|
| | | | | | Days to Death | | | |
| strain name | caps type | PspA type | B region clade | Log Challenge dose | 1 mg R36A + CFA | 4–5 valent mixture (0.5 μg each) + CFA | JY2141 + CFA | None |
| D39 | 2 | 25 | 2 | 4.76 | 3, 4x > 21 | 3, 4x > 21 | 3, 4, 5, 11, >21 | 3, 3, 4, 4, 8 |
| WU2 | 3 | 1 | 2 | 4.8 | 4x > 21 | 4x × 21 | 6, 3x > 21 | 3, 4, 2x > 21 |
| A66 | 3 | 13 | ? | 4.7 | 3, 3, >21, >21 | 2, 3x > 21 | 2, 2, 3, 4 | 2, 3, 4, 4 |
| BG9739 | 4 | 26 | 1 | 4.07–4.4 | 7, 8x > 21 | 3, 8x > 21 | 1, 5, 6, 6, 9, 4x > 21 | 3, 3, 3, 4, 6, 7, 7, 2x > 21 |
| L81905 | 4 | 23 | 1 | 6.90–6.96 | 2, 2, 2, 2, 5, 5, 4x >21 | 2, 6, 8, 9, 6x > 21 | 1, 1, 1, 1, 2, 3, 4, 5, 2x >21 | 1, 4x 2, 3x 3, 4, > 21 |
| EF5668 | 4 | 12 | 4 | 6.10–6.93 | 3, 3, 4, 7x >21 | 3x 3, 6x > 21 | 4x 3, 4, 4, 6, 6, >21 | 3, 5x 4, 6, >21 |
| DBL5 | 4 | 33 | 2 | 3.30 | 7, 14, 3x >21 | 3, 5, 5, 2x >21 | 2, 2, 2, 4, 6 | 4, 5, 5, 6, 9 |
| DBL6A | 6A | 19 | 1 | 4.34 | 6, 9, 10, 11, >21 | 10, 11, 12, 13, >21 | 3, 11, 11, 13, 16 | 8, 9, 11, 21, >21 |
| BG7322 | 6B | 21 | ? | 3.9 | 8, 8, 3x > 21 | 5x > 21 | 6, 6, 7, 8, 10 | 2, 5, 6, 8, 8 |

Note, JY2141 is a preparation from a strain that lacks PspA. None = no immunization.
Note, mice were given two immunizations with PspA two weeks apart and challenged intravenously 2 weeks after the last immunization. The first immunization was given with complete Freund's adjuvant (CFA) subcataneously, the second immunization was given intraperitoneally in saline.
[1] 4 valent vaccine mixture R36A, BG9739, EF5668, and DBL5 - all E180
[2] 4 valent vaccine mixture R36A, BG9739, DBL5, EF3296 D39 and DBL6A
[3] 5 avalent vaccine mixture R36A, BG9739, DBL5, EF3296, EF5668

Example 8
Ability of PspA immunogens to protect against individual challenge strains In example 7 some of the capsular type 2, 4, and 5 strains were not completely protected from death by immunization. In these studies the BALB/cByJ mouse was used instead of the hypersusceptible, immunodeficient CBA/N mouse used for the Example 7 studies. With the BALB/cJ mouse it was observed that immunization with PspA was in fact able to protect against death with capsular type 2, 4, and 5 pneumococci. This result is shown in the table below.

The data from Table 60A also demonstrates that a mixture of 4–5 full length PspAs was as effective, or more Effective than immunization with a single PspA.

Example 9
Characterization of PspA Epitopes within Pneumococcal Strains MC25–28

The strains examined came from a group of 13 capsular serotype 6B strains which have been identified that are members of a multiresistant clone, having resistance to penicillin, chloramphenicol, tetracycline, and some have acquired resistance to erythromycin. The pneumococcal isolates described in the following studies (MC25–28) are members of this 6B clone. Although previously thought to be geographically restricted to Spain (unlike the widespread multiresistant Spanish serotype 23F drone), members of this clone have been shown to be responsible for an increase in resistance to penicillin in Iceland (Soares, S., et al., J. Infect. Dis. 1993; 168: 158–163).

The following techniques were used to characterize the location of difference PspA epitopes:

Bacterial cell culture. Bacteria were grown in Todd-Hewitt broth with 0.5% yeast extract or on blood agar plates overnight at 37° C. in a candle jar. Capsular serotype was confirmed by cell agglutination using Danish antisera (Statens Seruminstitut, Copenhagen, Denmark). The isolates were subtyped as 6B by Quellung reaction, utilizing rabbit antisera against 6A or 6B capsule antigen.

Bacterial lysates. Cell lysates were prepared by incubating the bacterial cell pellet with 0.1% sodium deoxycholate, 0.01% sodium dodecylsufate (SDS), and 0.15 M sodium citrate, and then diluting the lysate in 0.5M Tris hydrochloride (pH 6.8). Total pneumococcal protein in the lysates was quantitated by the bicinchoninic acid method (BCA Protein Assay Reagent; Pierce Chemical Company, Rockford, Ill.).

PspA serotyping. Pneumococcal cell lysates were subjected to SDS-PAGE, transferred to nitrocellulose membranes, and developed as Western blots using a panel of seven MAbs to PspA. PspA serotypes were assigned based on the particular combination of MAbs with which each PspA was reactive.

Colony immunoblotting. A ten mL tube of Todd-Hewitt broth with 0.5% yeast extract was inoculated with overnight growth of MC25 from a blood agar plate. The isolate was allowed to grow to a concentration of 107 cells/mL as determined by an O.D. of 0.07 at 590 nm. MC25 was serially diluted and spread-plated on blood agar plates to give approximately 100 cells per plate. The plates were allowed to grow overnight in a candle jar, and a single blood agar plate with well-defined colonies was selected. Four nitrocellulose membranes were consecutively placed on the plate. Each membrane was lightly weighted and left in place for 5 min. In order to investigate the possibility of phase-variation between the two proteins detected on Western blots a single colony was picked from the plate, resuspended in ringer's solution, and spreadplated onto a blood agar plate. The membranes were developed as Western blots according to PspA serotyping methods.

Figure 14:
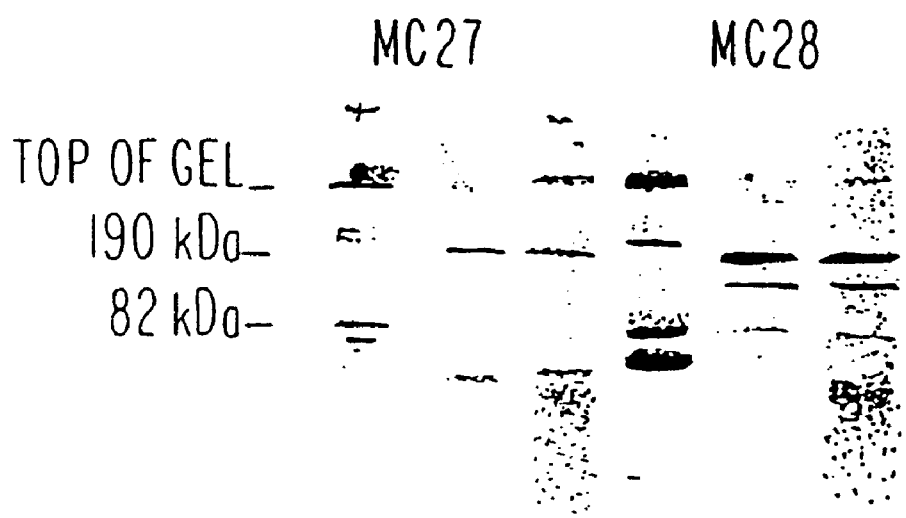
FIG. 14 shows: Cell lysates of pneumococcal isolates MC27 and MC28, subjected to SDS-PAGE and Western blotting with seven MAbs to PspA; 7D2 detected a protein of 82 kDa in each isolate, and Xi278 and 2A4 detected a protein of 190 kDa in each isolate; MAbs Xi64, Xi126, 1A4 and SR4W4 were not reactive; strains MC25 and MC26 yielded identical results (not shown).

When the strains MC25–28 were examined with the panel of seven MAbs specific for different PspA epitopes, all four demonstrated the same patterns of reactivity (FIG. 14). The MAbs XiR278 and 2A4 detected a PspA molecule with an apparent molecular weight of 190 kDa in each isolate. In accordance with the PspA serotyping system, the 190 kDa molecule was designated as PspA type 6 because of its reactivity with XiR278 and 2A4, but none of the five other MAbs in the typing system. Each isolate also produced a second PspA molecule with an apparent molecular weight of 82 kDa. The 82 kDa PspA of each isolate was detected only with the MAb 7D2 and was designated as type 34. No reactivity was detected with MAbs Xi126, Xi64, 1A4, or SR4Wr. Results from the colony immunoblotting showed that both PspAs were present simultaneously in these isolates under in vitro growth conditions. All colonies on the plate, as well as all of the progeny form a single colony, reacted with MAbs XiR278, 2A4, and 7D2.

Example 10
Southern Blot Analysis of Chromosomal Dna Isolated from Pneumococcal Strains MC25–28

Pneumococcal chromosomal DNA was prepared by the Youderian method (Sheffield, J. S., et al., Biotechniques, 1992; 12: 836–839). Briefly, for a 500 ml culture in THY or THY with 1% choline, cells were centrifuged at 8000 rpm in GSA rotor for 30 minutes at 4° C. The supernatant was decanted, and the cells were washed with 1 to 2 volumes of sterile water to remove choline, if used. This 'step was only necessary when sodium deoxycholate was used. The wasted cells were centrifued twice a 8000 rpm in GSA rotor for 10 minutes. Cells were resuspended in 3.5 ml TE buffer, containing 1% SDS or 1% sodium deoxycholate, and incubated at 37° C. for 15 minutes if sodium deoxycholate was used. If SDS was used, incubation at 37° C. was not necessary. The cells were incubated at 65° C. for 15 minutes, and 1/5 volume of 5.0 M potassium acetate was added, and the cell suspension was incubated for 30 minutes at 65° C.

The cells were placed on ice for 60 minutes, and Centrifuged at 12,000 rpm in an SS-34 rotor for 10 minutes. The supernatant was transferred to a clean centrifuge tube, and 2 volumes of cold 95% ethanol was added. After mixing, DNA was spooled on to a glass pasteur pipet, and air dried. The DNA was resuspended in 4 ml TE, and 4.0 g cesium chloride was added. The solution was split into two aliquots in ultracentrifuge tubes, and the tubes were filled to their maximum capacity using 1.0 g/ml cesium chloride in TE. Before closing the tubes, 300 ml of 10 ug/ml ethidium bromide was added.

The solution was centrifuged at 45,000 rpm overnight, or for 6 hours at 55,000 rpm. The chromosomal band was extracted using a gradient, at least 6 times with 1 volume each salt-saturated isopropanol. The aqueous phase was extracted by adding 2 volumes 95% ethanol. The DNA came out of solution immediately, and it was spooled on to a pasteur pipet. The DNA pellet was washed by dipping the spooled DNA in 5 ml 70% ethanol. The DNA was air dried, and resuspended in the desired volume of TE, e.g., 500 ul.

The cells were harvested, washed, lysed, and digested with 0.5% (st/vol) SDS and 100 $\mu$g/mL proteinase K at 37° C. for 1 h. The cell wall debris, proteins, and polysaccharides were complexed with 1% hexadecyl trimethyl ammonium bromide (CTAB) and 0.7M sodium chloride at 65° C. for 20 min., and then extracted with chloroform/isoamyl alcohol. DNA was precipitated with 0.6 volumes isopropanol, washed, and resuspended in 10 mM Tris-HCl, 1 mM EDTA, pH 8.0. DNA concentration was determined by spectrophotometric analysis at 260 nm (Meade, H. M. et al., J. Bacteriol 1982; 149: 114–122; Silhavy, T. J. et al., *Experiments with Gene Fusion, Cold Spring Harbor: Cold Spring Harbor Laboratory,* 1984; and Murray, M. G., et al., Nucleic Acids Res. p980; 8 4321–4325).

Probe preparation. 5' and 3' oligonucleotide primers homologous with nucleotides to 26 and 1967 to 1990 of Rx1 pspA (LSM13 and LSM2, respectively) were used to amplify the full length pspA and construct probe LSMpspA13/2 from Rx1 genomic DNA. 5' and 3' oligonucleotide primers homologous to nucleotides 161 to 187 and nucleotides 1093 to 1117 (LSM12 and LSM6, respectively) were used to amplify the variable α-helical region to construct probe LSMpspA12/6. PCR generated DNA was purified by Gene Clean (Bio101 Inc., Vista, Calif.) and random prime-labeled with digoxigenin-11-dUTP using the Genius 1 Nonradioactive DNA Labeling and Detection Kit as described by the manufacturer (Boehringer Mannheim, Indianapolis, Ind.).

DNA electrophoresis. For Southern blot analysis, approximately 10 μg of chromosomal DNA was digested to completion with a single restriction endonuclease (Hind III, Kpn 1, EcoRI, Dra I, or Pst I), then electrophoresed on a 0.7% agarose gel for 16–48 h at 35 volts. For PCR analysis, 5 μL of product were incubated with a single restriction endonuclease (Bcl 1, BamH I, Bst I, Pst I, Sac I, EcoR I, Sma I, and Kpn I), then electrophoresed on a 1.3% agarose gel for 2–3 h at 90 volts. In both cases, 1 kb DNA ladder was used for molecular weight markers (BRL, Gaithersburg, Md.), and gels were stained with ethidium bromide for 10 min and photographed with a ruler.

Southern blot hybridization. The DNA in the gel was depurinated in 0.25N HCl for 10 min, denatured in 0.5M NaOH and 1.5M NaCl for 30 min, and neutralized in 0.5M Tris-HCl (pH 7.2), 1.5M NaCl and 1 mM disodium EDTA for 30 min. DNA was transferred to a nylon membrane (Micron Separations INC, Mass.) using a POSIBLOT pressure blotter (Stratagene, LaJolla, Calif.) for 45 min and fixed by UV irradiation. The membranes were prehybridized for 3 h at 42° C. in 50% formamide, 5× SSC, 5× Denhardt solution, 25 mM sodium phosphate (pH 6.5), 0.5% SDS, 3% (wt/vol) dextran sulfate and 500 g/mL of denatured salmon sperm DNA. The membranes were then hybridized at 42° C. for 18 h in a solution containing 45% formamide, 5× SSC, 1× Denhardt solution, 20 mM sodium phosphate (pH 6.5), 0.5% SDS, 3% dextran sulfate, 250 μg/mL denatured sheared salmon sperm DNA, and about 20 ng of heat-denatured digoxigenin-labeled probe DNA. After hybridization, the membranes were washed twice in 0.1% SDS and 2× SSC for 3 min at room temperature. The membranes were washed twice to a final stringency of 0.1% SDS in 0.3× SSC at 65° C. for 15 min. This procedure yielded a stringency greater than 95 percent. The membranes were developed using the Genius 1 Nonradioactive DNA Labeling and Detection Kit as described by the manufacturer (Boehringer Mannheim, Indianapolis, Ind.). To perform additional Hybridization with other probes, the membranes were stripped in 0.2N NaOH/0.1% SDS at 40° C. for 30 min and then washed twice in 2× SSC. PCR. 5' and 3' primers homologous with the DNA encoding the N- and C-terminal ends of PspA (LSM13 and LSM2, respectively) were used. Reactions were conducted in 50 μL volumes containing 0.2 mM of each dNTP, and 1 μL of each primer at a working concentration of 50 mM. $MgCl_2$ was used at an optimal concentration of 1.75 mM with 0.25 units of Taq DNA polymerase. Ten to thirty ng of genomic DNA was added to each reaction tube. The amplification reactions were performed in a thermal cycler (M.J. Research, Inc.) using the following three step program: Step 1 consisted of a denaturing temperature of 94° C. for 2 min; Step 2 consisted of 9 complete cycles of a denaturing temperature of 94° C. for 1 min, an annealing temperature of 50° C. for 2 min, and an extension temperature of 72° C. for 3 min; Step 3 cycled for 19 times with a denaturing temperature 94° C. for 1 min, an annealing temperature of 60° C. for 2 min, and an extension temperature of 72° C. for 3 min; and at the end of the last cycle, the samples were held at 72° C. for 5 min to ensure complete extension.

Band size estimation. Fragment sizes in the molecular weight standard and in the Southern blot hybridization patterns were calculated from migration distances. The standard molecular sizes were fitted to a logarithmic regression model using Cricket Staph (Cricket Software, Malvern, Pa.). The molecular weights of the detected bands were estimated by entering the logarithmic line equation obtained by Cricket Graph into Microsoft Excel (Microsoft Corporation, Redmond, Wash.) in order to calculate molecular weights based on migration distances observed in the Southern blot.

Figure 15A:
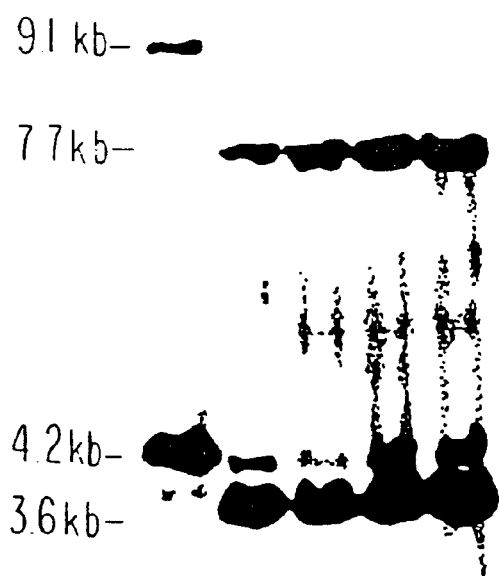
FIGS. 15A and 15B show: a Southern blot of Hind III digest of MC25–28 chromosomal DNA, using a digest of Rx1 DNA as a comparison; the blot was probed with LSMpspA13/2, a full length Rx1 probe (A), and LSMpspA12/6, a 5' probe of Rx1 pspA (B); the same concentration of Rx1 DNA was used in both panels, but the concentrations of MC25-28 DNA in B were half that used in A to avoid detection of partial digests.

Since most strains contain a pspA gene and a pspC gene, it was expected that if an extra gene were present one might observe at least three pspA homologous loci in isolates MC25–28. In Hind III digests of MC25–28 each strain revealed 7.7 and 3.6 kb bands when probed with LSMpspA13/2 (FIGS. 15A and 15C). In comparison, when Rx1 DNA was digested with Hind III and hybridized with LSMpspA13/2, homologous sequences were detected on 9.1 and 4.2 kb fragments, as expected from previous studies with PspA (FIG. 15A). Results consistent with two pspA-homologous genes in MC25–28 were obtained with two pspA-homologous genes in MC25–28 digested using four additional enzymes (Table 61).

TABLE 61

Chromosomal RFLPs with probe LSMpspA13/2 for isolates MC25–28 and Rx1

| Re-striction Enzyme | Strains Examined | | | | | Restriction Fragments (sizes in kilobases) | |
|---|---|---|---|---|---|---|---|
| | MC 25 | MC 26 | MC 27 | MC28 | RX1 | MC25–28 | Rx1 |
| Hind III | + | + | + | + | + | 7.7, 3.6 | 9.1, 4.2 |
| Kpn I | + | + | + | + | + | 11.6, 10.6 | 10.6, 9.8 |
| EcoR I | + | | | | + | 8.4, 7.6 | 7.8, 6.6 |
| Dra I | + | | | | + | 2.1, 1.1 | 1.9, 0.9 |
| Pst I | + | | | | + | >14, 6.1 | 10.0, 4.0 |

The four isolates examined are all members of a single clone of capsular type 6B pneumococci isolated from Spain. These four isolates are the first in which two PspAs have been observed, i.e., PspA and PspC, based on the observation that bands of different molecular weights were detected by different MAbs to PspA. Mutation and immunochemistry studies have demonstrated that all of the different sized PspA bands from Rx1 are made of a single gene capable of encoding a 69 kDa protein, supporting the assertion that two PspAs have been observed, i.e., PspA and PspC.

Figure 15B:
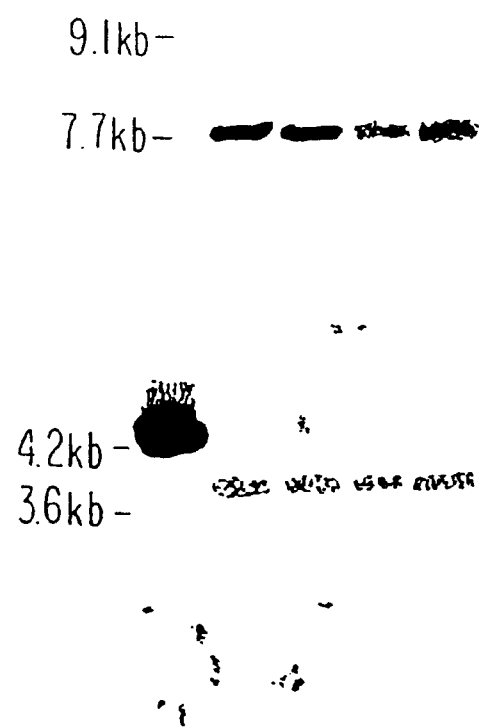

It has been observed that probes for the 5' half of pspA (encoding the α-helical half of the protein) bind the pspC sequence of most strains only at a stringency of around 90%. With chromosomal digests of MC25–28, it was observed that the 5' Rx1 probe LSMpspA12/6 (FIG. 15D) bound two pspA homologous bands at even higher stringency. The same probe bound only the pspA containing fragment of Rx1 at the higher stringency (FIG. 15B).

Figure 16:
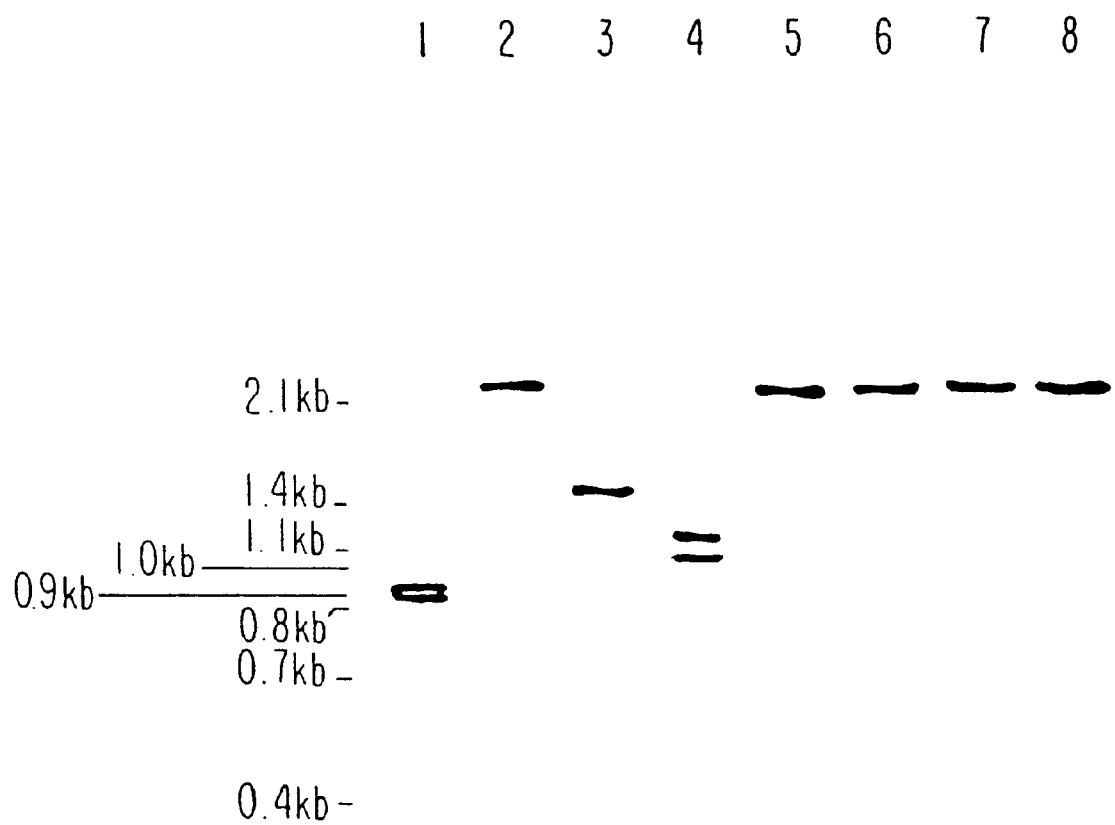
FIG. 16 shows: RFLP of amplified pspA, wherein PspA from MC25 was amplified by PCR using 5' and 3' primers for pspA (LSM13 and LSM2, respectively); the amplified DNA was digested with individual restriction endonucleases prior to electrophoresis and staining with ethidium bromide; Bcl I was used in lane 1; BamH I was used in lane 2; BstN I was used in lane 3; Pst I was used in lane 4; Sac I was used in lane 5; EcoR I was used in lane 6; Sma I was used in lane 7; and Kpn I was used in lane 8.

Further characterization of the pspA gene was done by RFLP analysis of PCR amplified pspA from each strain. Since previous studies indicated that individual strains yielded only one product, and since the amplification was conducted with primers based on a known pspA sequence, it was assumed that the Product amplified from each strain represented the pspA rather than the pspC gene. When MC25–28 were subjected to this procedure, an amplified pspA product of 2.1 kb was obtained from Mach of the four strains. When digested with Hha I, this fragment yielded bands of 1.1, 0.46, 0.21 and 0.19 kb for each of the four isolates. A single isolate, MC25, was analyzed with eight additional enzymes. Using each restriction enzyme, the sum of the fragments was always approximately equal to the size of whole pspA (FIG. 16). These results suggested that the 2.1 kb amplified DNA represents the amplified product of only a single pspA gene. Rx1 produced an amplified product of 2.0 kb and five fragments of 0.76. 0.468, 0.390, 0.349 and 0.120 kb when digested with Hha I as expected from its known pspA sequence.

There are several possible explanations for the observation of PspA and PspC in these strains but not in other strains. All isolates might make PspA and PspC in culture, but MAbs generally recognize only PspA (perhaps, in this isolate there has been a recombination between pspC DNA and the pspC locus, allowing that locus to make a product detected by MAb to PspA). All isolates can have PspA and PspC, but the expression of one of them generally does not occur under in vitro growth conditions. The pspC locus is normally a nonfunctional pseudogene sequence that, for an unexplained reason, has become functional in these isolates. Results from the colony immunoblotting of these isolates failed to show a detectable in vitro phase shift between either PspA type 6 (XIR278 and 2A4) or PspA type 34 (7D2) protein. This strengthens the second explanation, and suggests that the second PspA is these isolates is due to the pspC gene not being turned off during in vitro growth conditions.

Presumably, in these four strains, the second PspA protein is provided by the pspC DNA sequence. At high stringency, the probe comprising the coding. region of the α-helical half of PspA recognized both pspA homologous sequences of MC25–18, but not the pspC sequence of Rx1. The finding indicated that the pspC sequence of MC25–28 is more similar to the Rx1 pspA sequence than the Rx1 pspC sequence. If the pspC sequence of these strains is more similar to pspA than most pspC sequences, it could explain why the products of pspC genes cannot generally be identified by MAbs.

Example 11

Identification of conserved and variable regions of pspA and pspC sequences of S. pneumoniae The S. pneumoniae strains used in this study are listed in Table 62. The strains are human clinical isolates representing 12 capsular and 9 PspA serotypes. All strains were grown at 37° C. in 10 ml of Todd-Hewitt broth supplemented with 0.5% yeast extract to an approximate density of 5×10^8 cells/ml. After harvesting of the cells be centrifugation (2900 g, 10 min), the DNA was isolated, and stored at 4° C. in TE (10 mM Tris, 1 mM EDTA, pH8.0).

TABLE 62

Streptococcus pneumoniae strains used.

| Strain | Relevant phenotype | Reference |
|---|---|---|
| WU2 | Capsular type 3, PspA type 1 | Briles et al., 1981 |
| D39 | Capsular type 2, PspA type 25 | Avery et al., 1944 |
| R36A | Nonencapsuated mutant of D39, pspA type 25 | Avery et al., 1944 |
| Rx1 | Derivatitve of R36A, PspA type 25 | Shoemaker and Guild, 1974 |
| DBL5 | Capsular type 5, PspA type 33 | Yother et al., 1986 |
| DBL6A | Capsular type 6A, PspA type 19 | Yother et al., 1986 |
| A66 | Capsular type 3, PspA type 13 | Avery et al., 1944 |
| AC94 | Capsular type 9L, PspA type 0 | Waltman et al., 1992 |
| AC17 | Capsular type 9L, PspA type 0 | Waltman et al., 1992 |
| AC40 | Capsular type 9L, PspA type 0 | Waltman et al., 1992 |
| AC107 | Capsular type 9V, PspA type 0 | Waltman et al., 1992 |
| AC100 | Capsular type 9V, PspA type 0 | Waltman et al., 1992 |
| AC140 | Capsular type 9N, PspA type 18 | Waltman et al., 1992 |
| D109-1B | Capsular type 23, PspA type 12 | McDaniel et al., 1992 |
| BG9709 | Capsular type 9, PspA type 0 | McDaniel et al., 1992 |
| L81905 | Capsular type 4, PspA type 25 | McDaniel et al., 1992 |
| L82233 | Capsular type 14, PspA type 0 | McDaniel et al., 1992 |
| L82006 | Capsular type 1, PspA type 0 | McDaniel et al., 1992 |

Approximately 5 μg of chromosomal DNA was digested with HindIII according to the manufacturer's instructions (Promega, Inc., Madison, Wis.). The digested DNA was subjected to electrophoresis at 35 mV overnight in 0.8% agarose gels and then vacuum-blotted onto Nytran® membranes (Schleicher & Schuell, Keene, N.H.).

Figure 17:
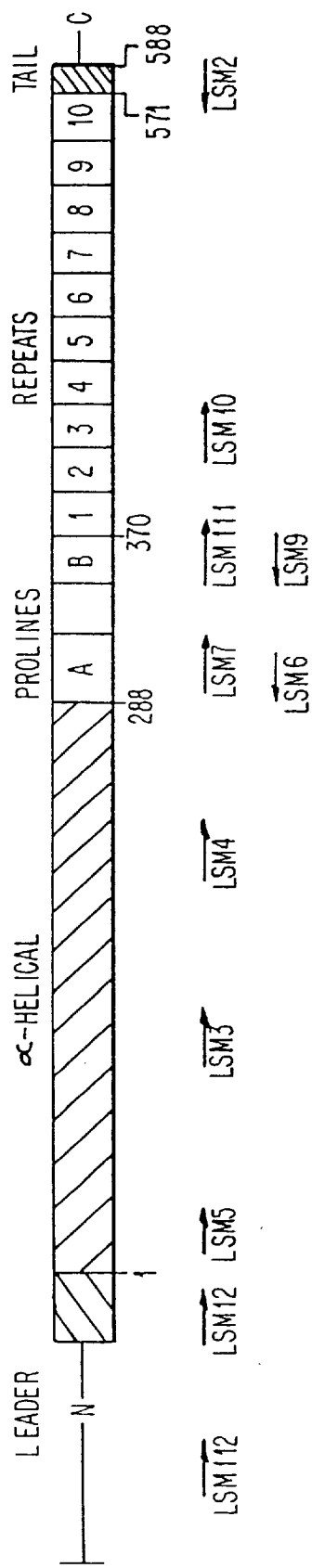
FIG. 17 shows: position and orientation of oligonucleotides relative to domains encoded by pspA; numbers along the bottom of the Figure represent amino acids in the mature PspA polypeptide from strain Rx1, and arrows represent the relative position (not to scale) and orientation of oligonucleotides.

The oligonucleotides uses were based on the previously determined sequence of Rx1 pspA. Their position and orientation relative to the structural domains of Rx1 pspA are shown in FIG. 17. Labeling of oligonucleotides and detection of probe-target hybrids were both performed with the Genius System® according to manufacturer's instructions (Boehringer-Mannhein, Indianapolis, Ind.). All hybridizations were done for 18 hours at 42° C. without formamide. By assuming that 1% base-pair mismatching results in a 1° C. decrease in $T_m$ arbitrary designations of "high" and "low" stringency were defined by salt concentration and temperature of post-hybridization washes. Homology between probe and target sequences was derived using calculated $T_m$ by established methods. High stringency is defined as ≧90%, and low stringency is ≦85% base-pair matching.

PCR primers, which were also used as oligonucleotide probes in Southern blotting and hybridizations, were designed based on the sequence of pspA from pneumococcal strain Rx1. These oligonucleotides were synthesized by Oligos, Etc. (Wilson, Oreg.), and are listed in Table 63.

TABLE 63

Oligonucleotide sequences.

| Primer | 5' -> 3' |
|---|---|
| LSM111 (SEQ ID NO: 22) | CCGGATCCAGCTCCTGCACCAAAAC |
| LSM2 (SEQ ID NO: 18) | GCGCGTCGACGCTTAAACCCATTCACCATTGG |
| LSM3 (SEQ ID NO: 23) | CCGGATCCTGAGCCAGAGCAGTTGGCTG |
| LSM4 (SEQ ID NO: 24) | CCGGATCCGCTCAAAGAGATTGATGAGTCTG |
| LSM5 (SEQ ID NO; 25) | GCGGATCCCGTAGCCAGTCAGTCTAAAGCTG |
| LSM6 (SEQ ID NO: 26) | CTGAGTCGACTGGAGTTTCTGGAGCTGGAGC |

TABLE 63-continued

Oligonucleotide sequences.

| Primer | 5' -> 3' |
|---|---|
| LSM7 (SEQ ID NO: 27) | CCGGATCCAGCTCCAGCTCCAGAAACTCCAG |
| LSM9 (SEQ ID NO: 28) | GTTTTTGGTGCAGGACCTGG |
| LSM10 (SEQ ID NO: 29) | GCTATGGCTACAGGTTG |
| LSM12 (SEQ ID NO: 30) | CCGGATCCAGCGTGCCTATCTTAGGGGCTGGT |
| LSM112 (SEQ ID NO: 31) | GCGGATCCTTGACCAATARRRACGGAGGAGGC |

PCR was done with an MJ Research, Inc., Programmable Thermal Cycler (Watertown, Mass.), using approximately 10 ng of genomic pneumococcal DNA as template with designated 5' and 3' primer pairs. The sample was brought to a total volume of 50 $\mu$l containing a final concentration of 50 mM KCl, 10 mM Tris-HCl (pH 8.3), 1.5 mM MgCl$_2$, 0.01% gelatin, 0.5 $\mu$M of each primer, 200 $\mu$M of each deoxynucleoside triphosphate, and 2.5 U of Taq DNA polymerase. The samples were denatured at 94° C. for 2 minutes and subjected to 10 cycles consisting of: 1 min at 94° C., 2 min at 50° C., and 3 min at 72° C., followed by 20 cycles of: 1 min at 94° C., 2 min at 60° C., and 3 min at 72° C. After 30 total cycles, the samples were held at 72° C. for an additional 5 min prior to cooling to 4° C. The amplicons were then analyzed by agarose gel electrophoresis.

Oligonucleosides were used to probe HindIII digests of DNA from 18 strains of S. pneumoniae under conditions of low and high stringency. Each strain was also screened using a full-length pspA probe. Table 64 summarizes the results for each strain under conditions of high stringency. Strain Rx1 is a laboratory derivative of the clinical isolate D39 and consequently, both strains showed identical hybridization patterns and are a single column in Table 64.

The only strain which did not have more than one pspA-homologous HindIII fragment was WU2, which was previously shown using a full-length pspA probe. Even at high stringency, six of the eight probes detected more than one fragment in at least one of the 18 strains (Table 64). LSM7, 10 and 12 hybridized with two fragments in more than one-half of the strains, and the fragments detected by the oligonucleotide probes were identical in size to those detected by the full-length pspA probe. Moreover, the same pairs of fragments were frequently detected by probes derived from the 3' as well as-the 5' region of Rx1 pspA. These results suggested that the HindIII fragments from different isolates include two separate but homologous sequences, rather than fragments of a single pspA gene. Based on the diversity of the hybridization patterns and the size of restriction fragments, it is clear that pspA and pspC sequences are highly diverse and that these loci have considerable sequence variability as determined by location of HindIII recognition sites.

Oligonucleotides which hybridize with a single restriction fragments in each strain were assumed to be specific for pspA. At high stringency, LSM3 and LSM4 detected only a single HindIII fragment in the strains with which they reacted. Restriction fragments containing homology to LSM3 or LSM4 were the same as those which hybridize with all of the other homologous probes. This suggested that LSM3 and LSM4 specifically detect pspA rather than the pspC sequence. That LSM3 hybridizes with a single restriction fragment of WU2 further confirmed that this oligonucleotide is specific for pspA. Sequences from the portion of the gene encoding the second proline region (LSM111) and the C-terminus (LSM2) appeared to be relatively specific for pspA since they generally detect only one of the HindIII fragments of each strain.

Oligonucleotides LSM12 and LSM10 were able to detect the most conserved epitopes of pspA and generally hybridize with multiple restriction fragments of each strain (Table 65). LSM7 was not as broadly cross-reactive, but detected two pspAs in 41% Id strains including almost 60% of the strains

TABLE 64

Summary of hybridization of oligonucleotides with HINDIII chromosomal restriction fragments.

Strains

| Probe | Rx1/ D39 | WU2 | DBL 5 | DBL 6A | A66 | AC 94 | AC 17 | AC 40 | AC107 | AC100 | AC140 | DB109 | BG9709 | BG58C | L8190 | L82233 | L82006 |
|---|---|---|---|---|---|---|---|---|---|---|---|---|---|---|---|---|---|
| FL-Rx1[a] | 4.0, 9.1[b] | 3.8 | 3.7, 5.8 | 3.0, 3.4 | 3.6, 4.3 | 3.6, 6.3 | 3.6, 6.3 | 3.2, 3.6 | 3.2, 3.6 | 4.0, 8.0 | 3.0, 4.0 | 3.3, 4.7 | 3.3, 4.7 | 1.4, 3.2, 3.6 | 3.6, 5.2 | 8.2, 3.7 | 4.3, 6.4 |
| LSM 12 | 4.0, 9.1 | 3.8 | 3.7, 5.8 | 3.0, 3.4 | 4.3 | —[c] | 3.6, 6.3 | 3.2, 3.6 | — | 4.0, 8.0 | 4.0 | — | 3.3, 4.7 | 2.2, 9.6 | 1.4, 3.2, 3.6 | 1.3, 3.7 | — |
| LSM 5 | 4.0 | — | — | — | — | 3.6, 6.3 | — | — | — | — | — | — | — | 2.2, 9.6 | 3.6 | 1.2, 2.3, 3.6 | — | — |
| LSM 3 | 4.0 | 3.8 | — | — | — | 6.3 | — | — | — | — | — | — | — | 2.2 | 3.6 | 3.6 | — | — |
| LSM 4 | 4.0 | — | — | — | — | — | — | — | — | — | — | — | — | 2.2 | 3.6 | 3.6 | 3.7 | — |
| LSM 7 | 4.0, 9.1 | 3.8 | 3.7 | 3.0, 3.4 | 3.6 | — | — | 3.2, 3.6 | — | — | 3.0, 4.0 | 3.3, 4.7 | 2.2, 9.6 | 3.6 | 3.6, 2.3 | 3.7 | — |
| LSM 11t | 4.0, 9.1 | 3.8 | 3.7, 5.8 | 3.4 | — | 6.3 | — | 3.2 | 3.6 | 4.0 | 4.0 | — | 2.2 | — | 5.2 | — | — |
| LSM 10 | 4.0, 9.1 | 3.8 | 3.7 | 3.4 | 3.6, 4.3 | — | 3.6, 6.3 | 3.2 | 3.6, 3.3 | 4.0 | 4.0 | 3.3, 4.7 | 2.2, 9.6 | 3.6, 3.2 | 3.6, 5.2 | 1.3, 3.7 | 4.3, 6.4 |
| LSM 2 | 4.0 | 0 | 3.7 | — | — | 3.6 | 3.6 | — | 3.6, 6.3 | 4.0 | 3.0, 4.0 | 4.7 | — | — | — | — | 4.3 |

[a]Full-length pspA of strain Rx1.
[b]numbers are size in kilobase pairs.
[c]no hybridization observed with corresponding probe.

with which it reacts. Thus, sequences representing the leader, first proline region, and the repeat region appear to be relatively conserved not only within pspA but between the pspA and pspC sequences. LSM3, 4, and 5 hybridize with the smallest number of strains of any oligonucleotides (29–35 percent), suggesting that the α-helical domain is the least conserved region within pspA. In strains BG58C and L81905 oligonucleotides detect more than two HindIII fragments containing sequences with homology to pspA. Because of the absence of HindIII restriction sites within any of the oligonucleotides it was unlikely that these multiple fragments result from the digestion of chromosomal DNA within the target regions. Also, the additional restriction fragments were detected at high stringency by more than one oligonucleotide. Possibly, in these two strains, there are three or four sequences with DNA homology to some portions of pspA. The probes most consistently reactive with these additional sequences are those for the leader, the alpha-helical region, and the proline-rich region.

The oligonucleotides used as hybridization probes were also tested for their utility as primers in the polymerase chain reaction (PCR). Amplification of pspA from 14 strains of S. pneumoniae comprising 12 different capsular types was attempted with the primers listed in Table 63. LSM2, derived from the 3' And of pspA, were able to amplify an apparent pspA sequence from each of 14 pneumococcal strains when used in combination with LSM111, which is within the sequence of pspA encoding the proline-rich region. Combinations of LSM2 with primers upstream in pspA were variably successful in amplifying sequences (Table 65). The lowest frequency of amplification was observed with LSM112 which was derived from the Rx1 sequence 5' to the pspA start site. This oligonucleotide was not used in the hybridization studies. DNA fragments generated by PCR were blotted and hybridized with a full-length pspA probe to confirm homology to pspA.

Further evidence for variability at the pspA locus comes from the differences in the sizes of the amplified pspA gene. When PCR primers LSM12 and LSM2 were used to amplify the entire coding region of PspA, PCR products from different pneumococcal isolates ranged in size from 1.9 to 2.3 kbp. The regions of pspA which encode the α-helical, proline-rich, and repeat domains were amplified from corresponding strains and variation in pspA appears to come from sequences within the α-helical coding region.

TABLE 65

Amplification of pspA by PCR using the indicated oligonucleotides as 5' primers in combination with the 3'-primer LSM2.

| 5'-primer | Domain | Amplified/ Tested | Percent Amplified |
|---|---|---|---|
| LSM112 | –35 (upstream) | 2/14 | 14 |
| LSM12 | leader | 8/14 | 57 |
| LSM3 | α-helical | 3/14 | 21 |
| LSM7 | proline | 12/14 | 86 |
| LSM111 | proline | 14/14 | 100 |

These studies have provided a finer resolution map of the location of conserved and variable sequences within pspA. Additionally, regions of divergence and identity between pspA and the pspC sequences have been identified. This data confirmed serological studies, and demonstrated that pspA and pspC sequences are highly variable at the DNA sequence level. The diversity of HindIII restriction fragment polymorphisms contained pspA and the pspC sequence supported earlier data using larger probes that detected extensive variability of the DNA in and around these sequences.

A useful pspA-specific DNA probe would identify Rx1 and WU2 pspA genes, in which restriction maps are known, and would identify only a single restriction fragment in most strains. Two probes, LSM3 and LSM4, do not hybridize with more than one HindIII restriction fragment in any strain of pneumococcus. Both of these oligonucleotides hybridize with Rx1 pspA and LSM3 hybridizes with WU2 pspA. However, each of these probes hybridize with only four of the other 15 strains. When these probes identify a fragment, however, it is generally also detected by all other Rx1-derived probes. Oligonucleotides from the second proline-rich region (LSM111) and the C-terminus of pspA (LSM2) generally identify only one pspA-homologous sequence at high stringency. Collectively, LSM111, 2, 3 and 4 react with 16 of the 17 isolates and in each case revealed a consensus DNA fragment recognized by most or all of the oligonucleotide probes.

When an oligonucleotide probe detected only a single DNA fragment it was presumed to be pspA. If the probe detected multiple fragments, it was presumed to hybridize with pspA. If the probe detected multiple fragments, it was presumed to hybridize with pspA and the pspC sequence. Based on these assumptions the most variable portion between pspA and pspC is the region immediately upstream from the –35 promoter region and that portion encoding the α-helical region. The most conserved portion between pspA and pspC was found to be the repeat region, the leader and the proline-rich region sequences. Although only one probe from within the repeat region was used, the high degree of conservation among the 10 repeats in the Rx1 sequence makes it likely that other probes within the repeat sequences would give similar results.

The portion of Rx1 pspA most similar to the pspC sequence was that encoding the leader peptide, the upstream portion of the proline-rich region, and the repeat region. The repeat region of PspA has been shown to be involved in the attachment of this protein to the pneumococcal cell surface. The conservation of the repeat region within pspC sequences suggests that if these loci encode a protein, it may have a similar functional attachment domain. The conservation of the leader sequence between pspA and the pspC sequence was also not surprising since similar conservation has been reported for the leader sequence of other proteins from gram positive organisms, such as M protein of group A streptococci (Haanes-Fritz, E. et al., Nucl. Acids Res. 1988; 16: 4667–4677).

In two strain, some oligonucleotide probes identified more than two pspA-homologous sequences. In these strains, there was a predominant sequence recognized by almost all of the probes, and two or three additional sequences share homology with DNA encoding the leader, α-helical, and proline region, and they have no homology with sequences encoding the repeat region in the C-terminus of PspA. These sequences might serve as cassettes which can recombine with pspA and/or the pspC sequences to generate antigenic diversity. Alternatively, the sequences might encode proteins with very different C-terminal regions and might not be surface attached by the mechanism of PspA.

Oligonucleotides which hybridize with a single chromosomal DNA fragment were used as primers in PCR to examine the variability of domains within pspA. These results demonstrate that full-length pspA varies in size among strains of pneumococci, and that this variability is almost exclusively the result of sequences in the alpha-helix coding region.

Example 12
Cloning of PspC

Figure 18:
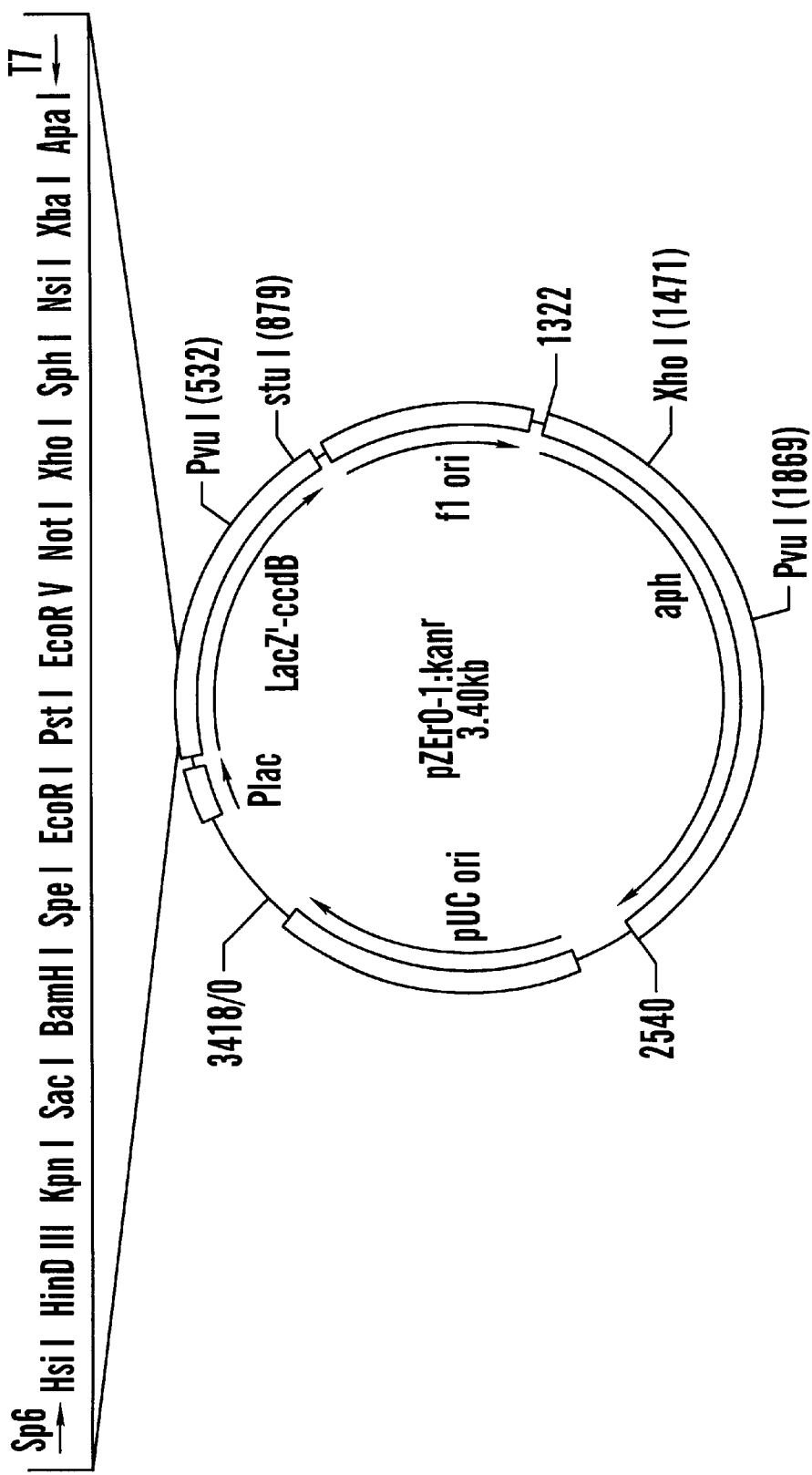
FIG. 18 shows: a restriction map of the pZero vector.

Chromosomal DNA from *S. pneumoniae* EF6796, serotype 6A clinical isolate, was isolated by methods including purification through a cesium chloride gradient, as described in Example 8. The HindII-EcoRI fragment of EF6796 was cloned in modified pZero vector (Invitrogen, San Diego, Calif.) in which the Zeocin-resistance cassette was replaced by a kanamycin cassette (shown in FIG. 18). Recombinant plasmids were electroporated into *Escherichia coli* TOP10F' cells [F' {lacI$^q$Tet$^R$} mcrA Δ(mrr-hsdRMS-mcrBC) φ80lacZΔM15 ΔlacX74 deoR recA1 araD139 Δ(ara-leu) 7967 galU galK rpsL endA1 nupG] (Invitrogen).

The 5' region of pspA.Rx1 does not hybridize to pspC sequence at high stringencies by Southern analysis. Utilizing both the full-length Rx1 pspA probe, and a probe containing the sequence encoding α-helical region of PspA, it was possible to identify which DNA fragment contained pspA and which fragment contained the pspC locus. The pspC locus and the pspA gene of EF6796 were mapped using restriction enzymes. After digestion of chromosomal DNA with HindIII, the pspC locus was localized to a fragment of approximately 6.8 kb. Following a double digest with HindIII and EcoRI, the pspC locus was located in a 3.5 kb fragment. To obtain the intact pspC gene of EF6796, chromosomal DNA was digested with HindIII, separated by agarose gel electrophoresis, the region between 6 and 7.5 kb purified, and subsequently digested with EcoRI. This digested DNA was analyzed by electrophoresis, and DNA fragments of 3.0 to 4.0 kb were purified (GeneClean, Bio101, Inc., Vista, Calif.). The size-fractionated DNA was then ligated in HindIII-EcoRI-digested pZero, and electroplated into *E. coli* TOP10F' cells. Kanamycin-resistant transformants were screened by colony blots and probed with full-length pspA. A transformant, LXS200, contained a vector with a 3.5 kb insert which hybridized to pspA.

*Escherichia coli* strain LXS200 which contains the cloned PspC gene from *Streptococcus pneumoniae* stain EP6796 was deposited on Jul. 24, 2001 under the terms of the Budapest Treaty with the American Type Culture Collection (ATCC), 12301 Parklawn Drive, Rockville, Maryland, 20852, USA, under accession number ATCC No. PTA-3526.

Sequencing of pspC in pLXS200 was completed using automated DNA sequencing on an ABI 377 (Applied Biosystems, Inc., PLACE). Sequence analyses were performed using the University Of Wisconsin Genetics Computer Group (GCG) programs supported by the Center for AIDS Research (P30 AI27767), MacVector 5.0, Sequencer 2.1, and DNA Strider programs. Sequence similarities of pspC were determined using the NCBI BLAST server. The coiled-coil structure predicted by pspC sequence was analyzed using Matcher. A gene probe for cloning the pspC locus. Two oligonucleotide primers, N192 and C558 (shown in FIG. 19), have been used previously to clone fragments homologous to the region of Rx1 pspA encoding amino acids 192–588 from various pneumococcal strains. These primers are modifications (altered restriction sites) of LSM4 and LSM2 which were previously shown to amplify DNA encoding the C-terminal 396 amino acids of PspA.Rx1 (FIG. 17); this includes approximately 100 amino acids of the α-helical region, the proline rich region, and the C-terminal choline-binding repeat region. Using primers N192 and C558, a 1.2 kb fragment from strain EF6796 was amplified by PCR, and subsequently cloned in pET-9A (designated PRCT135). This insert was then partially sequenced.

Independently, a larger pspA fragment from strain EF6796 was made using primers LSM13 and SKH2 (shown in FIG. 19) for the purpose of direct sequencing of serologically diverse pspA genes.

Figure 20:
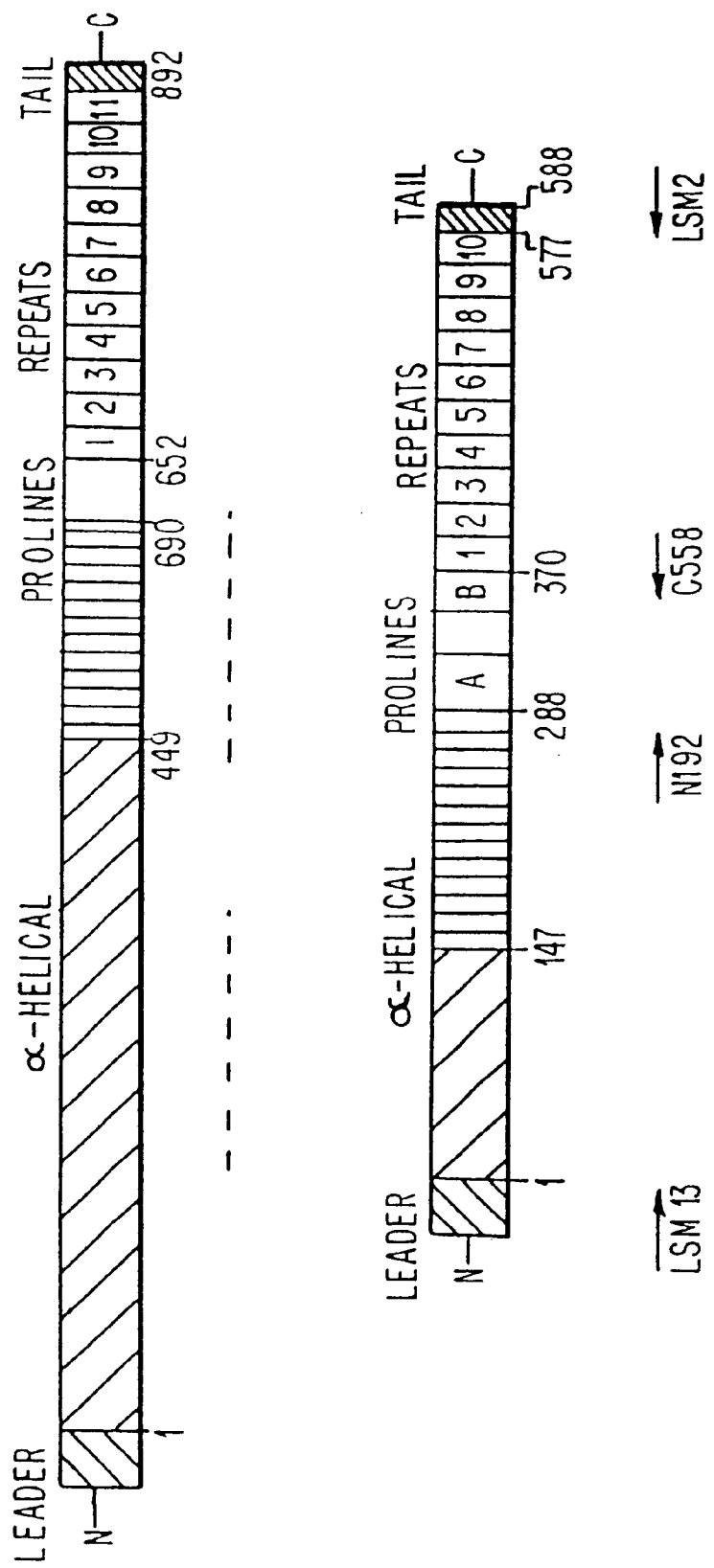
FIG. 20 shows: a comparison of the structural motifs of PspA and PspC; PspA has a smaller alpha-helical region, and does not contain the direct repeats within the alpha-helix (indicated by the dashed lines); the alpha-helical regions which are homologous between PspA and PspC are indicated by the dashed lines); the alpha-helical regions which are homologous between PspA and PspC are indicated by the striped pattern; and PCR primers are indicated by the arrows.

The LSM13 and SKH2 primer pair result in the amplification of the 5' end of most pspA gene(s) encoding the upstream promoter, the leader peptide, the α-helical, and the proline-rich regions (amino acid −15 to 450) (FIG. 20). From the strain EF6796, the LSM13 and SKH2 primers amplified a 1.3 kb fragment (pspA.EF6796), which was sequenced. The sequence from pRCT135 and the LSM13/SKH2 PCR-generated fragment pspA.EF6796 was not identical. The fragment obtained by PCR using primers LSM13 and SKH2 was designated pspA based on its location within the same chromosomal location as pspA.Rx1. The cloned fragment in pRCT135 was assumed to represent the sequence of the second gene locus, pspC, known to be present from Southern analysis. Both genes have significant similarity to the corresponding regions of the prototype pspA gene from strain Rx1. The second gene locus was called pspC, in recognition of its distinct chromosomal location, not sequence differences from the prototype pspA gene. Analysis of the nucleotide and amino acid sequence of pspC EF6796. To test the hypothesis that pRCT135 represented pspC of EF6796, and to further investigate pspC, the entire EF6796 pspC fine was cloned as a 3.4 kb HindIII-EcoR1 fragment forming pLXS200. DNA sequence of the pspC-containing clone pLXS200 revealed an open reading fram of 2782 nucleotides based on the analysis of putative transcriptional and translation start and stop sites (FIG. 21). The predicted open reading frame encodes a 105 kDa protein which has an estimated pI of 6.09.

PspA.Rx1 and PspC.EF6796 are similar in that they both contain an α-helical region followed by a proline-rich domain and repeat region (FIG. 20). However, there are several features of the amino acid sequence of PspC which are quite distinct from PspA. From comparisons at the nucleotide as well as the predicted amino acid sequence, it is apparent that the region of strong homology between PspC and PspA begins at amino acid 458 of PspC (amino acid 147 of PspA) and extends to the C-terminus of both proteins (positions 899 and 588 respectively). The predicted amino acid sequence of PspC.EF6796 and PspA.Rx1 are 76% similar and 68% identical based on GCG Bestfit program for this region (FIG. 22). The nucleotide sequence identity between pspC and pspA is 87% for the same region. Eight bases upstream of the ATG start site is putative ribosomal binding site, TAGAAGGA. The proposed transcriptional start −35 (TATACA) and −10 (TATAGT) regions are located between 258 to 263 and 280 to 285, respectively (FIG. 21). A potential transcriptional terminator occurs at a stem loop between nucleotides 3237 through 3287. The putative signal sequence of PspC is typical of other gram positive bacteria. This region consists of a charged region followed by a hydrophobic core of amino acids. A potential cleavage site of the signal peptide occurs at amino acid 37 following the Val-His-Ala. The first amino acid of the mature protein is a Glu residue.

Other than features similar to all signal sequences, there is no homology in this region between pspA and pspC. This confirms that pspC is present in a separate chromosomal locus from that of pspA. The signal sequence and upstream region have striking similarity to the similar regions of *S. agalactiae* β antigen (accession number X59771). The β antigen of Group B streptococci is a cell surface receptor that binds IgA. Similarity to the bac gene ends with the start of the mature protein of PspC, and the nucleotides are 75% identical in this region. Thus, although pspC is in a very similar chromosomal locus to the β antigen, it is clearly a distinct protein.

The N-terminus of PspC is quite different from the N-terminus of PspA. Prediction of the secondary structure utilizing Chou-Fausman analysis (Chao, P. Y. et al., Adv. Enzymol. Relat Areas Mol. Biol. 1978: 47: 45–148), suggests that the structure of amino acids 16 to 589 of PspC is predominately α-helical. The Matcher program was used to examine periodicity in the α-helical region of PspA. The characteristic seven residue periodicity is maintained by having hydrophobic residues at the first and fourth positions (a and d) and hydrophobic residues at the remaining positions. The coiled-coil region of the α-helix of PspC (between amino acid 32 to 600) has three breaks in the heptad repeat (FIG. 23). These disturbances in the 7 residue periodicity occur at amino acids 99 to 104, 224 to 267 and 346 to 350. The α-helical region of PspA has seven breaks in the motif, each break ranging from a few amino acids to 23 amino acids each. In contrast, the three breaks in the coiled-coil motif of PspC involve 5, 43 and 4 amino acids, respectively.

Figure 24:
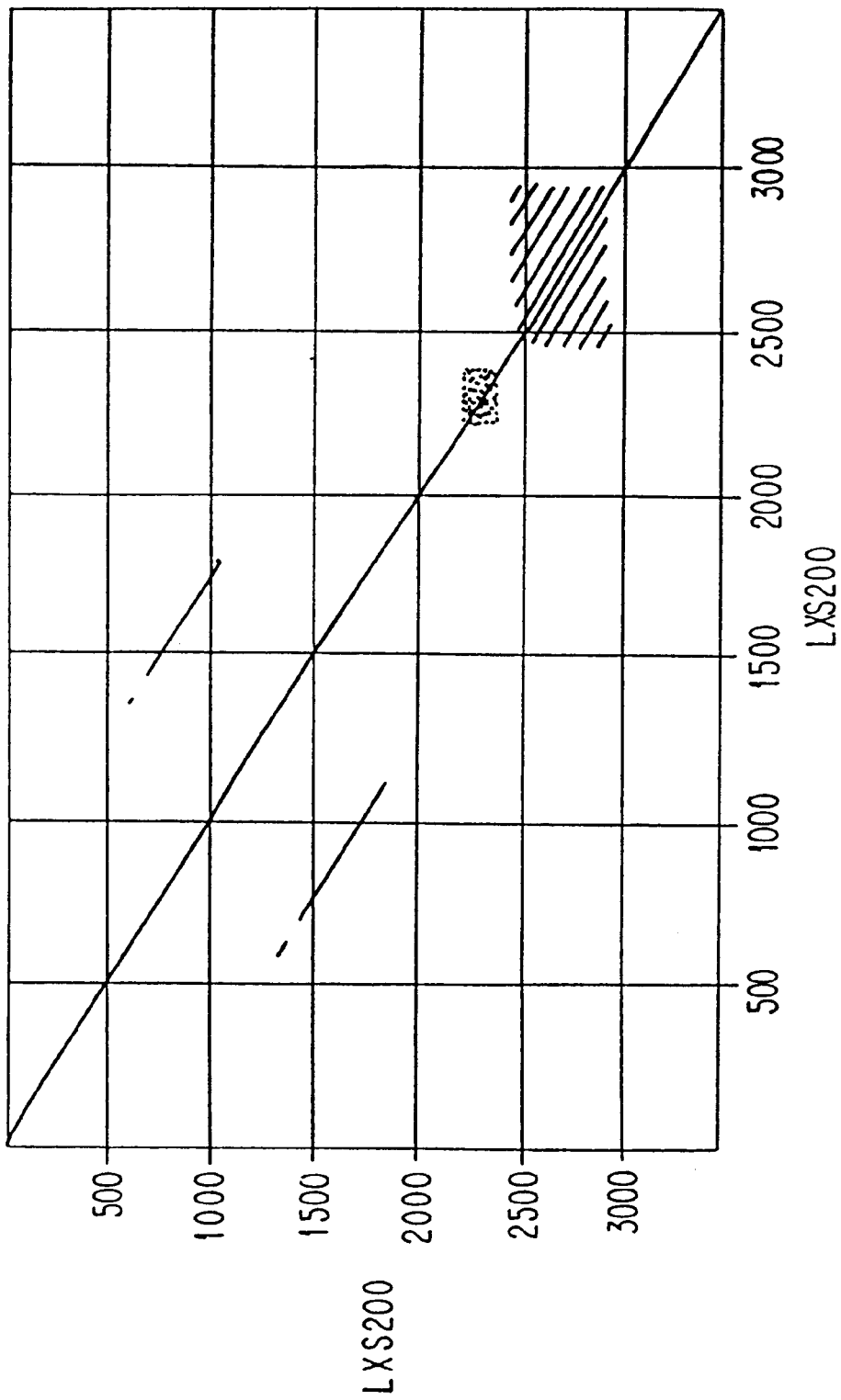
FIG. 24 shows: a matrix plot comparison of the repeat regions of the alpha-helical region of PspC.

The sequence encoding the α-helical region of PspC contains two direct repeats 483 nucleotides (160 amino acids) long which are 88% percent identical at the nucleotide level. These repeats, which occur between nucleotides 562 to 1045 and nucleotides 1312 to 1795, are conserved both at the nucleotide and amino acid level (amino acids 188 to 348 and 438 to 598) (FIG. 24). PspA lacks evidence for any repeats this prominent within the α-helical region. These repeat regions could provide a mechanism for recombination that could alter the N-terminal half of the PspC molecule. Although repeat motifs are common in bacterial surface proteins, a direct repeat this large or separated by a large spacer region is novel. The evolutionary significance of this region is not known. A Blast search of the repeat region and the 267 nucleotide bases between them revealed no sequence with significant homology at the nucleotide or amino acid level. However, one of the structural breaks in the coil-coiled region of PspC is the region between the two repeats. Perhaps some deviation from coiled-coil structure between the two repeats is critical to maintain the α-helical structure.

Previous studies have shown that a major cross-protective region of PspA comprises the C-terminal ⅓ of the α-helical region (between residues 192 and 260 of PspA.Rx1). This region accounts for the binding of 4 of 5 cross-protective immunity in mice. Homology between PspC and PspA begins at amino acid 148 of PspA, thus including the region from 192–299. The homology between PspA and the PspC includes the entire PspC sequence C-terminal of amino acid 486. Based on the fact that PspA and PspC are so similar in this region known to be protection-eliciting, PspC is also likely to be a protection-eliciting molecule. Because of close sequence and conformational similarity of the proteins in this region, antibodies specific for the region of PspA between amino acid 148 and 299 should cross-react with PspC and thus afford protection by reacting with PspC and PspA. Likewise, immunization with the PspC would be expected to elicit antibodies cross-protective against PspA. The differences between PspC of strain EF6796 and PspA of strain Rx1 is no greater than the differences between many additional PspAs, which have been shown to be highly cross-protective.

A proline-rich domain exists between amino acid 590 to 652. The sequence, PAPAPEK, is repeated six times in this region. This region is very similar to the proline-rich region of PspA.Rx1 which contains the sequence PAPAP repeated eight times in two proline-rich regions. These two regions of PspA.Rx1 are separated by 27 charge amino acids; no such spacer region is present in PspC.

Many cell surface proteins of other gram positive bacteria contain proline-rich regions. These are often associated with a domain of protein that is predicted to be near the cell wall murein layer when the protein is cell-associated. For example, in M proteins of S. pyogenes this domain contains both a Pro- and Gly-rich regions. The fibronectin-binding protein of S. pyogenes, S. dysgalactiae, and Staphylococcus aureus contains a proline-rich region with a three-residue periodicity (pro-charged-uncharged) that is not found in PspA or PspC. An M-like protein of S. equi contains a proline-rich region that is comprised of the tetrapeptide PEPK. This region lacks glycine normally found in the proline regions of M-proteins. The last proline repeat region of this molecule is PAPAK, which is more similar to the proline-region of PspA and PspC than it is to M-proteins.

Proline-rich regions of gram positive bacterial proteins have been reported previously to transit the cell wall. The differences in proline-rich regions of proteins from diverse bacteria may reflect differences in protein function or possibly subtle differences in cell wall function. Proline-rich regions are thought to be responsible for aberrant migration of these proteins through SDS-polyacrylamide gels.

The repeat region of PspC is a common motif found among several proteins in gram positive organisms. Autolysin of S. pneumoniae, toxins A and B of Clostridium difficile, glucosyltransferases from S. downei and S. mutans, and CspA of C. acetobitylicum all contain similar regions. In PspA these repeats are responsible for binding to the phosphatidylcholine of teichoic acid and lipoteichoic acid in cell wall of pneumococci. However, bacterial proteins containing C-terminal repeats are secreted, which may imply either a lost or gained function. Although all of these proteins have similar repeat regions the similarity of the repeat regions of PspA and PspC is much greater than that of PspC to the other proteins (Table 66).

Interestingly, PspC like PspA has a 17 amino acid partially hydrophobic tail. The function of this 17 amino acid region is unknown. In the case of PspA it has been shown that mutants lacking the tail bind the surface of pneumococci as well as PspAs in which the tail is expressed. Presently, it is now known whether PspC is attached to the cell surface or secreted.

PspA and PspC proteins both have α-helical coiled-coil regions, proline-rich central regions, repeat regions, with a choline binding motifs, and the C-terminal 17 amino acid tail. PspA and PspC share three regions of high sequence identity. One of these is a protection-eliciting region present within the helical domain. The other two regions are the proline-rich domain and a repeat domain shared with other choline binding proteins and thought to play a role in cell surface association. The similarity throughout most of the structure of the PspA and the PspC molecules raises the possibility that the two molecules may play at least slightly redundant functions. However, the fact that the N-terminal half of the protein is not homologous to any of the α-helical sequence of PspA suggests the PspC and PspA may have evolved for at least somewhat different roles on the cell surface. One of the most striking differences between the two molecules is the single repeat in the α-helical region of PspC. Although neither the exact function of PspA nor of PspC are known, the observation that a major cross-protective region of PspA is highly homologous with a similar region of PspC, raises the possibility that both molecules are protection-eliciting and elicit cross-protective antibodies.

The sequence similarity between the promoter region of the pspC gene and the bac gene from group B streptococci is very intriguing. It implies that an interspecies recombination event has occurred and, this interspecies recombination has contributed to the evolution of the pspC. The pspC gene thus has a chimeric structure, being partially like pspA and partially like the 6 antigen. In the latter case, all protein similarity is limited to the signal sequence. Similar interspecies recombination events have contributed to the evolution of the genes encoding penicillin binding protein.

Using analogous procedures, a second pspC sequence was isolated from strain D39 of S. pneumoniae. FIGS. 25 to 29 show the sequence data of PspC from strain D39, complete from upstream of the promoter through the proline-rich region. Strain D39 has the same genetic background as strains Rx1, from which pspA was sequenced. D39 and Rx1 have the same pspC gene based on Southern blot analysis.

The alpha-helical encoding region of the D39 pspC gene is one third of the size of the homologous region from the EF6796 pspC gene. The proline-rich region of the D39 pspC gene was more similar to Rx1 pspA than to EF6796 pspC. Even so, the two pspC genes were 86% identical at the nucleotide sequence, and 67% identical at the amino acid level.

In the alpha-helical sequence of EF6797 pspC a strong repeat was observed. This was absent in the pspC sequence of D39. The D39 pspC sequence also lacks a leader sequence, found in the EF6797 pspC sequence.

This data strongly indicates that there is variability in the structure of pspC, similar to previous observations for pspA. In the case of pspC, however, the extent of variability appears to be even greater than that which has been observed for pspA.

TABLE 66

PERCENT HOMOLOGY OF CHOLINE BINDING REGIONS

| Protein | Organism | Percent similarity/identity | |
|---|---|---|---|
| | | PspA | PspC |
| PspC | S. pneumoniae | 86/60 | 100/100 |
| Bacteriophage Cp-1 | S. pneumoniae | 56/30 | 56/28 |
| LytA | S. pneumoniae | 57/33 | 61/32 |
| PspA | C. perfringens | 64/45 | 59/42 |
| alpha toxin | C. novyi | 54/29 | 57/33 |
| CspB | C. acetobutylicum | 58/36 | 61/45 |

Having thus described in detail certain preferred embodiments of the present invention, it is to be understood that the invention defined by the appended claims is not to be limited by particular details set forth in the above description, as many apparent variations thereof are possible without departing from the spirit or scope thereof.

REFERENCES

Mufson M A. Streptococcus pneumoniae. In: Mandell G L, Douglas R G, Jr, Bennett J E, (eds.) Principles and Practice of Infectious Diseases. New York: Churchill Livingston, 1990:1539–50.

Cohen C, Parry D A D. alpha-helical coiled coils: more facts and better predictions. Science 1994;236:488–9.

Shapiro E D, Berg A T, Austrian R, et al. Protective efficacy of polyvalent pneumococcal polysaccharide vaccine. N Engl J Med 1991;325:1453–60.

Feldman C, Munro N C, Jeffery P K, et al. Pneumolysin induces the salient histologic features of pneumococcal infection in the rat lung in vivo. Am J Respir Cell Mol Biol 1992;5:416–23.

Lock R A, Paton J C, Hansman D. Comparative efficacy of pneumococcal neuraminidase and pneumolysin as immunogens protective against Streptococcus pneumoniae. Microb Pathog 1988;5:461–7.

Sampson J S, O'Connor S P, Stinson A R, Tharpe J A, Russell H. Cloning and nucleotide sequence analysis of psaA, the Streptococcus pneumoniae gene encoding a 37-kilodalton protein homologus to previously reported Streptococcus sp. adhesins. Infect Immun 1994;62:319–24.

McDaniel L S, Sheffield J S, Delucchi P, Briles D E. PspA, a surface protein of Streptococcus pneumoniae, is capable of eliciting protection against pneumococci of more than one capsular type. Infect Immun 1991;59:222–8.

Berry A M, Lock R A, Hansman D, Paton J C. Contribution of autolysin to virulence of Streptococcus pneumoniae. Infect Immun 1989;57:2324–30.

Berry A M, Yother J, Briles D E, Hansman D, Paton J C. Reduced virulence of a defined pneumolysin-negative mutant of Streptococcus pneumoniae. Infect Immun 1989;57:2037–42.

McDaniel L S, Yother J, Vijayakumar M, McGarry L, Guild W R, Briles D E. Use of insertional inactivation to facilitate studies of biological properties of pneumococcal surface protein A (PspA). J Exp Med 1987;165:381–94.

Waltman W D II, McDaniel L S, Gray B M, Briles D E. Variation in the molecular weight of PspA (Pneumococcal Surface Protein A) among Streptococcus pneumoniae. Microb Pathog 1990;8:61–9.

Crain M J, Waltman W D II, Turner J S, et al. Pneumococcal surface protein A (PspA) is serologically highly variable and is expressed by all clinically important capsular serotypes of Streptococcus pneumoniae. Infect Immun 1990;58:3293–9.

Yother J, Briles D E. Structural properties and evolutionary relationships of PspA, a surface protein of Streptococcus pneumoniae, as revealed by sequence analysis. J Bact 1992;174:601–9.

McDaniel L S, Scott G, Kearney J F, Briles D E. Monoclonal antibodies against protease sensitive pneumococcal antigens can protect mice from fatal infection with Streptococcus pneumoniae. J Exp Med 1984;160:386–97.

McDaniel L S, Ralph B A, McDaniel D O, Briles D E. Localization of protection-eliciting epitopes on PspA of Streptococcus pneumoniae between amino acids residues 192 and 260. Microb Path 1994;17:323–37.

Yother J, Forman C, Gray B M, Briles D E. Protection of mice from infection with Streptococcus pneumoniae by anti-phosphocholine antibody. Infect Immun 1982;36:184–8.

Briles D E, Crain M J, Gray B M, Forman C, Yother J. Strong association between capsular type and virulence for mice among human isolates of Streptococcus pneumoniae. Infect Immun 1992;60:111–6.

McDaniel L S, Sheffield J S, Swiatlo E, Yother J, Crain M J, Briles D E. Molecular localization of variable and conserved regions of pspA, and identification of additional pspA homologous sequences in Streptococcus pneumoniae. Microb Pathog 1992;13:261–9.

McDaniel L S, McDaniel D O. Analysis of the gene encoding type 12 PspA of S. pneumoniae EF5668. In: Ferretti J J, Gilmore M S, Klaenhammer T R, Brown F ed. Genetics of Streptococci, Enterococci and Lactococci. Basel: Karger, 1995:283–6.

Briles D E, Forman C, Crain M. Mouse antibody to phosphocholine can protect mice from infection with mouse-virulent human isolates of Streptococcus pneumoniae. Infect Immun 1992;60:1957–62.

Davis R W, Boststein D, Roth J R. A manual for genetic engineering: advanced bacterial genetics. Cold Spring Harbor, N.Y.: Cold Spring Harbor Laboratory Press, 1980.

Studier F W, Moffatt B A. Use of baceriophage T7 RNA polymerase to direct selective high-level expression of cloned genes. J Mol Biol 1986;189:113–30.

Hanahan D. Studies on transformation of *Escherichia coli* with plasmids. J Mol Biol 1983;166:557–80.

Laemmli UK. Cleavage of structural proteins during the assembly of the head of bacteriophage T4. Nature 1970;227:680–5.

Towbin H, Staehelin T, Gordon J. Electrophoretic transfer of proteins from polyacrylamide gels to nitrocellulose sheets: procedure and some applications. PNAS 1979;76:4350–4.

Amsbaugh D F, Hansen C T, Prescott B, Stashak P W, Barthold D R, Baker P J. Genetic control of the antibody response to type III pneumococcal polysaccharide in mice. I. evidence that an X-linked gene plays a decisive role in determining responsiveness. J Exp Med 1972;136:931–49.

Briles D E, Nahm M, Schroer K, et al. Antiphosphocholine antibodies found in normal mouse serum are protective against intravenous infection with type 3 *Streptococcus pneumoniae*. J Exp Med 1981;153:694–705.

Zar J H. Biostatistical Analysis. 2nd Ed. Englewood Cliffs, N. J.: Prentice-Hall, Inc., 1984:718.

Yother J, Handsome G L, Briles D E. Truncated forms of PspA that are secreted from *Streptococcus pneumoniae* and their use in functional studies and cloning of the pspA gene. J Bact 1992;174:610–8.

Talkington D F, Voellinger D C, McDaniel L S, Briles D E. Analysis of pneumococcal PspA microheterogeneity in SDS polyacrylamide gels and the association of PspA with the cell membrane. Microb Pathog 1992;13:343–55.

Talkington D F, Crimmins D L, Voellinger D C, Yother J, Briles DE. A 43-kilodalton pneumococcal surface protein, PspA: isolation, protective abilities, and structural analysis of the amino-terminal sequence. Infect Immun 1991;59:1285–9.

Schneewind O, Model P, Fischetti V A. Sorting of protein A to the staphylococcal cell wall. Cell 1992;70:267–81.

Yother J, White J M. Novel surface attachment mechanism for the streptococcus pneumoniae protein PspA. J Bact 1994;176:2976–85.

Gray B M. Pneumococcal infection in an era of multiple antibiotic resistance. Adv Ped Inf Dis 1995;In press.

Filice G. A., L. L. Van Etta, C. P. Darby and D. W. Fraser. 1986. Bacteremia in Charleston County, South Carolina. *Am. J. Epidemiol.* 123:128.

Gillespie S. H. 1989. Aspects of pneumococcal infection including bacterial virulence, host response and vaccination. *J. Med. Microbiol.* 28:237.

Musher D. M. 1992. Infections caused by *Streptococcus pneumoniae:* Clinical spectrum, pathogenesis, immunity, and treatment. *Clin. Infect. Dis.* 14:801.

Nordenstam G., B. Anderson, D. E. Briles, J. Brooks, A. Oden, A. Svanborg and C. S. Eden. 1990. High anti-phosphorylcholine antibody levels and mortality associated with pneumonia. *Scand. J. Infect. Dis.* 22:187.

Giebink G. S. 1989. The microbiology of otitis media. *Pediatr. Infect. Dis. J.* 8:S18.

Giebink G. S. 1985. Preventing pneumococcal disease in children: recommendations for using pneumococcal vaccine. *Pediatr. Infect Dis.* 4:343.

Siber G. R. 1994. Pneumococcal disease: prospects for a new generation of vaccines. *Science* 265:1385.

Cadoz M., J. Armand, F. Arminjon, J. -P. Michel, M. Michel, F. Denis and G. Schiffman. 1985. A new 23 valent pneumococcal vaccine: immunogenicity and reactogenicity in adults. *J. Biol. Stand.* 13:261.

Robbins J. B., R. Austrian, C. -J. Lee, S. C. Rastogi, G. Schiffman, J. Henrichsen, P. H. Makela, C. V. Broome, R. R. Facklam, R. H. Tiesjema and J. C. Parke Jr. 1983. Considerations for formulating the second-generation pneumococcal capsular polysaccharide vaccine with emphasis on the cross-reactive types within groups. *J. Infect. Dis.* 148:1136.

Forrester H. L., D. W. Jahigen and F. M. LaForce. 1987. Inefficacy of pneumococcal vaccine in a high-risk population. *Am. J. Med.* 83:425.

Douglas R. M. and H. B. Miles. 1984. Vaccination against *Streptococcus pneumoniae* in childhood: lack of demonstrable benefit in young Australian children. *J. Infect. Dis.* 149:861.

Douglas R. M., J. C. Paton, S. J. Duncan and D. J. Hansman. 1983. Antibody response to pneumococcal vaccination in children younger than five years of age. *J. Infect. Dis.* 148:131.

Leinonen M., A. Sakkinen, R. kalliokoski, J. Luotenen, M. Timonen and P. H. Mekela. 1986. Antibody response to 14-valent pneumococcal capsular polysaccharide vaccine in preschool age children. *Pediatr. Infect. Dis.* 5:39.

Makela P. H., M. Leinonen, J. Pukander and P. Karma. 1981. A study of the pneumococcal vaccine in prevention of clinically acute attacks of recurrent otitis media. *Rev. Infect. Dis.* 3 S124.

Riley I. D. and R. M. Douglas. 1981. An epidemiologic approach to pneumococcal disease. Rev. Infect. Dis. 3:233.

Wright P. F., S. H. Sell, W. K. Vaughn, C. Andrews, K. B. McConnell and G. Schiffman. 1981. Clinical studies of pneumococcal vaccines in infants. II. Efficacy and effect on nasopharyngeal carriage. *Rev. Infect. Dis.* 3:S108.

Lock R. A., J. C. Paton and D. Hansman. 1988. Comparative efficacy of pneumococcal neuraminidase and pneumolysin as immunogens protective against *Streptococcus pneumoniae*. *Microbial Pathogenesis* 5:461.

McDaniel L. S. and D. E. Briles. 1986. Monoclonal antibodies against bacteria. Orlando, Fla.: Academic Press, Inc., 143.

Paton J. C., R. A. Lock and D. J. Hansman. 1983. Effect of immunization with pneumolysin on survival time of mice challenged With *Streptococcus pneumoniae*. *Infect. Immun.* 40:548.

Talkington D. F., D. L. Crimmins, D. C. Voellinger, J. Mother and D. E. Briles. 1991. A 43-kilodalton pneumococcal surface protein, PspA: isolation, protective abilities, and structural analysis of the amino-terminal sequence. *Infect. Immun.* 59:1285.

Yother J., C. Forman, B. M. Gray and D. E. Briles. 1982. Protection of mice from infection with *Streptococcus pneumoniae* by anti-phosphocholine antibody. *Infect. Immun.* 36:184.

Crain M. J., W. D. Waltman, J. S. Turner, J. Yother, D. F. Talkington, L. S. McDaniel, B. M. Gray and D. E. Briles. 1990. Pneumococcal surface protein A (PspA) is serologically highly variable and is expressed by all clinically important capsular serotypes of *Streptococcus pneumoniae*. *Infect. Immun.* 58:3293.

Briles D. E., J. Yother and L. S. McDaniel. 1988. Role of pneumococcal surface protein A in the virulence of *Streptococcus pneumoniae*. *Rev. Infect. Dis.* 10:5372.

McDaniel L. S., J. Yother, M. Vijayakumar, L. McGarry, W. R. Guild and D. E. Briles. 1987. Use of insertional inactivation to facilitate studies of biological properties of pneumococcal surface protein A (PspA). *J. Exp. Med.* 165:381.

Waltman W. D., L. S. McDaniel, B. M. Gray and D. E. Briles. 1990. Variation in the molecular weight of PspA (pneumococcal surface protein A) among *Streptococcus pneumoniae. Microbial Pathogenesis* 8:61.

Yother J. and D. E. Briles. 1992. Structural properties and evolutionary relationships of PspA, a surface protein of *Streptococcus pneumoniae*, as revealed by sequence analysis. *J. Bacteriol.* 174:601.

Yother J. and J. M. White. 1994. Novel surface attachment mechanism for the Streptococcus pneumoniae protein PspA. *J. Bact.* 176:2976.

Yother J., G. L. Handsome and D. E. Briles. 1992. Truncated forms of PspA that are secreted from *Streptococcus pneumoniae* and their use in functional studies and cloning of the pspA gene. *J. Bacteriol.* 174:610.

McDaniel L. S., J. S. Sheffield, P. Delucchi and D. E. Briles. 1991. PspA, a surface protein of *Streptococcus pneumoniae*, is capable of eliciting protection against pneumococci of more than one capsular type. *Infect. Immun.* 9:222.

McDaniel L. S., B. A. Ralph, D. 0. McDaniel and D. E. Briles. 1994. Localization of protection-eliciting epitopes on PspA of *Streptococcus pneumoniae* between amino acid residues 192 and 260. *Micro. Pathogenesis* 17:323.

McDaniel L. S., K. Scott, J. F. Kearney and D. E. Briles. 1984. Monoclonal antibodies against protease sensitive pneumococcal antigens can protect mice from fatal infection with *Streptococcus pneumoniae. J. Exp. Med.* 160:386.

Davis R. W., W. D. Boststein and J. R. Roth. 1980. A manual for genetic engineering: Advanced bacterial genetics. Cold Spring Harbor, N.Y.: Cold Spring Harbor Laboratory, 201.

Hanahan D. 1983. Studies on transformation of *Escherichia coli* with plasmids. *J. Mol. Biol.* 166:557.

Birnboim H. C. and J. Doly. 1979. A rapid alkaline extraction procedure for screening recombinant plasmid DNA. *Nuc. Acids Res.* 7:1513.

Osborn M. J. and J. Munson. 1974. Separation of the inner (cytoplasmic) and outer membranes of gram negative bacteria. *Methods Enzymol.* 31A:642.

Wicker L. S. and I. Scher. 1986. X-linked immune deficiency (Xid) of CBA/N mice. New York: Apringer-Verlag, 86.

Amsbaugh D. F., C. T. Hansen, B. Prescott, P. W. Stashak, D. R. Barthold and P. J. Baker. 1972. Genetic control of the antibody response to type III pneumococcal polysaccharide in mice. I. Evidence that an X-linked gene plays a decisive role in determining responsiveness. *J. Exp. Med.* 136:931.

Briles D. E., M. Nahm, K. Schoer, J. Davie, P. Baker, J. F. Kearney and R. Barletta. 1981. Anti-phosphocholine antibodies found in normal mouse serum are protective against intravenous infection with type 3 *S. pneumoniae. J. Exp. Med.* 153:694.

McDaniel L. S., J. S. Sheffield, E. Swiatlo, J. Yother, M. J. Crain and D. E. Briles. 1992. Molecular localization of variable and conserved regions of pspA and identification of additional pspA homologous sequences in *Streptococcus pneumoniae. Microbial Pathogenesis* 13:261.

Alexander, J. E., Lock, R. A., Peeters, C. C. A. M., Poolman, J. T., Andrew, P. W., Mitchell, T. J., Hansman, D., and Paton, J. C. (1994) Immunization of mice with pneumolysin toxoid confers a significant degree of protection against at least nine serotypes of *Streptococcus pneumoniae. Infect Immun* 62: 5683–5688.

Avery, O. T., McLeod, C. M., and McCarty, M. (1944) Studies on the chemical nature of the substance inducing transformation of pneumococcal types. Induction of transformation by a desoxyribonucleic acid fraction isolated from pneumococcus type III. *J Exp Med* 79: 137–158.

Briles, D. E., Nahm, M., Schroer, K., Davie, J., Baker, P., Kearney, J. F., and Barletta, R. (1981) Anti-phosphocholine antibodies found in normal mouse serum are protective against intravenous infection with type 3 *S. pneumoniae. J Exp Med* 153: 694–705.

Crain, M. J., Waltman, W. D. II, Turner, J. S., Yother, J., Talkington, D. E., McDaniel, L. M., Gray, B. M., and Briles, D. E. (1990) Pneumococcal surface protein A (PspA) is serologically highly variable and is expressed by all clinically important capsular serotypes of *Streptococcus pneumoniae. Infect Immun* 58: 393–3299.

Haanes-Fritz, E., Kraus, W., Burdett, V., Dale, J. B., Beachey, E. H., and Cleary, P. (1988) Comparison of the leader sequences of four group A streptococcal M protein genes. *Nucl Acids Res* 16: 4667–4677.

McDaniel, L. S., Yother, J., Vijayakumar, M., McGarry, L., Guild, W. R., and Briles, D. E. (1987) Use of insertional inactivation to facilitate studies of biological properties of pneumococcal surface protein A (PspA). *J Exp Med* 165: 381–394.

McDaniel, L. S., Sheffield, J. S., Delucchi, P., and Briles, D. E. (1991) PspA, a surface protein of *Streptococcus pneumoniae*, is capable of eliciting protection against pneumococci of more than one capsular type. *Infect Immun* 59: 222–228.

McDaniel, L. S., Sheffield, J. S., Swiatlo, E., Yother, J. Crain, M. J., and Briles, D. E. (1992) Molecular localization of variable and conserved regions of pspA, and identification of additional pspA-homologous sequences in *Streptococcus pneumoniae. Microbial Pathogenesis* 13: 261–269.

McDaniel, L. S., Ralph, B. A., McDaniel, D. O., and Briles, D. E. (1994) Localization of protection-eliciting epitopes on PspA of *Streptococcus pneumoniae* between amino acid residues 192 and 260. *Microbial Pathogenesis* 17: 323–337.

Meinkoth, J., and Wahl, G. (1984) Hybridization of nucleic acids immobilized on solid supports. *Anal Biochem* 138: 267–284.

Sampson, J. S., O'Connor, S. P., Stinson, A. R., Tharpe, J. A., and Russell, H. (1994) Cloning and nucleotide sequence analysis of psaA, the Streptococcus pneumoniae gene encoding a 37-kilodalton protein homologous to previously reported Streptococcus sp. adhesins. *Infect Immun* 62: 319–324.

Shoemaker, N. B., and Guild, W. R. (1974) Destruction of low efficiency markers is a slow process occurring at a heteroduplex stage of transformation. *Mol Gen Genet* 128: 283–290.

Siber, G. R. (1994) Pneumococcal disease: prospects for a new generation of vaccines. *Science* 265: 1385–1387.

Talkington, D. F., Crimmins, D. L., Voellinger, D. C., Yother, J., and Briles, D. E. (1991) A 43-kilodalton pneumococcal surface protein, PspA: isolation, protective abilities, and structural analysis of the amino-terminal sequence. *Infect Immun* 59: 1285–1289.

Waltman, W. D. II, McDaniel, L. S., Gray, B. M., and Briles, D. E. (1990) Variation in the molecular weight of PspA (pneumococcal surface protein A) among Streptococcus pneumoniae. *Microbial Pathogenesis* 8: 61–69.

Yother, J., McDaniel, L. S., and Briles, D. E. (1986) Transformation of encapsulated *Streptococcus pneumoniae*. *J Bacteriol* 168: 1463–1465.

Yother, J., and Briles, D. E. (1992) Structural properties and evolutionary relationships of PspA, a surface protein of *Streptococcus pneumoniae*, as revealed by sequence analysis. *J Bacteriol* 174: 601–609.

Yother, J., Handsome, G. L., and Briles, D. E. (1992) Truncated forms of PspA that are secreted from *Streptococcus pneumoniae* and their use in functional studies and cloning of the pspA gene. *J Bacteriol* 174: 610–618.

Yother, J., and White, J. M. (1994) Novel surface attachment mechanism of the *Streptococcus pneumoniae* protein PspA. *J Bacteriol* 176: 2976–2985.

Anonymous. Pneumococcal polysaccharide vaccine. *MMWR* 1981, 30, 410–419.

Farley, J. J., King, J. C., Nair, P., Hines, S. E., Tressler, R. L., Vink, P. E. Invasive pneumococcal disease among infected and uninfected children of mothers with immunodeficiency virus infection. *J. Pediatr.* 1994, 124, 853–858.

Schwartz, B., Gove, S., Lob-Lovit, J., Kirkwood, B. R. Potential interactions for the prevention of childhood pneumonia in developing countries: etiology of accute lower respiratory infections among young children in developing countries. *Ped. Infect. Dis.* in Press.

Avery, O. T., Goebel, W. F. Chemoimmunological studies of the soluble specific substance of pneumococcus. I. The isolation and properties of the acetyl polysaccharide of pneumococcus type 1. *J. Exp. Med.* 1933, 58, 731–755.

Austrian, R. Pneumococcal Vaccine: Development and Prospects. *Am. J. Med* 1979, 67, 547–549.

Shapiro, E. D., Berg, A. T., Austrian, R., Schroeder, D., Parcells, V., Margolis, A., Adair, R. K., Clemmens, J. D. Protective efficacy of polyvalent pneumococcal polysaccharide vaccine. *N. Engl. J. Med* 1991, 325, 1453–1460.

Fedson, D. S. Pneumococcal vaccination in the prevention of community-acquired pneumonia: an optimistic view of cost-effectiveness. *Sem. Resp. Infect.* 1993, 8, 285–293.

Gotschlich, E.C., Goldschneider, I., Lepow, M. L., Gold, R. The immune response to bacterial polysaccharides in man. In: *Antibodies in human diagnosis and therapy,* (Ed. Haber, E., Krause, R. M.) Raven, N.Y., 1977, 391–402.

Cowan, M. J., Ammann, A. J., Wara, D. W., Howie, V. M., Schultz, L., Doyle, N., Kaplan, M. Pneumococcal polysaccharide immunization in infants and children. *Pediatrics* 1978, 62, 721–727.

Mond, J. J., Lees, A., Snapper, C. M. T cell-independent antigens type 2. *Ann. Rev. Immunol.* 1995, 13, 655–692.

Stein, K. E. Thymus-independent and thymus-dependent responses to polysaccharide antigens. *J. Infect. Dis.* 1992, 162, S49.

Chiu, S. S., Greenberg, P. D., Marcy, S. M., Wong, V. K., Chang, S. J., Chiu, C. Y., Ward, J. I. Mucosal antibody responses in infants following immunization with *Haemophzilus influenzae*. *Pediatr. Res. Abstract.* 1994, 35, 10A.

Kauppi, M., Eskola, J., Kathty, H. H. influenzae type b (Hib) conjugate vaccines induce mucosal IgA1 and IgA2 antibody responses in infants and children. *ICAAC Abstracts* 1993, 33, 174.

Dagen, R., Melamed, R., Abramson, O., Piglansky, L., Greenberg, D., Mendelman, P. M., Bohidar, N., Ter-Minassian, D., Cvanovich, N., Lov, D., Rusk, C., Donnelly, J., Yagupsky, P. Effect of heptavalent pneumococcal-OMPC conjugate vaccine on nasopharyngeal carriage when administered during the 2nd year of life. *Pediatr. Res.* 1995, 37, 172A.

Fattom, A., Vann, W. F., Szu, S. C., Sutton, A., Bryla, D., Shiffman, G., Robbins, J. B., Schneerson, R. Synthesis and physiochemical and immunological characterization of pneumococcus type 12F polysaccharide-diptheria toxoid conjugates. *Infect. Immun.* 1988, 56, 2292–2298.

Kennedy, D., Derousse, C., E., A. Immunologic response of 12–18 month old children to licensed pneumococcal polysaccharide vaccine primed with *Streptococcus pneumoniae* 19F conjugate vaccine. *ICAAC* 1994, 34th annual meeting, 236.

McDaniel, L. S., Ralph, B. A., McDaniel, D. O., Briles, D. E. Localization of protection-eliciting epitopes on PspA of Streptococcus pneumoniae between amino acid residues 192 and 260. *Microb. Pathog.* 1994, 17, 323–337.

Langermann, S., Palaszynski, S. R., Burlein, J. E., Koenig, S., Hanson, M. S., Briles, D. E., Stover, C. K. Protective humoral response against pneumococcal infection in mice elicited by recombinant Bacille Calmette-Gurin vaccines expressing PspA. *J. Exp. Med.* 1994, 180, 2277–2286.

Siber, G. R. Pneumococcal disease: prospects for a new generation of vaccines. *Science* 1994, 265, 1385–1387.

Lock, R. A., Hansman, D., Paton, J. C. Comparative efficacy of autolysin and pneumolysin as immunogens protecting mice against infection by *Streptococcus pneumoniae*. *Microb. Pathog.* 1992, 12, 137–143.

Sampson, J. S., O'Connor, S. P., Stinson, A. R., Tharpe, J. A., Russell, H. Cloning and nucleotide sequence analysis of psaA, the *Streptococcus pneumoniae* gene encoding a 37-kilodalton protein homologus to previously reported Streptococcus sp. adhesins. *Infect. Immun.* 1994, 62, 319.

Paton, J. C., Lock, R. A., Lee, C. -J., Li, J. P., Berry, A. M., Mitchell. Purification and immunogenicity of genetically obtained pneumolysin toxoids and their conjugation to *Streptococcus pneumoniae* type 19F polysaccharide. *Infect. Immun.* 1991, 59, 2297–2304.

McDaniel, L. S., Scott, G., Kearney, J. F., Briles, D. E. Monoclonal antibodies against protease sensitive pneumococcal antigens can protect mice from fatal infection with *Streptococcus pneumoniae*. *J. Exp. Med.* 1984, 160, 386–397.

Briles, D. E., Forman, C., Horowitz, J. C., Volanakis, J. E., Benjamin, W. H., Jr., McDaniel, L. S., Eldridge, J., Brooks, J. Antipneumococcal effects of C-reactive protein and monoclonal antibodies to pneumococcal cell wall and capsular antigens. *Infect. Immun.* 1989, 57, 1457–1464.

McDaniel, L. S., Sheffield, J. S., Delucchi, P., Briles, D. E. PspA, a surface protein of *Streptococcus pneumoniae*, is capable of eliciting protection against pneumococci of more than one capsular type. *Infect. Immun.* 1991, 59, 222–228.

McDaniel, L. S., Yother, J., Vijayakumar, M., McGarry, L., Guild, W. R., Briles, D. E. Use of insertional inactivation to facilitate studies of biological properties of pneumococcal surface protein A (PspA). *J. Exp. Med.* 1987, 165, 381–394.

Yother, J., McDaniel, L. S., Crain, M. J., Talkington, D. F., Briles, D. E. Pneumococcal surface protein A: Structural analysis and biological significance In: *Genetics and Molecular Biology of Streptococci, Lactococci, and Enterococci,* (Ed. Dunny, G. M., Cleary, P. P., McKay, L. L.) American Society for Microbiology, Washington, DC, 1991, 88–91.

Waltman, W. D., II, McDaniel, L. S., Gray, B. M., Briles, D. E. Variation in the molecular weight of PspA (Pneumococcal Surface Protein A) among *Streptococcus pneumoniae*. *Microb. Pathog.* 1990, 8, 61–69.

Crain, M. J., Waltman, W. D., II, Turner, J. S., Yother, J., Talkington, D. E., McDaniel, L. M., Gray, B. M., Briles, D. E. Pneumococcal surface protein A (PspA) is serologically highly variable and is expressed by all clinically important capsular serotypes of *Streptococcus pneumoniae*. *Infect. Immun.* 1990, 58, 3293–3299.

McDaniel, L. S., Scott, G., Widenhofer, K., Carroll, Briles, D. E. Analysis of a surface protein of *Streptococcus pneumoniae* recognized by protective monoclonal antibodies. *Microb. Pathog.* 1986, 1, 519–531.

Tart, R. C., McDaniel, L. S., Ralph, B. A., Briles, D. E. Truncated *Streptocccus pneumoniae* PspA molecules elicit cross-protective immunity against pneumococcal challenge in mice. *J. Infect. Dis.* 1995, In Press.

Yother, J., Briles, D. E. Structural properties and evolutionary relationships of PspA, a surface protein of *Streptococcus pneumoniae*, as revealed by sequence analysis. *J. Bact.* 1992, 174, 601–609.

Talkington, D. F., Crimmins, D. L., Voellinger, D. C., Jother, J., Briles, D. E. A 43-kilodalton pneumococcal surface protein, PspA: isolation, protective abilities, and structural analysis of the amino-terminal sequence. *Infect. Immun.* 1991, 59:, 1285–1289.

McDaniel, L. S., McDaniel, D. O. Genetic analysis of the gene encoding type 12 PspA of *Streptococcus pneumoniae* strain EF5668 In: *Genetics of the streptococci, enterocococci, and lactococci,* (Ed. Feretti, J. J., Gilmore, M. S., Khenhammer, T. R., Brown, F.) Dev. Biol. Stand. Basel Krager, Basel, 1995, 283–286.

Fischetti, V. A., Pancholi, V., Schneewind, O. Conservation of a hexapeptide sequence in the anchor region of surface proteins from gram-positive cocci. *Mol. Microbiol* 1990, 4, 1603–1605.

Schneewind, O., Fowler, A., Faull, K. F. Structure of cell wall anchor of cell surface proteins in *Staphylococcus aureus*. *Science* 1995, 268, 103–106.

Yother, J., White, J. M. Novel surface attachment mechanism for the *Streptococcus pneumoniae* protein PspA. *J. Bact.* 1994, 176, 2976–2985.

McDaniel, L. S., Brooks-Walter, A., Briles, D. E., Swiatlo, E. Oligonucleotides identify conserved and variable regions of pspA and pspA-like sequences of *Streptococcus pneumoniae*. *Mol. Microbiol.* Submitted.

Yother, J., Handsome, G. L., Briles, D. E. Truncated forms of PspA that are secreted from *Streptococcus pneumoniae* and their use in functional studies and cloning of the pspA gene. *J. Bact.* 1992, 174, 610–618.

Talkington, D. F., Voellinger, D. C., McDaniel, L. S., Briles, D. E. Analysis of pneumococcal PspA microheterogeneity in SDS polyacrylamide gels and the association of PspA with the cell membrane. *Microb. Pathog.* 1992, 13, 343–355.

Smith, M.D., Guild, W.R. A plasmid in *Streptococcus pneumoniae*. *J. Bacteriol.* 1979, 137, 735–739.

Shoemaker, N. B., Guild, W. R. Destruction of low efficiency markers is a slow process occurring at a heteroduplex stage of transformation. *Mol. Gen. Genet.* 1974, 128, 283–290.

Raven, A. W. Reciprocal capsular transformations of pneumococci. *J. Bact.* 1959, 17, 296–309.

McDaniel, L. S., Sheffield, J. S., Swiatlo, E., Yother, J., Crain, M. J., Briles, D. E. Molecular localization of variable and conserved regions of pspA, and idnetification of additional pspA homologous sequences in Streptococcus pneumoniae. *Microb. Pathog.* 1992, 13, 261–269.

Brooks-Walter, A., McDaniel, L. S., Hollingshead, S. K., Briles, D. E. Restriction fragment length polymorphisms of pspA of *Streptococcus pneumoniae* reveal a genetic polymorphism. Submitted.

van de Rijn, I., Kessler, R. E. Growth characteristics of Group A Streptococci in a new chemically defined medium. *Infec. Immun.* 1980, 27, 444–448.

Waltman, W. D., II, McDaniel, L. S., Andersson, B., Bland, L., Gray, B. M., Svanborg-Eden, C., Briles, D. E. Protein serotyping of *Streptococcus pneumoniae* based on reactivity to six monoclonal antibodies. *Microb. Pathog.* 1988, 5, 159–167.

Tomasz, A. Surface components of *Streptococcus pneumoniae*. *Rev. Infect. Dis* 1981, 3, 190–211.

Garcia, J. L., Garcia, E., Lopez, R. Overproduction and rapid purifcation of the amidase of *Streptococcus pneumoniae*. *Arch. Microbiol.* 1987, 149, 52–56.

Osborn, M. J., Munson, J. Separation of the inner (cytoplasmic) and outer membranes of gram negative bacteria. *Method Enzymol.* 1974, 31A, 642–653.

Briles, D. E., Horowitz, J., McDaniel, L. S., Benjamin, W. H., Jr., Claflin, J. L., Booker, C. L., Scott, G., Forman, C. Genetic control of susceptibility to pneumococcal infection. *Curr. Top. Microbiol. Immunol.* 1986, 124, 103–120.

Briles, D. E., Crain, M. J., Gray, B. M., Forman, C., Yother, J. A strong association between capsular type and mouse virulence among human isolates of *Streptococcus pneumoniae*. *Infect. Immun.* 1992, 60, 111–116.

Musher, D. M., Raizan, K. R., Weinstein, L. The effect of *Listeria monocytogenes* on resistance to pneumococcal infection. *Soc. Exp. Bio. and Med.* 1970, 135, 557–560.

Roberts, P., Jeffery, P. K., Mitchell, T. J., Andrew, P. W., Boulnois, G. J., Feldman, C., Cole, P. J., Wilson, R. Effect of immunization with Freund's adjuvant and pneummolysin on histologic features of pneumococcal infection in the rat lung in vivo. *Infect. Immun.* 1992, 60, 4969–4972.

Weigle, W. O. Immunological unresponsiveness In: *Adv. Immunol,* (Ed. Dixon, J. F., Kunkel, H. G.) Academic Press, New York, N.Y., 1973, 61–162.

Alexander, J. E., Lock, R. A., Peeters, C. C. A. M., Poolman, J. T., Andrew, P. W., Mitchell, T. J., Hansman, D., Paton, J. C. Immunization of mice with pneumolysin toxoid confers a significant degreee of protection against at least nine serotypes of *Streptococcus pneumoniae*. *Infection and Immunity* 1994, 62, 5683–5688.

Berry, A. M., Lock, R. A., Hansman, D., Paton, J. C. Contribution of autolysin to virulence of *Streptococcus pneumoniae*. *Infect. Immun.* 1989, 57, 2324–2330.

Lock, R. A., Paton, J. C., Hansman, D. Purification and immunologic characterization of neuraminidase produced by *Streptococcus pneumoniae*. *Microb. Pathog.* 1988, 4, 33–43.

Talkington, D., Koenig, A., Russell, H. The 37 kDa protein of *Streptococcus pneumoniae* protects mice against fatal challenge. *American Society of Microbiology Abstracts* 1992, 149.

Dillard, J. P., Yother, J. Genetic and molecular characterization of capsular polysaccharide biosynthesis in *Streptococcus pneumoniae* type 3. *Mol. Microbiol.* 1994, 12, 99–972.

Tomasz, A. Biological consequences of the replacement of choline by ethanolamine in the cell wall of pneumococcus: chain formation, loss of transformability, and loss of autolysis. *Proc. Natl. Acad. Sci. USA* 1968, 59, 86–93.

Briles, D. E., Nahm, M., Schroer, K., Davie, J., Baker, P., Kearney, J., Barletta, R. Antiphosphocholine antibodies found in normal mouse serum are protective against intravenous infection with type 3 *Streptococcus pneumoniae*. *J. Exp. Med.* 1981, 153, 694–705.

Amsbaugh, D. F., Hansen, C. T., Prescott, B., Stashak, P. W., Barthold, D. R., Baker, P. J. Genetic control of the antibody response to type III pneumococcal polysaccharide in mice. I. Evidence that an X-linked gene plays a decisive role in determining responsiveness. *J. Exp. Med* 1972, 136, 931–949.

Avery, O. T., MacLeod, C. M., McCarty, M. Studies on the chemical nature of the substance inducing transformation of pneumococcal types. Induction of transformation by a desoxyribonucleic acid fraction isolated from pneumococcus type III. *J. Exp. Med* 1944, 79, 137–158.

McCarty, M. *The transforming principle.* Norton, N.Y., 1985, 252.

What is claimed is:

1. An isolated amino acid molecule comprising pneumococcal surface protein C, PspC, of *Streptococcus pneumoniae* having alpha-helical, proline rich and repeat regions.

2. An immunological composition consisting essentially of the isolated amino acid molecule of claim 1.

3. An isolated amino acid molecule of claim 1 comprising amino acid residue 458 to the C-terminus of PspC as set forth in FIG. 21.

4. An isolated amino acid molecule of claim 1, further comprising a signal sequence consisting essentially of a charged region followed by a hydrophobic core of amino acids.

5. An isolated amino acid molecule of claim 1, wherein the alpha-helical region further comprises a seven residue periodicity and a coiled coil region having three breaks in a heptad repeat.

6. An isolated amino acid molecule comprising pneumococcal surface protein C, PspC, of *S. pneumoniae* having alpha-helical, proline rich and repeat regions, wherein the alpha-helical region comprises a C-terminus having substantial homology with a protection-eliciting region of PspA.

7. An immunological composition consisting essentially of the isolated amino acid molecule of claim 6.

8. An isolated amino acid molecule of claim 1, further comprising a 17 amino acid, partially hydrophobic tail.

9. An isolated amino acid molecule of claim 6, further comprising a 17 amino acid, partially hydrophobic tail.

* * * * *